US012410228B2

(12) United States Patent
Menting et al.

(10) Patent No.: US 12,410,228 B2
(45) Date of Patent: *Sep. 9, 2025

(54) INSULIN ANALOGS

(71) Applicants: UNIVERSITY OF UTAH RESEARCH FOUNDATION, Salt Lake City, UT (US); THE WALTER AND ELIZA HALL INSTITUTE OF MEDICAL RESEARCH, Parkville (AU)

(72) Inventors: John Gerbrandt Tasman Menting, Bulleen (AU); Brian Smith, Bundoora (AU); Danny Hung-Chieh Chou, Salt Lake City, UT (US); Helena Safavi-Hemami, Salt Lake City, UT (US); Michael Colin Lawrence, Newport (AU); Baldomero M. Olivera, Salt Lake City, UT (US)

(73) Assignees: UNIVERSITY OF UTAH RESEARCH FOUNDATION, Salt Lake City, UT (US); THE WALTER AND ELIZA HALL INSTITUTE OF MEDICAL RESEARCH, Parkville (AU)

( * ) Notice: Subject to any disclaimer, the term of this patent is extended or adjusted under 35 U.S.C. 154(b) by 447 days.

This patent is subject to a terminal disclaimer.

(21) Appl. No.: 17/568,698

(22) Filed: Jan. 4, 2022

(65) Prior Publication Data
US 2022/0340636 A1  Oct. 27, 2022

Related U.S. Application Data

(63) Continuation of application No. 16/319,450, filed as application No. PCT/AU2017/050758 on Jul. 21, 2017, now Pat. No. 11,248,034.

(60) Provisional application No. 62/483,118, filed on Apr. 7, 2017.

(30) Foreign Application Priority Data

Jul. 22, 2016 (AU) ................................ 2016902883

(51) Int. Cl.
*C07K 14/62* (2006.01)
*C07K 14/435* (2006.01)
*C30B 7/02* (2006.01)
*C30B 29/58* (2006.01)
*G16B 15/00* (2019.01)
*A61K 38/00* (2006.01)
*A61P 3/10* (2006.01)

(52) U.S. Cl.
CPC ........ *C07K 14/62* (2013.01); *C07K 14/43509* (2013.01); *C30B 7/02* (2013.01); *C30B 29/58* (2013.01); *G16B 15/00* (2019.02); *A61K 38/00* (2013.01); *A61P 3/10* (2018.01); *C07K 2299/00* (2013.01)

(58) Field of Classification Search
CPC .............. C07K 14/62; C07K 17/43509; C07K 2299/00; G16B 15/00; G16B 15/30; C30B 7/02; C30B 29/58; A61P 3/10; A61P 3/08; A61K 38/00; A61K 38/28
See application file for complete search history.

(56) References Cited

U.S. PATENT DOCUMENTS

| 8,575,096 | B2* | 11/2013 | Olsen ..................... C07K 14/62 |
| | | | 514/6.9 |
| 11,248,034 | B2 | 2/2022 | Menting |
| 2008/0146492 | A1 | 6/2008 | Zimmerman |
| 2011/0077196 | A1 | 3/2011 | Weiss |
| 2013/0022592 | A1 | 1/2013 | Vaughn |
| 2014/0128319 | A1 | 5/2014 | Weiss |
| 2022/0389073 | A1* | 12/2022 | Chou ....................... A61P 3/10 |

FOREIGN PATENT DOCUMENTS

| RU | 2104305 | 2/1998 |
| WO | 2005095443 | 10/2005 |
| WO | 2008034881 | 3/2008 |
| WO | 2010014946 | 2/2010 |
| WO | 2010066636 | 6/2010 |
| WO | 2012174480 | 12/2012 |
| WO | 2014145593 | 9/2014 |
| WO | 2014158900 | 10/2014 |
| WO | 2018014091 | 1/2018 |

OTHER PUBLICATIONS

Chiral Mutagenesis of Insulin: Contribution of The B20-B23 beta-Turn to Activity and Stability. The Journal of Biological Chemistry, vol. 281, No. 31, pp. 22386-22396. (Year: 2006).*
Smith, L. et al., "Amino acid sequences of Insulins", Diabetes, 21(2 Suppl):457-60, (1972).
Abraham, M. et al., "Gromacs: High Performance Molecular Simulations Through Multi-Level Parallelism from Laptops to Supercomputers", SoftwareX 1-2:19-25, (2015).
Adams, M. et al., "Structure of Rhombohedral 2 Zinc Insulin Crystals", Nature, 224:491-5, (1969).
Adams, P. et al., "Phenix: A Comprehensive Python-Based System for Macromolecular Structure Solution", Acta Crystallogr D Biol Crystallogr., 66(Pt 2):213-21, (2010).
AU Patent Application No. 2016902883; Provisional Application as filed, dated Jul. 22, 2016; 203 pages.

(Continued)

*Primary Examiner* — Catherine S Hibbert
(74) *Attorney, Agent, or Firm* — BALLARD SPAHR LLP

(57) ABSTRACT

The present invention relates to insulin analogs, particularly insulin analogs having shortened B chains. The present invention also relates to the crystal structure of insulin from the venom of cone snails and to methods of using the crystal and related structural information to screen for and design insulin analogs that interact with or modulate the insulin receptor. The present invention also relates to therapeutic and prophylactic methods using insulin analogs.

Figure 2:
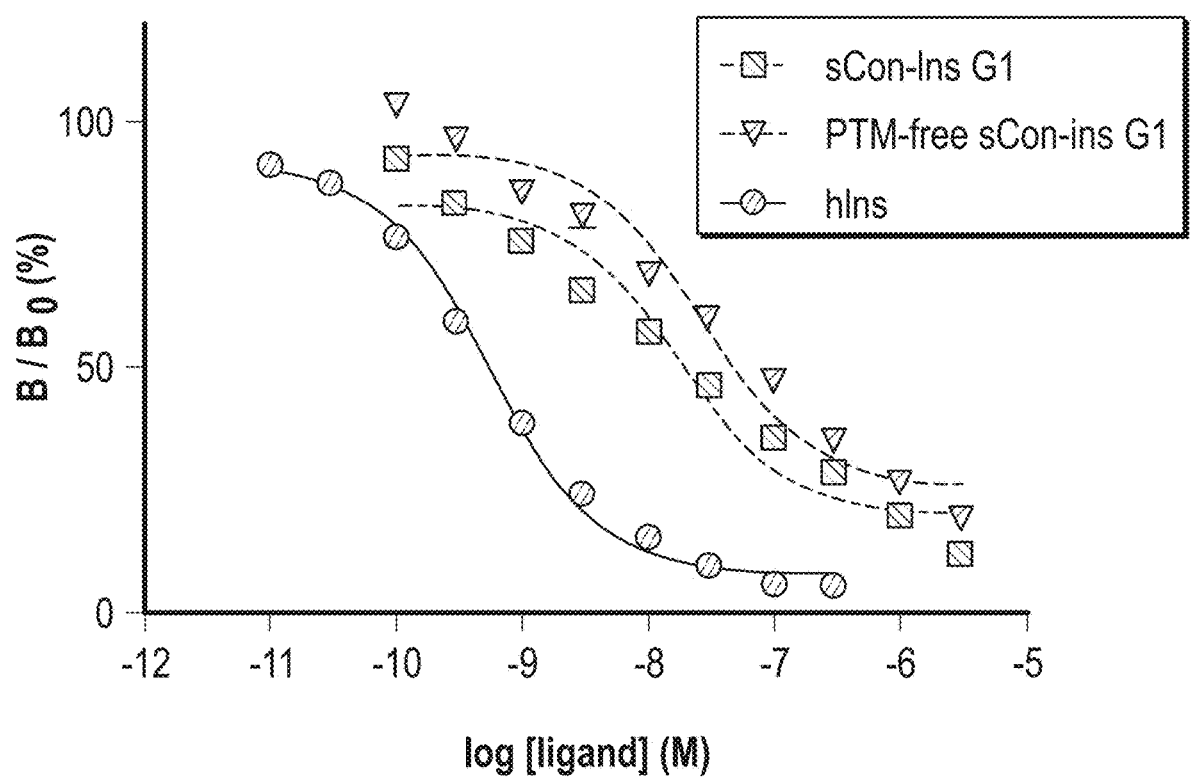

18 Claims, 32 Drawing Sheets
Specification includes a Sequence Listing.

(56) References Cited

OTHER PUBLICATIONS

Bajaj, M. et al., "Coypu Insulin. Primary Structure, Conformation and Biological Properties of a Hystricomorph Rodent Insulin", Biochem J., 238(2):345-51, (1986).
Bao, S. et al., "Crystal Structure of Desheptapeptide (B24-B30) Insulin at 1.6 A Resolution: Implications for Receptor Binding", Proc Natl Acad Sci USA, 94(7):2975-80, (1997).
Bentley, G., "[35] Phase Translation Function", Methods Enzymol., 276:611-9, (1997).
Berendsen, H. et al., "Molecular Dynamics with Coupling to an External Bath", J Chem Phys., 81:3684-90, (1984).
Best, R. et al., "Optimization of the Additive Charmm All-Atom Protein Force Field Targeting Improved Sampling of the Backbone φ, ψ and Side-Chain χ(1) and χ(2) Dihedral Angles", J Chem Theory Comput., 8(9):3257-73, (2012).
Brünger, A. et al., "Crystallography & NMR System: A New software Suite for Macromolecular Structure Determination", Acta Cystallogr D Biol Crystallogr., 54(Pt 5):905-21, (1998).
Brünger, A., "[32] Patterson Correlation Searches and Refinement", Methods Enzymol., 276:558-80, (1997).
Bussi, G. et al., "Canonical Sampling Through Velocity Rescaling", J Chem Phys., 126(1):014101, (2007).
CAS RN 102961-54-6, STN Entry Date Jun. 28, 1986 (see whole registry entry).
CAS RN 135317-44-1, STN Entry Date Aug. 2, 1991 (see whole registry entry).
CAS RN 1353849-21-4, STN Entry Date Jan. 23, 2012 (see whole registry entry).
CAS RN 177150-87-7, STN Entry Date Jun. 7, 1996 (see whole registry entry).
CAS RN 53123-87-8, STN Entry Date Nov. 16, 1984 (see whole registry entry).
CAS RN 556776-12-6, STN Entry Date Jul. 29, 2003 (see whole registry entry).
Chen, Z. et al., "Conformational Changes in Conantokin-G Induced Upon Binding of Calcium and Magnesium as Revealed by NMR Structural Analysis", J Biol Chem., 273(26):16248-58, (1998).
Cnudde, S. et al., "The Crystal Structure of the Calcium-Bound Con-G[Q6A] Peptide Reveals a Novel Metal-Dependent Helical Trimer", J Biol Inorg Chem., 16(2):257-66, (2011).
Dai, Q. et al., "Ca 2+-Induced Self-Assembly in Designed Peptides with Optimally Spaced Gamma-Carboxyglutamic Acid Residues", J Inorg Biochem., 105(1):52-7, (2011).
Denley, A. et al., "Structural Determinants for High-Affinity Binding of Insulin-Like Growth Factor II to Insulin Receptor (IR)-A, the Exon 11 Minus Isoform of the IR", Mol Endocrinol., 18(10):2502-12, (2004).
Dodson, G. et al., "The Role of Assembly in Insulin's Biosynthesis", Curr Opin Struct Biol., 8(2):189-94, (1998).
Emsley, P. et al., "Coot: Model-Building Tools for Molecular Graphics", Acta Crystallogr D Biol Crystallogr., 60(Pt 12 Pt 1):2126-32, (2004).
Essmann, U. et al., "A Smooth Particle Mesh Ewald Method", J Chem Phys., 103(19): 8577-93, (1995).
Galande, A. et al., "An Effective Method of On-Resin Disulfide Bond Formation in Peptides", J Comb Chem., 7(2):174-7, (2005).
Gauguin, L. et al., "Structural basis for the lower affinity of the insulin-like growth factors for the insulin receptor", J Biol Chem., 283(5):2604-13, (2008).
Glendorf, T. et al., "Engineering of Insulin Receptor Isoform-Selective Insulin Analogues", PLoS One, 6(5):e20288, (2011).
Guvench, O. et al., "Charmm Additive All-Atom Force Field for Carbohydrate Derivatives and its Utility in Polysaccharide and Carbohydrate-Protein Modeling", J Chem Theory Comput., 7(10):3162-80, (2011).
Heni, M. et al., "Impaired Insulin Action in the Human Brain: Causes and Metabolic Consequences", Nat Rev Endocrinol., 11(12):701-11, (2015).

Hess, B., "P-Lincs: A Parallel Linear Constraint Solver for Molecular Simulation", J Chem Theory Comput., 4(1):116-22, (2008).
Holm, L. et al., "Dali Server: Conservation Mapping in 3D", Nucleic Acids Res., 38(Web Server Issue): W545-9, (2010).
Houtman, J. et al., "Studying Multisite Binary and Ternary Protein Interactions by Global Analysis of Isothermal Titration Calorimetry Data in Sedphat: Application to Adaptor Protein Complexes in Cell Signaling", Protein Sci., 16(1):30-42, (2007).
Hua, Q. et al., "Insulin: a small protein with a long journey", Protein Cell, 1(6):537-51, (2010).
Hua, Q. et al., "Structure of a Protein in a Kinetic Trap", Nat Struct Biol., 2(2):129-38, (1995).
International Application No. PCT/AU2017/050758; International Search Report and Written Opinion of the International Searching Authority, date of mailing Sep. 15, 2017; 19 pages.
Jones, T. et al., "Improved Methods for Building Protein Models in Electron Density Maps and the Location of Errors in These Models", Acta Crystallogr., A47(Pt 2): 110-9, (1991).
Kabsch, W., "Integration, Scaling, Space-Group Assignment and Post-Refinement", Acta Crystallogr D Biol Crystallogr., 66(Pt 2):133-44, (2010).
King, G., "Venoms as a Platform for Human Drugs: Translating Toxins into Therapeutics", Expert Opin Biol Ther., 11(11):1469-84, (2011).
Kleywegt, G. et al., "A Super Position", News from the Uppsala Software Factory—4, pp. 1-4, (1994).
Krissinel, E. et al., "Secondary-Structure Matching (SSM), a New Tool for Fast Protein Structure Alignment in Three Dimensions", Acta Crystallogr D Biol Crystallogr., 60(Pt 12 Pt 1):2256-68, (2004).
Kristensen, C. et al., "Alanine Scanning Mutagenesis of Insulin", The Journal of Biological Chemistry, 272(20):12978-83, (1997).
Lattman, E., "Diffraction Methods for Biological Macromolecules. Use of the Rotation and Translation Functions", Methods Enzymol., 115:55-77, (1985).
Lawrence, C. et al., "Insulin Mimetic Peptide Disrupts the Primary Binding Site of the Insulin Receptor", J Biol Chem., 291(30):15473-81, (2016).
Marsh, B. et al., "Molecular Regulation of GLUT-4 Targeting in 3T3-L1 Adipocytes", J Cell Biol., 130(5):1081-91, (1995).
McCoy, A. et al., "Phaser Crystallographic Software", J Appl Crystallogr., 40(Pt4):658-74, (2007).
Menting, J. et al., "How Insulin Engages its Primary Binding Site on the Insulin Receptor", Nature, 493(7431):241-5, (2013).
Menting, J. et al., "Protective Hinge in Insulin Opens to Enable its Receptor Engagement", Proc Natl Acad Sci USA, 111(33):E3395-E3404, (2014).
Menting, J. et al., "Structural Congruency of Ligand Binding to the Insulin and Insulin/Type 1 Insulin-like Growth Factor Hybrid Receptors", Structure, 23(7):1270-82, (2015).
Moody, A. et al., "A Simple Free Fat Cell Bioassay for Insulin", Horm Metab Res., 6(1):12-6, (1974).
Morton, T. et al., "Kinetic Analysis of Macromolecular Interactions Using Surface Plasmon Resonance Biosensors", Methods Enzymol., 295:268-94, (1998).
Murshudov, G. et al., "Refinement of Macromolecular Structures by the Maximum-Likelihood Method", Acta Crystallogr D Biol Crystallogr., 53(Pt 3):240-55, (1997).
Muttenthaler, M et al., "p-Nitrobenzyl Protection for Cysteine and Selenocysteine: A More Stable Alternative to the Acetamidomethyl Group", Biopolymers, 94(4):423-32, (2010).
Nakagawa, S. et al., "Chiral mutagenesis of insulin. Contribution of the B20-B23 beta-turn to activity and stability", J Biol Chem., 281(31):22386-96, (2006).
Navaza, J. et al., "[33] AMoRe: An Automated Molecular Replacement Program Package", Methods Enzymol., 276:581-94, (1997).
Nice, E. et al., "Instrumental Biosensors: New Perspectives for the Analysis of Biomolecular Interactions", Bioessays, 21(4):339-52, (1999).
Olefsky, J., "Mechanisms of the Ability of Insulin to Activate the Glucose-Transport System in Rat Adipocytes", Biochem J., 172(1):137-45, (1978).
Owens, D., "New Horizons-Alternative Routes for Insulin Therapy", Nat Rev Drug Discov., 1(7):529-40, (2002).

(56) References Cited

OTHER PUBLICATIONS

Pandyarajan, V. et al., "Aromatic Anchor at an Invariant Hormone-Receptor Interface", J Biol Chem., 289(50):34709-27, (2014).
Pettersen, E. et al., "UCSF Chimera—A Visualization System for Exploratory Research and Analysis", J Comput Chem., 25(13):1605-12, (2004).
Phillips, J. et al., "Scalable Molecular Dynamics with Namd", J Comput Chem., 26(16):1781-802, (2005).
Pronk, S. et al., "Gromacs 4.5: A High-Throughput and Highly Parallel Open Source Molecular Simulation Toolkit", Bioinformatics, 29(7):845-54, (2013).
River, J. et al., "Total Synthesis and Further Characterization of the Gamma-Carboxyglutamate-Containing "Sleeper" Peptide from Conus Geographus Venom", Biochemistry, 26(26):8508-12, (1987).
Robinson, L. et al., "Insulin-Regulated Sorting of Glucose Transporters in 3T3-L1 Adipocytes", Am J Physiol., 263(2 Pt 1):E383-93, (1992).
Safavi-Hemami, H. et al., "Specialized Insulin is Used for Chemical Warfare by Fish-Hunting Cone Snails", Proc Natl Acad Sci USA, 112(6):1743-8, (2015).
Schymkowitz, J. et al., "The FoldX Web Server: An Online Force Field", Nucleic Acids Res., 33(Web Server Issue):W382-8, (2005).
Simon, J. et al., "Evolution of Preproinsulin Gene in Birds", Mol Phylogenet Evol., 30(3):755-66, (2004).
Smith, G. et al., "The Structure of T6 Human Insulin at 1.0 A Resolution", Acta Crystallogr D Biol Crystallogr, 59(Pt 3):474-82, (2003).
Soos, M. et al., "Monoclonal Antibodies Reacting with Multiple Epitopes on the Human Insulin Receptor", Biochem J., 235(1):199-208, (1986).
Sparrow, L. et al., "N-Linked Glycans of the Human Insulin Receptor and Their Distribution Over the Crystal Structure", Proteins, 71(1):426-39, (2008).
Tong, L. et al., "Rotation Function Calculations with GLRF Program", Methods Enzymol., 276:594-611, (1997).
U.S. Appl. No. 16/319,450; Corrected Notice of Allowance, dated Oct. 20, 2021; 4 pages.
U.S. Appl. No. 16/319,450; Examiner-Initiated Interview Summary, dated Feb. 16, 2021; 1 page.
U.S. Appl. No. 16/319,450; Examiner-Initiated Interview Summary, dated Oct. 14, 2021; 1 page.
U.S. Appl. No. 16/319,450; Examiner-Initiated Interview Summary, Feb. 19, 2021; 2 pages.
U.S. Appl. No. 16/319,450; Non-Final Office Action, dated Feb. 24, 2021; 16 pages.
U.S. Appl. No. 16/319,450; Notice of Allowance, dated Oct. 5, 2021; 24 pages.
U.S. Appl. No. 62/483,118; Provisional Application as filed, dated Apr. 7, 2017; 39 pages.
Walewska, A. et al., "Integrated Oxidative Folding of Cysteine/Selenocysteine Containing Peptides: Improving Chemical Synthesis of Conotoxins", Angew Chem Int Ed Engl., 48(12):2221-4, (2009).
Webb, B. et al., "Comparative Protein Structure Modeling Using Modeller", Curr Protoc Bioinformatics, 47:5.6.1-32, (2014).
Weiss, M., "The Structure and Function of Insulin: Decoding the TR Transition", Vitam Horm., 80:33-49, (2009).
Zambelli, V. et al., "Harnessing the Knowledge of Animal Toxins to Generate Drugs", Pharmacol Res., 112:30-6, (2016).

\* cited by examiner

A-chain
Con-Ins G1   1 GVVYHCHRPCSNAEFKKYC* 20 (SEQ ID NO: 22)
hIns         1 GIVEQCCTSICSLYQLENYCN 21 (SEQ ID NO: 24)

B-chain
Con-Ins G1  -1 TFDTOKHRCGSYITNSYMDLCYR        21 (SEQ ID NO: 23)
hIns         1 FVNQHLCGSHLVEALYLVCGERGFFYTPKT 30 (SEQ ID NO: 25)

| | GlyA1 | IleA2 | ValA3 | GlnA4 | GlnA5 | ThrA8 | SerA9 | IleA10 | SerA.2 | LeuA.3 | TyrA14 | GlnA15 | LeuA16 | GluA17 | AsnA18 | TyrA19 | AsnA21 |
|---|---|---|---|---|---|---|---|---|---|---|---|---|---|---|---|---|---|
| G | 0.00234646 | 4.689710000 | 2.375930000 | -0.592227100 | 4.009608100 | 0.501115000 | 1.759780000 | 1.108860000 | 0.571175000 | -1.505310000 | -2.480930000 | -1.634080000 | -3.559240000 | -1.264590000 | -1.598070000 | -4.855750000 | 0.125014000 |
| A | -1.779300000 | -1.817100000 | -1.457310000 | -0.816097100 | -0.790896011 | 0.120398001 | -1.604800000 | -1.172110000 | -0.987294100 | -0.760101000 | -1.941680001 | -0.302014100 | -3.234520000 | 1.386093001 | -1.058020001 | -1.913180001 | 0.230415100 |
| L | -2.624070000 | -0.094432600 | -1.201480000 | 0.455197000 | -0.791710000 | -0.709971700 | -1.559440200 | 0.098688700 | -1.043290000 | 0.022867601 | -1.990610000 | -0.436693000 | -0.003320730 | 0.578907700 | -1.409870000 | 0.338456000 | 0.046242200 |
| V | 5.540320000 | 1.371590000 | 0.000000000 | 0.445353000 | 2.037230000 | 0.006278850 | 1.630990000 | 0.444778000 | 1.394370000 | 0.949893000 | 2.272910000 | 0.213419000 | 2.506150000 | 1.042840000 | 2.516630000 | 1.802980000 | 0.536612000 |
| I | -6.544360000 | -0.000065746 | 0.414220000 | -0.144407700 | -1.726180000 | -0.523831000 | 1.369930000 | 0.000000000 | -1.012560000 | 0.637399000 | -2.013830000 | 0.323103000 | 4.240920000 | -0.368434000 | -2.684340000 | -1.540790000 | -0.205372000 |
| P | -1.509840000 | -1.379050000 | -1.826980000 | -1.293550000 | -3.409500000 | -0.785195000 | -4.599040000 | 0.086197000 | 0.533055000 | -0.329706000 | -0.981637000 | 0.133202000 | -5.224290000 | -4.245700000 | -2.883750000 | -0.842933000 | 0.344724000 |
| R | -1.114952000 | -6.176100000 | -1.464490000 | 0.172260000 | -0.911682000 | -1.162080000 | 0.796600000 | -1.871846000 | 1.559410000 | -0.658523000 | -0.119980000 | -0.593236410 | -3.123890000 | 0.678894400 | -2.283675000 | -1.123790000 | 0.660799700 |
| T | -6.346200000 | -3.995520000 | -0.151883500 | -0.257094000 | -0.716922200 | 0.000000000 | -0.664950000 | -0.445532000 | -0.942600000 | 1.015390000 | -1.999810000 | -0.397386000 | 4.953440000 | -0.852949000 | 1.930660000 | -2.490400000 | -0.596455000 |
| S | 1.411340000 | 4.941610000 | 2.040660000 | 0.014053001 | 1.182570000 | 0.663974000 | 0.000000000 | 1.371470000 | 0.000000000 | 1.208500000 | 1.965100000 | 1.369490000 | 2.744420000 | 0.335617000 | 1.705730000 | 2.208460000 | 0.694490000 |
| C | 1.836460000 | 3.702730000 | -0.892670000 | -0.453404500 | 4.197470000 | 0.454656000 | 1.414230000 | -0.595018000 | 0.818851000 | -1.236730000 | -2.297790000 | -1.170380000 | -2.526460000 | 7.441430000 | 1.403830000 | -2.166180000 | -0.144792000 |
| M | -2.203740000 | 0.395970000 | -0.600760000 | 0.000000000 | -0.377763900 | -0.493092000 | 1.271040000 | -0.293930000 | -0.610094700 | 0.386082600 | 4.777772000 | 0.399736000 | 0.160595300 | 0.509810000 | 0.215152000 | -1.420800000 | 0.090631870 |
| K | -4.581420000 | 0.000000000 | -0.600295400 | 0.275995500 | 0.239504000 | 0.000000000 | -0.777215670 | -0.456777200 | -0.889661000 | -0.484508000 | -1.983130000 | 0.363526800 | 4.317610000 | -0.509810000 | 1.769100000 | -1.429250000 | -0.362048000 |
| E | -2.831945000 | -4.264380000 | -2.278050000 | 0.000000000 | 0.000000000 | 0.482909000 | 0.584680800 | 0.305575000 | 0.109133000 | 0.477289500 | -0.787810000 | -0.000648077 | 2.936300000 | -0.000643000 | 3.665270000 | 3.557940000 | 0.483110000 |
| Q | -2.666390000 | 3.811155000 | -1.432850000 | 0.067192100 | 0.000000000 | 0.420610000 | 0.988513000 | 0.184230000 | 1.223630000 | 0.361984400 | 1.392690000 | 0.006747410 | 2.021150000 | 0.481277200 | 1.840000000 | 3.836220000 | 0.542307000 |
| D | -2.091300000 | -5.065390000 | -2.995180000 | 0.811375600 | -0.529296000 | 0.253691000 | 1.260000000 | -0.857232000 | 2.173270000 | 0.192735000 | 1.622575000 | 0.298305500 | 3.394470000 | 1.698440000 | -2.829130000 | 4.242730000 | -0.011538700 |
| N | -2.919760000 | 4.535410000 | -1.493790000 | 0.254735000 | -0.014566200 | 0.885244000 | 1.613130000 | -0.956065000 | 0.021341000 | -1.097350000 | -2.388160000 | -0.842089000 | -2.450650000 | -0.566670000 | -0.005392610 | -2.474610000 | 0.000000000 |
| W | -1.233450000 | 1.695500000 | -2.028550000 | -0.842171200 | 4.017420000 | -0.716036000 | 1.261280000 | -0.351820000 | 1.363540000 | -0.094532400 | -2.180840000 | -0.423493000 | -0.297905000 | 1.243970000 | -4.064710000 | 0.297602000 | 0.073311700 |
| Y | 2.711800000 | -5.571270000 | -2.418410000 | 0.123366000 | -0.592181000 | -0.932491000 | -1.422700000 | 1.654320000 | -0.870707000 | 0.403147000 | 1.654320000 | -0.262730000 | 3.194690000 | 1.648100000 | -1.982620000 | -0.000066919 | -0.345476000 |
| F | -2.381330000 | -2.378910000 | 4.797160000 | 0.418951001 | -0.177295500 | 0.927160000 | 1.422700000 | -0.659893100 | -0.681317000 | 0.221982000 | -1.527610000 | -0.827387000 | -0.382219300 | 0.596157500 | -1.270420000 | 0.688641000 | -0.201897000 |
| H | 3.031570000 | -1.252140000 | -3.483390000 | -0.330510000 | 4.105470000 | 0.149270000 | -1.584530000 | 0.731091000 | 1.084140000 | -0.501544000 | -2.485670000 | 1.316410000 | -2.066690000 | 0.131641000 | -2.597800000 | 4.335780000 | -0.645149000 |

FIG. 19A

FIG. 19B

SEQUENCE LISTING

<160> NUMBER OF SEQ ID NOS: 58

<210> SEQ ID NO 1
<211> LENGTH: 34
<212> TYPE: PRT
<213> ORGANISM: Artificial Sequence
<220> FEATURE:
<223> OTHER INFORMATION: A chain
<220> FEATURE:
<221> NAME/KEY: X
<222> LOCATION: (2)..(2)
<223> OTHER INFORMATION: Val or Ile
<220> FEATURE:
<221> NAME/KEY: X
<222> LOCATION: (3)..(3)
<223> OTHER INFORMATION: Val or Ala
<220> FEATURE:
<221> NAME/KEY: X
<222> LOCATION: (4)..(4)
<223> OTHER INFORMATION: Glu, Asp, Cys or gamma carboxyglutamate
<220> FEATURE:
<221> NAME/KEY: X
<222> LOCATION: (5)..(5)
<223> OTHER INFORMATION: Gln, Glu, gamma carboxyglutamate, His or Val
<220> FEATURE:
<221> NAME/KEY: X
<222> LOCATION: (6)..(6)
<223> OTHER INFORMATION: Cys or selenocysteine
<220> FEATURE:
<221> NAME/KEY: X
<222> LOCATION: (7)..(7)
<223> OTHER INFORMATION: Cys or selenocysteine
<220> FEATURE:
<221> NAME/KEY: X
<222> LOCATION: (8)..(8)
<223> OTHER INFORMATION: Thr, His, Asp, Gln, Tyr, Lys, Ala or Val
<220> FEATURE:
<221> NAME/KEY: X
<222> LOCATION: (9)..(9)
<223> OTHER INFORMATION: Ser, Arg, Asn, Gly, His or Lys
<220> FEATURE:
<221> NAME/KEY: X
<222> LOCATION: (10)..(10)
<223> OTHER INFORMATION: Ile, Pro, Tyr, Ala, Ser, Val, Phe, His or Thr -continued

```
<220> FEATURE:
<221> NAME/KEY: X
<222> LOCATION: (11)..(11)
<223> OTHER INFORMATION: Cys or selenocysteine
<220> FEATURE:
<221> NAME/KEY: X
<222> LOCATION: (12)..(12)
<223> OTHER INFORMATION: Ser or Thr
<220> FEATURE:
<221> NAME/KEY: X
<222> LOCATION: (13)..(13)
<223> OTHER INFORMATION: Leu, Asn, Val, Arg or Asp
<220> FEATURE:
<221> NAME/KEY: X
<222> LOCATION: (14)..(14)
<223> OTHER INFORMATION: Tyr, Ala, Gln, His, Asp or Glu
<220> FEATURE:
<221> NAME/KEY: X
<222> LOCATION: (15)..(15)
<223> OTHER INFORMATION: Gln, Glu or Thr
<220> FEATURE:
<221> NAME/KEY: X
<222> LOCATION: (16)..(16)
<223> OTHER INFORMATION: Phe, Leu, or Ala
<220> FEATURE:
<221> NAME/KEY: X
<222> LOCATION: (17)..(17)
<223> OTHER INFORMATION: Glu, Gln, Lys, Arg, Ile, Met, Thr or Ser
<220> FEATURE:
<221> NAME/KEY: X
<222> LOCATION: (18)..(18)
<223> OTHER INFORMATION: Lys, Ser, Thr, Asn, Gln or Glu
<220> FEATURE:
<221> NAME/KEY: X
<222> LOCATION: (19)..(19)
<223> OTHER INFORMATION: Tyr or Phe
<220> FEATURE:
<221> NAME/KEY: X
<222> LOCATION: (20)..(20)
<223> OTHER INFORMATION: Cys, selenocysteine, amidated Cys, or amidated
      selenocysteine
<220> FEATURE:
<221> NAME/KEY: X
<222> LOCATION: (21)..(21)
<223> OTHER INFORMATION: Asn, Pro, His, Ser, Gly, Ala, or is absent
<220> FEATURE:
<221> NAME/KEY: X
<222> LOCATION: (22)..(22)
<223> OTHER INFORMATION: Pro, Asn, Thr, Leu, Ser or is absent
<220> FEATURE:
<221> NAME/KEY: X
<222> LOCATION: (23)..(23)
<223> OTHER INFORMATION: Thr, Leu, Val, Ser or is absent
<220> FEATURE:
<221> NAME/KEY: X
<222> LOCATION: (24)..(24)
<223> OTHER INFORMATION: Arg, Thr, Met, Gln, Leu or is absent
<220> FEATURE:
<221> NAME/KEY: X
<222> LOCATION: (25)..(25)
<223> OTHER INFORMATION: Glu, Gly or is absent
<220> FEATURE:
<221> NAME/KEY: X
<222> LOCATION: (26)..(26)
<223> OTHER INFORMATION: Ser, Leu or is absent
<220> FEATURE:
<221> NAME/KEY: X
<222> LOCATION: (27)..(31)
<223> OTHER INFORMATION: Ser or absent
<220> FEATURE:
<221> NAME/KEY: X
<222> LOCATION: (32)..(32)
<223> OTHER INFORMATION: Ala, Ser or is absent
<220> FEATURE:
<221> NAME/KEY: X
<222> LOCATION: (33)..(33)
<223> OTHER INFORMATION: Ala, Val or is absent
<220> FEATURE:
<221> NAME/KEY: X
```

-continued

```
<222> LOCATION: (34)..(34)
<223> OTHER INFORMATION: Ala or is absent

<400> SEQUENCE: 1

Gly Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa

<210> SEQ ID NO 2
<211> LENGTH: 39
<212> TYPE: PRT
<213> ORGANISM: Artificial Sequence
<220> FEATURE:
<223> OTHER INFORMATION: B chain
<220> FEATURE:
<221> NAME/KEY: X
<222> LOCATION: (1)..(1)
<223> OTHER INFORMATION: Thr, Asn, Ser or is absent
<220> FEATURE:
<221> NAME/KEY: X
<222> LOCATION: (2)..(2)
<223> OTHER INFORMATION: Phe, Ser, Asn, Thr, Gln or is absent
<220> FEATURE:
<221> NAME/KEY: X
<222> LOCATION: (3)..(3)
<223> OTHER INFORMATION: Ala, Asp, Gly, Pro, Leu, Phe, or His
<220> FEATURE:
<221> NAME/KEY: X
<222> LOCATION: (4)..(4)
<223> OTHER INFORMATION: Ala, Thr, Pro, Asp, Val or Gly
<220> FEATURE:
<221> NAME/KEY: X
<222> LOCATION: (5)..(5)
<223> OTHER INFORMATION: Asn, Pro, His, Thr, Arg, Ser or hydroxyproline
<220> FEATURE:
<221> NAME/KEY: X
<222> LOCATION: (6)..(6)
<223> OTHER INFORMATION: Lys, Glu, Asn, Asp, Arg, Gln or Gly
<220> FEATURE:
<221> NAME/KEY: X
<222> LOCATION: (7)..(7)
<223> OTHER INFORMATION: His, Tyr, Arg or Ile
<220> FEATURE:
<221> NAME/KEY: X
<222> LOCATION: (8)..(8)
<223> OTHER INFORMATION: Arg, Thr, Ile, Ser, Leu, Tyr or Lys
<220> FEATURE:
<221> NAME/KEY: X
<222> LOCATION: (9)..(9)
<223> OTHER INFORMATION: Cys or selenocysteine
<220> FEATURE:
<221> NAME/KEY: X
<222> LOCATION: (10)..(10)
<223> OTHER INFORMATION: Gly, Gln or Asp
<220> FEATURE:
<221> NAME/KEY: X
<222> LOCATION: (11)..(11)
<223> OTHER INFORMATION: Ser, Leu, Gly or Pro
<220> FEATURE:
<221> NAME/KEY: X
<222> LOCATION: (12)..(12)
<223> OTHER INFORMATION: His, Glu, gamma carboxyglutamate, Asp, or Asn
<220> FEATURE:
<221> NAME/KEY: X
<222> LOCATION: (13)..(13)
<223> OTHER INFORMATION: Ile, Leu, Asp, Val or Ala
<220> FEATURE:
<221> NAME/KEY: X
<222> LOCATION: (14)..(14)
<223> OTHER INFORMATION: Thr, Ala, Pro, Val or Arg
<220> FEATURE:
<221> NAME/KEY: X
<222> LOCATION: (15)..(15)
```

```
<223> OTHER INFORMATION: Asn, Asp, Ala, Val, Thr, Pro or Glu
<220> FEATURE:
<221> NAME/KEY: X
<222> LOCATION: (16)..(16)
<223> OTHER INFORMATION: Ala, Ser, Gln, His, Tyr, Arg or Gly
<220> FEATURE:
<221> NAME/KEY: X
<222> LOCATION: (17)..(17)
<223> OTHER INFORMATION: Thr, Tyr, Pro, Leu or Gly
<220> FEATURE:
<221> NAME/KEY: X
<222> LOCATION: (18)..(18)
<223> OTHER INFORMATION: Tyr, Met, Val, Gln, Ile, Asp, Gly, Asn or Leu
<220> FEATURE:
<221> NAME/KEY: X
<222> LOCATION: (19)..(19)
<223> OTHER INFORMATION: Leu, Asp, Gln, Gly, Lys, Glu, Arg or Thr
<220> FEATURE:
<221> NAME/KEY: X
<222> LOCATION: (20)..(20)
<223> OTHER INFORMATION: Val, Leu or Lys
<220> FEATURE:
<221> NAME/KEY: X
<222> LOCATION: (21)..(21)
<223> OTHER INFORMATION: Cys, amidated Cys, selenocysteine or amidated
      selenocysteine
<220> FEATURE:
<221> NAME/KEY: X
<222> LOCATION: (22)..(22)
<223> OTHER INFORMATION: Val, Tyr, Phe, His, Gly, Gln, Leu, amidated
      His, amidated Val or is absent
<220> FEATURE:
<221> NAME/KEY: X
<222> LOCATION: (23)..(23)
<223> OTHER INFORMATION: Glu, Arg, Ser, Gly or is absent
<220> FEATURE:
<221> NAME/KEY: X
<222> LOCATION: (24)..(24)
<223> OTHER INFORMATION: Arg, Asp, Val or is absent
<220> FEATURE:
<221> NAME/KEY: X
<222> LOCATION: (25)..(25)
<223> OTHER INFORMATION: Gly, Leu, Val or is absent
<220> FEATURE:
<221> NAME/KEY: X
<222> LOCATION: (26)..(26)
<223> OTHER INFORMATION: Phe, Val, Ile or is absent
<220> FEATURE:
<221> NAME/KEY: X
<222> LOCATION: (27)..(27)
<223> OTHER INFORMATION: Phe, Asn, Pro, Glu or is absent
<220> FEATURE:
<221> NAME/KEY: X
<222> LOCATION: (28)..(28)
<223> OTHER INFORMATION: Tyr, Cys, His or is absent
<220> FEATURE:
<221> NAME/KEY: X
<222> LOCATION: (29)..(29)
<223> OTHER INFORMATION: Thr, His, Ile, Leu, Ser, Tyr or is absent
<220> FEATURE:
<221> NAME/KEY: X
<222> LOCATION: (30)..(30)
<223> OTHER INFORMATION: Pro, Glu, Leu, Ile, Arg or is absent
<220> FEATURE:
<221> NAME/KEY: X
<222> LOCATION: (31)..(31)
<223> OTHER INFORMATION: Ile, Lys or is absent
<220> FEATURE:
<221> NAME/KEY: X
<222> LOCATION: (32)..(32)
<223> OTHER INFORMATION: Ala, Asp, Ser, Thr, Lys, Leu, Gln or is absent
<220> FEATURE:
<221> NAME/KEY: X
<222> LOCATION: (33)..(33)
<223> OTHER INFORMATION: Cys or is absent
<220> FEATURE:
<221> NAME/KEY: X
<222> LOCATION: (34)..(34)
<223> OTHER INFORMATION: Glu, Pro, Val or is absent
```

```
<220> FEATURE:
<221> NAME/KEY: X
<222> LOCATION: (35)..(35)
<223> OTHER INFORMATION: Glu, Gly or is absent
<220> FEATURE:
<221> NAME/KEY: X
<222> LOCATION: (36)..(36)
<223> OTHER INFORMATION: Glu, Gly or is absent
<220> FEATURE:
<221> NAME/KEY: X
<222> LOCATION: (37)..(37)
<223> OTHER INFORMATION: Glu, Val or is absent
<220> FEATURE:
<221> NAME/KEY: X
<222> LOCATION: (38)..(38)
<223> OTHER INFORMATION: Ala, Asp or is absent
<220> FEATURE:
<221> NAME/KEY: X
<222> LOCATION: (39)..(39)
<223> OTHER INFORMATION: Ala or is absent

<400> SEQUENCE: 2

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa
        35

<210> SEQ ID NO 3
<211> LENGTH: 39
<212> TYPE: PRT
<213> ORGANISM: Artificial Sequence
<220> FEATURE:
<223> OTHER INFORMATION: B chain
<220> FEATURE:
<221> NAME/KEY: X
<222> LOCATION: (1)..(1)
<223> OTHER INFORMATION: Thr, Asn, Ser or is absent
<220> FEATURE:
<221> NAME/KEY: X
<222> LOCATION: (2)..(2)
<223> OTHER INFORMATION: Phe, Ser, Asn, Thr, Gln or is absent
<220> FEATURE:
<221> NAME/KEY: X
<222> LOCATION: (3)..(3)
<223> OTHER INFORMATION: Asp, Gly, Pro, Leu, Phe, or His
<220> FEATURE:
<221> NAME/KEY: X
<222> LOCATION: (4)..(4)
<223> OTHER INFORMATION: Thr, Pro, Asp, Val or Gly
<220> FEATURE:
<221> NAME/KEY: X
<222> LOCATION: (5)..(5)
<223> OTHER INFORMATION: Asn, Pro, His, Thr, Arg, Ser or hydroxyproline
<220> FEATURE:
<221> NAME/KEY: X
<222> LOCATION: (6)..(6)
<223> OTHER INFORMATION: Lys, Glu, Asn, Asp, Arg, Gln or Gly
<220> FEATURE:
<221> NAME/KEY: X
<222> LOCATION: (7)..(7)
<223> OTHER INFORMATION: His, Tyr, Arg or Ile
<220> FEATURE:
<221> NAME/KEY: X
<222> LOCATION: (8)..(8)
<223> OTHER INFORMATION: Arg, Thr, Ile, Ser, Leu, Tyr or Lys
<220> FEATURE:
<221> NAME/KEY: X
<222> LOCATION: (9)..(9)
<223> OTHER INFORMATION: Cys or selenocysteine
<220> FEATURE:
<221> NAME/KEY: X
<222> LOCATION: (10)..(10)
<223> OTHER INFORMATION: Gly, Gln or Asp
```

```
<220> FEATURE:
<221> NAME/KEY: X
<222> LOCATION: (11)..(11)
<223> OTHER INFORMATION: Ser, Leu, Gly or Pro
<220> FEATURE:
<221> NAME/KEY: X
<222> LOCATION: (12)..(12)
<223> OTHER INFORMATION: His, Glu, gamma carboxyglutamate, Asp, or Asn
<220> FEATURE:
<221> NAME/KEY: X
<222> LOCATION: (13)..(13)
<223> OTHER INFORMATION: Ile, Leu, Asp, Val or Ala
<220> FEATURE:
<221> NAME/KEY: X
<222> LOCATION: (14)..(14)
<223> OTHER INFORMATION: Thr, Ala, Pro, Val or Arg
<220> FEATURE:
<221> NAME/KEY: X
<222> LOCATION: (15)..(15)
<223> OTHER INFORMATION: Asn, Asp, Ala, Val, Thr, Pro or Glu
<220> FEATURE:
<221> NAME/KEY: X
<222> LOCATION: (16)..(16)
<223> OTHER INFORMATION: Ala, Ser, Gln, His, Tyr, Arg or Gly
<220> FEATURE:
<221> NAME/KEY: X
<222> LOCATION: (17)..(17)
<223> OTHER INFORMATION: Tyr or Leu
<220> FEATURE:
<221> NAME/KEY: X
<222> LOCATION: (18)..(18)
<223> OTHER INFORMATION: Tyr, Met, Val, Gln, Ile, Asp, Gly, Asn or Leu
<220> FEATURE:
<221> NAME/KEY: X
<222> LOCATION: (19)..(19)
<223> OTHER INFORMATION: Leu, Asp, Gln, Gly, Lys, Glu, Arg or Thr
<220> FEATURE:
<221> NAME/KEY: X
<222> LOCATION: (20)..(20)
<223> OTHER INFORMATION: Val, Leu or Lys
<220> FEATURE:
<221> NAME/KEY: X
<222> LOCATION: (21)..(21)
<223> OTHER INFORMATION: Cys, amidated Cys, selenocysteine or amidated
      selenocysteine
<220> FEATURE:
<221> NAME/KEY: X
<222> LOCATION: (22)..(22)
<223> OTHER INFORMATION: Tyr, Phe or His
<220> FEATURE:
<221> NAME/KEY: X
<222> LOCATION: (23)..(23)
<223> OTHER INFORMATION: Glu, Arg, Ser, Gly or is absent
<220> FEATURE:
<221> NAME/KEY: X
<222> LOCATION: (24)..(24)
<223> OTHER INFORMATION: Arg, Asp, Val or is absent
<220> FEATURE:
<221> NAME/KEY: X
<222> LOCATION: (25)..(25)
<223> OTHER INFORMATION: Gly, Leu, Val or is absent
<220> FEATURE:
<221> NAME/KEY: X
<222> LOCATION: (26)..(26)
<223> OTHER INFORMATION: Phe, Val, Ile or is absent
<220> FEATURE:
<221> NAME/KEY: X
<222> LOCATION: (27)..(27)
<223> OTHER INFORMATION: Phe, Asn, Pro, Glu or is absent
<220> FEATURE:
<221> NAME/KEY: X
<222> LOCATION: (28)..(28)
<223> OTHER INFORMATION: Tyr, Cys, His or is absent
<220> FEATURE:
<221> NAME/KEY: X
<222> LOCATION: (29)..(29)
<223> OTHER INFORMATION: Thr, His, Leu, Tyr or is absent
<220> FEATURE:
<221> NAME/KEY: X
```

```
<222> LOCATION: (30)..(30)
<223> OTHER INFORMATION: Pro, Glu, Leu, Ile, Arg or is absent
<220> FEATURE:
<221> NAME/KEY: X
<222> LOCATION: (31)..(31)
<223> OTHER INFORMATION: Ile, Lys or is absent
<220> FEATURE:
<221> NAME/KEY: X
<222> LOCATION: (32)..(32)
<223> OTHER INFORMATION: Thr, Lys, Leu, Gln or is absent
<220> FEATURE:
<221> NAME/KEY: X
<222> LOCATION: (33)..(33)
<223> OTHER INFORMATION: Cys or is absent
<220> FEATURE:
<221> NAME/KEY: X
<222> LOCATION: (34)..(34)
<223> OTHER INFORMATION: Glu, Pro, Val or is absent
<220> FEATURE:
<221> NAME/KEY: X
<222> LOCATION: (35)..(35)
<223> OTHER INFORMATION: Glu, Gly or is absent
<220> FEATURE:
<221> NAME/KEY: X
<222> LOCATION: (36)..(36)
<223> OTHER INFORMATION: Glu, Gly or is absent
<220> FEATURE:
<221> NAME/KEY: X
<222> LOCATION: (37)..(37)
<223> OTHER INFORMATION: Glu, Val or is absent
<220> FEATURE:
<221> NAME/KEY: X
<222> LOCATION: (38)..(38)
<223> OTHER INFORMATION: Ala, Asp or is absent
<220> FEATURE:
<221> NAME/KEY: X
<222> LOCATION: (39)..(39)
<223> OTHER INFORMATION: Ala or is absent

<400> SEQUENCE: 3

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa
        35

<210> SEQ ID NO 4
<211> LENGTH: 39
<212> TYPE: PRT
<213> ORGANISM: Artificial Sequence
<220> FEATURE:
<223> OTHER INFORMATION: B chain
<220> FEATURE:
<221> NAME/KEY: X
<222> LOCATION: (1)..(1)
<223> OTHER INFORMATION: Thr, Asn, Ser or is absent
<220> FEATURE:
<221> NAME/KEY: X
<222> LOCATION: (2)..(2)
<223> OTHER INFORMATION: Phe, Ser, Asn, Thr, Gln or is absent
<220> FEATURE:
<221> NAME/KEY: X
<222> LOCATION: (3)..(3)
<223> OTHER INFORMATION: Asp, Gly, Pro, Leu, Phe, or His
<220> FEATURE:
<221> NAME/KEY: X
<222> LOCATION: (4)..(4)
<223> OTHER INFORMATION: Thr, Pro, Asp, Val or Gly
<220> FEATURE:
<221> NAME/KEY: X
<222> LOCATION: (5)..(5)
<223> OTHER INFORMATION: Asn, Pro, His, Thr, Arg, Ser or hydroxyproline
<220> FEATURE:
<221> NAME/KEY: X
```

```
<222> LOCATION: (6)..(6)
<223> OTHER INFORMATION: Lys, Glu, Asn, Asp, Arg, Gln or Gly
<220> FEATURE:
<221> NAME/KEY: X
<222> LOCATION: (7)..(7)
<223> OTHER INFORMATION: His, Tyr, Arg or Ile
<220> FEATURE:
<221> NAME/KEY: X
<222> LOCATION: (8)..(8)
<223> OTHER INFORMATION: Arg, Thr, Ile, Ser, Leu, Tyr or Lys
<220> FEATURE:
<221> NAME/KEY: X
<222> LOCATION: (9)..(9)
<223> OTHER INFORMATION: Cys or selenocysteine
<220> FEATURE:
<221> NAME/KEY: X
<222> LOCATION: (10)..(10)
<223> OTHER INFORMATION: Gly, Gln or Asp
<220> FEATURE:
<221> NAME/KEY: X
<222> LOCATION: (11)..(11)
<223> OTHER INFORMATION: Ser, Leu, Gly or Pro
<220> FEATURE:
<221> NAME/KEY: X
<222> LOCATION: (12)..(12)
<223> OTHER INFORMATION: His, Glu, gamma carboxyglutamate, Asp, or Asn
<220> FEATURE:
<221> NAME/KEY: X
<222> LOCATION: (13)..(13)
<223> OTHER INFORMATION: Ile, Leu, Asp, Val or Ala
<220> FEATURE:
<221> NAME/KEY: X
<222> LOCATION: (14)..(14)
<223> OTHER INFORMATION: Thr, Ala, Pro, Val or Arg
<220> FEATURE:
<221> NAME/KEY: X
<222> LOCATION: (15)..(15)
<223> OTHER INFORMATION: Asn, Asp, Ala, Val, Thr, Pro or Glu
<220> FEATURE:
<221> NAME/KEY: X
<222> LOCATION: (16)..(16)
<223> OTHER INFORMATION: Ala, Ser, Gln, His, Tyr, Arg or Gly
<220> FEATURE:
<221> NAME/KEY: X
<222> LOCATION: (17)..(17)
<223> OTHER INFORMATION: Tyr or Leu
<220> FEATURE:
<221> NAME/KEY: X
<222> LOCATION: (18)..(18)
<223> OTHER INFORMATION: Tyr, Met, Val, Gln, Ile, Asp, Gly, Asn or Leu
<220> FEATURE:
<221> NAME/KEY: X
<222> LOCATION: (19)..(19)
<223> OTHER INFORMATION: Leu, Asp, Gln, Gly, Lys, Glu, Arg or Thr
<220> FEATURE:
<221> NAME/KEY: X
<222> LOCATION: (20)..(20)
<223> OTHER INFORMATION: Val, Leu or Lys
<220> FEATURE:
<221> NAME/KEY: X
<222> LOCATION: (21)..(21)
<223> OTHER INFORMATION: Cys, amidated Cys, selenocysteine or amidated
     selenocysteine
<220> FEATURE:
<221> NAME/KEY: X
<222> LOCATION: (22)..(22)
<223> OTHER INFORMATION: Tyr, Phe or His
<220> FEATURE:
<221> NAME/KEY: X
<222> LOCATION: (23)..(23)
<223> OTHER INFORMATION: Glu, Arg, Ser, Gly or is absent
<220> FEATURE:
<221> NAME/KEY: X
<222> LOCATION: (24)..(39)
<223> OTHER INFORMATION: absent

<400> SEQUENCE: 4

Xaa Xaa Xaa Xaa Xaa Xaa Xaa Xaa Xaa Xaa Xaa Xaa Xaa Xaa Xaa Xaa
```

```
         1               5                  10                 15
Xaa Xaa Xaa Xaa Xaa Xaa Xaa Xaa Xaa Xaa Xaa Xaa Xaa Xaa Xaa
             20                 25                 30
Xaa Xaa Xaa Xaa Xaa Xaa Xaa
         35

<210> SEQ ID NO 5
<211> LENGTH: 39
<212> TYPE: PRT
<213> ORGANISM: Artificial Sequence
<220> FEATURE:
<223> OTHER INFORMATION: B chain
<220> FEATURE:
<221> NAME/KEY: X
<222> LOCATION: (1)..(1)
<223> OTHER INFORMATION: Thr, Asn, Ser or is absent
<220> FEATURE:
<221> NAME/KEY: X
<222> LOCATION: (2)..(2)
<223> OTHER INFORMATION: Phe, Ser, Asn, Thr, Gln or is absent
<220> FEATURE:
<221> NAME/KEY: X
<222> LOCATION: (3)..(3)
<223> OTHER INFORMATION: Asp, Gly, Pro, Leu, Phe, or His
<220> FEATURE:
<221> NAME/KEY: X
<222> LOCATION: (4)..(4)
<223> OTHER INFORMATION: Thr, Pro, Asp, Val or Gly
<220> FEATURE:
<221> NAME/KEY: X
<222> LOCATION: (5)..(5)
<223> OTHER INFORMATION: Asn, Pro, His, Thr, Arg, Ser or hydroxyproline
<220> FEATURE:
<221> NAME/KEY: X
<222> LOCATION: (6)..(6)
<223> OTHER INFORMATION: Lys, Glu, Asn, Asp, Arg, Gln or Gly
<220> FEATURE:
<221> NAME/KEY: X
<222> LOCATION: (7)..(7)
<223> OTHER INFORMATION: His, Tyr, Arg or Ile
<220> FEATURE:
<221> NAME/KEY: X
<222> LOCATION: (8)..(8)
<223> OTHER INFORMATION: Arg, Thr, Ile, Ser, Leu, Tyr or Lys
<220> FEATURE:
<221> NAME/KEY: X
<222> LOCATION: (9)..(9)
<223> OTHER INFORMATION: Cys or selenocysteine
<220> FEATURE:
<221> NAME/KEY: X
<222> LOCATION: (12)..(12)
<223> OTHER INFORMATION: His, Glu, gamma carboxyglutamate, Asp, or Asn
<220> FEATURE:
<221> NAME/KEY: X
<222> LOCATION: (13)..(13)
<223> OTHER INFORMATION: Ile, Leu, Asp, Val or Ala
<220> FEATURE:
<221> NAME/KEY: X
<222> LOCATION: (14)..(14)
<223> OTHER INFORMATION: Thr, Ala, Pro, Val or Arg
<220> FEATURE:
<221> NAME/KEY: X
<222> LOCATION: (15)..(15)
<223> OTHER INFORMATION: Asn, Asp, Ala, Val, Thr, Pro or Glu
<220> FEATURE:
<221> NAME/KEY: X
<222> LOCATION: (16)..(16)
<223> OTHER INFORMATION: Ala, Ser, Gln, His, Tyr, Arg or Gly
<220> FEATURE:
<221> NAME/KEY: X
<222> LOCATION: (17)..(17)
<223> OTHER INFORMATION: Tyr or Leu
<220> FEATURE:
<221> NAME/KEY: X
<222> LOCATION: (18)..(18)
<223> OTHER INFORMATION: Tyr, Met, Val, Gln, Ile, Asp, Gly, Asn or Leu
```

```
<220> FEATURE:
<221> NAME/KEY: X
<222> LOCATION: (19)..(19)
<223> OTHER INFORMATION: Leu, Asp, Gln, Gly, Lys, Glu, Arg or Thr
<220> FEATURE:
<221> NAME/KEY: X
<222> LOCATION: (20)..(20)
<223> OTHER INFORMATION: Val, Leu or Lys
<220> FEATURE:
<221> NAME/KEY: X
<222> LOCATION: (21)..(21)
<223> OTHER INFORMATION: Cys, amidated Cys, selenocysteine or amidated
      selenocysteine
<220> FEATURE:
<221> NAME/KEY: X
<222> LOCATION: (22)..(22)
<223> OTHER INFORMATION: Tyr, Phe or His
<220> FEATURE:
<221> NAME/KEY: X
<222> LOCATION: (23)..(23)
<223> OTHER INFORMATION: Glu, Arg, Ser, Gly or is absent
<220> FEATURE:
<221> NAME/KEY: X
<222> LOCATION: (24)..(24)
<223> OTHER INFORMATION: Arg, Asp, Val or is absent
<220> FEATURE:
<221> NAME/KEY: X
<222> LOCATION: (25)..(25)
<223> OTHER INFORMATION: Gly, Leu, Val or is absent
<220> FEATURE:
<221> NAME/KEY: X
<222> LOCATION: (26)..(26)
<223> OTHER INFORMATION: Phe, Val, Ile or is absent
<220> FEATURE:
<221> NAME/KEY: X
<222> LOCATION: (27)..(27)
<223> OTHER INFORMATION: Phe, Asn, Pro, Glu or is absent
<220> FEATURE:
<221> NAME/KEY: X
<222> LOCATION: (28)..(28)
<223> OTHER INFORMATION: Tyr, Cys, His or is absent
<220> FEATURE:
<221> NAME/KEY: X
<222> LOCATION: (29)..(29)
<223> OTHER INFORMATION: Thr, His, Leu, Tyr or is absent
<220> FEATURE:
<221> NAME/KEY: X
<222> LOCATION: (30)..(30)
<223> OTHER INFORMATION: Pro, Glu, Leu, Ile, Arg or is absent
<220> FEATURE:
<221> NAME/KEY: X
<222> LOCATION: (31)..(31)
<223> OTHER INFORMATION: Ile, Lys or is absent
<220> FEATURE:
<221> NAME/KEY: X
<222> LOCATION: (32)..(32)
<223> OTHER INFORMATION: Thr, Lys, Leu, Gln or is absent
<220> FEATURE:
<221> NAME/KEY: X
<222> LOCATION: (33)..(33)
<223> OTHER INFORMATION: Cys or is absent
<220> FEATURE:
<221> NAME/KEY: X
<222> LOCATION: (34)..(34)
<223> OTHER INFORMATION: Glu, Pro, Val or is absent
<220> FEATURE:
<221> NAME/KEY: X
<222> LOCATION: (35)..(35)
<223> OTHER INFORMATION: Glu, Gly or is absent
<220> FEATURE:
<221> NAME/KEY: X
<222> LOCATION: (36)..(36)
<223> OTHER INFORMATION: Glu, Gly or is absent
<220> FEATURE:
<221> NAME/KEY: X
<222> LOCATION: (37)..(37)
<223> OTHER INFORMATION: Glu, Val or is absent
<220> FEATURE:
<221> NAME/KEY: X
```

```
<222> LOCATION: (38)..(38)
<223> OTHER INFORMATION: Ala, Asp or is absent
<220> FEATURE:
<221> NAME/KEY: X
<222> LOCATION: (39)..(39)
<223> OTHER INFORMATION: Ala or is absent

<400> SEQUENCE: 5

Xaa Xaa Xaa Xaa Xaa Xaa Xaa Xaa Xaa Gly Ser Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa
        35

<210> SEQ ID NO 6
<211> LENGTH: 39
<212> TYPE: PRT
<213> ORGANISM: Artificial Sequence
<220> FEATURE:
<223> OTHER INFORMATION: B chain
<220> FEATURE:
<221> NAME/KEY: X
<222> LOCATION: (1)..(1)
<223> OTHER INFORMATION: Thr, Asn, Ser or is absent
<220> FEATURE:
<221> NAME/KEY: X
<222> LOCATION: (2)..(2)
<223> OTHER INFORMATION: Phe, Ser, Asn, Thr, Gln or is absent
<220> FEATURE:
<221> NAME/KEY: X
<222> LOCATION: (3)..(3)
<223> OTHER INFORMATION: Asp, Gly, Pro, Leu, Phe, or His
<220> FEATURE:
<221> NAME/KEY: X
<222> LOCATION: (4)..(4)
<223> OTHER INFORMATION: Thr, Pro, Asp, Val or Gly
<220> FEATURE:
<221> NAME/KEY: X
<222> LOCATION: (5)..(5)
<223> OTHER INFORMATION: Asn, Pro, His, Thr, Arg, Ser or hydroxyproline
<220> FEATURE:
<221> NAME/KEY: X
<222> LOCATION: (6)..(6)
<223> OTHER INFORMATION: Lys, Glu, Asn, Asp, Arg, Gln or Gly
<220> FEATURE:
<221> NAME/KEY: X
<222> LOCATION: (7)..(7)
<223> OTHER INFORMATION: His or Tyr
<220> FEATURE:
<221> NAME/KEY: X
<222> LOCATION: (8)..(8)
<223> OTHER INFORMATION: Arg, Thr, Ile, Ser, Leu, Tyr or Lys
<220> FEATURE:
<221> NAME/KEY: X
<222> LOCATION: (9)..(9)
<223> OTHER INFORMATION: Cys or selenocysteine
<220> FEATURE:
<221> NAME/KEY: X
<222> LOCATION: (12)..(12)
<223> OTHER INFORMATION: His, Glu, gamma carboxyglutamate, Asp, or Asn
<220> FEATURE:
<221> NAME/KEY: X
<222> LOCATION: (13)..(13)
<223> OTHER INFORMATION: Ile, Leu, Asp, Val or Ala
<220> FEATURE:
<221> NAME/KEY: X
<222> LOCATION: (14)..(14)
<223> OTHER INFORMATION: Thr, Ala, Pro, Val or Arg
<220> FEATURE:
<221> NAME/KEY: X
<222> LOCATION: (15)..(15)
<223> OTHER INFORMATION: Asn, Asp, Ala, Val, Thr, Pro or Glu
<220> FEATURE:
<221> NAME/KEY: X
```

```
<222> LOCATION: (16)..(16)
<223> OTHER INFORMATION: Ala, Ser, Gln, His, Tyr, Arg or Gly
<220> FEATURE:
<221> NAME/KEY: X
<222> LOCATION: (17)..(17)
<223> OTHER INFORMATION: Tyr or Leu
<220> FEATURE:
<221> NAME/KEY: X
<222> LOCATION: (18)..(18)
<223> OTHER INFORMATION: Tyr, Met, Val, Gln, Ile, Asp, Gly, Asn or Leu
<220> FEATURE:
<221> NAME/KEY: X
<222> LOCATION: (19)..(19)
<223> OTHER INFORMATION: Leu, Asp, Gln, Gly, Lys, Glu, Arg or Thr
<220> FEATURE:
<221> NAME/KEY: X
<222> LOCATION: (20)..(20)
<223> OTHER INFORMATION: Val or Leu
<220> FEATURE:
<221> NAME/KEY: X
<222> LOCATION: (21)..(21)
<223> OTHER INFORMATION: Cys, amidated Cys, selenocysteine or amidated
      selenocysteine
<220> FEATURE:
<221> NAME/KEY: X
<222> LOCATION: (22)..(22)
<223> OTHER INFORMATION: Tyr, Phe or His
<220> FEATURE:
<221> NAME/KEY: X
<222> LOCATION: (23)..(23)
<223> OTHER INFORMATION: Glu, Arg, Ser, Gly or is absent
<220> FEATURE:
<221> NAME/KEY: X
<222> LOCATION: (24)..(24)
<223> OTHER INFORMATION: Arg, Asp, Val or is absent
<220> FEATURE:
<221> NAME/KEY: X
<222> LOCATION: (25)..(25)
<223> OTHER INFORMATION: Gly, Leu, Val or is absent
<220> FEATURE:
<221> NAME/KEY: X
<222> LOCATION: (26)..(26)
<223> OTHER INFORMATION: Phe, Val, Ile or is absent
<220> FEATURE:
<221> NAME/KEY: X
<222> LOCATION: (27)..(27)
<223> OTHER INFORMATION: Phe, Asn, Pro, Glu or is absent
<220> FEATURE:
<221> NAME/KEY: X
<222> LOCATION: (28)..(28)
<223> OTHER INFORMATION: Tyr, Cys, His or is absent
<220> FEATURE:
<221> NAME/KEY: X
<222> LOCATION: (29)..(29)
<223> OTHER INFORMATION: Thr, His, Leu, Tyr or is absent
<220> FEATURE:
<221> NAME/KEY: X
<222> LOCATION: (30)..(30)
<223> OTHER INFORMATION: Pro, Glu, Leu, Ile, Arg or is absent
<220> FEATURE:
<221> NAME/KEY: X
<222> LOCATION: (31)..(31)
<223> OTHER INFORMATION: Ile, Lys or is absent
<220> FEATURE:
<221> NAME/KEY: X
<222> LOCATION: (32)..(32)
<223> OTHER INFORMATION: Thr, Lys, Leu, Gln or is absent
<220> FEATURE:
<221> NAME/KEY: X
<222> LOCATION: (33)..(33)
<223> OTHER INFORMATION: Cys or is absent
<220> FEATURE:
<221> NAME/KEY: X
<222> LOCATION: (34)..(34)
<223> OTHER INFORMATION: Glu, Pro, Val or is absent
<220> FEATURE:
<221> NAME/KEY: X
<222> LOCATION: (35)..(35)
<223> OTHER INFORMATION: Glu, Gly or is absent
```

-continued

```
<220> FEATURE:
<221> NAME/KEY: X
<222> LOCATION: (36)..(36)
<223> OTHER INFORMATION: Glu, Gly or is absent
<220> FEATURE:
<221> NAME/KEY: X
<222> LOCATION: (37)..(37)
<223> OTHER INFORMATION: Glu, Val or is absent
<220> FEATURE:
<221> NAME/KEY: X
<222> LOCATION: (38)..(38)
<223> OTHER INFORMATION: Ala, Asp or is absent
<220> FEATURE:
<221> NAME/KEY: X
<222> LOCATION: (39)..(39)
<223> OTHER INFORMATION: Ala or is absent

<400> SEQUENCE: 6

Xaa Xaa Xaa Xaa Xaa Xaa Xaa Xaa Xaa Gly Ser Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa
        35

<210> SEQ ID NO 7
<211> LENGTH: 23
<212> TYPE: PRT
<213> ORGANISM: Artificial Sequence
<220> FEATURE:
<223> OTHER INFORMATION: B chain
<220> FEATURE:
<221> NAME/KEY: X
<222> LOCATION: (1)..(1)
<223> OTHER INFORMATION: Thr, Asn or is absent
<220> FEATURE:
<221> NAME/KEY: X
<222> LOCATION: (2)..(2)
<223> OTHER INFORMATION: Phe, Ser or is absent
<220> FEATURE:
<221> NAME/KEY: X
<222> LOCATION: (3)..(3)
<223> OTHER INFORMATION: Phe or Asp
<220> FEATURE:
<221> NAME/KEY: X
<222> LOCATION: (4)..(4)
<223> OTHER INFORMATION: Thr or Val
<220> FEATURE:
<221> NAME/KEY: X
<222> LOCATION: (5)..(5)
<223> OTHER INFORMATION: Pro, Asn or hydroxyproline
<220> FEATURE:
<221> NAME/KEY: X
<222> LOCATION: (6)..(6)
<223> OTHER INFORMATION: Lys, Asn or Gln
<220> FEATURE:
<221> NAME/KEY: X
<222> LOCATION: (7)..(7)
<223> OTHER INFORMATION: His or Tyr
<220> FEATURE:
<221> NAME/KEY: X
<222> LOCATION: (8)..(8)
<223> OTHER INFORMATION: Arg, Ile or Leu
<220> FEATURE:
<221> NAME/KEY: X
<222> LOCATION: (9)..(9)
<223> OTHER INFORMATION: Cys or selenocysteine
<220> FEATURE:
<221> NAME/KEY: X
<222> LOCATION: (12)..(12)
<223> OTHER INFORMATION: His, Asp, Glu or gamma carboxyglutamate
<220> FEATURE:
<221> NAME/KEY: X
<222> LOCATION: (13)..(13)
<223> OTHER INFORMATION: Val, Ile or Leu
```

```
<220> FEATURE:
<221> NAME/KEY: X
<222> LOCATION: (14)..(14)
<223> OTHER INFORMATION: Thr, Ala, Pro, or Val
<220> FEATURE:
<221> NAME/KEY: X
<222> LOCATION: (15)..(15)
<223> OTHER INFORMATION: Glu, Val, Asn or Asp
<220> FEATURE:
<221> NAME/KEY: X
<222> LOCATION: (16)..(16)
<223> OTHER INFORMATION: Ser, Gln, Tyr or Ala
<220> FEATURE:
<221> NAME/KEY: X
<222> LOCATION: (17)..(17)
<223> OTHER INFORMATION: Tyr or Leu
<220> FEATURE:
<221> NAME/KEY: X
<222> LOCATION: (18)..(18)
<223> OTHER INFORMATION: Tyr, Asp, Met or Val
<220> FEATURE:
<221> NAME/KEY: X
<222> LOCATION: (19)..(19)
<223> OTHER INFORMATION: Leu, Asp, Gln or Lys
<220> FEATURE:
<221> NAME/KEY: X
<222> LOCATION: (20)..(20)
<223> OTHER INFORMATION: Leu or Val
<220> FEATURE:
<221> NAME/KEY: X
<222> LOCATION: (21)..(21)
<223> OTHER INFORMATION: Cys, amidated Cys, selenocysteine or amidated
     selenocysteine
<220> FEATURE:
<221> NAME/KEY: X
<222> LOCATION: (22)..(22)
<223> OTHER INFORMATION: Tyr or Gly
<220> FEATURE:
<221> NAME/KEY: X
<222> LOCATION: (23)..(23)
<223> OTHER INFORMATION: Glu, Arg, Gly or is absent

<400> SEQUENCE: 7

Xaa Xaa Xaa Xaa Xaa Xaa Xaa Xaa Xaa Gly Ser Xaa Xaa Xaa Xaa Xaa
1               5                   10                  15

Xaa Xaa Xaa Xaa Xaa Xaa Xaa
            20

<210> SEQ ID NO 8
<211> LENGTH: 23
<212> TYPE: PRT
<213> ORGANISM: Artificial Sequence
<220> FEATURE:
<223> OTHER INFORMATION: B chain
<220> FEATURE:
<221> NAME/KEY: X
<222> LOCATION: (1)..(1)
<223> OTHER INFORMATION: Thr or is absent
<220> FEATURE:
<221> NAME/KEY: X
<222> LOCATION: (2)..(2)
<223> OTHER INFORMATION: Phe or is absent
<220> FEATURE:
<221> NAME/KEY: X
<222> LOCATION: (3)..(3)
<223> OTHER INFORMATION: Phe or Asp
<220> FEATURE:
<221> NAME/KEY: X
<222> LOCATION: (4)..(4)
<223> OTHER INFORMATION: Thr or Val
<220> FEATURE:
<221> NAME/KEY: X
<222> LOCATION: (5)..(5)
<223> OTHER INFORMATION: Pro, Asn or hydroxyproline
<220> FEATURE:
<221> NAME/KEY: X
```

```
<222> LOCATION: (6)..(6)
<223> OTHER INFORMATION: Lys or Gln
<220> FEATURE:
<221> NAME/KEY: X
<222> LOCATION: (8)..(8)
<223> OTHER INFORMATION: Arg or Leu
<220> FEATURE:
<221> NAME/KEY: X
<222> LOCATION: (12)..(12)
<223> OTHER INFORMATION: His, Glu or gamma carboxyglutamate
<220> FEATURE:
<221> NAME/KEY: X
<222> LOCATION: (13)..(13)
<223> OTHER INFORMATION: Ile or Leu
<220> FEATURE:
<221> NAME/KEY: X
<222> LOCATION: (14)..(14)
<223> OTHER INFORMATION: Thr, or Val
<220> FEATURE:
<221> NAME/KEY: X
<222> LOCATION: (15)..(15)
<223> OTHER INFORMATION: Glu, or Asn
<220> FEATURE:
<221> NAME/KEY: X
<222> LOCATION: (16)..(16)
<223> OTHER INFORMATION: Ser or Ala
<220> FEATURE:
<221> NAME/KEY: X
<222> LOCATION: (17)..(17)
<223> OTHER INFORMATION: Tyr or Leu
<220> FEATURE:
<221> NAME/KEY: X
<222> LOCATION: (18)..(18)
<223> OTHER INFORMATION: Tyr or Met
<220> FEATURE:
<221> NAME/KEY: X
<222> LOCATION: (19)..(19)
<223> OTHER INFORMATION: Leu or Asp
<220> FEATURE:
<221> NAME/KEY: X
<222> LOCATION: (20)..(20)
<223> OTHER INFORMATION: Leu or Val
<220> FEATURE:
<221> NAME/KEY: X
<222> LOCATION: (22)..(22)
<223> OTHER INFORMATION: Tyr
<220> FEATURE:
<221> NAME/KEY: X
<222> LOCATION: (23)..(23)
<223> OTHER INFORMATION: Glu, Arg, Gly or is absent

<400> SEQUENCE: 8

Xaa Xaa Xaa Xaa Xaa Xaa His Xaa Cys Gly Ser Xaa Xaa Xaa Xaa Xaa
1               5                   10                  15

Xaa Xaa Xaa Xaa Cys Xaa Xaa
            20

<210> SEQ ID NO 9
<211> LENGTH: 34
<212> TYPE: PRT
<213> ORGANISM: Artificial Sequence
<220> FEATURE:
<223> OTHER INFORMATION: A chain
<220> FEATURE:
<221> NAME/KEY: X
<222> LOCATION: (2)..(2)
<223> OTHER INFORMATION: Val or Ile
<220> FEATURE:
<221> NAME/KEY: X
<222> LOCATION: (3)..(3)
<223> OTHER INFORMATION: Val or Ala
<220> FEATURE:
<221> NAME/KEY: X
<222> LOCATION: (4)..(4)
<223> OTHER INFORMATION: Glu, gamma carboxyglutamate or Cys
<220> FEATURE:
```

-continued

```
<221> NAME/KEY: X
<222> LOCATION: (5)..(5)
<223> OTHER INFORMATION: Gln, Glu, gamma carboxyglutamate, His or Val
<220> FEATURE:
<221> NAME/KEY: X
<222> LOCATION: (6)..(7)
<223> OTHER INFORMATION: Cys or selenocysteine
<220> FEATURE:
<221> NAME/KEY: X
<222> LOCATION: (8)..(8)
<223> OTHER INFORMATION: Thr, His, Asp, Gln, Tyr, Lys or Val
<220> FEATURE:
<221> NAME/KEY: X
<222> LOCATION: (9)..(9)
<223> OTHER INFORMATION: Ser, Arg, Asn, His or Lys
<220> FEATURE:
<221> NAME/KEY: X
<222> LOCATION: (10)..(10)
<223> OTHER INFORMATION: Ile, Pro, Tyr, Ala, Ser, Phe, His or Thr
<220> FEATURE:
<221> NAME/KEY: X
<222> LOCATION: (11)..(11)
<223> OTHER INFORMATION: Cys or selenocysteine
<220> FEATURE:
<221> NAME/KEY: X
<222> LOCATION: (12)..(12)
<223> OTHER INFORMATION: Ser or Thr
<220> FEATURE:
<221> NAME/KEY: X
<222> LOCATION: (13)..(13)
<223> OTHER INFORMATION: Leu, Asn, Val or Asp
<220> FEATURE:
<221> NAME/KEY: X
<222> LOCATION: (14)..(14)
<223> OTHER INFORMATION: Tyr, Ala, Gln, Asp or Glu
<220> FEATURE:
<221> NAME/KEY: X
<222> LOCATION: (15)..(15)
<223> OTHER INFORMATION: Gln, Glu or Thr; or Ala
<220> FEATURE:
<221> NAME/KEY: X
<222> LOCATION: (17)..(17)
<223> OTHER INFORMATION: Glu, Lys, Arg, Ile, Met, Thr or Ser
<220> FEATURE:
<221> NAME/KEY: X
<222> LOCATION: (18)..(18)
<223> OTHER INFORMATION: Lys, Thr, Asn, Gln or Glu
<220> FEATURE:
<221> NAME/KEY: X
<222> LOCATION: (19)..(19)
<223> OTHER INFORMATION: Tyr or Phe
<220> FEATURE:
<221> NAME/KEY: X
<222> LOCATION: (20)..(20)
<223> OTHER INFORMATION: Cys, selenocysteine, amidated Cys, or amidated
      selenocysteine
<220> FEATURE:
<221> NAME/KEY: X
<222> LOCATION: (21)..(21)
<223> OTHER INFORMATION: Asn, Pro, His, Ser, Gly, Ala, or is absent
<220> FEATURE:
<221> NAME/KEY: X
<222> LOCATION: (22)..(22)
<223> OTHER INFORMATION: Pro, Asn, Thr, Leu, Ser or is absent
<220> FEATURE:
<221> NAME/KEY: X
<222> LOCATION: (23)..(23)
<223> OTHER INFORMATION: Thr, Leu, Val, Ser or is absent
<220> FEATURE:
<221> NAME/KEY: X
<222> LOCATION: (24)..(24)
<223> OTHER INFORMATION: Arg, Thr, Met, Gln, Leu or is absent
<220> FEATURE:
<221> NAME/KEY: X
<222> LOCATION: (25)..(25)
<223> OTHER INFORMATION: Glu, Gly or is absent
<220> FEATURE:
<221> NAME/KEY: X
<222> LOCATION: (26)..(26)
```

```
<223> OTHER INFORMATION: Ser, Leu or is absent
<220> FEATURE:
<221> NAME/KEY: X
<222> LOCATION: (27)..(31)
<223> OTHER INFORMATION: Ser or is absent
<220> FEATURE:
<221> NAME/KEY: X
<222> LOCATION: (32)..(32)
<223> OTHER INFORMATION: Ala, Ser or is absent
<220> FEATURE:
<221> NAME/KEY: X
<222> LOCATION: (33)..(33)
<223> OTHER INFORMATION: Ala, Val or is absent
<220> FEATURE:
<221> NAME/KEY: X
<222> LOCATION: (34)..(34)
<223> OTHER INFORMATION: Ala or is absent

<400> SEQUENCE: 9

Gly Xaa Xaa Xaa Xaa Xaa Xaa Xaa Xaa Xaa Xaa Xaa Xaa Xaa Phe
1               5                   10                  15

Xaa Xaa Xaa Xaa Xaa Xaa Xaa Xaa Xaa Xaa Xaa Xaa Xaa Xaa Xaa
                20                  25                  30

Xaa Xaa

<210> SEQ ID NO 10
<211> LENGTH: 21
<212> TYPE: PRT
<213> ORGANISM: Artificial Sequence
<220> FEATURE:
<223> OTHER INFORMATION: A chain
<220> FEATURE:
<221> NAME/KEY: X
<222> LOCATION: (2)..(2)
<223> OTHER INFORMATION: Val or Ile
<220> FEATURE:
<221> NAME/KEY: X
<222> LOCATION: (4)..(4)
<223> OTHER INFORMATION: Glu or gamma carboxyglutamate
<220> FEATURE:
<221> NAME/KEY: X
<222> LOCATION: (5)..(5)
<223> OTHER INFORMATION: His or Gln
<220> FEATURE:
<221> NAME/KEY: X
<222> LOCATION: (6)..(7)
<223> OTHER INFORMATION: Cys or selenocysteine
<220> FEATURE:
<221> NAME/KEY: X
<222> LOCATION: (8)..(8)
<223> OTHER INFORMATION: His or Thr
<220> FEATURE:
<221> NAME/KEY: X
<222> LOCATION: (9)..(9)
<223> OTHER INFORMATION: Arg or Ser
<220> FEATURE:
<221> NAME/KEY: X
<222> LOCATION: (10)..(10)
<223> OTHER INFORMATION: Pro or Ile
<220> FEATURE:
<221> NAME/KEY: X
<222> LOCATION: (11)..(11)
<223> OTHER INFORMATION: Cys or selenocysteine
<220> FEATURE:
<221> NAME/KEY: X
<222> LOCATION: (13)..(13)
<223> OTHER INFORMATION: Asn or Leu
<220> FEATURE:
<221> NAME/KEY: X
<222> LOCATION: (14)..(14)
<223> OTHER INFORMATION: Ala or Tyr
<220> FEATURE:
<221> NAME/KEY: X
<222> LOCATION: (15)..(15)
<223> OTHER INFORMATION: Glu or Gln
```

-continued

```
<220> FEATURE:
<221> NAME/KEY: X
<222> LOCATION: (16)..(16)
<223> OTHER INFORMATION: Phe or Leu
<220> FEATURE:
<221> NAME/KEY: X
<222> LOCATION: (17)..(17)
<223> OTHER INFORMATION: Lys or Glu
<220> FEATURE:
<221> NAME/KEY: X
<222> LOCATION: (18)..(18)
<223> OTHER INFORMATION: Lys or Asn
<220> FEATURE:
<221> NAME/KEY: X
<222> LOCATION: (20)..(20)
<223> OTHER INFORMATION: Cys, selenocysteine, amidated Cys, or amidated
      selenocysteine
<220> FEATURE:
<221> NAME/KEY: X
<222> LOCATION: (21)..(21)
<223> OTHER INFORMATION: Asn or absent

<400> SEQUENCE: 10

Gly Xaa Val Xaa Xaa Cys Cys Xaa Xaa Xaa Cys Ser Xaa Xaa Xaa Xaa
1               5                   10                  15

Xaa Xaa Tyr Cys Xaa
            20

<210> SEQ ID NO 11
<211> LENGTH: 23
<212> TYPE: PRT
<213> ORGANISM: Artificial Sequence
<220> FEATURE:
<223> OTHER INFORMATION: B chain
<220> FEATURE:
<221> NAME/KEY: X
<222> LOCATION: (1)..(1)
<223> OTHER INFORMATION: Thr or is absent
<220> FEATURE:
<221> NAME/KEY: X
<222> LOCATION: (2)..(2)
<223> OTHER INFORMATION: Phe or is absent
<220> FEATURE:
<221> NAME/KEY: X
<222> LOCATION: (3)..(3)
<223> OTHER INFORMATION: Phe or Asp
<220> FEATURE:
<221> NAME/KEY: X
<222> LOCATION: (4)..(4)
<223> OTHER INFORMATION: Thr or Val
<220> FEATURE:
<221> NAME/KEY: X
<222> LOCATION: (5)..(5)
<223> OTHER INFORMATION: Pro, Asn or hydroxyproline
<220> FEATURE:
<221> NAME/KEY: X
<222> LOCATION: (6)..(6)
<223> OTHER INFORMATION: Lys or Gln
<220> FEATURE:
<221> NAME/KEY: X
<222> LOCATION: (8)..(8)
<223> OTHER INFORMATION: Arg or Leu
<220> FEATURE:
<221> NAME/KEY: X
<222> LOCATION: (9)..(9)
<223> OTHER INFORMATION: Cys or selenocysteine
<220> FEATURE:
<221> NAME/KEY: X
<222> LOCATION: (12)..(12)
<223> OTHER INFORMATION: His, Glu or gamma carboxyglutamate
<220> FEATURE:
<221> NAME/KEY: X
<222> LOCATION: (13)..(13)
<223> OTHER INFORMATION: Ile or Leu
<220> FEATURE:
<221> NAME/KEY: X
```

```
<222> LOCATION: (14)..(14)
<223> OTHER INFORMATION: Thr, or Val
<220> FEATURE:
<221> NAME/KEY: X
<222> LOCATION: (15)..(15)
<223> OTHER INFORMATION: Glu, or Asn
<220> FEATURE:
<221> NAME/KEY: X
<222> LOCATION: (16)..(16)
<223> OTHER INFORMATION: Ser or Ala
<220> FEATURE:
<221> NAME/KEY: X
<222> LOCATION: (17)..(17)
<223> OTHER INFORMATION: Tyr or Leu
<220> FEATURE:
<221> NAME/KEY: X
<222> LOCATION: (18)..(18)
<223> OTHER INFORMATION: Tyr or Met
<220> FEATURE:
<221> NAME/KEY: X
<222> LOCATION: (19)..(19)
<223> OTHER INFORMATION: Leu or Asp
<220> FEATURE:
<221> NAME/KEY: X
<222> LOCATION: (20)..(20)
<223> OTHER INFORMATION: Leu or Val
<220> FEATURE:
<221> NAME/KEY: X
<222> LOCATION: (21)..(21)
<223> OTHER INFORMATION: Cys, selenocysteine, amidated Cys, or amidated
      selenocysteine
<220> FEATURE:
<221> NAME/KEY: X
<222> LOCATION: (22)..(22)
<223> OTHER INFORMATION: Gly or Tyr
<220> FEATURE:
<221> NAME/KEY: X
<222> LOCATION: (23)..(23)
<223> OTHER INFORMATION: Glu or Arg

<400> SEQUENCE: 11

Xaa Xaa Xaa Xaa Xaa Xaa His Xaa Cys Gly Ser Xaa Xaa Xaa Xaa Xaa
1               5                   10                  15

Xaa Xaa Xaa Xaa Xaa Xaa Xaa
            20

<210> SEQ ID NO 12
<211> LENGTH: 21
<212> TYPE: PRT
<213> ORGANISM: Artificial Sequence
<220> FEATURE:
<223> OTHER INFORMATION: A chain
<220> FEATURE:
<221> NAME/KEY: X
<222> LOCATION: (2)..(2)
<223> OTHER INFORMATION: Val or Ile
<220> FEATURE:
<221> NAME/KEY: X
<222> LOCATION: (4)..(4)
<223> OTHER INFORMATION: Glu or gamma carboxyglutamate
<220> FEATURE:
<221> NAME/KEY: X
<222> LOCATION: (5)..(5)
<223> OTHER INFORMATION: His or Gln
<220> FEATURE:
<221> NAME/KEY: X
<222> LOCATION: (8)..(8)
<223> OTHER INFORMATION: His or Thr
<220> FEATURE:
<221> NAME/KEY: X
<222> LOCATION: (9)..(9)
<223> OTHER INFORMATION: Arg or Ser
<220> FEATURE:
<221> NAME/KEY: X
<222> LOCATION: (10)..(10)
<223> OTHER INFORMATION: Pro or Ile
```

```
<220> FEATURE:
<221> NAME/KEY: X
<222> LOCATION: (13)..(13)
<223> OTHER INFORMATION: Asn or Leu
<220> FEATURE:
<221> NAME/KEY: X
<222> LOCATION: (14)..(14)
<223> OTHER INFORMATION: Ala or Tyr
<220> FEATURE:
<221> NAME/KEY: X
<222> LOCATION: (15)..(15)
<223> OTHER INFORMATION: Glu or Gln
<220> FEATURE:
<221> NAME/KEY: X
<222> LOCATION: (17)..(17)
<223> OTHER INFORMATION: Lys or Glu
<220> FEATURE:
<221> NAME/KEY: X
<222> LOCATION: (18)..(18)
<223> OTHER INFORMATION: Lys or Asn
<220> FEATURE:
<221> NAME/KEY: X
<222> LOCATION: (21)..(21)
<223> OTHER INFORMATION: Asn or absent

<400> SEQUENCE: 12

Gly Xaa Val Xaa Xaa Cys Cys Xaa Xaa Xaa Cys Ser Xaa Xaa Xaa Phe
1               5                   10                  15

Xaa Xaa Tyr Cys Xaa
            20

<210> SEQ ID NO 13
<211> LENGTH: 23
<212> TYPE: PRT
<213> ORGANISM: Artificial Sequence
<220> FEATURE:
<223> OTHER INFORMATION: B chain
<220> FEATURE:
<221> NAME/KEY: X
<222> LOCATION: (1)..(1)
<223> OTHER INFORMATION: Thr or is absent
<220> FEATURE:
<221> NAME/KEY: X
<222> LOCATION: (2)..(2)
<223> OTHER INFORMATION: Phe or is absent
<220> FEATURE:
<221> NAME/KEY: X
<222> LOCATION: (3)..(3)
<223> OTHER INFORMATION: Phe or Asp
<220> FEATURE:
<221> NAME/KEY: X
<222> LOCATION: (4)..(4)
<223> OTHER INFORMATION: Thr or Val
<220> FEATURE:
<221> NAME/KEY: X
<222> LOCATION: (5)..(5)
<223> OTHER INFORMATION: Pro, Asn or hydroxyproline
<220> FEATURE:
<221> NAME/KEY: X
<222> LOCATION: (6)..(6)
<223> OTHER INFORMATION: Lys or Gln
<220> FEATURE:
<221> NAME/KEY: X
<222> LOCATION: (8)..(8)
<223> OTHER INFORMATION: Arg or Leu
<220> FEATURE:
<221> NAME/KEY: X
<222> LOCATION: (12)..(12)
<223> OTHER INFORMATION: His, Glu or gamma carboxyglutamate
<220> FEATURE:
<221> NAME/KEY: X
<222> LOCATION: (13)..(13)
<223> OTHER INFORMATION: Ile or Leu
<220> FEATURE:
<221> NAME/KEY: X
<222> LOCATION: (14)..(14)
```

```
<223> OTHER INFORMATION: Thr, or Val
<220> FEATURE:
<221> NAME/KEY: X
<222> LOCATION: (15)..(15)
<223> OTHER INFORMATION: Glu, or Asn
<220> FEATURE:
<221> NAME/KEY: X
<222> LOCATION: (16)..(16)
<223> OTHER INFORMATION: Ser or Ala
<220> FEATURE:
<221> NAME/KEY: X
<222> LOCATION: (17)..(17)
<223> OTHER INFORMATION: Tyr or Leu
<220> FEATURE:
<221> NAME/KEY: X
<222> LOCATION: (18)..(18)
<223> OTHER INFORMATION: Tyr or Met
<220> FEATURE:
<221> NAME/KEY: X
<222> LOCATION: (19)..(19)
<223> OTHER INFORMATION: Leu or Asp
<220> FEATURE:
<221> NAME/KEY: X
<222> LOCATION: (20)..(20)
<223> OTHER INFORMATION: Leu or Val
<220> FEATURE:
<221> NAME/KEY: X
<222> LOCATION: (23)..(23)
<223> OTHER INFORMATION: Glu or Arg

<400> SEQUENCE: 13

Xaa Xaa Xaa Xaa Xaa Xaa His Xaa Cys Gly Ser Xaa Xaa Xaa Xaa Xaa
1               5                   10                  15

Xaa Xaa Xaa Xaa Cys Tyr Xaa
            20

<210> SEQ ID NO 14
<211> LENGTH: 21
<212> TYPE: PRT
<213> ORGANISM: Artificial Sequence
<220> FEATURE:
<223> OTHER INFORMATION: A chain
<220> FEATURE:
<221> NAME/KEY: X
<222> LOCATION: (4)..(4)
<223> OTHER INFORMATION: Glu or gamma carboxyglutamate
<220> FEATURE:
<221> NAME/KEY: X
<222> LOCATION: (5)..(5)
<223> OTHER INFORMATION: His or Gln
<220> FEATURE:
<221> NAME/KEY: X
<222> LOCATION: (6)..(7)
<223> OTHER INFORMATION: Cys or selenocysteine
<220> FEATURE:
<221> NAME/KEY: X
<222> LOCATION: (8)..(8)
<223> OTHER INFORMATION: His or Thr
<220> FEATURE:
<221> NAME/KEY: X
<222> LOCATION: (9)..(9)
<223> OTHER INFORMATION: Arg or Ser
<220> FEATURE:
<221> NAME/KEY: X
<222> LOCATION: (10)..(10)
<223> OTHER INFORMATION: Pro or Ile
<220> FEATURE:
<221> NAME/KEY: X
<222> LOCATION: (11)..(11)
<223> OTHER INFORMATION: Cys or selenocysteine
<220> FEATURE:
<221> NAME/KEY: X
<222> LOCATION: (13)..(13)
<223> OTHER INFORMATION: Asn or Leu
<220> FEATURE:
<221> NAME/KEY: X
```

```
<222> LOCATION: (14)..(14)
<223> OTHER INFORMATION: Ala or Tyr
<220> FEATURE:
<221> NAME/KEY: X
<222> LOCATION: (15)..(15)
<223> OTHER INFORMATION: Glu or Gln
<220> FEATURE:
<221> NAME/KEY: X
<222> LOCATION: (17)..(17)
<223> OTHER INFORMATION: Lys or Glu
<220> FEATURE:
<221> NAME/KEY: X
<222> LOCATION: (18)..(18)
<223> OTHER INFORMATION: Lys or Asn
<220> FEATURE:
<221> NAME/KEY: X
<222> LOCATION: (20)..(20)
<223> OTHER INFORMATION: Cys, selenocysteine, amidated Cys, or amidated
      selenocysteine
<220> FEATURE:
<221> NAME/KEY: X
<222> LOCATION: (21)..(21)
<223> OTHER INFORMATION: Asn or absent

<400> SEQUENCE: 14

Gly Val Val Xaa Xaa Cys Cys Xaa Xaa Xaa Cys Ser Xaa Xaa Xaa Phe
1               5                   10                  15

Xaa Xaa Tyr Cys Xaa
            20

<210> SEQ ID NO 15
<211> LENGTH: 23
<212> TYPE: PRT
<213> ORGANISM: Artificial Sequence
<220> FEATURE:
<223> OTHER INFORMATION: B chain
<220> FEATURE:
<221> NAME/KEY: X
<222> LOCATION: (1)..(1)
<223> OTHER INFORMATION: Thr or is absent
<220> FEATURE:
<221> NAME/KEY: X
<222> LOCATION: (2)..(2)
<223> OTHER INFORMATION: Phe or is absent
<220> FEATURE:
<221> NAME/KEY: X
<222> LOCATION: (3)..(3)
<223> OTHER INFORMATION: Phe or Asp
<220> FEATURE:
<221> NAME/KEY: X
<222> LOCATION: (4)..(4)
<223> OTHER INFORMATION: Thr or Val
<220> FEATURE:
<221> NAME/KEY: X
<222> LOCATION: (5)..(5)
<223> OTHER INFORMATION: Pro, Asn or hydroxyproline
<220> FEATURE:
<221> NAME/KEY: X
<222> LOCATION: (6)..(6)
<223> OTHER INFORMATION: Lys or Gln
<220> FEATURE:
<221> NAME/KEY: X
<222> LOCATION: (12)..(12)
<223> OTHER INFORMATION: His, Glu or gamma carboxyglutamate
<220> FEATURE:
<221> NAME/KEY: X
<222> LOCATION: (14)..(14)
<223> OTHER INFORMATION: Thr, or Val
<220> FEATURE:
<221> NAME/KEY: X
<222> LOCATION: (15)..(15)
<223> OTHER INFORMATION: Glu, or Asn
<220> FEATURE:
<221> NAME/KEY: X
<222> LOCATION: (16)..(16)
<223> OTHER INFORMATION: Ser or Ala
```

```
<220> FEATURE:
<221> NAME/KEY: X
<222> LOCATION: (17)..(17)
<223> OTHER INFORMATION: Tyr or Leu
<220> FEATURE:
<221> NAME/KEY: X
<222> LOCATION: (18)..(18)
<223> OTHER INFORMATION: Tyr or Met
<220> FEATURE:
<221> NAME/KEY: X
<222> LOCATION: (19)..(19)
<223> OTHER INFORMATION: Leu or Asp
<220> FEATURE:
<221> NAME/KEY: X
<222> LOCATION: (23)..(23)
<223> OTHER INFORMATION: Glu or Arg

<400> SEQUENCE: 15

Xaa Xaa Xaa Xaa Xaa His Arg Cys Gly Ser Xaa Ile Xaa Xaa Xaa
1               5                   10                  15

Xaa Xaa Xaa Leu Cys Tyr Xaa
            20

<210> SEQ ID NO 16
<211> LENGTH: 21
<212> TYPE: PRT
<213> ORGANISM: Artificial Sequence
<220> FEATURE:
<223> OTHER INFORMATION: A chain

<400> SEQUENCE: 16

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 17
<211> LENGTH: 21
<212> TYPE: PRT
<213> ORGANISM: Artificial Sequence
<220> FEATURE:
<223> OTHER INFORMATION: B chain
<220> FEATURE:
<221> NAME/KEY: X
<222> LOCATION: (15)..(15)
<223> OTHER INFORMATION: aromatic residue or large aliphatic residue

<400> SEQUENCE: 17

Phe Val Asn Gln His Leu Cys Gly Ser His Leu Val Glu Ala Xaa Tyr
1               5                   10                  15

Leu Val Cys Gly Glu
            20

<210> SEQ ID NO 18
<211> LENGTH: 21
<212> TYPE: PRT
<213> ORGANISM: Artificial Sequence
<220> FEATURE:
<223> OTHER INFORMATION: A chain

<400> SEQUENCE: 18

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 19
```

```
<211> LENGTH: 21
<212> TYPE: PRT
<213> ORGANISM: Artificial Sequence
<220> FEATURE:
<223> OTHER INFORMATION: B chain
<220> FEATURE:
<221> NAME/KEY: X
<222> LOCATION: (20)..(20)
<223> OTHER INFORMATION: aromatic residue or large aliphatic residue

<400> SEQUENCE: 19

Phe Val Asn Gln His Leu Cys Gly Ser His Leu Val Glu Ala Leu Tyr
1               5                   10                  15

Leu Val Cys Xaa Glu
            20

<210> SEQ ID NO 20
<211> LENGTH: 21
<212> TYPE: PRT
<213> ORGANISM: Artificial Sequence
<220> FEATURE:
<223> OTHER INFORMATION: A chain

<400> SEQUENCE: 20

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 21
<211> LENGTH: 21
<212> TYPE: PRT
<213> ORGANISM: Artificial Sequence
<220> FEATURE:
<223> OTHER INFORMATION: B chain
<220> FEATURE:
<221> NAME/KEY: X
<222> LOCATION: (15)..(15)
<223> OTHER INFORMATION: aromatic residue or large aliphatic residue
<220> FEATURE:
<221> NAME/KEY: X
<222> LOCATION: (20)..(20)
<223> OTHER INFORMATION: aromatic residue or large aliphatic residue

<400> SEQUENCE: 21

Phe Val Asn Gln His Leu Cys Gly Ser His Leu Val Glu Ala Xaa Tyr
1               5                   10                  15

Leu Val Cys Xaa Glu
            20

<210> SEQ ID NO 22
<211> LENGTH: 20
<212> TYPE: PRT
<213> ORGANISM: Conus geographus
<220> FEATURE:
<221> NAME/KEY: X
<222> LOCATION: (4)..(4)
<223> OTHER INFORMATION: gamma-carboxylated glutamic acid
<220> FEATURE:
<221> NAME/KEY: X
<222> LOCATION: (20)..(20)
<223> OTHER INFORMATION: amidated Cys (at N-terminus)

<400> SEQUENCE: 22

Gly Val Val Xaa His Cys Cys His Arg Pro Cys Ser Asn Ala Glu Phe
1               5                   10                  15

Lys Lys Tyr Xaa
            20
```

<210> SEQ ID NO 23
<211> LENGTH: 23
<212> TYPE: PRT
<213> ORGANISM: Conus geographus
<220> FEATURE:
<221> NAME/KEY: X
<222> LOCATION: (5)..(5)
<223> OTHER INFORMATION: hydroxyproline
<220> FEATURE:
<221> NAME/KEY: X
<222> LOCATION: (12)..(12)
<223> OTHER INFORMATION: gamma-carboxylated glutamic acid

<400> SEQUENCE: 23

Thr Phe Asp Thr Tyr Lys His Arg Cys Gly Ser Xaa Ile Thr Asn Ser
1               5                   10                  15

Tyr Met Asp Leu Cys Tyr Arg
            20

<210> SEQ ID NO 24
<211> LENGTH: 21
<212> TYPE: PRT
<213> ORGANISM: Homo sapiens

<400> SEQUENCE: 24

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 25
<211> LENGTH: 30
<212> TYPE: PRT
<213> ORGANISM: Homo sapiens

<400> SEQUENCE: 25

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 26
<211> LENGTH: 21
<212> TYPE: PRT
<213> ORGANISM: Artificial Sequence
<220> FEATURE:
<223> OTHER INFORMATION: A chain
<220> FEATURE:
<221> NAME/KEY: X
<222> LOCATION: (2)..(2)
<223> OTHER INFORMATION: Val or Ile
<220> FEATURE:
<221> NAME/KEY: X
<222> LOCATION: (4)..(4)
<223> OTHER INFORMATION: Glu or gamma carboxyglutamate,
<220> FEATURE:
<221> NAME/KEY: X
<222> LOCATION: (5)..(5)
<223> OTHER INFORMATION: His or Gln
<220> FEATURE:
<221> NAME/KEY: X
<222> LOCATION: (8)..(8)
<223> OTHER INFORMATION: His or Thr
<220> FEATURE:
<221> NAME/KEY: X
<222> LOCATION: (9)..(9)
<223> OTHER INFORMATION: Arg or Ser
<220> FEATURE:

```
<221> NAME/KEY: X
<222> LOCATION: (10)..(10)
<223> OTHER INFORMATION: Pro or Ile,
<220> FEATURE:
<221> NAME/KEY: X
<222> LOCATION: (13)..(13)
<223> OTHER INFORMATION: Asn or Leu
<220> FEATURE:
<221> NAME/KEY: X
<222> LOCATION: (14)..(14)
<223> OTHER INFORMATION: Ala or Tyr
<220> FEATURE:
<221> NAME/KEY: X
<222> LOCATION: (15)..(15)
<223> OTHER INFORMATION: Glu or Gln
<220> FEATURE:
<221> NAME/KEY: X
<222> LOCATION: (17)..(17)
<223> OTHER INFORMATION: Lys or Glu
<220> FEATURE:
<221> NAME/KEY: X
<222> LOCATION: (18)..(18)
<223> OTHER INFORMATION: Lys or Asn
<220> FEATURE:
<221> NAME/KEY: X
<222> LOCATION: (21)..(21)
<223> OTHER INFORMATION: Asn or absent

<400> SEQUENCE: 26

Gly Xaa Val Xaa Xaa Cys Cys Xaa Xaa Xaa Cys Ser Xaa Xaa Xaa Phe
1               5                   10                  15

Xaa Xaa Tyr Cys Xaa
            20

<210> SEQ ID NO 27
<211> LENGTH: 23
<212> TYPE: PRT
<213> ORGANISM: Artificial Sequence
<220> FEATURE:
<223> OTHER INFORMATION: B chain
<220> FEATURE:
<221> NAME/KEY: X
<222> LOCATION: (1)..(1)
<223> OTHER INFORMATION: Thr or is absent
<220> FEATURE:
<221> NAME/KEY: X
<222> LOCATION: (2)..(2)
<223> OTHER INFORMATION: Phe or is absent
<220> FEATURE:
<221> NAME/KEY: X
<222> LOCATION: (3)..(3)
<223> OTHER INFORMATION: Phe or Asp
<220> FEATURE:
<221> NAME/KEY: X
<222> LOCATION: (4)..(4)
<223> OTHER INFORMATION: Thr or Val
<220> FEATURE:
<221> NAME/KEY: X
<222> LOCATION: (5)..(5)
<223> OTHER INFORMATION: Pro, Asn or hydroxyproline
<220> FEATURE:
<221> NAME/KEY: X
<222> LOCATION: (6)..(6)
<223> OTHER INFORMATION: Lys or Gln
<220> FEATURE:
<221> NAME/KEY: X
<222> LOCATION: (8)..(8)
<223> OTHER INFORMATION: Arg or Leu
<220> FEATURE:
<221> NAME/KEY: X
<222> LOCATION: (12)..(12)
<223> OTHER INFORMATION: His, Glu or gamma carboxyglutamate
<220> FEATURE:
<221> NAME/KEY: X
<222> LOCATION: (13)..(13)
<223> OTHER INFORMATION: Ile or Leu
```

```
<220> FEATURE:
<221> NAME/KEY: X
<222> LOCATION: (14)..(14)
<223> OTHER INFORMATION: Thr, or Val
<220> FEATURE:
<221> NAME/KEY: X
<222> LOCATION: (15)..(15)
<223> OTHER INFORMATION: Glu, or Asn
<220> FEATURE:
<221> NAME/KEY: X
<222> LOCATION: (16)..(16)
<223> OTHER INFORMATION: Ser or Ala
<220> FEATURE:
<221> NAME/KEY: X
<222> LOCATION: (18)..(18)
<223> OTHER INFORMATION: Tyr or Met
<220> FEATURE:
<221> NAME/KEY: X
<222> LOCATION: (19)..(19)
<223> OTHER INFORMATION: Leu or Asp
<220> FEATURE:
<221> NAME/KEY: X
<222> LOCATION: (20)..(20)
<223> OTHER INFORMATION: Leu or Val
<220> FEATURE:
<221> NAME/KEY: X
<222> LOCATION: (22)..(22)
<223> OTHER INFORMATION: Gly or Tyr
<220> FEATURE:
<221> NAME/KEY: X
<222> LOCATION: (23)..(23)
<223> OTHER INFORMATION: Glu or Arg

<400> SEQUENCE: 27

Xaa Xaa Xaa Xaa Xaa Xaa His Xaa Cys Gly Ser Xaa Xaa Xaa Xaa Xaa
1               5                   10                  15

Tyr Xaa Xaa Xaa Cys Xaa Xaa
            20

<210> SEQ ID NO 28
<211> LENGTH: 21
<212> TYPE: PRT
<213> ORGANISM: Artificial Sequence
<220> FEATURE:
<223> OTHER INFORMATION: A chain
<220> FEATURE:
<221> NAME/KEY: X
<222> LOCATION: (4)..(4)
<223> OTHER INFORMATION: Glu or gamma carboxyglutamate
<220> FEATURE:
<221> NAME/KEY: X
<222> LOCATION: (5)..(5)
<223> OTHER INFORMATION: His or Gln
<220> FEATURE:
<221> NAME/KEY: X
<222> LOCATION: (8)..(8)
<223> OTHER INFORMATION: His or Thr
<220> FEATURE:
<221> NAME/KEY: X
<222> LOCATION: (9)..(9)
<223> OTHER INFORMATION: Arg or Ser
<220> FEATURE:
<221> NAME/KEY: X
<222> LOCATION: (10)..(10)
<223> OTHER INFORMATION: Pro or Ile
<220> FEATURE:
<221> NAME/KEY: X
<222> LOCATION: (13)..(13)
<223> OTHER INFORMATION: Asn or Leu
<220> FEATURE:
<221> NAME/KEY: X
<222> LOCATION: (14)..(14)
<223> OTHER INFORMATION: Ala or Tyr
<220> FEATURE:
<221> NAME/KEY: X
<222> LOCATION: (15)..(15)
```

```
<223> OTHER INFORMATION: Glu or Gln
<220> FEATURE:
<221> NAME/KEY: X
<222> LOCATION: (17)..(17)
<223> OTHER INFORMATION: Lys or Glu
<220> FEATURE:
<221> NAME/KEY: X
<222> LOCATION: (18)..(18)
<223> OTHER INFORMATION: Lys or Asn
<220> FEATURE:
<221> NAME/KEY: X
<222> LOCATION: (21)..(21)
<223> OTHER INFORMATION: Asn or absent

<400> SEQUENCE: 28

Gly Val Val Xaa Xaa Cys Cys Xaa Xaa Xaa Cys Ser Xaa Xaa Xaa Phe
1               5                   10                  15

Xaa Xaa Tyr Cys Xaa
            20

<210> SEQ ID NO 29
<211> LENGTH: 23
<212> TYPE: PRT
<213> ORGANISM: Artificial Sequence
<220> FEATURE:
<223> OTHER INFORMATION: B chain
<220> FEATURE:
<221> NAME/KEY: X
<222> LOCATION: (1)..(1)
<223> OTHER INFORMATION: Thr or is absent
<220> FEATURE:
<221> NAME/KEY: X
<222> LOCATION: (2)..(2)
<223> OTHER INFORMATION: Phe or is absent
<220> FEATURE:
<221> NAME/KEY: X
<222> LOCATION: (3)..(3)
<223> OTHER INFORMATION: Phe or Asp
<220> FEATURE:
<221> NAME/KEY: X
<222> LOCATION: (4)..(4)
<223> OTHER INFORMATION: Thr or Val
<220> FEATURE:
<221> NAME/KEY: X
<222> LOCATION: (5)..(5)
<223> OTHER INFORMATION: Pro, Asn or hydroxyproline
<220> FEATURE:
<221> NAME/KEY: X
<222> LOCATION: (6)..(6)
<223> OTHER INFORMATION: Lys or Gln
<220> FEATURE:
<221> NAME/KEY: X
<222> LOCATION: (12)..(12)
<223> OTHER INFORMATION: His, Glu or gamma carboxyglutamate
<220> FEATURE:
<221> NAME/KEY: X
<222> LOCATION: (14)..(14)
<223> OTHER INFORMATION: Thr, or Val
<220> FEATURE:
<221> NAME/KEY: X
<222> LOCATION: (15)..(15)
<223> OTHER INFORMATION: Glu, or Asn
<220> FEATURE:
<221> NAME/KEY: X
<222> LOCATION: (16)..(16)
<223> OTHER INFORMATION: Ser or Ala
<220> FEATURE:
<221> NAME/KEY: X
<222> LOCATION: (18)..(18)
<223> OTHER INFORMATION: Tyr or Met
<220> FEATURE:
<221> NAME/KEY: X
<222> LOCATION: (19)..(19)
<223> OTHER INFORMATION: Leu or Asp
<220> FEATURE:
<221> NAME/KEY: X
```

```
<222> LOCATION: (22)..(22)
<223> OTHER INFORMATION: Gly or Tyr
<220> FEATURE:
<221> NAME/KEY: X
<222> LOCATION: (23)..(23)
<223> OTHER INFORMATION: Glu or Arg

<400> SEQUENCE: 29

Xaa Xaa Xaa Xaa Xaa Xaa His Arg Cys Gly Ser Xaa Ile Xaa Xaa Xaa
1               5                   10                  15

Tyr Xaa Xaa Leu Cys Xaa Xaa
            20

<210> SEQ ID NO 30
<211> LENGTH: 22
<212> TYPE: PRT
<213> ORGANISM: Artificial Sequence
<220> FEATURE:
<223> OTHER INFORMATION: B Chain

<400> SEQUENCE: 30

Phe Val Asn Gln His Leu Cys Gly Ser Glu Leu Val Glu Ala Leu Tyr
1               5                   10                  15

Leu Val Cys Tyr Glu Arg
            20

<210> SEQ ID NO 31
<211> LENGTH: 22
<212> TYPE: PRT
<213> ORGANISM: Artificial Sequence
<220> FEATURE:
<223> OTHER INFORMATION: B chain

<400> SEQUENCE: 31

Phe Val Asn Gln His Leu Cys Gly Ser Glu Leu Val Glu Ala Leu Tyr
1               5                   10                  15

Leu Val Cys Phe Glu Arg
            20

<210> SEQ ID NO 32
<211> LENGTH: 22
<212> TYPE: PRT
<213> ORGANISM: Artificial Sequence
<220> FEATURE:
<223> OTHER INFORMATION: B chain

<400> SEQUENCE: 32

Phe Val Asn Gln His Leu Cys Gly Ser Glu Leu Val Glu Ala Leu Tyr
1               5                   10                  15

Leu Val Cys Pro Glu Arg
            20

<210> SEQ ID NO 33
<211> LENGTH: 22
<212> TYPE: PRT
<213> ORGANISM: Artificial Sequence
<220> FEATURE:
<223> OTHER INFORMATION: B chain

<400> SEQUENCE: 33

Phe Val Asn Gln His Leu Cys Gly Ser Asp Leu Val Glu Ala Leu Tyr
1               5                   10                  15

Leu Val Cys Tyr Glu Arg
            20
```

```
<210> SEQ ID NO 34
<211> LENGTH: 22
<212> TYPE: PRT
<213> ORGANISM: Artificial Sequence
<220> FEATURE:
<223> OTHER INFORMATION: B chain

<400> SEQUENCE: 34

Phe Val Asn Gln His Leu Cys Gly Ser Asp Leu Val Glu Ala Leu Tyr
1               5                   10                  15

Leu Val Cys Phe Glu Arg
            20

<210> SEQ ID NO 35
<211> LENGTH: 22
<212> TYPE: PRT
<213> ORGANISM: Artificial Sequence
<220> FEATURE:
<223> OTHER INFORMATION: B chain

<400> SEQUENCE: 35

Phe Val Asn Gln His Leu Cys Gly Ser Asp Leu Val Glu Ala Leu Tyr
1               5                   10                  15

Leu Val Cys Pro Glu Arg
            20

<210> SEQ ID NO 36
<211> LENGTH: 22
<212> TYPE: PRT
<213> ORGANISM: Artificial Sequence
<220> FEATURE:
<223> OTHER INFORMATION: B chain

<400> SEQUENCE: 36

Phe Val Asn Gln His Leu Cys Gly Ser Gln Leu Val Glu Ala Leu Tyr
1               5                   10                  15

Leu Val Cys Tyr Glu Arg
            20

<210> SEQ ID NO 37
<211> LENGTH: 22
<212> TYPE: PRT
<213> ORGANISM: Artificial Sequence
<220> FEATURE:
<223> OTHER INFORMATION: B chain

<400> SEQUENCE: 37

Phe Val Asn Gln His Leu Cys Gly Ser Gln Leu Val Glu Ala Leu Tyr
1               5                   10                  15

Leu Val Cys Phe Glu Arg
            20

<210> SEQ ID NO 38
<211> LENGTH: 22
<212> TYPE: PRT
<213> ORGANISM: Artificial Sequence
<220> FEATURE:
<223> OTHER INFORMATION: B chain

<400> SEQUENCE: 38

Phe Val Asn Gln His Leu Cys Gly Ser Gln Leu Val Glu Ala Leu Tyr
1               5                   10                  15

Leu Val Cys Pro Glu Arg
            20
```

```
<210> SEQ ID NO 39
<211> LENGTH: 21
<212> TYPE: PRT
<213> ORGANISM: Artificial Sequence
<220> FEATURE:
<223> OTHER INFORMATION: A chain

<400> SEQUENCE: 39

Gly Ile Val Glu Gln Cys Cys His Arg Ile Cys Ser Leu Tyr Gln Leu
1               5                   10                  15

Glu Asn Tyr Cys Asn
            20

<210> SEQ ID NO 40
<211> LENGTH: 21
<212> TYPE: PRT
<213> ORGANISM: Artificial Sequence
<220> FEATURE:
<223> OTHER INFORMATION: A chain

<400> SEQUENCE: 40

Gly Ile Val Glu Gln Cys Cys Tyr Arg Ile Cys Ser Leu Tyr Gln Leu
1               5                   10                  15

Glu Asn Tyr Cys Asn
            20

<210> SEQ ID NO 41
<211> LENGTH: 21
<212> TYPE: PRT
<213> ORGANISM: Artificial Sequence
<220> FEATURE:
<223> OTHER INFORMATION: A chain

<400> SEQUENCE: 41

Gly Ile Val Glu Gln Cys Cys Lys Arg Ile Cys Ser Leu Tyr Gln Leu
1               5                   10                  15

Glu Asn Tyr Cys Asn
            20

<210> SEQ ID NO 42
<211> LENGTH: 22
<212> TYPE: PRT
<213> ORGANISM: Artificial Sequence
<220> FEATURE:
<223> OTHER INFORMATION: B chain

<400> SEQUENCE: 42

Phe Val Asn Gln His Leu Cys Gly Ser His Leu Val Glu Ala Leu Tyr
1               5                   10                  15

Leu Val Cys Gly Glu Arg
            20

<210> SEQ ID NO 43
<211> LENGTH: 22
<212> TYPE: PRT
<213> ORGANISM: Artificial Sequence
<220> FEATURE:
<223> OTHER INFORMATION: B chain

<400> SEQUENCE: 43

Phe Val Asn Gln His Leu Cys Gly Ser His Leu Val Glu Ala Tyr Tyr
1               5                   10                  15

Leu Val Cys Gly Glu Arg
```

20

<210> SEQ ID NO 44
<211> LENGTH: 22
<212> TYPE: PRT
<213> ORGANISM: Artificial Sequence
<220> FEATURE:
<223> OTHER INFORMATION: B chain

<400> SEQUENCE: 44

Phe Val Asn Gln His Leu Cys Gly Ser His Leu Val Glu Ala Leu Tyr
1               5                   10                  15

Leu Val Cys Tyr Glu Arg
            20

<210> SEQ ID NO 45
<211> LENGTH: 22
<212> TYPE: PRT
<213> ORGANISM: Artificial Sequence
<220> FEATURE:
<223> OTHER INFORMATION: B chain

<400> SEQUENCE: 45

Phe Val Asn Gln His Leu Cys Gly Ser His Leu Val Glu Ala Tyr Tyr
1               5                   10                  15

Leu Val Cys Tyr Glu Arg
            20

<210> SEQ ID NO 46
<211> LENGTH: 22
<212> TYPE: PRT
<213> ORGANISM: Artificial Sequence
<220> FEATURE:
<223> OTHER INFORMATION: B chain
<220> FEATURE:
<221> NAME/KEY: X
<222> LOCATION: (20)..(20)
<223> OTHER INFORMATION: D-tyrosine, O-methyl-L-tyrosine,
      L-phenylalanine, 4-phenyl-L-phenylalanine, 4-tert-butyl-L-
      phenylalanine, L-tryptophan
<220> FEATURE:
<221> NAME/KEY: X
<222> LOCATION: (20)..(20)
<223> OTHER INFORMATION: Xaa = D-tyrosine, O-methyl-L-tyrosine,
      L-phenylalanine, 4-phenyl-L-phenylalanine, 4-tert-butyl-L-
      phenylalanine, L-tryptophan

<400> SEQUENCE: 46

Phe Val Asn Gln His Leu Cys Gly Ser Glu Leu Val Glu Ala Leu Tyr
1               5                   10                  15

Leu Val Cys Xaa Glu Arg
            20

<210> SEQ ID NO 47
<211> LENGTH: 21
<212> TYPE: PRT
<213> ORGANISM: Artificial Sequence
<220> FEATURE:
<223> OTHER INFORMATION: A chain

<400> SEQUENCE: 47

Gly Ile Val Glu Gln Cys Cys His Ser Ile Cys Ser Leu Tyr Gln Leu
1               5                   10                  15

Glu Asn Tyr Cys Asn
            20

```
<210> SEQ ID NO 48
<211> LENGTH: 22
<212> TYPE: PRT
<213> ORGANISM: Artificial Sequence
<220> FEATURE:
<223> OTHER INFORMATION: B chain

<400> SEQUENCE: 48

Phe Val Asn Gln His Leu Cys Gly Ser Glu Leu Val Glu Ala Leu Tyr
1               5                   10                  15

Leu Val Cys Gly Glu Arg
            20

<210> SEQ ID NO 49
<211> LENGTH: 21
<212> TYPE: PRT
<213> ORGANISM: Artificial Sequence
<220> FEATURE:
<223> OTHER INFORMATION: A chain

<400> SEQUENCE: 49

Gly Ile Val Glu Gln Cys Cys Thr Arg Ile Cys Ser Leu Tyr Gln Leu
1               5                   10                  15

Glu Asn Tyr Cys Asn
            20

<210> SEQ ID NO 50
<211> LENGTH: 20
<212> TYPE: PRT
<213> ORGANISM: Artificial Sequence
<220> FEATURE:
<223> OTHER INFORMATION: A chain

<400> SEQUENCE: 50

Gly Val Val Tyr His Cys Cys His Arg Pro Cys Ser Asn Ala Glu Phe
1               5                   10                  15

Lys Lys Phe Cys
            20

<210> SEQ ID NO 51
<211> LENGTH: 20
<212> TYPE: PRT
<213> ORGANISM: Artificial Sequence
<220> FEATURE:
<223> OTHER INFORMATION: A chain

<400> SEQUENCE: 51

Gly Val Val Tyr His Cys Cys Tyr Arg Pro Cys Ser Asn Ala Glu Phe
1               5                   10                  15

Lys Lys Phe Cys
            20

<210> SEQ ID NO 52
<211> LENGTH: 20
<212> TYPE: PRT
<213> ORGANISM: Artificial Sequence
<220> FEATURE:
<223> OTHER INFORMATION: A chain

<400> SEQUENCE: 52

Gly Val Val Tyr His Cys Cys Lys Arg Ala Cys Ser Asn Ala Glu Phe
1               5                   10                  15

Met Gln Phe Cys
            20
```

-continued

```
<210> SEQ ID NO 53
<211> LENGTH: 22
<212> TYPE: PRT
<213> ORGANISM: Artificial Sequence
<220> FEATURE:
<223> OTHER INFORMATION: B chain

<400> SEQUENCE: 53

Asn Ser Asp Thr Pro Lys Tyr Arg Cys Gly Ser Tyr Ile Pro Asn Ser
1               5                   10                  15

Tyr Ile Asp Leu Cys Phe
            20

<210> SEQ ID NO 54
<211> LENGTH: 22
<212> TYPE: PRT
<213> ORGANISM: Artificial Sequence
<220> FEATURE:
<223> OTHER INFORMATION: B chain

<400> SEQUENCE: 54

Asn Ser Asp Thr Pro Lys Tyr Arg Cys Gly Ser Asp Ile Pro Asn Ser
1               5                   10                  15

Tyr Met Asp Leu Cys Phe
            20

<210> SEQ ID NO 55
<211> LENGTH: 23
<212> TYPE: PRT
<213> ORGANISM: Artificial Sequence
<220> FEATURE:
<223> OTHER INFORMATION: B chain

<400> SEQUENCE: 55

Asn Ser Asp Thr Pro Trp Asn Arg Cys Gly Ser Gln Ile Thr Asp Ser
1               5                   10                  15

Tyr Arg Tyr Leu Cys Pro His
            20

<210> SEQ ID NO 56
<211> LENGTH: 21
<212> TYPE: PRT
<213> ORGANISM: Artificial Sequence
<220> FEATURE:
<223> OTHER INFORMATION: A chain
<220> FEATURE:
<221> NAME/KEY: X
<222> LOCATION: (8)..(8)
<223> OTHER INFORMATION: his, tyr, or lys
<220> FEATURE:
<221> NAME/KEY: X
<222> LOCATION: (9)..(9)
<223> OTHER INFORMATION: arg
<220> FEATURE:
<221> NAME/KEY: X
<222> LOCATION: (21)..(21)
<223> OTHER INFORMATION: asp or gly

<400> SEQUENCE: 56

Gly Ile Val Glu Gln Cys Cys Xaa Xaa Ile Cys Ser Leu Tyr Gln Leu
1               5                   10                  15

Glu Asn Tyr Cys Xaa
            20

<210> SEQ ID NO 57
<211> LENGTH: 22
```

```
<212> TYPE: PRT
<213> ORGANISM: Artificial Sequence
<220> FEATURE:
<223> OTHER INFORMATION: B chain
<220> FEATURE:
<221> NAME/KEY: X
<222> LOCATION: (10)..(10)
<223> OTHER INFORMATION: glu, asp, or gln
<220> FEATURE:
<221> NAME/KEY: X
<222> LOCATION: (20)..(20)
<223> OTHER INFORMATION: tyr, phe, or pro

<400> SEQUENCE: 57

Phe Val Asn Gln His Leu Cys Gly Ser Xaa Leu Val Glu Ala Leu Tyr
1               5                   10                  15

Leu Val Cys Xaa Glu Arg
            20

<210> SEQ ID NO 58
<211> LENGTH: 21
<212> TYPE: PRT
<213> ORGANISM: Artificial Sequence
<220> FEATURE:
<223> OTHER INFORMATION: A chain

<400> SEQUENCE: 58

Gly Ile Val Glu Gln Cys Cys His Arg Ile Cys Ser Leu Tyr Gln Leu
1               5                   10                  15

Glu Asn Tyr Cys Gly
            20
```

INSULIN ANALOGS

The present application is a continuation of U.S. application Ser. No. 16/319,450, filed Jan. 21, 2019, which is a national stage entry under 35 U.S.C. § 371 of International Application No. PCT/AU2017/050758, filed Jul. 21, 2017, which claims priority from Australian provisional application number AU2016902883, filed Jul. 22, 2016, and also claims priority from U.S. provisional application No. 62/483,118, filed Apr. 4, 2017, which are hereby incorporated by reference in their entireties.

STATEMENT REGARDING FEDERALLY SPONSORED RESEARCH

This invention, in part, was made with government support under GM 48677 awarded by National Institutes of Health. The government has certain rights in the invention.

INCORPORATION OF SEQUENCE LISTING

The sequence listing that is contained in the file named "MONO0002520US_ST25," which is 46.9 kilobytes as measured in Microsoft Windows operating system and was created on Dec. 23, 2020, is filed electronically herewith and incorporated herein by reference.

FIELD OF THE INVENTION

The present invention relates generally to insulin analogs. More particularly, the present invention relates to rapid acting insulin analogs having shortened B chains. The present invention also relates to the crystal structure of insulin from the venom of cone snails and to methods of using the crystal and related structural information to screen for and design insulin analogs that interact with or modulate the insulin receptor.

BACKGROUND TO THE INVENTION

Insulin is a polypeptide hormone that plays a central role in the regulation of glucose metabolism, reproduction and cognition. Human insulin monomer consists of two polypeptide chains, the A- and B-chains, which are covalently linked by two disulfide bridges (CysA7-CysB7 and CysA19-B20). The A-chain consists of 21 amino acids and the B chain consists of 30 amino acids. A third disulfide bridge is located within the A chain (CysA6-CysA11). In the body, insulin exists as monomers, dimers and hexamers. The hexamer consists of three insulin dimers held together by two central zinc ions. Human insulin is stored in pancreatic β-cells as the hexamer. The biologically active form that binds the insulin receptor is monomeric. Insulin hexamer-monomer conversion is crucial to its bioavailability.

Disturbance of insulin regulation is associated with often severe clinical manifestations, such as diabetes myelitis, hyperglycemia, as well as other similar conditions. Diabetes mellitus (referred to as diabetes) is a group of disorders that is characterized by high blood sugar levels over a prolonged period of time. Diabetes can arise if the pancreas does not produce enough insulin or if the body does not respond properly to insulin. Administration of insulin or insulin analogs remains the most effective method of treating conditions such as diabetes. Treatment of diabetes often involves administration of a combination of rapid acting, pre-prandial insulin as well as a longer-acting insulin to maintain basal levels of the hormone.

Rapid-acting insulin analogs have a fast onset of activity. Typically, they are either monomeric or rapidly dissociate into the monomeric form on injection into an affected individual. Structurally, these insulin analogs differ from normal human insulin by having modifications within the B-chain C-terminal region (residues B26-B30) that are deleterious to insulin multimerization. However, further C-terminal truncation of the B chain in order to abolish self-association has led to near complete loss of activity, presumably because PheB24 is critical for activity. For example, des-octapeptide[B23-B30] insulin (DOI), a monomeric analogue, preserves less than 0.1% bioactivity (Bao at al., 1997). PheB24 lies immediately C-terminal to a Type 1 β-turn formed by residues GlyB20-GluB21-ArgB22-GlyB23, with both the triplet PheB24-PheB25-TyrB26 and the Type 1 β-turn being highly conserved in vertebrate insulins.

There is a need for new insulin analogs, and methods for designing such analogs, which are monomeric, fast acting, and retain the human insulin receptor signalling activity.

SUMMARY OF THE INVENTION

The inventors have characterised the newly identified insulin Con-Ins G1 from the venom of *Conus geographus* and show that it is monomeric, but still binds to the human insulin receptor and retains signalling activity. The inventors further successfully produced crystals of Con-Ins G1 and elucidated its three-dimensional structure using X-ray crystallography. The structural data presented herein have now enabled identification, for the first time, the key amino acid positions and interactions that permit Con-Ins G1 to retain its activity, despite lacking the aromatic triplet, PheB24-PheB25-TyrB26, of human insulin.

In an aspect, the present invention provides an insulin analog comprising an A chain peptide and a B chain peptide, wherein the B chain comprises an aromatic or large aliphatic residue at a position corresponding to amino acid number 20 of the B chain of human insulin and/or an aromatic or large aliphatic residue at a position corresponding to amino acid number 15 of the B chain of human insulin, wherein the analog comprises at least one amino acid found in human insulin but lacking in the corresponding position of *Conus geographus* venom insulin, and wherein the A chain peptide and the B chain peptide are bonded together across at least one pair of cysteine residues.

In some embodiments, the aromatic residue is selected from the group consisting of tyrosine, phenylalanine, tryptophan, histidine and 4-methylphenylalanine. In some embodiments, the large aliphatic residue is selected from the group consisting of isoleucine, cyclohexylalanine, cyclopentylalanine and methionine. In some embodiments, the aromatic or large aliphatic residue at a position corresponding to amino acid number 20 of the B chain of human insulin is selected from the group consisting of tyrosine, phenylalanine, 4-methylphenylalanine, histidine, tryptophan, methionine, cyclopentylalanine and cyclohexylalanine. In some embodiments, the aromatic or large aliphatic residue at a position corresponding to amino acid number 15 of the B chain of human insulin is selected from the group consisting of tyrosine, phenylalanine, 4-methylphenylalanine, histidine, tryptophan, methionine, cyclopentylalanine and cyclohexylalanine.

In some embodiments, the B chain is truncated at the C-terminal end when compared to human insulin. In some embodiments, the B chain is lacking one or more or all of the nine C-terminal amino acids of human insulin. In some embodiments, the B chain is at least lacking PheB24 of human insulin. In some embodiments, the B chain is at least lacking the human B chain aromatic triplet (amino acids PheB24-PheB25-TyrB26 of human insulin).

In some embodiments, the insulin analog comprises an A chain peptide comprising the sequence Gly-$X_{A2}$-$X_{A3}$-$X_{A4}$-$X_{A5}$-$Cys_{A6}$-$Cys_{A7}$-$X_{A8}$-$X_{A9}$-$X_{A10}$-$Cys_{A11}$-$X_{A12}$-$X_{A13}$-$X_{A14}$-$X_{A15}$-$X_{A16}$-$X_{A17}$-$X_{A18}$-$X_{A19}$-$Cys_{A20}$-$X_{A21}$-$X_{A22}$-$X_{A23}$-$X_{A24}$-$X_{A25}$-$X_{A26}$-$X_{A27}$-$X_{A28}$-$X_{A29}$-$X_{A30}$-$X_{A31}$-$X_{A32}$-$X_{A33}$-$X_{A34}$, wherein $X_{A2}$=Val or Ile; $X_{A3}$=Val or Ala; $X_{A4}$=Glu, Asp, Cys or gamma carboxyglutamate; $X_{A5}$=Gln, Glu, gamma carboxyglutamate, His or Val; $Cys_{A6}$, $Cys_{A7}$, and $Cys_{A11}$ are independently Cys or selenocysteine; $X_{A8}$=Thr, His, Asp, Gln, Tyr, Lys, Ala or Val; $X_{A9}$=Ser, Arg, Asn, Gly, His or Lys; $X_{A10}$=Ile, Pro, Tyr, Ala, Ser, Val, Phe, His or Thr; $X_{A12}$=Ser or Thr; $X_{A13}$=Leu, Asn, Val, Arg or Asp; $X_{A14}$=Tyr, Ala, Gln, His, Asp or Glu; $X_{A15}$=Gln, Glu or Thr; $X_{A16}$=Phe, Leu, or Ala; $X_{A17}$=Glu, Gln, Lys, Arg, Ile, Met, Thr or Ser; $X_{A18}$=Lys, Ser, Thr, Asn, Gln or Glu; $X_{A19}$=Tyr or Phe; $Cys_{A20}$=Cys, selenocysteine, amidated Cys, or amidated selenocysteine; $X_{A21}$=Asn, Pro, His, Ser, Gly, Ala, or is absent; $X_{A22}$=Pro, Asn, Thr, Leu, Ser or is absent; $X_{A23}$=Thr, Leu, Val, Ser or is absent; $X_{A24}$=Arg, Thr, Met, Gln, Leu or is absent; $X_{A25}$=Glu, Gly or is absent; from $X_{A26}$=Ser, Leu or is absent; $X_{A27}$ to $X_{A31}$ are independently Ser or are absent; $X_{A32}$=Ala, Ser or is absent; $X_{A33}$=Ala, Val or is absent; and $X_{A34}$=Ala or is absent (SEQ ID NO: 1); and a B chain peptide comprising the sequence $X_{B1}$-$X_{B2}$-$X_{B3}$-$X_{B4}$-$X_{B5}$-$X_{B6}$-$X_{B7}$-$X_{B8}$-$Cys_{B9}$-$X_{B10}$-$X_{B11}$-$X_{B12}$-$X_{B13}$-$X_{B14}$-$X_{B15}$-$X_{B16}$-$X_{B17}$-$X_{B18}$-$X_{B19}$-$X_{B20}$-$Cys_{B21}$-$X_{B22}$-$X_{B23}$-$X_{B24}$-$X_{B25}$-$X_{B26}$-$X_{B27}$-$X_{B28}$-$X_{B29}$-$X_{B30}$-$X_{B31}$-$X_{B32}$-$X_{B33}$-$X_{B34}$-$X_{B35}$-$X_{B36}$-$X_{B37}$-$X_{B38}$-$X_{B39}$, wherein $X_{B1}$=Thr, Asn, Ser or is absent; $X_{B2}$=Phe, Ser, Asn, Thr, Gln or is absent; $X_{B3}$=Ala, Asp, Gly, Pro, Leu, Phe, or His; $X_{B4}$=Ala, Thr, Pro, Asp, Val or Gly; $X_{B5}$=Asn, Pro, His, Thr, Arg, Lys, Ser or hydroxyproline; $X_{B6}$=Lys, Glu, Asn, Asp, Arg, Gln or Gly; $X_{B7}$=His, Tyr, Arg or Ile; $X_{B8}$=Arg, Thr, Ile, Ser, Leu, Tyr or Lys; $Cys_{B9}$=Cys or selenocysteine; $X_{B10}$=Gly, Gln or Asp; $X_{B11}$=Ser, Leu, Gly or Pro; $X_{B12}$=His, Glu, gamma carboxyglutamate, Asp, or Asn; $X_{B13}$=Ile, Leu, Asp, Val or Ala; $X_{B14}$=Thr, Ala, Pro, Val or Arg; $X_{B15}$=Asn, Asp, Ala, Val, Thr, Pro or Glu; $X_{B16}$=Ala, Ser, Gln, His, Tyr, Arg or Gly; $X_{B17}$=Tyr, Pro, Leu or Gly; $X_{B18}$=Tyr, Met, Val, Gln, Ile, Asp, Gly, Asn or Leu; $X_{B19}$=Leu, Asp, Gln, Gly, Lys, Glu, Arg, Ser or Thr; $X_{B20}$=Val, Leu or Lys; $C_{B21}$=Cys, amidated Cys, selenocysteine or amidated selenocysteine; $X_{B22}$=Val, Tyr, Phe, His, Gly, Gln, Leu, amidated His, amidated Val or is absent; $X_{B23}$=Glu, Asp, Arg, Ser, Gly or is absent; $X_{B24}$=Arg, Asp, Val or is absent; $X_{B25}$=Gly, Leu, Val or is absent; $X_{B26}$=Phe, Val, Ile or is absent; $X_{B27}$=Phe, Asn, Pro, Glu or is absent; $X_{B28}$=Tyr, Cys, His or is absent; $X_{B29}$=Thr, His, Ile, Leu, Ser, Tyr or is absent; $X_{B30}$=Pro, Glu, Leu, Ile, Arg or is absent; $X_{B31}$=Ile, Lys or is absent; $X_{B32}$=Ala, Asp, Ser, Thr, Lys, Leu, Gln or is absent; $X_{B33}$=Cys or is absent; $X_{B34}$=Glu, Pro, Val or is absent; $X_{B35}$=Glu, Gly or is absent; $X_{B36}$=Glu, Gly or is absent; $X_{B37}$=Glu, Val or is absent; $X_{B38}$=Ala, Asp or is absent; and $X_{B39}$=Ala or is absent (SEQ ID NO: 2).

In some embodiments, the B chain peptide comprises the sequence $X_{B1}$-$X_{B2}$-$X_{B3}$-$X_{B4}$-$X_{B5}$-$X_{B6}$-$X_{B7}$-$X_{B8}$-$Cys_{B9}$-$X_{B10}$-$X_{B11}$-$X_{B12}$-$X_{B13}$-$X_{B14}$-$X_{B15}$-$X_{B16}$-$X_{B17}$-$X_{B18}$-$X_{B19}$-$X_{B20}$-$Cys_{B21}$-$X_{B22}$-$X_{B23}$-$X_{B24}$-$X_{B25}$-$X_{B26}$-$X_{B27}$-$X_{B28}$-$X_{B29}$-$X_{B30}$-$X_{B31}$-$X_{B32}$-$X_{B33}$-$X_{B34}$-$X_{B35}$-$X_{B36}$-$X_{B37}$-$X_{B38}$-$X_{B39}$, wherein $X_{B1}$=Thr, Asn, Ser or is absent; $X_{B2}$=Phe, Ser, Asn, Thr, Gln or is absent; $X_{B3}$=Asp, Gly, Pro, Leu, Phe, or His; $X_{B4}$=Thr, Pro, Asp, Val or Gly; $X_{B5}$=Asn, Pro, His, Thr, Arg, Ser or hydroxyproline; $X_{B6}$=Lys, Glu, Asn, Asp, Arg, Gln or Gly; $X_{B7}$=His, Tyr, Arg or Ile; $X_{B8}$=Arg, Thr, Ile, Ser, Leu, Tyr or Lys; $Cys_{B9}$=Cys or selenocysteine; $X_{B10}$=Gly, Gln or Asp; $X_{B11}$=Ser, Leu, Gly or Pro; $X_{B12}$=His, Glu, gamma carboxyglutamate, Asp, or Asn; $X_{B13}$=Ile, Leu, Asp, Val or Ala; $X_{B14}$=Thr, Ala, Pro, Val or Arg; $X_{B15}$=Asn, Asp, Ala, Val, Thr, Pro or Glu; $X_{B16}$=Ala, Ser, Gln, His, Tyr, Arg or Gly; $X_{B17}$=Tyr or Leu; $X_{B18}$=Tyr, Met, Val, Gln, Ile, Asp, Gly, Asn or Leu; $X_{B19}$=Leu, Asp, Gln, Gly, Lys, Glu, Arg or Thr; $X_{B20}$=Val, Leu or Lys; $C_{B21}$=Cys, amidated Cys, selenocysteine or amidated selenocysteine; $X_{B22}$=Tyr, Phe or His; $X_{B23}$=Glu, Arg, Ser, Gly or is absent; $X_{B24}$=Arg, Asp, Val or is absent; $X_{B25}$=Gly, Leu, Val or is absent; $X_{B26}$=Phe, Val, Ile or is absent; $X_{B27}$=Phe, Asn, Pro, Glu or is absent; $X_{B28}$=Tyr, Cys, His or is absent; $X_{B29}$=Thr, His, Leu, Tyr or is absent; $X_{B30}$=Pro, Glu, Leu, Ile, Arg or is absent; $X_{B31}$=Ile, Lys or is absent; $X_{B32}$=Thr, Lys, Leu, Gln or is absent; $X_{B33}$=Cys or is absent; $X_{B34}$=Glu, Pro, Val or is absent; $X_{B35}$=Glu, Gly or is absent; $X_{B36}$=Glu, Gly or is absent; $X_{B37}$=Glu, Val or is absent; $X_{B38}$=Ala, Asp or is absent; and $X_{B39}$=Ala or is absent (SEQ ID NO: 3).

In some embodiments, the B chain peptide comprises the sequence $X_{B1}$-$X_{B2}$-$X_{B3}$-$X_{B4}$-$X_{B5}$-$X_{B6}$-$X_{B7}$-$X_{B8}$-$Cys_{B9}$-$X_{B1}$-$X_{B11}$-$X_{B12}$-$X_{B13}$-$X_{B14}$-$X_{B15}$-$X_{B16}$-$X_{B17}$-$X_{B18}$-$X_{B19}$-$X_{B20}$-$Cys_{B21}$-$X_{B22}$-$X_{B23}$-$X_{B24}$-$X_{B25}$-$X_{B26}$-$X_{B27}$-$X_{B28}$-$X_{B29}$-$X_{B30}$-$X_{B31}$-$X_{B32}$-$X_{B33}$-$X_{B34}$-$X_{B35}$-$X_{B36}$-$X_{B37}$-$X_{B38}$-$X_{B39}$, wherein $X_{B1}$=Thr, Asn, Ser or is absent; $X_{B2}$=Phe, Ser, Asn, Thr, Gln or is absent; $X_{B3}$=Asp, Gly, Pro, Leu, Phe, or His; $X_{B4}$=Thr, Pro, Asp, Val or Gly; $X_{B5}$=Asn, Pro, His, Thr, Arg, Ser or hydroxyproline; $X_{B6}$=Lys, Glu, Asn, Asp, Arg, Gln or Gly; $X_{B7}$=His, Tyr, Arg or Ile; $X_{B8}$=Arg, Thr, Ile, Ser, Leu, Tyr or Lys; $Cys_{B9}$=Cys or selenocysteine; $X_{B10}$=Gly, Gln or Asp; $X_{B11}$=Ser, Leu, Gly or Pro; $X_{B12}$=His, Glu, gamma carboxyglutamate, Asp, or Asn; $X_{B13}$=Ile, Leu, Asp, Val or Ala; $X_{B14}$=Thr, Ala, Pro, Val or Arg; $X_{B15}$=Asn, Asp, Ala, Val, Thr, Pro or Glu; $X_{B16}$=Ala, Ser, Gln, His, Tyr, Arg or Gly; $X_{B17}$=Tyr or Leu; $X_{B18}$=Tyr, Met, Val, Gln, Ile, Asp, Gly, Asn or Leu; $X_{B19}$=Leu, Asp, Gln, Gly, Lys, Glu, Arg or Thr; $X_{B20}$=Val, Leu or Lys; $C_{B21}$=Cys, amidated Cys, selenocysteine or amidated selenocysteine; $X_{B22}$=Tyr, Phe or His; $X_{B23}$=Glu, Arg, Ser, Gly or is absent; and $X_{B24}$, $X_{B25}$, $X_{B26}$, $X_{B27}$, $X_{B28}$, $X_{B29}$, $X_{B30}$, $X_{B31}$, $X_{B32}$, $X_{B33}$, $X_{B34}$, $X_{B35}$, $X_{B36}$, $X_{B37}$, $X_{B38}$ and $X_{B39}$ are absent (SEQ ID NO: 4).

In some embodiments, the B chain peptide comprises the sequence $X_{B1}$-$X_{B2}$-$X_{B3}$-$X_{B4}$-$X_{B5}$-$X_{B6}$-$X_{B7}$-$X_{B8}$-$Cys_{B9}$-Gly-Ser-$X_{B12}$-$X_{B13}$-$X_{B14}$-$X_{B15}$-$X_{B16}$-$X_{B17}$-$X_{B18}$-$X_{B19}$-$X_{B20}$-$Cys_{B21}$-$X_{B22}$-$X_{B23}$-$X_{B24}$-$X_{B25}$-$X_{B26}$-$X_{B27}$-$X_{B28}$-$X_{B29}$-$X_{B30}$-$X_{B31}$-$X_{B32}$-$X_{B33}$-$X_{B34}$-$X_{B35}$-$X_{B36}$-$X_{B37}$-$X_{B38}$-$X_{B39}$, where $X_{B1}$=Thr, Asn, Ser or is absent; $X_{B2}$=Phe, Ser, Asn, Thr, Gln or is absent; $X_{B3}$=Asp, Gly, Pro, Leu, Phe, or His; $X_{B4}$=Thr, Pro, Asp, Val or Gly; $X_{B5}$=Asn, Pro, His, Thr, Arg, Ser or hydroxyproline; $X_{B6}$=Lys, Glu, Asn, Asp, Arg, Gln or Gly; $X_{B7}$=His, Tyr, Arg or Ile; $X_{B8}$=Arg, Thr, Ile, Ser, Leu, Tyr or Lys; $Cys_{B9}$=Cys or selenocysteine; $X_{B12}$=His, Glu, gamma carboxyglutamate, Asp, or Asn; $X_{B13}$=Ile, Leu, Asp, Val or Ala; $X_{B14}$=Thr, Ala, Pro, Val or Arg; $X_{B15}$=Asn, Asp, Ala, Val, Thr, Pro or Glu; $X_{B16}$=Ala, Ser, Gln, His, Tyr, Arg or Gly; $X_{B17}$=Tyr or Leu; $X_{B18}$=Tyr, Met, Val, Gln, Ile, Asp, Gly, Asn or Leu; $X_{B19}$=Leu, Asp, Gln, Gly, Lys, Glu, Arg or Thr; $X_{B20}$=Val, Leu or Lys; $C_{B21}$=Cys, amidated Cys, selenocysteine or amidated selenocysteine; $X_{B22}$=Tyr, Phe or His; $X_{B23}$=Glu, Arg, Ser, Gly or is absent; $X_{B24}$=Arg, Asp, Val or is absent; $X_{B25}$=Gly, Leu, Val or is absent; $X_{B26}$=Phe, Val, Ile or is absent; $X_{B27}$=Phe, Asn, Pro, Glu or is absent; $X_{B28}$=Tyr, Cys, His or is absent; $X_{B29}$=Thr, His, Leu, Tyr or is absent; $X_{B30}$=Pro, Glu, Leu, Ile, Arg or is absent; $X_{B31}$=Ile, Lys or is absent; $X_{B32}$=Thr, Lys, Leu, Gln or is absent; $X_{B33}$=Cys or is absent; $X_{B34}$=Glu, Pro, Val or is absent; $X_{B35}$=Glu, Gly or is absent; $X_{B36}$=Glu, Gly or is absent; $X_{B37}$=Glu, Val or is absent; $X_{B38}$=Ala, Asp or is absent; and $X_{B39}$=Ala or is absent (SEQ ID NO: 5).

In some embodiments, the B chain peptide comprises the sequence $X_{B1}$-$X_{B2}$-$X_{B3}$-$X_{B4}$-$X_{B5}$-$X_{B6}$-$X_{B7}$-$X_{B8}$-Cys$_{B9}$-Gly-Ser-$X_{B12}$-$X_{B13}$-$X_{B14}$-$X_{B15}$-$X_{B16}$-$X_{B17}$-$X_{B18}$-$X_{B19}$-$X_{B20}$-Cys$_{B21}$-$X_{B22}$-$X_{B23}$-$X_{B24}$-$X_{B25}$-$X_{B26}$-$X_{B27}$-$X_{B28}$-$X_{B29}$-$X_{B30}$-$X_{B31}$-$X_{B32}$-$X_{B33}$-$X_{B34}$-$X_{B35}$-$X_{B36}$-$X_{B37}$-$X_{B38}$-$X_{B39}$, where $X_{B1}$=Thr, Asn, Ser or is absent; $X_{B2}$=Phe, Ser, Asn, Thr, Gln or is absent; $X_{B3}$=Asp, Gly, Pro, Leu, Phe, or His; $X_{B4}$=Thr, Pro, Asp, Val or Gly; $X_{B5}$=Asn, Pro, His, Thr, Arg, Ser or hydroxyproline; $X_{B6}$=Lys, Glu, Asn, Asp, Arg, Gln or Gly; $X_{B7}$=His or Tyr; $X_{B8}$=Arg, Thr, Ile, Ser, Leu, Tyr or Lys; Cys$_{B9}$=Cys or selenocysteine; $X_{B12}$=His, Glu, gamma carboxyglutamate, Asp, or Asn; $X_{B13}$=Ile, Leu, Asp, Val or Ala; $X_{B14}$=Thr, Ala, Pro, Val or Arg; $X_{B15}$=Asn, Asp, Ala, Val, Thr, Pro or Glu; $X_{B16}$=Ala, Ser, Gln, His, Tyr, Arg or Gly; $X_{B17}$=Tyr or Leu; $X_{B18}$=Tyr, Met, Val, Gln, Ile, Asp, Gly, Asn or Leu; $X_{B19}$=Leu, Asp, Gln, Gly, Lys, Glu, Arg or Thr; $X_{B20}$=Val or Leu; $C_{B21}$=Cys, amidated Cys, selenocysteine or amidated selenocysteine; $X_{B22}$=Tyr, Phe or His; $X_{B23}$=Glu, Arg, Ser, Gly or is absent; $X_{B24}$=Arg, Asp, Val or is absent; $X_{B25}$=Gly, Leu, Val or is absent; $X_{B26}$=Phe, Val, Ile or is absent; $X_{B27}$=Phe, Asn, Pro, Glu or is absent; $X_{B28}$=Tyr, Cys, His or is absent; $X_{B29}$=Thr, His, Leu, Tyr or is absent; $X_{B30}$=Pro, Glu, Leu, Ile, Arg or is absent; $X_{B31}$ Ile, Lys or is absent; $X_{B32}$=Thr, Lys, Leu, Gln or is absent; $X_{B33}$=Cys or is absent; $X_{B34}$=Glu, Pro, Val or is absent; $X_{B35}$=Glu, Gly or is absent; $X_{B36}$=Glu, Gly or is absent; $X_{B37}$=Glu, Val or is absent; $X_{B38}$=Ala, Asp or is absent; and $X_{B39}$=Ala or is absent (SEQ ID NO: 6).

In some embodiments, the B chain peptide comprises the sequence $X_{B1}$-$X_{B2}$-$X_{B3}$-$X_{B4}$-$X_{B5}$-$X_{B6}$-$X_{B7}$-$X_{B8}$-Cys$_{B9}$-Gly-Ser-$X_{B12}$-$X_{B13}$-$X_{B14}$-$X_{B15}$-$X_{B16}$-$X_{B17}$-$X_{B18}$-$X_{B19}$-$X_{B20}$-Cys$_{B21}$-$X_{B22}$-$X_{B23}$, wherein $X_{B1}$=Thr, Asn or is absent; $X_{B2}$=Phe, Ser or is absent; $X_{B3}$=Phe or Asp; $X_{B4}$=Thr or Val; $X_{B5}$=Pro, Asn or hydroxyproline; $X_{B6}$=Lys, Asn or Gln; $X_{B7}$=His or Tyr; $X_{B8}$=Arg, Ile or Leu; $X_{B12}$=His, Asp, Glu or gamma carboxyglutamate; Cys$_{B9}$=Cys or selenocysteine; $X_{B13}$=Val, Ile or Leu; $X_{B14}$=Thr, Ala, Pro, or Val; $X_{B15}$=Glu, Val, Asn or Asp; $X_{B16}$=Ser, Gln, Tyr or Ala; $X_{B17}$=Tyr or Leu; $X_{B18}$=Tyr, Asp, Met or Val; $X_{B19}$=Leu, Asp, Gln or Lys; $X_{B20}$=Leu or Val; Cys$_{B21}$=Cys, amidated Cys, selenocysteine or amidated selenocysteine; $X_{B22}$=Tyr or Gly; and $X_{B23}$=Glu, Arg, Gly or is absent (SEQ ID NO: 7).

In some embodiments, the B chain peptide comprises the sequence $X_{B1}$-$X_{B2}$-$X_{B3}$-$X_{B4}$-$X_{B5}$-$X_{B6}$-His-$X_{B8}$-Cys$_{B9}$-Gly-Ser-$X_{B12}$-$X_{B13}$-$X_{B14}$-$X_{B15}$-$X_{B16}$-$X_{B17}$-$X_{B18}$-$X_{B19}$-$X_{B20}$-Cys$_{B21}$-$X_{B22}$-$X_{B23}$, wherein $X_{B1}$=Thr or is absent; $X_{B2}$=Phe or is absent; $X_{B3}$=Phe or Asp; $X_{B4}$=Thr or Val; $X_{B5}$=Pro, Asn or hydroxyproline; $X_{B6}$=Lys or Gln; $X_{B8}$=Arg or Leu; $X_{B12}$=His, Glu or gamma carboxyglutamate; $X_{B13}$=Ile or Leu; $X_{B14}$=Thr, or Val; $X_{B15}$=Glu, or Asn; $X_{B16}$=Ser or Ala; $X_{B17}$=Tyr or Leu, $X_{B18}$=Tyr or Met; $X_{B19}$=Leu or Asp, $X_{B20}$=Leu or Val; $X_{B22}$=Tyr; and $X_{B23}$=Glu or Arg (SEQ ID NO: 8).

In some embodiments, $X_{B17}$ and $X_{B22}$ are Tyr. In some embodiments, $X_{B22}$ is Tyr. In some embodiments, $X_{B17}$ is Tyr.

In some embodiments, the A chain peptide comprises the sequence Gly-$X_{A2}$-$X_{A3}$-$X_{A4}$-$X_{A5}$-Cys$_{A6}$-Cys$_{A7}$-$X_{A8}$-$X_{A9}$-$X_{A10}$-Cys$_{A11}$-$X_{A12}$-$X_{A13}$-$X_{A14}$-$X_{A15}$-Phe-$X_{A17}$-$X_{A18}$-$X_{A19}$-Cys$_{A20}$-$X_{A21}$-$X_{A22}$-$X_{A23}$-$X_{A24}$-$X_{A25}$-$X_{A26}$-$X_{A27}$-$X_{A28}$-$X_{A29}$-$X_{A30}$-$X_{A31}$-$X_{A32}$-$X_{A33}$-$X_{A34}$, wherein $X_{A2}$=Val or Ile; $X_{A3}$=Val or Ala; $X_{A4}$=Glu, gamma carboxyglutamate or Cys; $X_{A5}$=Gln, Glu, gamma carboxyglutamate, His or Val; Cys$_{A6}$, Cys$_{A7}$, and Cys$_{A11}$ are independently Cys or selenocysteine; $X_{A8}$=Thr, His, Asp, Gln, Tyr, Lys or Val; $X_{A9}$=Ser, Arg, Asn, His or Lys; $X_{A10}$=Ile, Pro, Tyr, Ala, Ser, Phe, His or Thr; $X_{A12}$=Ser or Thr; $X_{A13}$=Leu, Asn, Val or Asp; $X_{A14}$=Tyr, Ala, Gln, Asp or Glu; $X_{A15}$=Gln, Glu or Thr; or Ala; $X_{A17}$=Glu, Lys, Arg, Ile, Met, Thr or Ser; $X_{A18}$=Lys, Thr, Asn, Gln or Glu; $X_{A19}$=Tyr or Phe; Cys$_{A20}$=Cys, selenocysteine, amidated Cys, or amidated selenocysteine; $X_{A21}$=Asn, Pro, His, Ser, Gly, Ala, or is absent; $X_{A22}$=Pro, Asn, Thr, Leu, Ser or is absent; $X_{A23}$=Thr, Leu, Val, Ser or is absent; $X_{A24}$=Arg, Thr, Met, Gln, Leu or is absent; $X_{A25}$=Glu, Gly or is absent; from $X_{A26}$=Ser, Leu or is absent; $X_{A27}$ to $X_{A31}$ are independently Ser or are absent; $X_{A32}$=Ala, Ser or is absent; $X_{A33}$=Ala, Val or is absent; and $X_{A34}$=Ala or is absent (SEQ ID NO: 9).

In some embodiments, the insulin analog comprises an A chain peptide comprising a sequence Gly-$X_{A2}$-Val-$X_{A4}$-$X_{A5}$-Cys$_{A6}$-Cys$_{A7}$-$X_{A8}$-$X_{A9}$-$X_{A10}$-Cys$_{A11}$-Ser-$X_{A13}$-$X_{A14}$-$X_{A15}$-$X_{A16}$-$X_{A17}$-$X_{A18}$-Tyr-Cys$_{A20}$-$X_{A21}$, wherein $X_{A2}$ is Val or Ile, $X_{A4}$ is Glu or gamma carboxyglutamate, $X_{A5}$ is His or Gln, $X_{A8}$ is His or Thr, $X_{A9}$ is Arg or Ser, $X_{A10}$ is Pro or Ile, $X_{A13}$ is Asn or Leu, $X_{A14}$ is Ala or Tyr, $X_{A15}$ is Glu or Gln, $X_{A16}$ is Phe or Leu, $X_{A17}$ is Lys or Glu, $X_{A18}$ is Lys or Asn and $X_{A21}$ is Asn or absent (SEQ ID NO: 10); and a B chain peptide comprising the sequence $X_{B1}$-$X_{B2}$-$X_{B3}$-$X_{B4}$-$X_{B5}$-$X_{B6}$-His-$X_{B8}$-Cys$_{B9}$-Gly-Ser-$X_{B12}$-$X_{B13}$-$X_{B14}$-$X_{B15}$-$X_{B16}$-$X_{B17}$-$X_{B18}$-$X_{B19}$-$X_{B20}$-Cys$_{B21}$-$X_{B22}$-$X_{B23}$, wherein $X_{B1}$=Thr or is absent; $X_{B2}$=Phe or is absent; $X_{B3}$=Phe or Asp; $X_{B4}$=Thr or Val; $X_{B5}$=Pro, Asn or hydroxyproline; $X_{B6}$=Lys or Gln; $X_{B8}$=Arg or Leu; $X_{B12}$=His, Glu or gamma carboxyglutamate; $X_{B13}$=Ile or Leu; $X_{B14}$=Thr, or Val; $X_{B15}$=Glu, or Asn; $X_{B16}$=Ser or Ala; $X_{B17}$=Tyr or Leu; $X_{B18}$=Tyr or Met; $X_{B19}$=Leu or Asp, $X_{B20}$=Leu or Val; $X_{B22}$=Gly or Tyr; and $X_{B23}$=Glu or Arg (SEQ ID NO: 11).

In some embodiments, the insulin analog comprises an A chain peptide comprising a sequence Gly-$X_{A2}$-Val-$X_{A4}$-$X_{A5}$-Cys$_{A6}$-Cys$_{A7}$-$X_{A8}$-$X_{A9}$-$X_{A10}$-Cys$_{A11}$-Ser-$X_{A13}$-$X_{A14}$-$X_{A15}$-Phe-$X_{A17}$-$X_{A18}$-Tyr-Cys$_{A20}$-$X_{A21}$, wherein $X_{A2}$ is Val or Ile, $X_{A4}$ is Glu or gamma carboxyglutamate, $X_{A5}$ is His or Gln, $X_{A8}$ is His or Thr, $X_{A9}$ is Arg or Ser, $X_{A10}$ is Pro or Ile, $X_{A13}$ is Asn or Leu, $X_{A14}$ is Ala or Tyr, $X_{A15}$ is Glu or Gln, $X_{A17}$ is Lys or Glu, $X_{A18}$ is Lys or Asn and $X_{A21}$ is Asn or absent (SEQ ID NO: 12); and an B chain peptide comprising the sequence $X_{B1}$-$X_{B2}$-$X_{B3}$-$X_{B4}$-$X_{B5}$-$X_{B6}$-His-$X_{B8}$-Cys$_{B9}$-Gly-Ser-$X_{B12}$-$X_{B13}$-$X_{B14}$-$X_{B15}$-$X_{B16}$-$X_{B17}$-$X_{B18}$-$X_{B19}$-$X_{B20}$-Cys$_{B21}$-Tyr-$X_{B23}$, wherein $X_{B1}$=Thr or is absent; $X_{B2}$=Phe or is absent; $X_{B3}$=Phe or Asp; $X_{B4}$=Thr or Val; $X_{B5}$=Pro, Asn or hydroxyproline; $X_{B6}$=Lys or Gln; $X_{B8}$=Arg or Leu; $X_{B12}$=His, Glu or gamma carboxyglutamate; $X_{B13}$=Ile or Leu; $X_{B14}$=Thr, or Val; $X_{B15}$=Glu, or Asn; $X_{B16}$=Ser or Ala; $X_{B17}$=Tyr or Leu; $X_{B18}$=Tyr or Met; $X_{B19}$=Leu or Asp, $X_{B20}$=Leu or Val; and $X_{B23}$=Glu or Arg (SEQ ID NO: 13).

In some embodiments, the insulin analog comprises an A chain peptide comprising a sequence Gly-Val-Val-$X_{A4}$-$X_{A5}$-Cys$_{A6}$-Cys$_{A7}$-$X_{A8}$-$X_{A9}$-$X_{A10}$-Cys$_{A11}$-Ser-$X_{A13}$-$X_{A14}$-$X_{A15}$-Phe-$X_{A17}$-$X_{A18}$-Tyr-Cys$_{A20}$-$X_{A21}$, wherein $X_{A4}$ is Glu or gamma carboxyglutamate, $X_{A5}$ is His or Gln, $X_{A8}$ is His or Thr, $X_{A9}$ is Arg or Ser, $X_{A10}$ is Pro or Ile, $X_{A13}$ is Asn or Leu, $X_{A14}$ is Ala or Tyr, $X_{A15}$ is Glu or Gln, $X_{A17}$ is Lys or Glu, $X_{A18}$ is Lys or Asn and $X_{A21}$ is Asn or absent (SEQ ID NO: 14); and an B chain peptide comprising the sequence $X_{B1}$-$X_{B2}$-$X_{B3}$-$X_{B4}$-$X_{B5}$-$X_{B6}$-His-Arg-Cys$_{B9}$-Gly-Ser-$X_{B12}$-Ie-$X_{B14}$-$X_{B15}$-$X_{B16}$-$X_{B17}$-$X_{B18}$-$X_{B19}$-Leu-Cys$_{B21}$-Tyr-$X_{B23}$, wherein $X_{B1}$=Thr or is absent; $X_{B2}$=Phe or is absent; $X_{B3}$=Phe or Asp; $X_{B4}$=Thr or Val; $X_{B5}$=Pro, Asn or hydroxyproline; $X_{B6}$=Lys or Gln; $X_{B12}$=His, Glu or gamma carboxyglutamate; $X_{B14}$=Thr, or Val; $X_{B15}$=Glu, or Asn; $X_{B16}$=Ser or Ala; $X_{B17}$=Tyr or Leu; $X_{B18}$=Tyr or Met; $X_{B19}$=Leu or Asp, and $X_{B23}$=Glu or Arg (SEQ ID NO: 15).

In an embodiment, the insulin analog is identical to human insulin with the exception of a truncated B-chain at the C-terminus and an aromatic residue or large aliphatic residue at amino acid number 15 and/or 20 of the B chain. Examples are provided, but are not limited to, the three below embodiments where Xaa is an aromatic residue or large aliphatic residue.

In some embodiments, the insulin analog comprises an A chain peptide comprising the sequence Gly-Ile-Val-Glu-Gln-Cys-Cys-Thr-Ser-Ile-Cys-Ser-Leu-Tyr-Gln-Leu-Glu-Asn-Tyr-Cys-Asn (SEQ ID NO: 16); and a B chain peptide comprising the sequence Phe-Val-Asn-Gln-His-Leu-Cys-Gly-Ser-His-Leu-Val-Glu-Ala-Xaa-Tyr-Leu-Val-Cys-Gly-Glu, where Xaa is an aromatic residue or large aliphatic residue (SEQ ID NO: 17).

In some embodiments, the insulin analog comprises an A chain peptide comprising the sequence Gly-Ile-Val-Glu-Gln-Cys-Cys-Thr-Ser-Tie-Cys-Ser-Leu-Tyr-Gln-Leu-Glu-Asn-Tyr-Cys-Asn (SEQ ID NO: 18); and a B chain peptide comprising the sequence Phe-Val-Asn-Gln-His-Leu-Cys-Gly-Ser-His-Leu-Val-Glu-Ala-Leu-Tyr-Leu-Val-Cys-Xaa-Glu, where Xaa is an aromatic residue or large aliphatic residue (SEQ ID NO: 19).

In some embodiments, the insulin analog comprises an A chain peptide comprising the sequence Gly-Ile-Val-Glu-Gln-Cys-Cys-Thr-Ser-Ile-Cys-Ser-Leu-Tyr-Gln-Leu-Glu-Asn-Tyr-Cys-Asn (SEQ ID NO: 20); and a B chain peptide comprising the sequence Phe-Val-Asn-Gln-His-Leu-Cys-Gly-Ser-His-Leu-Val-Glu-Ala-Xaa-Tyr-Leu-Val-Cys-Xaa-Glu (SEQ ID NO: 21), where Xaa is an aromatic residue or large aliphatic residue.

In some embodiments, the insulin analog comprises a number of modified amino acids. In some embodiments, the insulin analog comprises one or more or all of the following:
i) $X_{A4}$ is gamma carboxyglutamate,
ii) $X_{B5}$=hydroxyproline; and
iii) $X_{B12}$=gamma carboxyglutamate.

In some embodiments, $Cys_{B9}$ of the B chain peptide is bonded to $Cys_{A6}$ of the A chain peptide. In some embodiments, $Cys_{B21}$ of the B chain peptide is bonded to $Cys_{A20}$ of the A chain peptide. In some embodiments, $Cys_{A7}$ is bonded to $Cys_{A11}$.

In some embodiments, the A chain peptide and the B chain peptide are linked together at one pair of their respective terminal ends. In some embodiments, the A chain peptide and the B chain peptide are linked together at both terminal ends.

In some embodiments, the insulin analog has an $IC_{50}$ against the human IR-B receptor of less than $10^{-6}$ M. In some embodiments, the insulin analog does not bind human IGF-IR or binds IGF-IR weakly. In some embodiments, the analog has an affinity ($K_d$) for human IGF-IR of weaker than 100 nM.

In some embodiments, the insulin analog is predominantly monomeric. In some embodiments, at least 75% of the analog is monomeric in solution.

In some embodiments, the insulin analog has increased bioavailability when administered to a human when compared human insulin. In some embodiments, the insulin analog has a peak bioavailability within 0.5 to 3 hours of administration to a human. In some embodiments, the insulin analog has an onset of activity within 10 minutes of administration.

In a further aspect, the present invention provides a pharmaceutical composition, comprising the insulin analog as defined herein or a pharmaceutically acceptable salt thereof and one or more pharmaceutically acceptable carriers.

In still a further aspect, the present invention provides a method for treating and/or preventing an insulin-related condition, comprising administering a therapeutically effective amount of the insulin analog as defined herein to a subject in need thereof. In some embodiments, the insulin related condition is hyperglycemia, insulin resistance, type-1 diabetes, gestational diabetes or type-2 diabetes.

In still a further aspect, the present invention provides a method for decreasing blood glucose levels, comprising administering a therapeutically effective amount of the insulin analog as defined herein to a subject in need thereof.

In still a further aspect, the present invention provides use of the insulin analog as defined herein in the manufacture of a medicament for treating and/or preventing an insulin-related condition in a subject. In still a further aspect, the present invention provides use of the insulin analog as defined herein in the manufacture of a medicament for decreasing blood glucose levels in a subject.

In still a further aspect, the present invention provides an insulin analog as defined herein for use in treating and/or preventing an insulin-related condition in a subject. In still a further aspect, the present invention provides an insulin analog as defined herein for use in decreasing blood glucose levels in a subject.

In still a further aspect, the present invention provides peptides comprising an insulin A chain peptide and an insulin B chain peptide, wherein the B chain peptide comprises a substitution at amino acid 10 and amino acid 20. In some instances, the substitution at amino acid 20 is G20Y, G20F, or G20P. In some instances, the substitution at amino acid 10 is H10E, H10D or H10Q.

In some embodiments, the peptides comprise an insulin A chain peptide and an insulin B chain peptide, wherein the B chain peptide comprises a substitution at amino acid and amino acid 20, further comprising at least one substitution in the A chain peptide. In some instances, the at least one substitution in the A chain peptide is T8H, T8Y, T8K, or S9R.

In some embodiments, the peptides comprise an insulin A chain peptide and an insulin B chain peptide, wherein the B chain peptide comprises a substitution at amino acid and amino acid 20, further comprising at least two substitutions in the A chain peptide.

In some instances, the at least two substitutions in the A chain peptide are two of the substitutions selected from: T8H, T8Y, T8K, and S9R.

In some embodiments, the peptide is a des-octapeptide insulin. In some instances, the B chain peptide comprises the sequence of FVNQHLCGSELVEALYLVCYER (SEQ ID NO: 30). In some instances, the A chain comprises the sequence of (SEQ ID NO: 39)
GIVEQCCHRICSLYQLENYCN.

In some embodiments, the A chain peptide and B chain peptide are bonded via at least one disulfide bond. In some embodiments, the peptide is a monomer.

In some embodiments, the insulin A chain peptide is at least 70% identical to wild type human insulin A chain peptide.

In yet another aspect, the present invention provides pharmaceutical compositions comprising an insulin analog, peptide or compound as defined herein. In some embodiments, the present invention provides pharmaceutical compositions comprising a peptide comprising an insulin A chain peptide and an insulin B chain peptide, wherein the B chain peptide comprises a substitution at amino acid 10 and amino acid 20 and a pharmaceutically acceptable carrier.

In yet another aspect, the present invention provides methods of increasing insulin receptor activation in a subject comprising administering a therapeutically effective amount of an insulin analog, peptide or compound as defined herein. In some embodiments, the present invention provides methods of increasing insulin receptor activation in a subject comprising administering a therapeutically effective amount of a peptide comprising an insulin A chain peptide and an insulin B chain peptide, wherein the B chain peptide comprises a substitution at amino acid 10 and amino acid 20 to a subject in need thereof.

In yet another aspect, the present invention provides methods of lowering the blood sugar in a subject comprising administering a therapeutically effective amount of an insulin analog, peptide or compound as defined herein. In some embodiments, the present invention provides methods of lowering the blood sugar in a subject comprising administering a therapeutically effective amount of a peptide comprising an insulin A chain peptide and an insulin B chain peptide, wherein the B chain peptide comprises a substitution at amino acid and amino acid 20 to a subject in need thereof.

In yet another aspect, the present invention methods of treating type 1 diabetes in a subject comprising administering a therapeutically effective amount of an insulin analog, peptide or compound as defined herein. In some embodiments, the present invention provides methods of treating type 1 diabetes in a subject comprising administering a therapeutically effective amount of a peptide comprising an insulin A chain peptide and an insulin B chain peptide, wherein the B chain peptide comprises a substitution at amino acid and amino acid 20 to a subject in need thereof. In some instances, the subject has been diagnosed with type 1 diabetes prior to administering the peptide.

In still a further aspect, there is provided a therapeutic protein having an A chain peptide bonded to a B chain peptide via at least one disulfide bond, wherein the A chain comprises the sequence of GIVEQCCHRICSLYQLENYCN (SEQ ID NO: 39), and wherein the B chain peptide comprises the sequence of FVNQHLCGSELVEALYLVCYER (SEQ ID NO: 30).

In still a further aspect, the present invention provides a method of redesigning or modifying a polypeptide which is known to bind to an insulin receptor (IR) comprising performing structure-based evaluation of a structure defined by the atomic coordinates of Appendix I or a subset thereof and redesigning or chemically modifying the polypeptide as a result of the evaluation. In some embodiments, the structure-based evaluation comprises comparison of the structure defined by the atomic coordinates of Appendix I or a subset thereof, with the atomic coordinates of insulin or a subset thereof. In some embodiments, the structure-based evaluation further comprises molecular modelling of a complex formed between the structure defined by the atomic coordinates of Appendix I or a subset thereof with the atomic coordinates of an insulin receptor or a subset thereof. In some embodiments, the method further comprises synthesising or obtaining the redesigned or chemically modified polypeptide and testing for its ability to bind IR. In some embodiments, the method further comprises synthesising or obtaining the redesigned or chemically modified polypeptide and determining the ability of the redesigned or chemically modified polypeptide to modulate IR activation. In some embodiments, the method further comprises synthesising or obtaining the redesigned or chemically modified polypeptide and determining the ability of the redesigned or chemically modified polypeptide to lower blood glucose levels. In some embodiments, the polypeptide which is known to bind to IR is insulin. In some embodiments, the insulin is human insulin. In another aspect, there is also provided a polypeptide which has been redesigned or modified by the method as defined herein. In some embodiments, the polypeptide is monomeric.

In another aspect, the present invention provides an isolated molecule which is an IR agonist, wherein the molecule is identified and/or designed based on the 3D structure of Con-Ins G1 defined by the atomic coordinates of Appendix I or a subset thereof. In some embodiments, the molecule is a peptide, polypeptide or peptidomimetic. In some embodiments, the molecule is monomeric. In some embodiments, the molecule has an $IC_{50}$ against the human IR-B receptor of less than $10^{-6}$ M.

In another aspect, the present invention provides a method of identifying a compound which binds IR, the method comprising:
 i) generating a three-dimensional structure model of a polypeptide having
    a) a structure defined by the atomic coordinates of Appendix I or a subset thereof, or
    b) a structure having a root mean square deviation less than about 2.0 Å when superimposed on the corresponding backbone atoms of a), and
ii) designing or screening for a compound which potentially binds the IR.

In some embodiments, generating a three-dimensional structure model comprises generating a model of the polypeptide bound to IR or regions thereof. In some embodiments, the method further comprises synthesising the compound which potentially binds the JR. In some embodiments, the compound modulates at least one biological activity of IR. In some embodiments, the compound is monomeric. In some embodiments, the method further comprises testing the compound designed or screened for in ii) for its ability to modulate blood glucose levels. In some embodiments, steps i) and ii) are performed in silico.

In another aspect, the present invention provides a computer-based method of identifying a compound which mimics insulin activity, the method comprising i) generating a three-dimensional structure model of a polypeptide having
   a) a structure defined by the atomic coordinates of Appendix I or a subset thereof, or
   b) a structure having a root mean square deviation less than about 2.0 Å when superimposed on the corresponding backbone atoms of a), and
ii) designing or screening for a compound which mimics insulin activity.

In some embodiments, generating a three-dimensional structure model comprises generating a model of the polypeptide bound to IR or regions thereof. In some embodiments, the method further comprises synthesising the compound which potentially binds the IR. In some embodiments, the compound modulates at least one biological activity of IR. In some embodiments, the compound is monomeric. In some embodiments, the method further comprises testing the compound designed or screened for in ii) for its ability to modulate blood glucose levels. In some embodiments, steps i) and ii) are performed in silico.

In a further aspect, the present invention provides a compound identified using a method defined herein.

In a further aspect, the present invention provides a crystal of Con-Ins G1 polypeptide having a space group P432 with unit cell dimensions of a=b=c=74.91 Å with up to about 2% variation in any cell dimension.

In a further aspect, the present invention provides the structure of Con-Ins G1 polypeptide as defined by the atomic coordinates of Appendix I.

In a further aspect, the present invention provides for the use of the structure of Con-Ins G1 polypeptide as defined by the atomic coordinates of Appendix T as a structural model. In some embodiments, the structural model is used for identification of insulin analogs. The present invention also provides insulin analogs identified by the use defined herein.

In yet another aspect, the present invention provides a pharmaceutical composition comprising the insulin analog, polypeptide molecule and/or compound as defined herein.

Any embodiment herein shall be taken to apply mutatis mutandis to any other embodiment unless specifically stated otherwise. For instance, as the skilled person would understand examples of insulin analogs, peptides and health conditions outlined herein for the methods of the invention equally apply to the use and pharmaceutical compositions of the invention. It is also intended that embodiments of the present invention include manufacturing steps such as incorporating the compound into a pharmaceutical composition in the manufacture of a medicament.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims.

The invention is hereinafter described by way of the following non-limiting Examples and with reference to the accompanying figures. The present invention is not to be limited in scope by the specific embodiments described herein, which are intended for the purpose of exemplification only. Functionally-equivalent products, compositions and methods are clearly within the scope of the invention, as described herein.

BRIEF DESCRIPTION OF THE ACCOMPANYING FIGURES

The accompanying drawings, which are incorporated in and constitute a part of this specification, illustrate several embodiments of the disclosed method and compositions and together with the description, serve to explain the principles of the disclosed method and compositions.

FIG. 1: Sequence comparison with human insulin. The sequence of Con-Ins G1 and comparison with human insulin. The conserved cysteine residues and aromatic triplet are boxed. The disulphide bonds are indicated with a solid line connecting the two cysteine residues. γ: γ-carboxylated-glutamate; O: hydroxyproline; *: C-terminal amidation.

FIG. 2 Characterization of Con-Ins G1. Competition binding analysis to human IR (isoform B) of Con-Ins G1 (n=9), PTM-free sCon-Ins G1 (n=9) and human insulin (n=21). Error bars depict SEM (when absent error bars are smaller than marker size). sCon-Ins G1: Con-Ins G1 with diselenide bond between SecA6 and SecA10.

FIG. 3: Insulin signalling measured by Akt phosphorylation analysis. Akt phosphorylation analysis of sCon-Ins G1, PTM-free sCon-Ins G1 and hIns (n=4). Error bars depict SEM (when absent error bars are smaller than marker size).

FIG. **4*a***: The x-ray crystal structure of Con-Ins G1. Superposition of Con-Ins G1 and hIns (PDB entry 1MSO). The backbones of the Con-Ins G1 B and A chains are shown in black, and the backbones of the hIns B and A chains are shown in white.

FIG. **4*b***: The hydrophobic core of Con-Ins G1. Core structure of Con-Ins G1 compared to that of hIns.

FIGS. **4*c*, 4*d* and 4*f***: Post-translational modifications of Con-Ins G1. Side chain interactions of GlaA4, GlaB10 and HypB3 (respectively, with that of GlaA4 being compared to that of hIns GluA4).

FIG. **4*e*: The hydrophobic core of Con-Ins G1. Core structure of Con-Ins G1 compared to that of hIns. Shows a different view of the same interactions as those presented in FIG. 4*b***.

FIG. 5: The x-ray crystal structure of Con-Ins G1. Stereo image showing the arrangement within the crystal of Con-Ins G1 monomers around the crystallographic four-fold axis. Four sulphate molecules (centre) are modelled—with unrestrained coordinates and effective occupancy each of 0.25—into a relatively featureless blob of difference electron density on the four-fold axis. The sulphate ion forms part of a charge-compensated cluster comprising the amino-terminal group of GlyA1 and a side-chain carboxylate of GlaA4 from each Con-Ins G1 monomer.

FIG. 6: Con-ins G1 binding hIR. Molecular model of Con-Ins G1 in the context of the primary insulin binding site of the human insulin receptor. hIns residues B22-B27 (in their hIR-bound form from PDB entry 4OGA) are overlaid in black. The Figure illustrates how the side chain of Con-Ins G1 TyrB15, once rotated from its receptor free conformation, may together with that of Con-Ins G1 TyrB20 act as a surrogate for that of hIns PheB24 in formation of the Con-Ins G1/hIR complex. The A chain of Con-Ins G1 (foreground) is transparent for clarity.

FIG. 7: TyrB15 and TyrB20. Isosurface representation of the ($2mF_{obs}-DF_{calc}$) difference electron density in the vicinity of Con-Ins G1 residues TyrB15 and TyrB20, contoured at the 1.5σ level. The side chains of both these residues appear disordered compared to those of neighbouring residues (for example, that of TyrA19).

FIG. 8: GlaA4 of Con-Ins G1. Schematic diagram showing the interaction of the side chain of Con-Ins G1 PTM residue GlaA4 with side chain of hIR αCT residue Asn711, as observed within the molecular model of the complex of Con-Ins G1 with the primary binding site of hIR. The molecular surface is that of the hIR L1 domain.

FIG. 9: Insulin signalling measured by Akt phosphorylation analysis. Akt phosphorylation analysis of hIns, hIns[DOI] and hIns[TyrB15, TyrB20, DOI].

FIG. 10: Characterization of Con-Ins G1. Sedimentation equilibrium analysis of Con-Ins G1 at 30,000 rpm (shaded dots) and 45,000 rpm (unshaded dots) with the best fit (lines) to a single species of apparent MW 5380±55 g/mol.

FIG. 11: Con-InsG1 in co-complex with Fv83-7.IR310.T and IR-$A^{704-719}$. Two orthogonal views of an overlay of the two copies in the asymmetric unit of crystal structure of the complex of Con-InsG1 in co-complex with Fv83-7.IR310.T and IR-A$^{704-719}$. Within each Panel, one copy is shown as a Cα trace with thick linkages and the other as a Cα trace with thin linkages. The overlay is based on common residues within the IR310.T moiety. The CR domains and their attached Fv83-7 are omitted for clarity.

Figure 12:
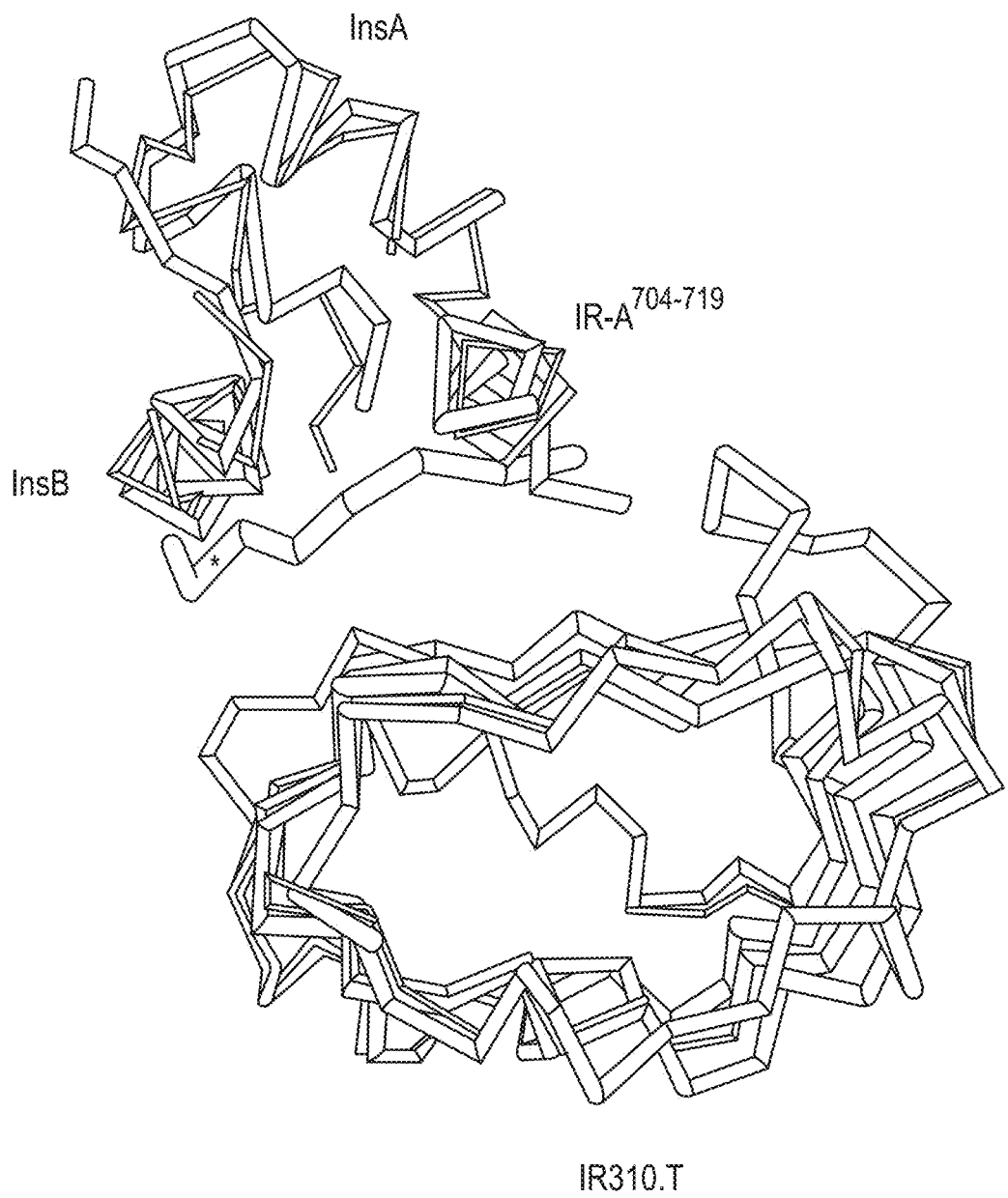

FIG. 12: Con-InsG1 in co-complex with Fv83-7.IR310.T and IR-A$^{704-719}$. Overlay of the crystal structure of Con-InsG1 in co-complex with Fv83-7.IR310.T and IR-A$^{704-719}$ with the crystal structure of hIns in co-complex with Fab83-7.IR310.T and IR-A$^{704-719}$ (PDB entry 4OGA). The Con-InsG1 complex is shown as a Cα trace with thicker lines and the hIns complex as a Cα trace with thinner lines, except for residues B22-B30 which are shown as a thick line with an asterisk). The overlay is based on common residues within the IR310.T moiety. The cysteine-rich domain of IR310.T and its attached antibody fragment are omitted for clarity.

Figure 13:
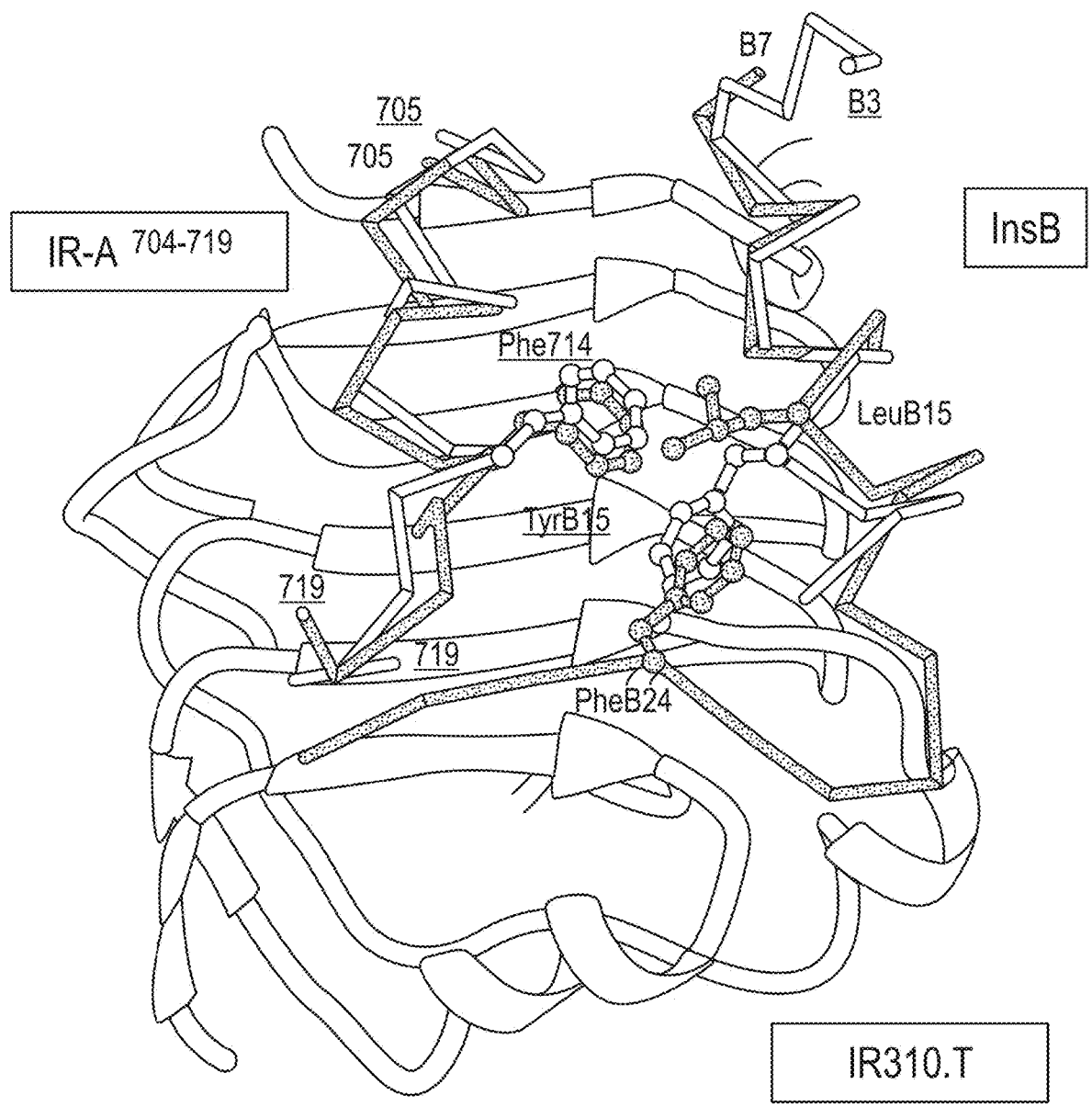

FIG. 13: TyrB15 and TyrB20. Overlay of hIns in complex with Fab83-7, IR310.T and IR-A$^{704-719}$ (PDB entry 4OGA; labelled) and Con-Ins G1 in complex with Fv83-7, IR310.T and IR-A$^{704-719}$ (underlined labels) based on the common domain L1 of IR310.T. The L1 domain of IR310.T is shown in cartoon ribbon representation, while hIns, Con-Ins G1 and IR-A$^{704-719}$ are shown in Cα trace representation. The CR domain of IR310.T is omitted for clarity. The side chains and Cα atoms of hIR Phe714, hIns LeuB15 and Phe B24 and Con-Ins G1 TyrB15 are shown in ball-and-stick representation. The spatial correspondence of the side chains of hIns PheB24 and Con-InsG1 TyrB15 is evident. No interpretable electron density is present for Con-Ins G1 TyrB20. The respective A chains of Con-Ins G1 and of hIns are omitted for clarity.

Figure 14:
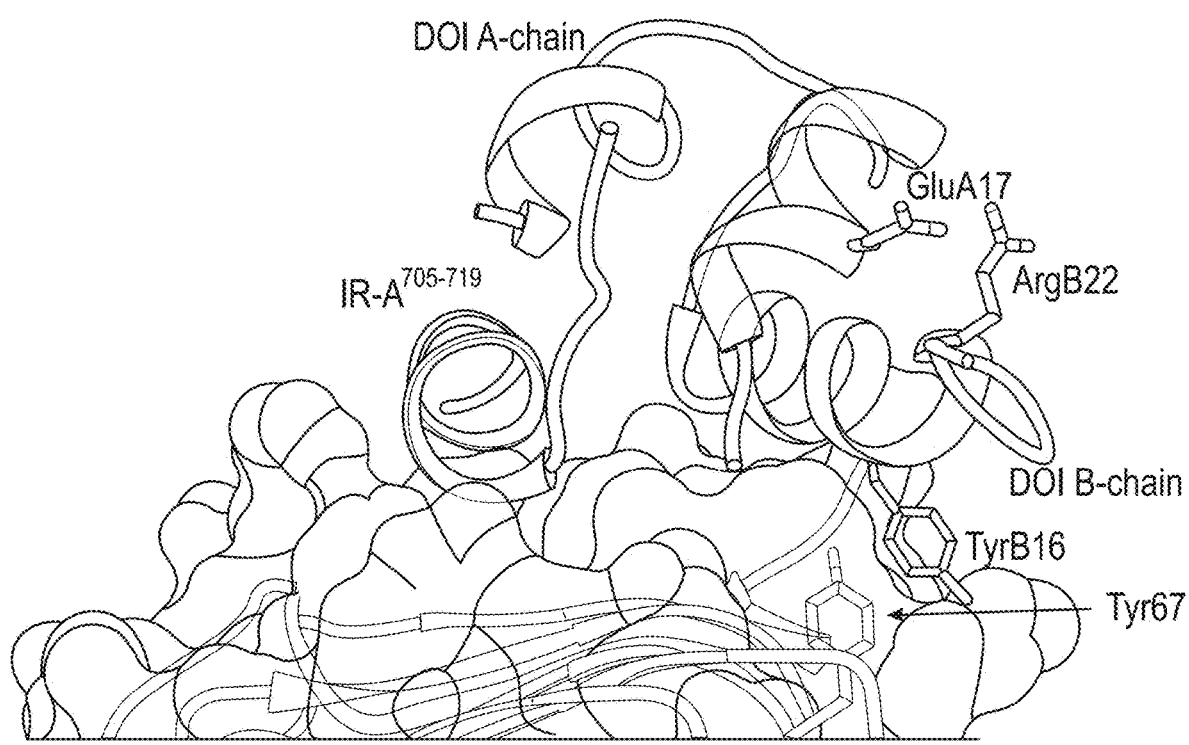

FIG. 14: Molecular modelling of hIns[DOI] bound to components that comprise the primary binding site (site 1) of the hIR. Molecular model of hIns[DOI] in complex with the IR L1 domain (residues Gly5 to Cys155) and the IR-A$^{704-719}$ segment (residues Phe705 to Ser719 of the IR-A isoform). The IR-A$^{704-719}$ segment is shown in cartoon ribbon representation. The hIns[DOI] A chain and B chain are shown in cartoon ribbon representation and are labelled. The transparent molecular surface is that of the hIR L1 domain. The hIR L1 domain is shown in cartoon ribbon representation with the side chain of Tyr67 shown.

Figure 15:
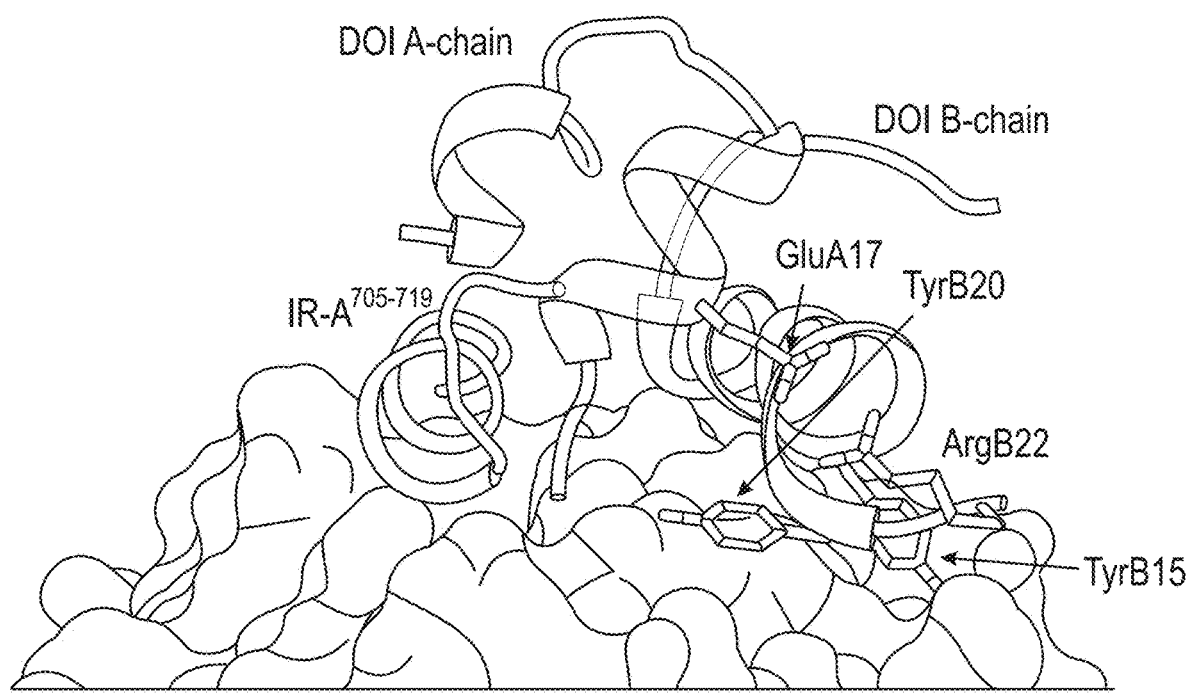

FIG. 15: Molecular modelling of hIns[TyrB15, DOI] bound to components that comprise the primary binding site (site 1) of the hIR. Molecular model of hIns[TyrB15, DOT] in complex with the JR L1 domain (residues Gly5 to Cys155) and the JR-A segment Phe705 to Ser719 (IR-A$^{704-719}$). The IR-A$^{704-719}$ segment is shown in cartoon ribbon representation. The hIns[TyrB15, DOI] A chain and B chain are shown in cartoon ribbon representation and are labelled. The molecular surface is that of the hIR L1 domain. The figure illustrates how the side-chain of TyrB15 projects into the hydrophobic core of the DOI-(IR-A$^{704-719}$)-L1 interface occupying space otherwise occupied by hIns LeuB15.

Figure 16:
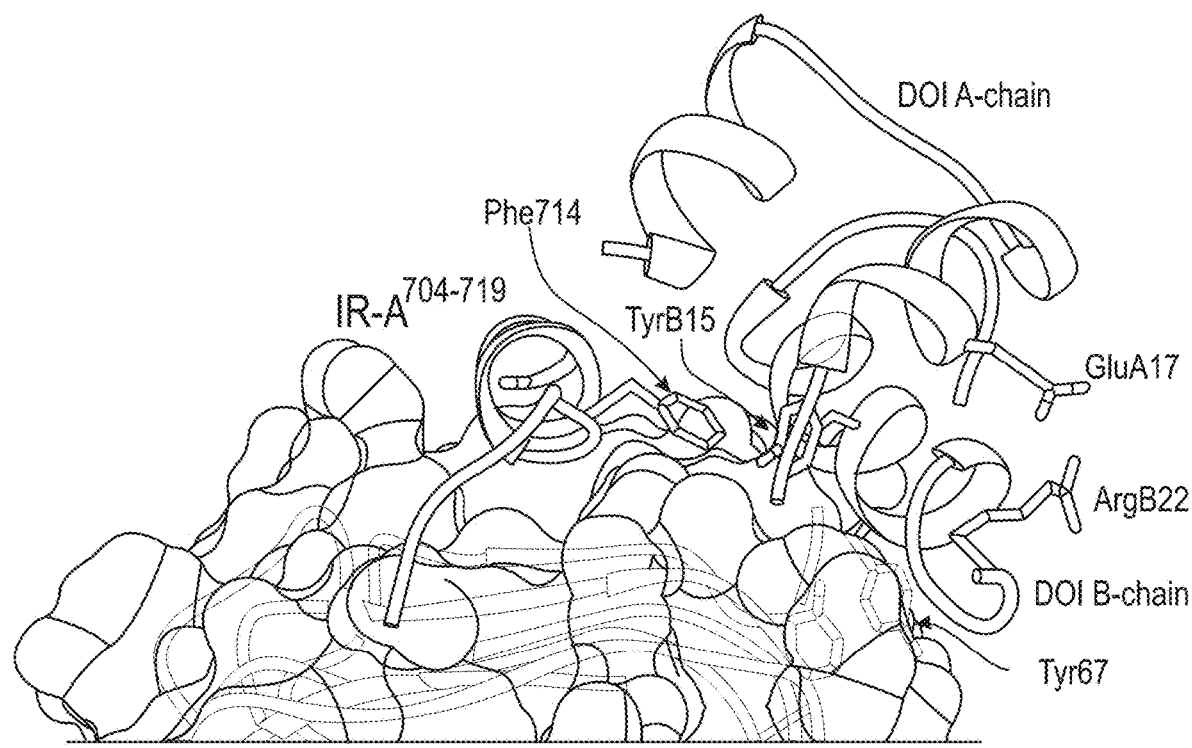

FIG. 16: Molecular modelling of hIns[DOI, TyrB20] bound to components that comprise the primary binding site (site 1) of the hIR Molecular model of hIns[TyrB20, DOI] in complex with the IR L1 domain (residues Gly5 to Cys155) and the IR-A$^{704-719}$. The figure illustrates how the side-chain of TyrB20 remained in the hIns B24 binding site, with all other interactions with the receptor appearing native-like. The IR-A$^{704-719}$ segment is shown in cartoon ribbon representation. The hIns[TyrB20, DOI] A chain and B chain are shown in cartoon ribbon representation and are labelled. The transparent molecular surface is that of the hIR L1 domain. The hIR L1 domain is shown in cartoon ribbon representation with the side chain of Tyr67 shown.

Figure 17A:
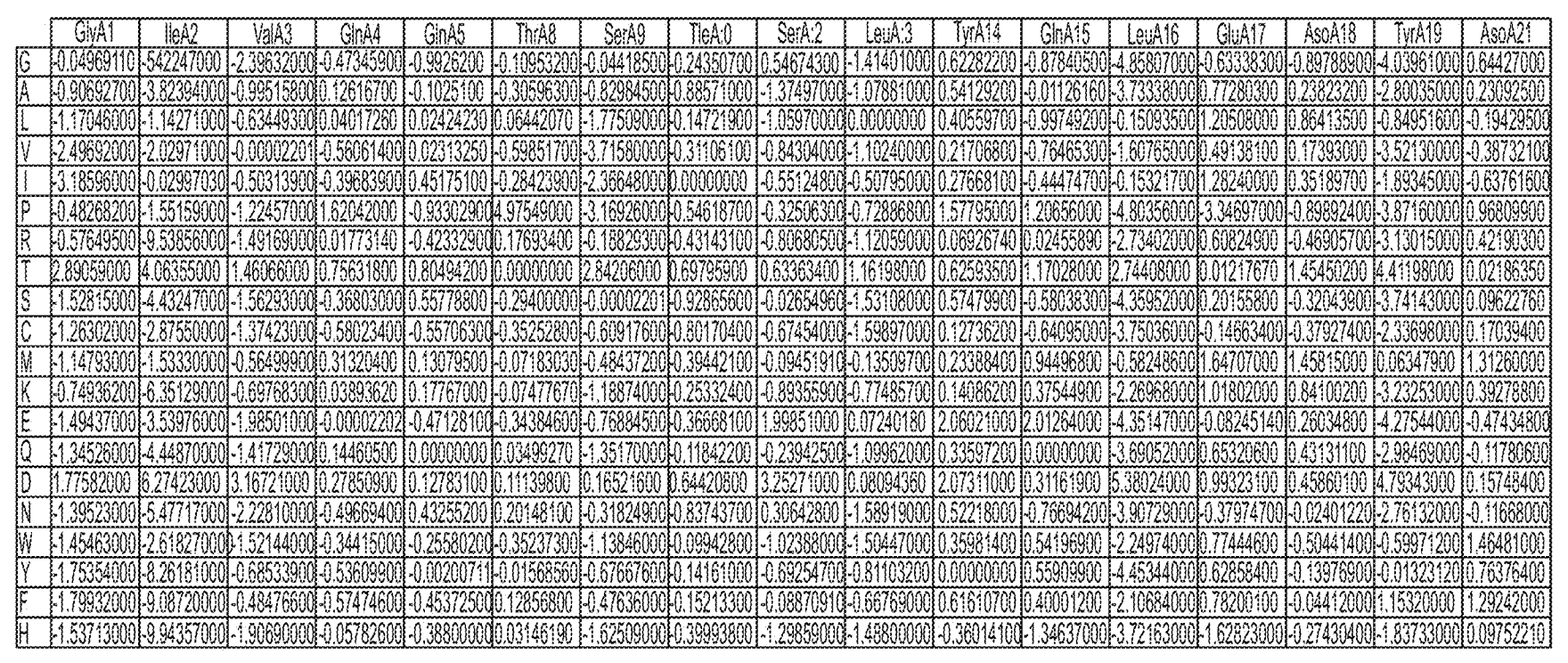
Figure 17B:
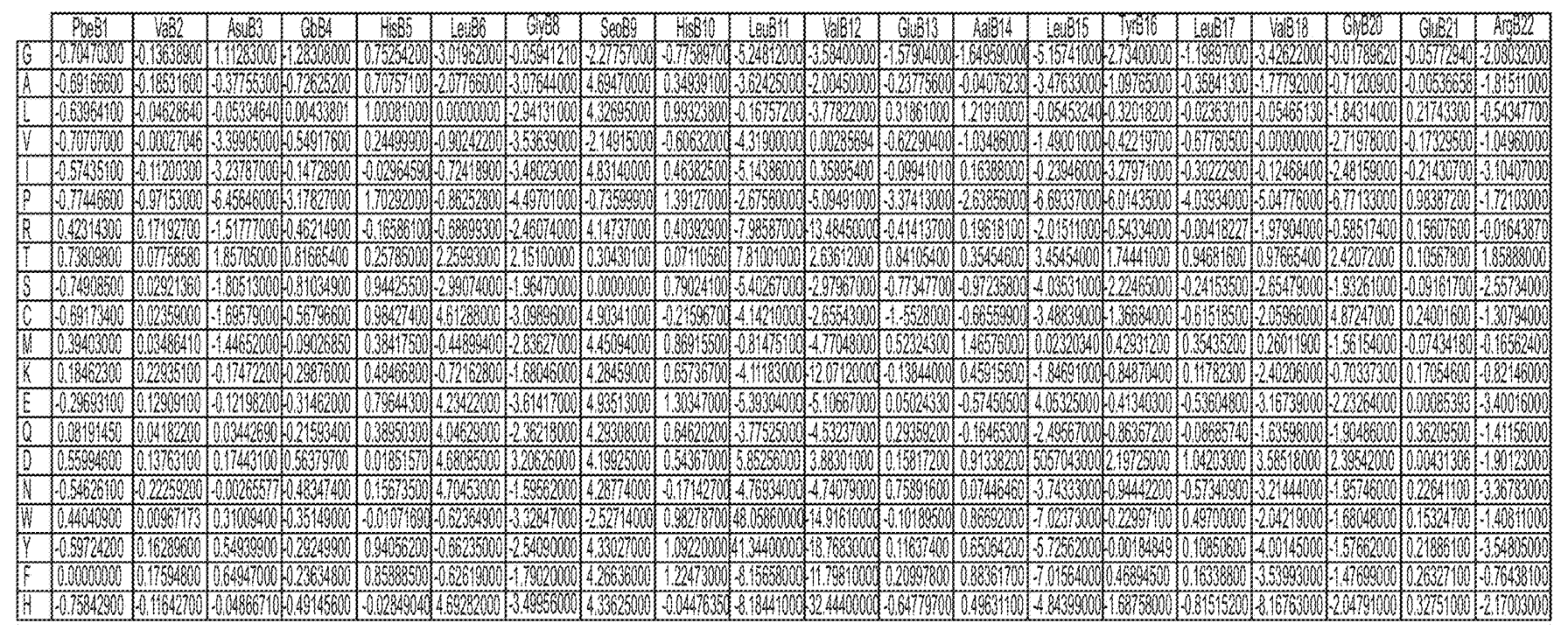

FIG. 17A and FIG. 17B: Positional scan of hIns[DOI]. The resultant mutational ΔΔG (kcal/mol) contribution at each site of hIns[DOI].

Figure 18A:
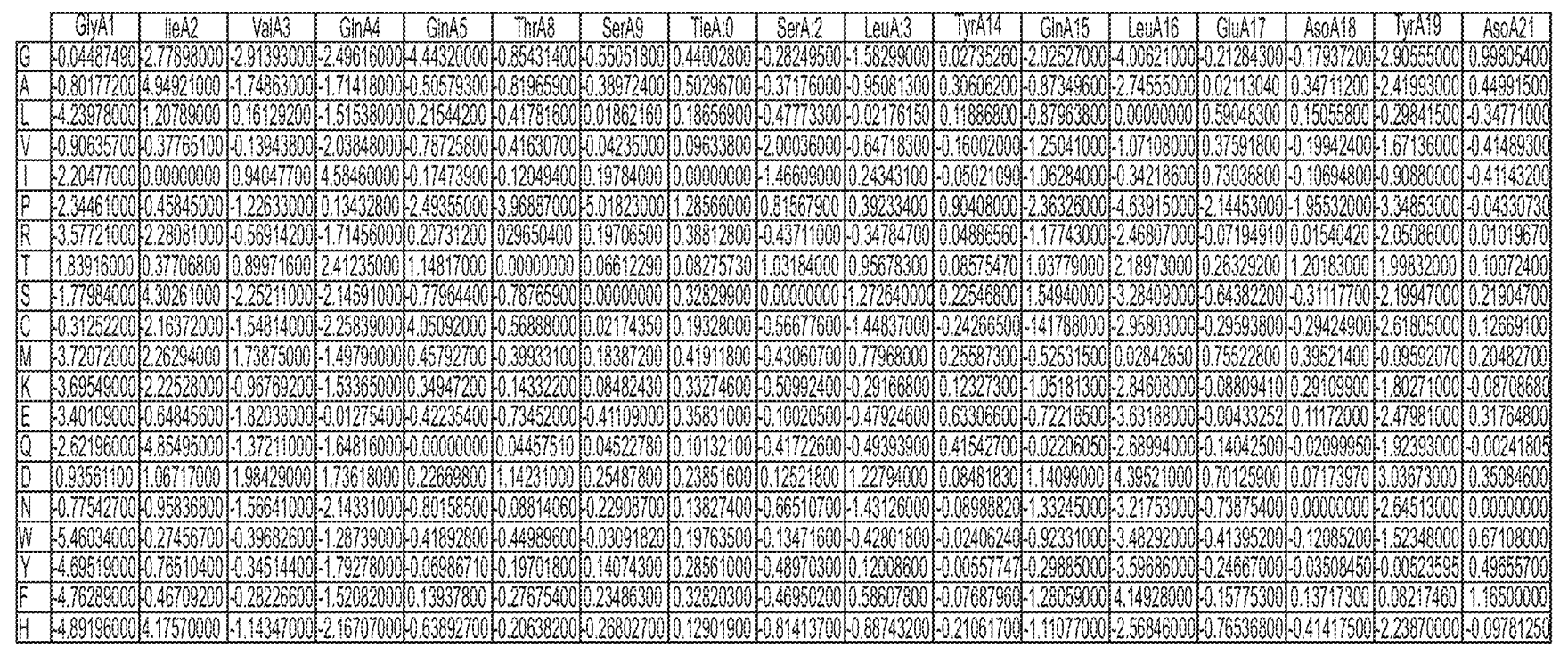
Figure 18B:
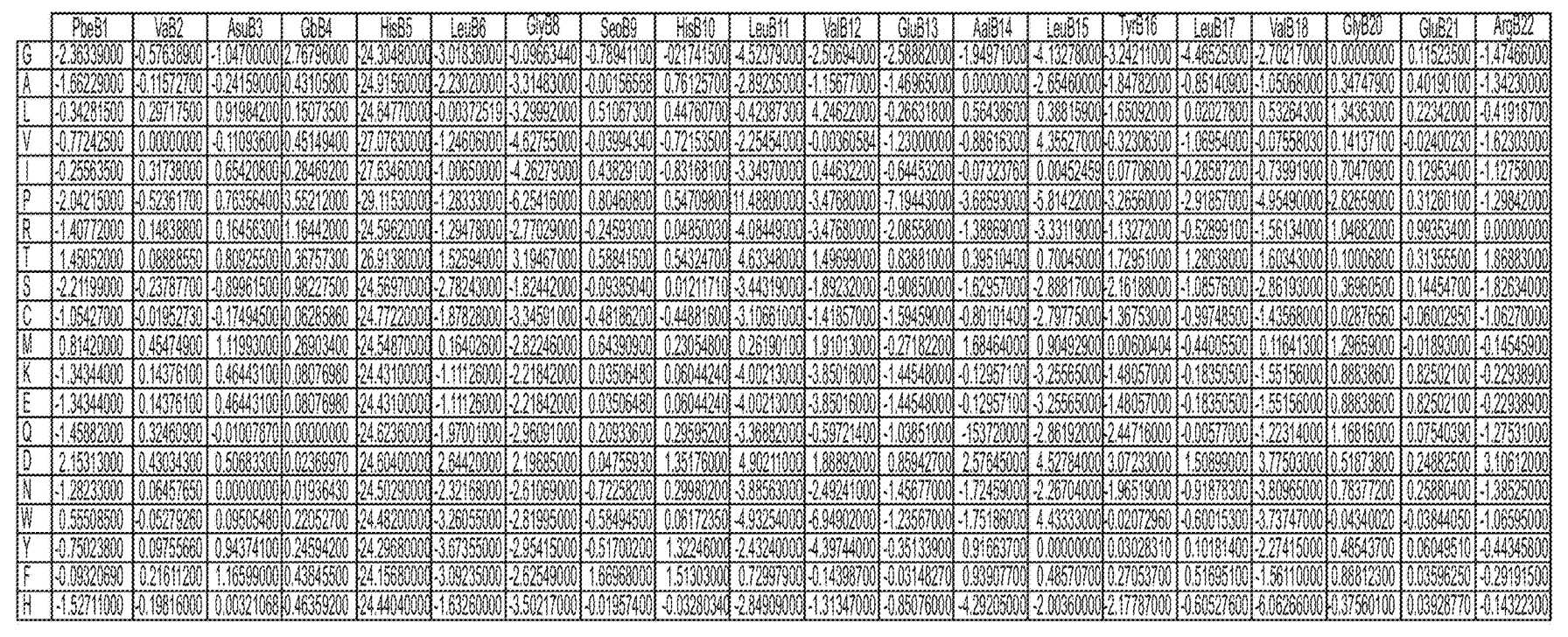

FIG. 18A and FIG. 18B: Positional scan of hIns[TyrB15, DOI]. The resultant mutational ΔΔG (kcal/mol) contribution at each site of hIns[TyrB15, DOI].

Figure 19B:
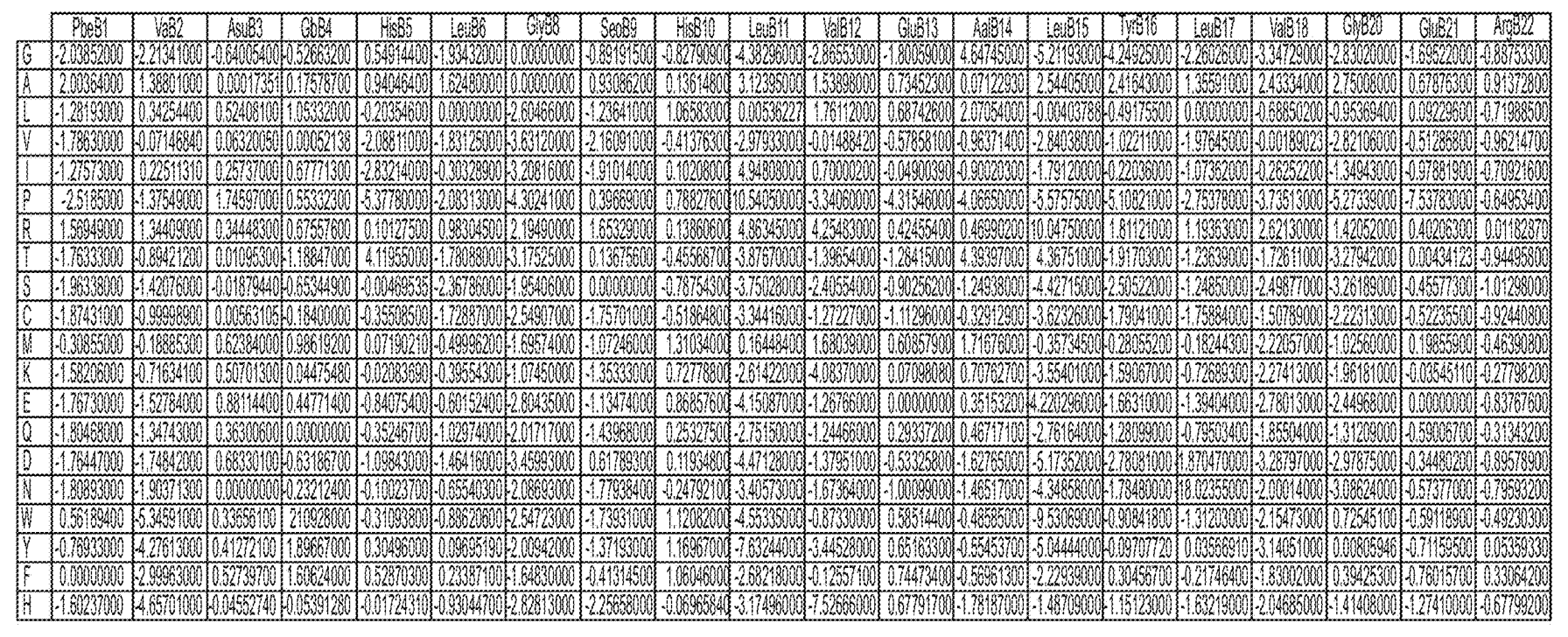

FIG. 19A and FIG. 19B: Positional scan of hIns[TyrB20, DOI]. The resultant mutational ΔΔG (kcal/mol) contribution at each site of hIns[TyrB20, DOI].

Figure 20:
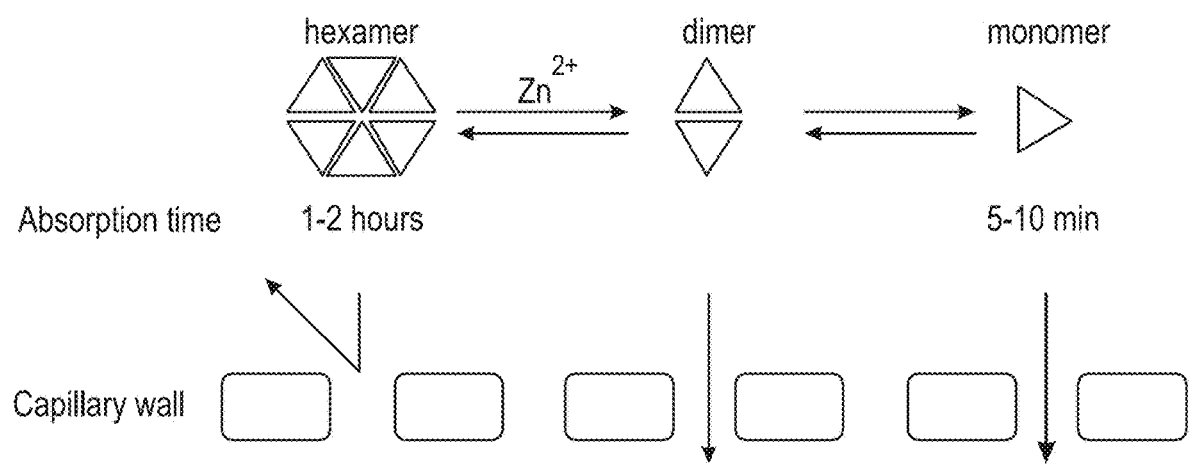

FIG. 20: Schematic of insulin multimer equilibrium. Figure shows that insulin monomerization slows absorption rate.

Figure 21:
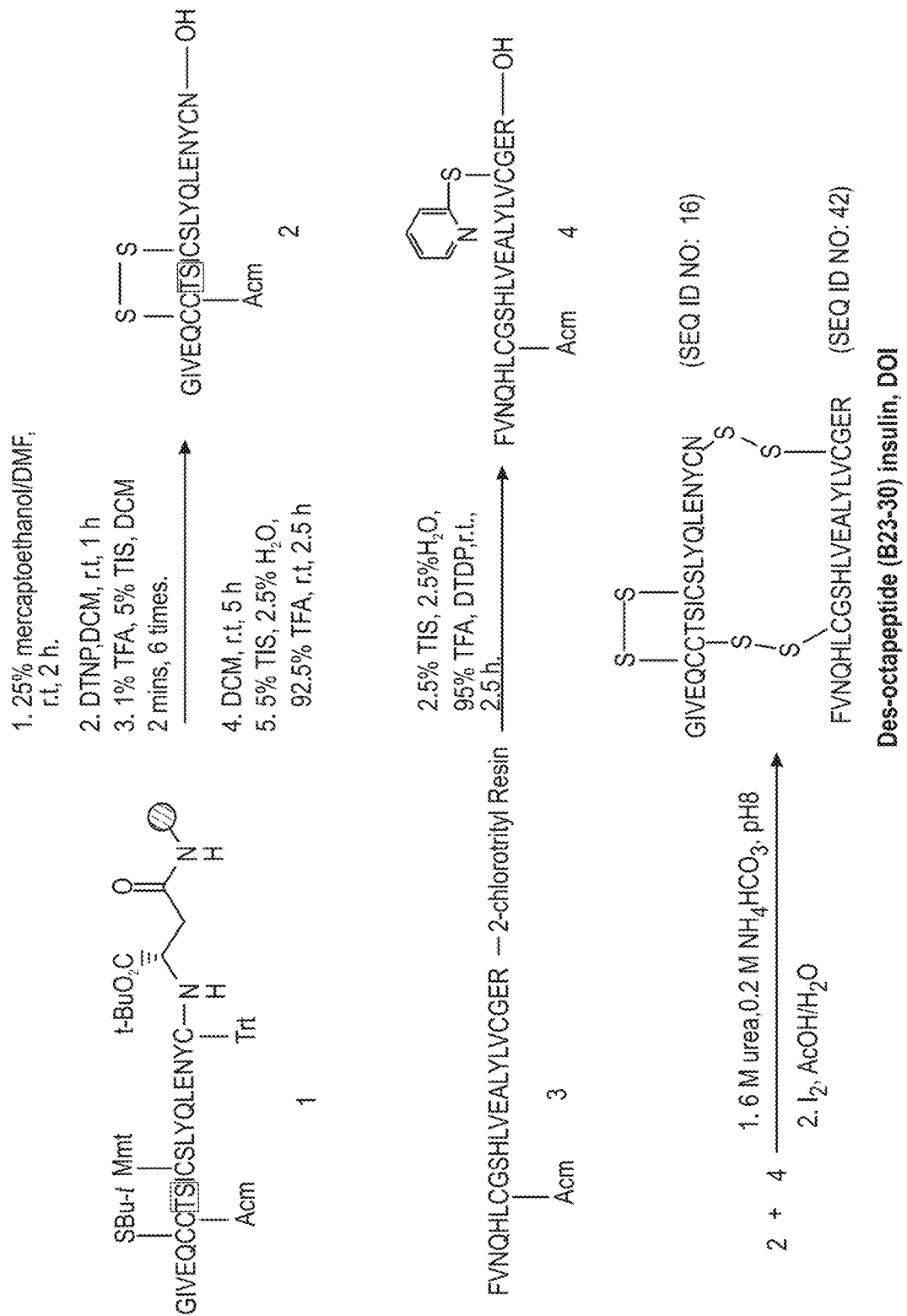

FIG. 21: Chemical total synthesis of human DOI insulin. Figure shows the chemical total synthesis of human DOI insulin. Thr-Ser isopeptide (boxed) was used to increase the solubility of insulin A chain.

Figure 22:
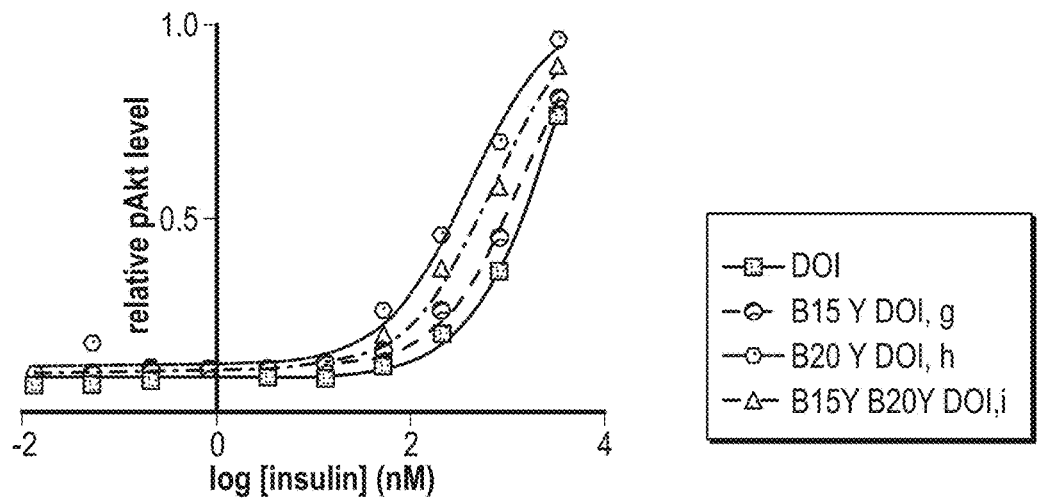
Figure 22:
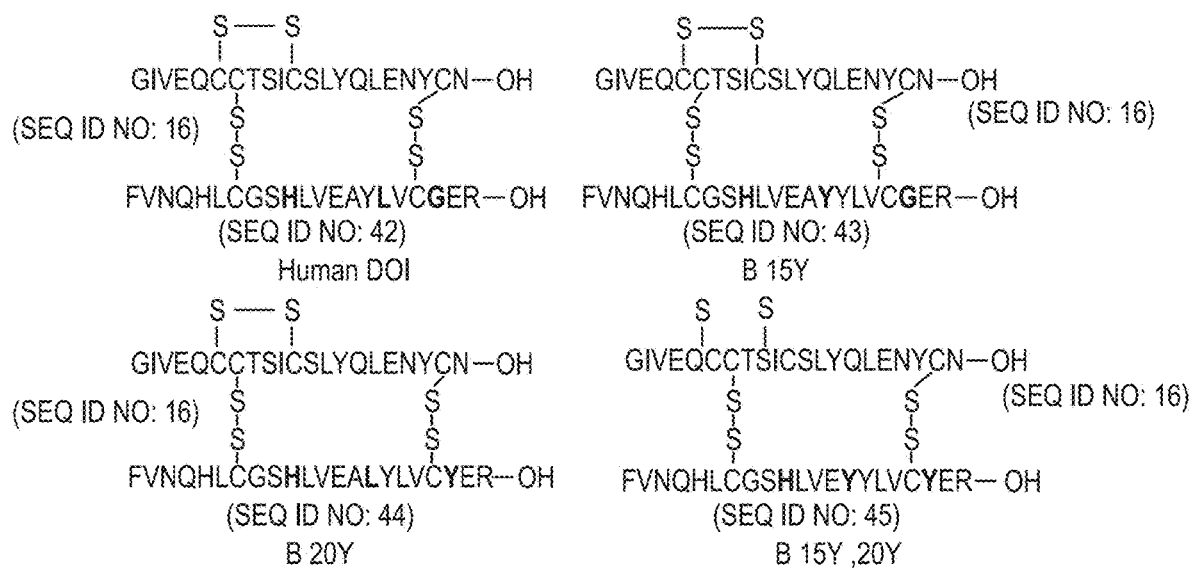

FIG. 22: Insulin signalling activation by exemplified insulin analogs. Figure shows the effects of B15 Tyr and B20 Tyr on hIR activation. The sequence for each peptide used is also shown.

Figure 23:
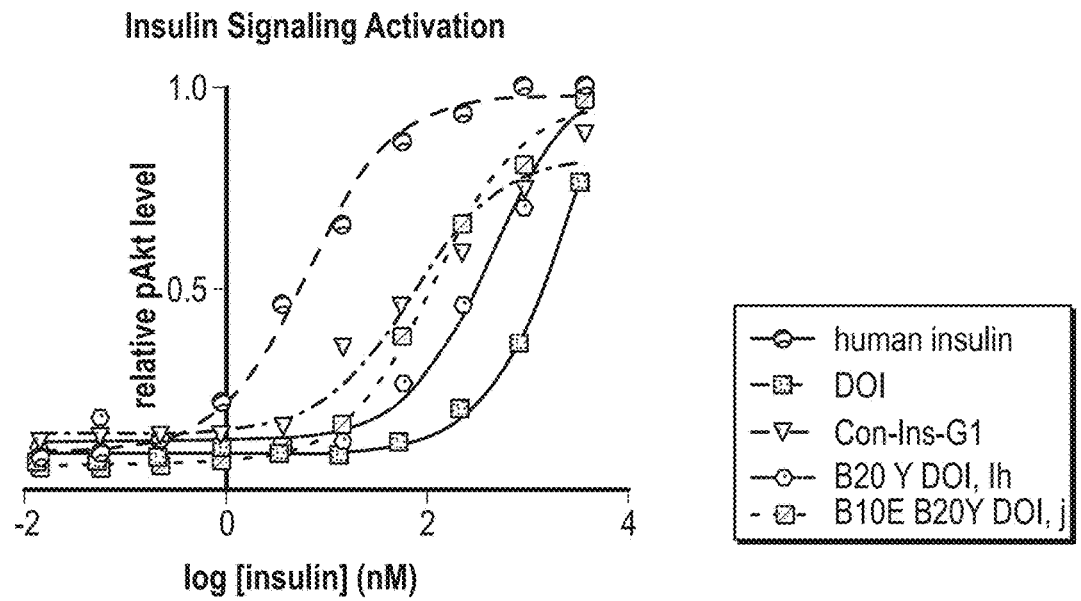
Figure 23:
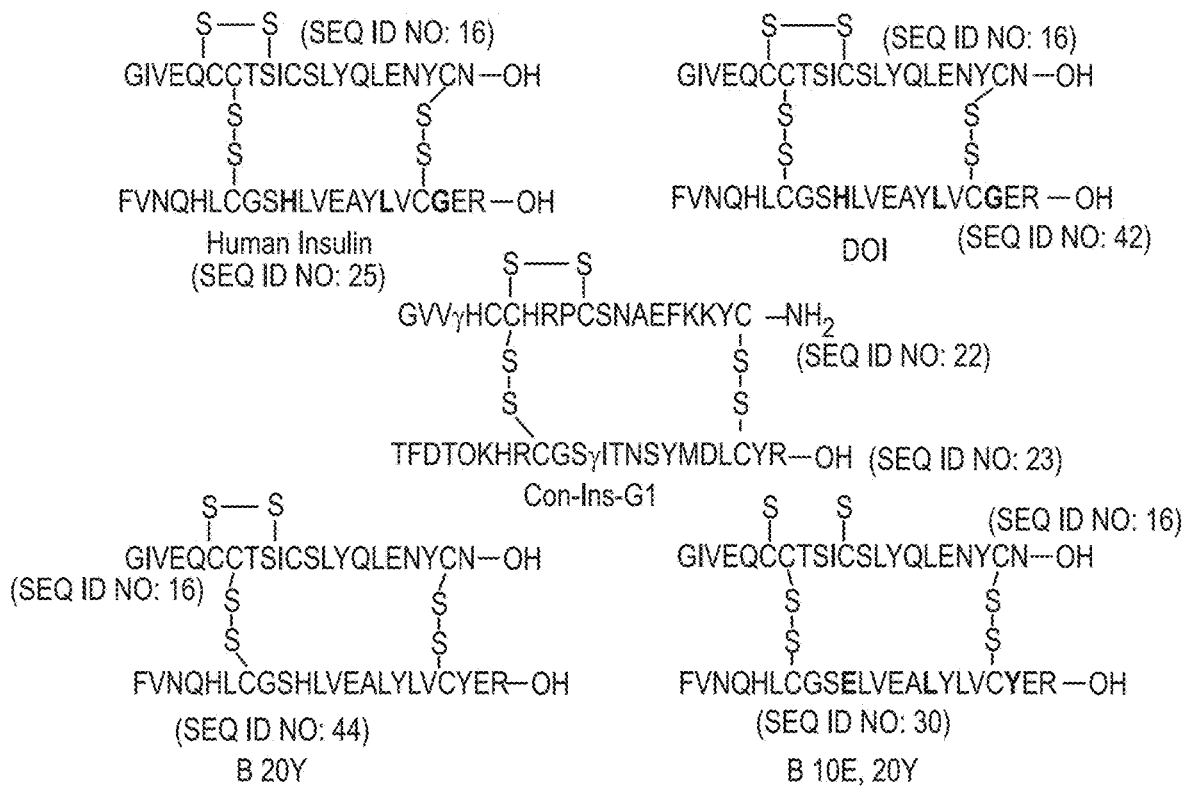

FIG. 23: Insulin signalling activation by exemplified insulin analogs. Figure shows the effects of B10 Glu, B20 Tyr on hIR activation. The sequence for each peptide used is also shown.

Figure 24A:
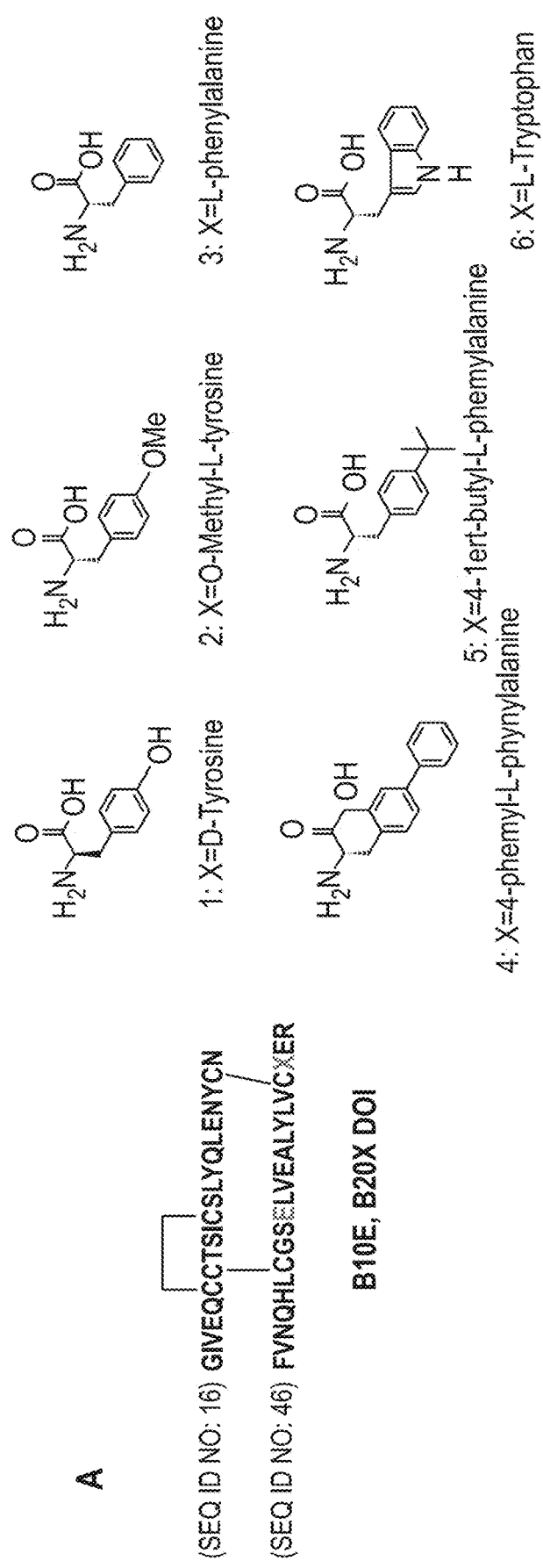

FIG. 24A: Insulin signalling activation by exemplified insulin analogs. Figure shows peptide sequences/modified amino acids.

Figure 24B:
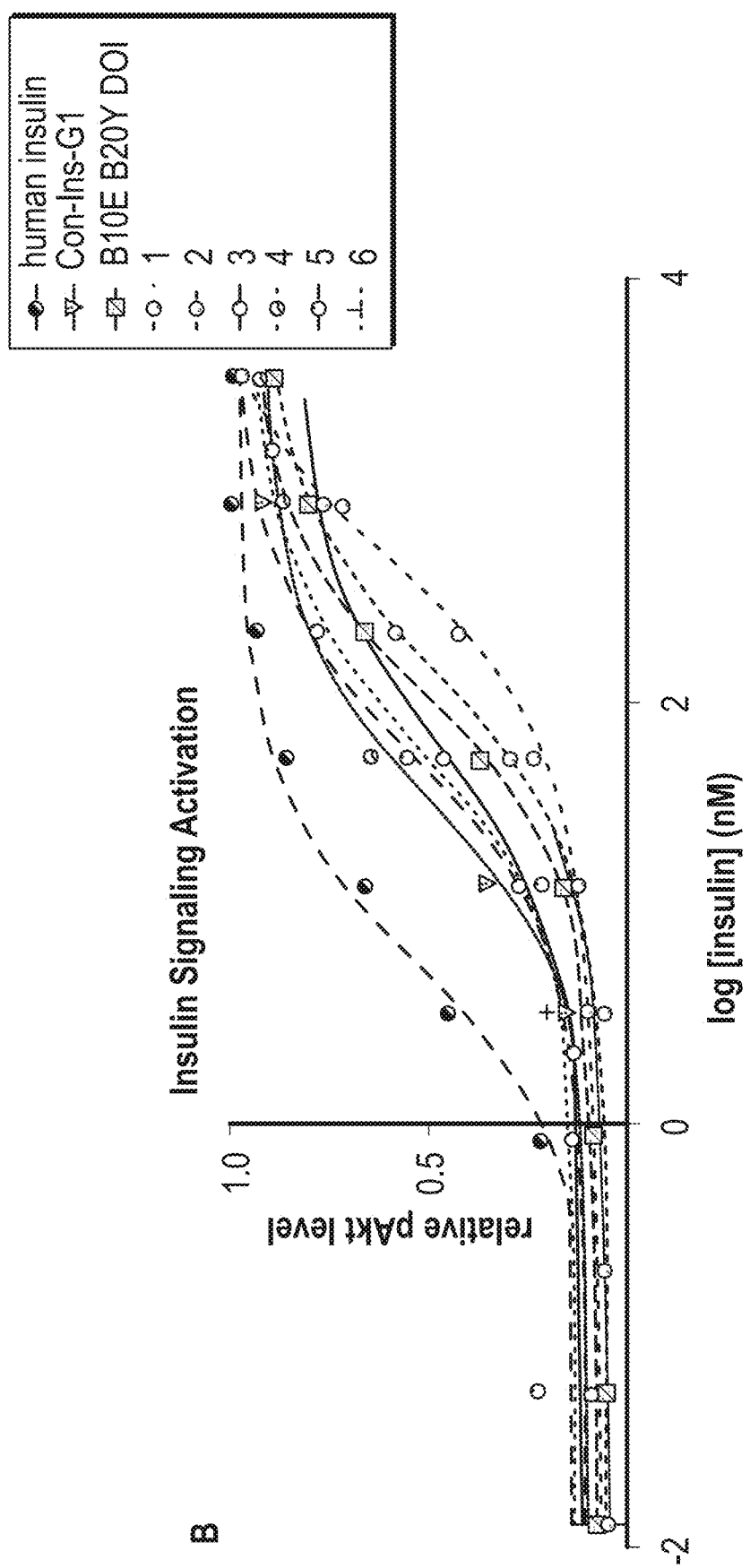

FIG. 24B: Insulin signalling activation by exemplified insulin analogs. FIG. 24B shows effects of B20 residues in activating insulin signaling.

Figure 25:
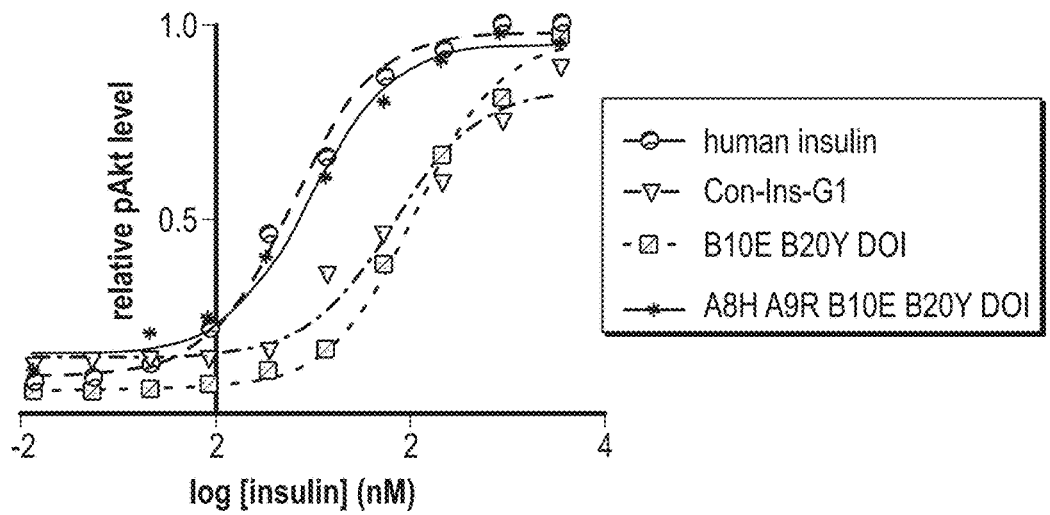
Figure 25:
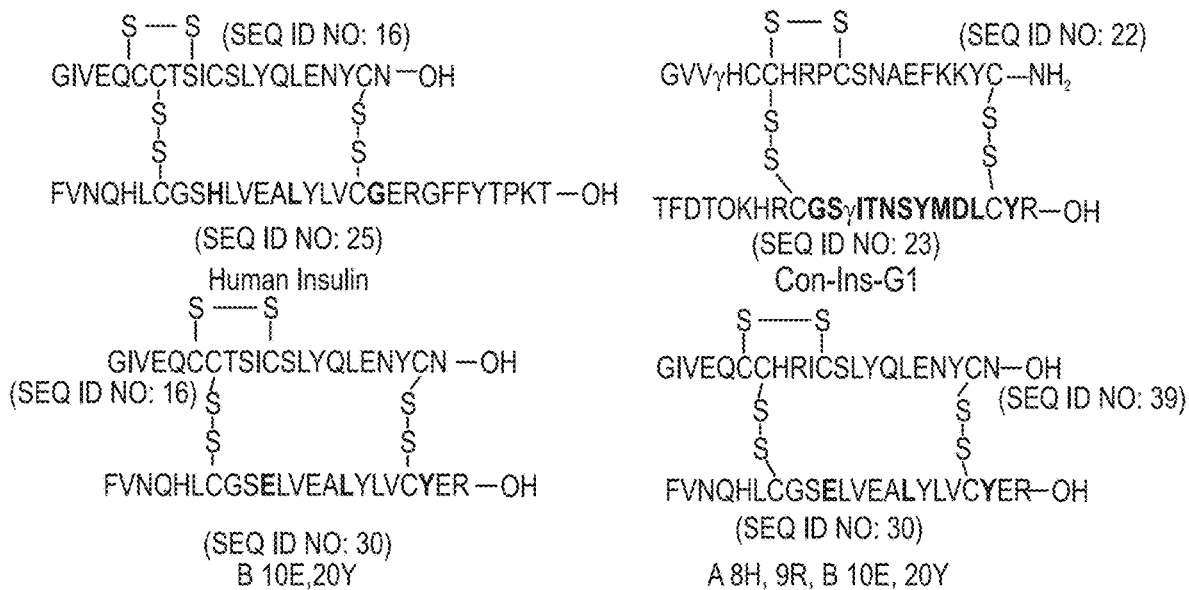

FIG. 25: Insulin signalling activation by exemplified insulin analogs. Figure shows the effects of A8 His, A9 Arg on hIR activation. The sequence for each peptide used is also shown.

Figure 26:
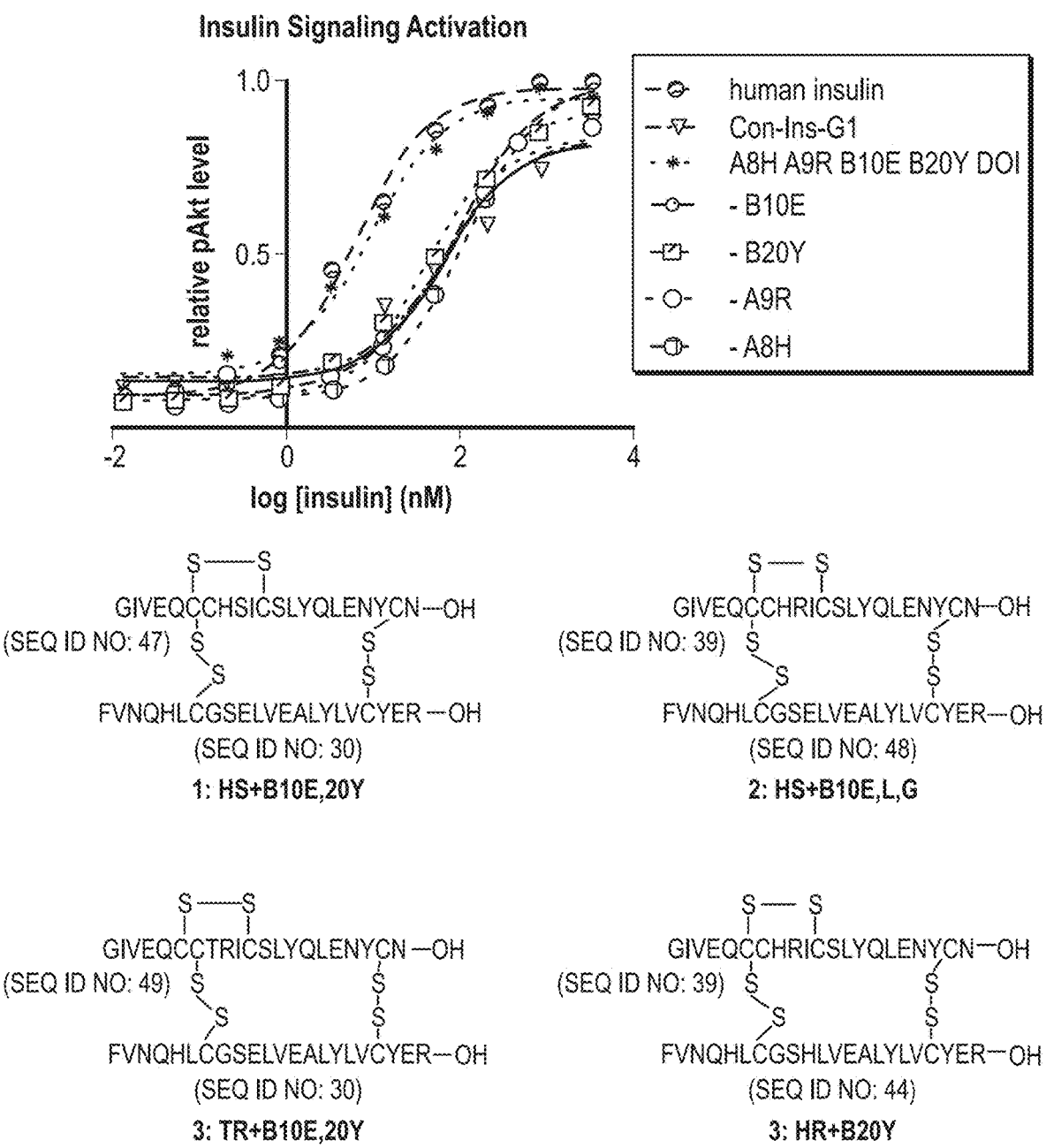

FIG. 26: Insulin signalling activation by exemplified insulin analogs. Figure shows the individual effect of A8, A9, B10 and B20 on hIR activation.

Figure 27:
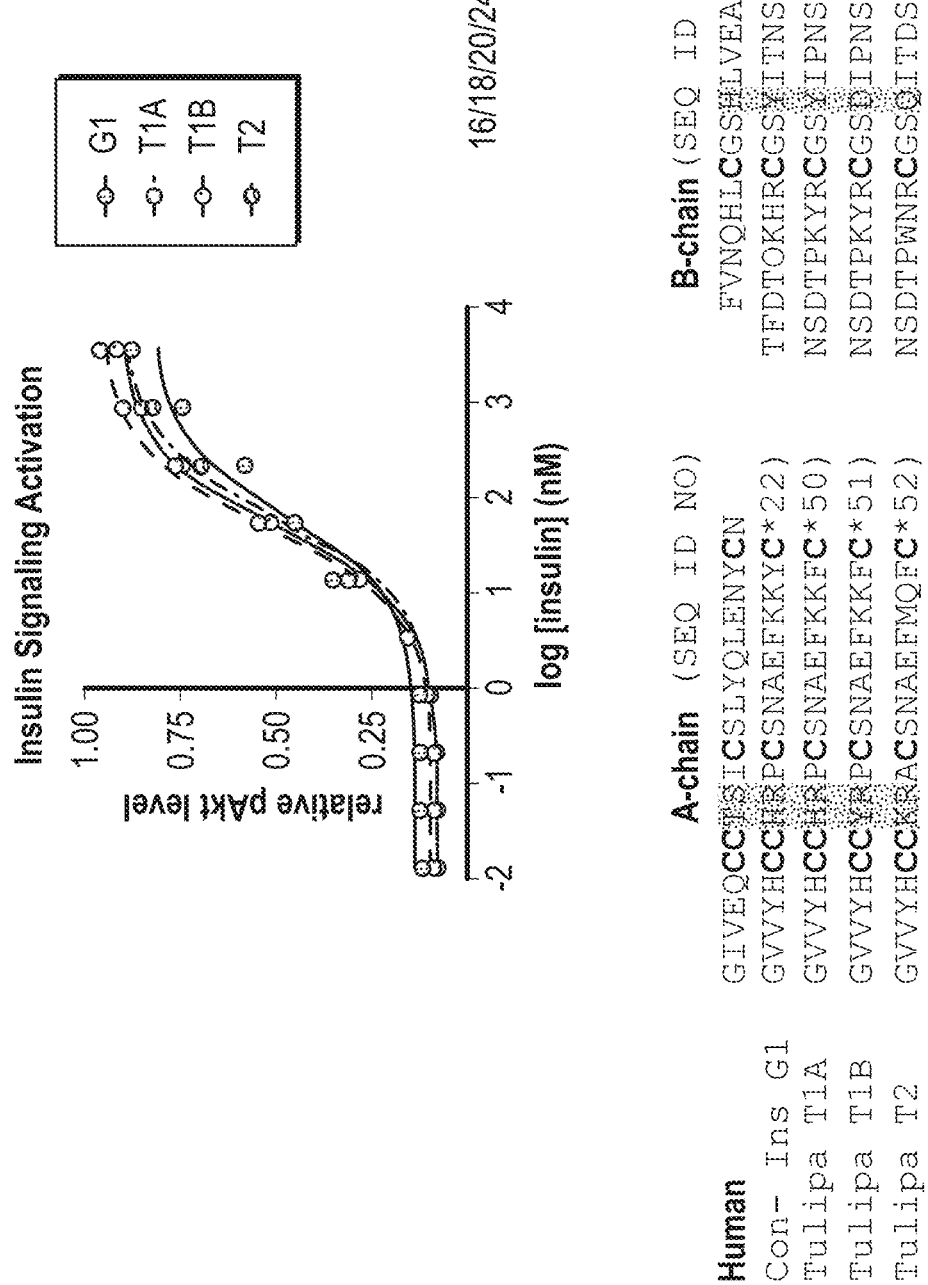

FIG. 27: Insulin signalling activation by venom insulins. Figure shows the insulin signaling activation of several venom insulins with similar potencies to Con-Ins G1 (top panel). Sequence alignment of these venom insulins (bottom panel). Residues at position 9 and 10 in the A chain and 10 and 20 in the B chain are shaded. γ and * denote post-translational modifications (gamma-carboxyglutmate and C-terminal amidation, respectively).

KEY TO THE SEQUENCE LISTING

SEQ ID NO: 1-58: Insulin analogs, peptides and/or compounds according to embodiments of the present disclosure.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., molecular genetics, pharmacology, protein crystallography, protein chemistry, biochemistry and the like).

Unless otherwise indicated, the techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The term "and/or", e.g., "X and/or Y" shall be understood to mean either "X and Y" or "X or Y" and shall be taken to provide explicit support for both meanings or for either meaning. In addition, the articles "a" and "an" as used in this application and the appended claims may generally be construed to mean "one or more" unless specified otherwise or clear from context to be directed to a singular form.

The term "insulin" means human insulin, pig insulin, guinea pig insulin, chicken insulin, mouse insulin, beef insulin or venom insulin. In some embodiments, insulin means human insulin. The term "venom insulin" means a cone snail venom insulin. Preferably, venom insulin means Con-Ins G1.

The term "insulin analog" as used herein refers to any agent that is capable of mimicking the activity of insulin. In some embodiments, the insulin analog is at least an insulin receptor agonist. In some embodiments, the insulin analog binds to the insulin receptor. Preferably insulin analogs may be peptides, polypeptides, proteins or peptidomimetics. In some embodiments, the insulin analog is a peptide. As the person skilled in the art would understand, unless the context indicates otherwise, the terms "insulin analog", "peptide" and insulin peptide" are used interchangeably. Insulin analogs also include the IR agonists, molecules, compounds and the like identified by the methods disclosed herein.

The term "peptide," as used herein, refers to a polymer of amino acids ranging from two to about fifty amino acids (e.g., 4, 6, 8, 10, 12, 15, 20, 25, 30, 35, 40, or 45 amino acids in length). The term peptide encompasses both unmodified peptides, modified peptides, and otherwise chemically derivatized peptides (for example phosphorylated, sulphated, amidated and the like). In some embodiments, the peptide may be an unnatural peptide oligomer, such as those described in Sadowsky et al. (2005) and Sadowsky et al. (2007). The term "polypeptide," or "protein" as used interchangeably herein, refers to a polymer of amino acids generally greater than about 50 amino acids in total length and typically having stable characteristic secondary and tertiary structures. The term "polypeptide" or "protein" may also include a combination of such polymers (for example two or more) associating with stable tertiary quaternary structure resulting either through their non-covalent or covalent association.

In some embodiments, the peptide, protein or polypeptide comprises amino acids that occur naturally in the subject to be treated. In some embodiments, the peptide or polypeptide comprises one or more unnatural amino acids, modified amino acids or synthetic amino acid analogues. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, cyclopentylalanine, β-alanine, fluoro-amino acids, designer amino acids such as β-methyl amino acids, Cα-methyl amino acids, Nα-methyl amino acids, and amino acid analogues in general. Also included within the scope are peptides, polypeptides or proteins which are differentially modified during or after synthesis, for example, by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the peptide, protein or polypeptide.

The term amino acid "modification" refers to a substitution of an amino acid, or the derivation of an amino acid by the addition and/or removal of chemical groups to/from the amino acid, and includes substitution with any of the 20 amino acids commonly found in human proteins, as well as atypical or non-naturally occurring amino acids. Commercial sources of atypical amino acids include Sigma-Aldrich (Milwaukee, Wis.), ChemPep Inc. (Miami, Fla.), and Genzyme Pharmaceuticals (Cambridge, Mass.). Atypical amino acids may be purchased from commercial suppliers, synthesized de novo, or chemically modified or derivatized from naturally occurring amino acids.

As used herein an amino acid "substitution" refers to the replacement of one amino acid residue by a different amino acid residue. The substituted amino acid may be any of the amino acids commonly found in human proteins, as well as atypical or non-naturally occurring amino acids.

The terms "A chain peptide" and "B chain peptide" are interchangeable with "insulin A chain peptide" and "insulin B chain peptide."

As used herein, reference to a compound that is a "derivative thereof" refers to a compound that is adapted or modified from an ancestral compound and has a similar but new structure and which has a similar biological activity as the ancestral compound. In some embodiments, the ancestral compound is a small molecule, a peptide, polypeptide, protein or an insulin analog as described herein. In some embodiments, the ancestral compound is a peptide, polypeptide, protein or insulin analog which may be modified to include any chemical modification, comprise single or multiple substitutions, deletions and/or additions of any molecules associated with the protein or peptide, such as carbohydrates, lipids and/or proteins or peptides. In one embodiment, "derivatives" of proteins, polypeptides or peptides include those modified analogues resulting from glycosylation, acetylation, phosphorylation, amidation, palmitoylation, myristoylation, isoprenylation, lipidation, alkylation, derivatization, introduction of protective/blocking groups, proteolytic cleavage or binding to an antibody or to another cellular ligand.

Throughout the application, all references to a particular amino acid position by letter and number (e.g. position A5 or B5) refer to the amino acid at that position of either the A chain (e.g. position A5) or the B chain (e.g. position B5) in the respective A chain or B chain of venom insulin Con-G1 Ins from *Conus geographus*, or the corresponding amino acid position in any analogs thereof. For example, a reference herein to "position B17" absent any further elaboration would mean the corresponding position B15 of the B chain of human insulin as Con-Ins G1 has two additional N-terminal B chain residues.

As used herein, the phrase "at a position corresponding to amino acid number" refers to the relative position of the amino acid compared to surrounding amino acids with reference to a defined amino acid sequence. For instance, in some embodiments, when compared to human insulin (see FIG. 1) the B chain of the insulin analog of the invention may have one or two additional N-terminal amino acids, such as present in Con-Ins G1. In an example, upon performing a protein alignment the skilled person would readily comprehend that the leucine ($15^{th}$ amino acid) of the B chain of naturally occurring human insulin corresponds to the $17^{th}$ amino acid of the B chain Con-Ins G1 (see FIG. 1). In a preferred embodiment of the invention, this $15^{th}$ amino acid of the B chain of naturally occurring human insulin is an aromatic residue or a large aliphatic residue and/or 20' amino acid of the B chain of naturally occurring human insulin is an aromatic residue or a large aliphatic residue.

The term "monomeric insulin" refers to insulin and insulin analogs that are less prone to forming higher order species (such as dimers, tetramers, hexamers etc) than human insulin. Preferably, the insulin or insulin analog is fully or substantially monomeric, e.g., at least 50%, 60%, 70%, 75%, 80%, 85%, 90%, 95%, 97%, 98%, 99%, or 100% monomeric.

As would be understood by the person skilled in the art, the term "therapeutic" refers to a treatment, therapy, or drug that can treat a disease or condition or that can ameliorate one or more symptoms associated with a disease or condition. As used herein, a therapeutic can refer to a therapeutic compound, including, but not limited to proteins, peptides, nucleic acids (e.g. CpG oligonucleotides), small molecules, vaccines, allergenic extracts, antibodies, gene therapies, other biologics or small molecules.

As used herein, the term "subject" refers to any organism susceptible to insulin related disorders. As would be understood by the person skilled in the art, the term "subject" and "patient" can be used interchangeably. For example, the subject can be a mammal, avian, arthropod, chordate, amphibian or reptile. Exemplary subjects include but are not limited to human, primate, livestock (e.g. sheep, cow, chicken, horse, donkey, pig), companion animals (e.g. dogs, cats), laboratory test animals (e.g. mice, rabbits, rats, guinea pigs, hamsters), captive wild animal (e.g. fox, deer). In one example, the subject is a mammal. In one example, the subject is human.

The term "treating" as used herein, includes prophylaxis of the specific disorder or condition, or alleviation of the symptoms associated with a specific disorder or condition and/or preventing or eliminating said symptoms. For example, as used herein the term "treating diabetes" will refer in general to maintaining glucose blood levels within acceptable levels and may include increasing or decreasing blood glucose levels depending on a given situation.

As the skilled person would understand, insulin analogs will be administered in a therapeutically effective amount. The terms "effective amount" or "therapeutically effective amount," as used herein, refer to an amount of an insulin analog being administered sufficient to relieve to some extent one or more of the symptoms of the disease or condition being treated. The result can be reduction and/or alleviation of the signs, symptoms, or causes of a disease, or any other desired alteration of a biological system. For example one symptom would be the prevention or treatment of hyperglycemia. An "effective amount" of an insulin analog is an amount effective to achieve a desired pharmacologic effect or therapeutic improvement without undue adverse side effects. By way of example only, therapeutically effective amounts may be determined by routine experimentation, including but not limited to a dose escalation clinical trial. The term "therapeutically effective amount" includes, for example, a prophylactically effective amount. It is understood that "an effective amount" or "a therapeutically effective amount" can vary from subject to subject, due to variation in metabolism of the compound of any of age, weight, general condition of the subject, the condition being treated, the severity of the condition being treated, and the judgment of the prescribing physician. Thus, it is not always possible to specify an exact "effective amount." However, an appropriate "effective" amount in any individual case may be determined by one of ordinary skill in the art using routine experimentation. Where more than one therapeutic agent is used in combination, a "therapeutically effective amount" of each therapeutic agent can refer to an amount of the therapeutic agent that would be therapeutically effective when used on its own, or may refer to a reduced amount that is therapeutically effective by virtue of its combination with one or more additional therapeutic agents.

The term "onset" of activity, as used herein refers to the length of time before insulin reaches the blood stream and begins to lower blood glucose levels, "peak" refers to the time period when the insulin analog best lowers blood glucose levels and "duration" refers to how long the insulin continues to work, i.e. lower blood glucose levels. The person skilled in the art would be aware that onset, peak and duration of an insulin analog may vary depending on factors such as the patient, the condition of the patient, and the route of administration.

The term "IR" as used herein includes wild-type IR and variants thereof including allelic variants and naturally occurring mutations and genetically engineered variants. It will be readily apparent to the skilled person that IR may be derived from other species not specifically disclosed herein. Furthermore, the skilled person will have no difficulties identifying such other suitable IR given the known conservation of IR sequences from primitive organisms through to mammals and humans.

Venom Insulin Crystals

In an aspect, the present invention provides a crystal comprising venom insulin. As used herein, the term "crystal" means a structure (such as a three dimensional (3D) solid aggregate) in which the plane faces intersect at definite angles and in which there is a regular structure (such as internal structure) of the constituent chemical species. The term "crystal" refers in particular to a solid physical crystal form such as an experimentally prepared crystal.

Crystals according to the invention may be prepared using venom insulin from organisms in the genus *Conus*, such as *Conus geographus* and *Conus tulipa*. Some embodiments relate to insulins from the venom of *Conus geographus*. However, the venom insulin may also be from other species. Typically, these insulins comprise a 20 amino acid A chain and a 23 amino acid B, however the length of the A and B chain can vary. The amino acids in the A and B chain may be post-translationally modified; example post-translational modifications include but are not limited to glutamic acid may be replaced by γ-carboxylated glutamic acid (also referred to as the conjugate base gamma carboxyglutamate), proline may be replaced by hydroxyproline, the C-terminus may be amidated, cysteine may be replaced by seleoncysteine. The person skilled in the art will recognize that other post-translation modifications are possible.

In a preferred embodiment the venom insulin is Con-Ins G1 and has the sequence shown below:

```
A-chain:
                                          (SEQ ID NO: 22)
GVVyHCCHRPCSNAEFKKYC*

B-chain:
                                          (SEQ ID NO: 23)
TFDTOKHRCGSyITNSYMDLCYR
``` where γ is 7-carboxylated glutamic acid, O is hydroxyproline and *the C-terminus of the A-chain is amidated. However, the insulin polypeptide may also be obtained from other species or a non-native designed sequence.

Crystals may be constructed with wild-type sequences or variants thereof, including naturally occurring mutations as well as genetically engineered variants. Typically, variants have at least 90, 95 or 98% sequence identity with a corresponding wild-type venom insulin.

The production of a crystal comprising venom insulin is described below.

In preferred embodiments, the present invention provides a crystal of Con-Ins G1 having a space group P432 with unit cell dimensions of a=b=c=74.91 Å with up to about 2% variation in any cell dimension.

In a preferred embodiment, a crystal comprising venom insulin has the atomic coordinates set forth in Appendix I. As used herein, the term "atomic coordinates" refer to a set of values which define the position of one or more atoms with reference to a system of axes. It will be understood by those skilled in the art that atomic coordinates may be varied, without affecting significantly the accuracy of models derived therefrom; thus, although the invention provides a very precise definition of a preferred atomic structure, it will be understood that minor variations are envisaged and the claims are intended to encompass such variations. Preferred are variants in which the root mean square deviation (RMSD) of the x, y and z co-ordinates for all backbone atoms other than hydrogen is less than 2.0 Å (preferably less than 1.5 Å, 1.3 Å, 1 Å, 0.7 Å or less than 0.3 Å) compared with the coordinates given in Appendix I. It will be readily appreciated by those skilled in the art that a 3D rigid body rotation and/or translation of the atomic coordinates does not alter the structure of the molecule concerned.

Crystal Structure of Venom Insulin

In further aspects, a crystal structure of a venom insulin, or a region thereof is also provided. In some embodiments, the venom insulin is Con-Ins G1. In some embodiments, the crystal structure of a venom insulin is the structure of Con-Ins G1 as defined by the atomic coordinates of Appendix I.

The atomic coordinates obtained experimentally for venom insulin are shown in Appendix I. However, a person skilled in the art will appreciate that a set of atomic coordinates determined by X-ray crystallography is not without standard error. Accordingly, any set of structure coordinates for venom insulin that has a root mean square deviation of protein backbone atoms of less than 0.75 Å when superimposed (using backbone atoms) on the atomic coordinates listed in Appendix I shall be considered identical.

The present invention also comprises the atomic coordinates of venom insulin that substantially conform to the atomic coordinates listed in Appendix I. A structure that "substantially conforms" to a given set of atomic coordinates is a structure wherein at least about 50% of such structure has an RMSD of less than about 2.0 Å for the backbone atoms in secondary structure elements in each domain, preferably less than about 1.5 Å for the backbone atoms in secondary structure elements in each domain, and more preferably, less than about 1.3 Å for the backbone atoms in secondary structure elements in each domain, and, in increasing preference, less than about 1.0 Å, less than about 0.7 Å, less than about 0.5 Å, and most preferably, less than about 0.3 Å for the backbone atoms in secondary structure elements in each domain.

In a more preferred embodiment, a structure that substantially conforms to a given set of atomic coordinates is a structure wherein at least about 75% of such structure has the recited RMSD value, and more preferably, at least about 90% of such structure has the recited RMSD value, and most preferably, about 100% of such structure has the recited RMSD value.

In an even more preferred embodiment, the above definition of "substantially conforms" can be extended to include atoms of amino acid side chains. As used herein, the phrase "common amino acid side chains" refers to amino acid side chains that are common to both the structure which substantially conforms to a given set of atomic coordinates and the structure that is actually represented by such atomic coordinates.

It will be appreciated that a set of atomic coordinates for a polypeptide is a relative set of points that define a shape in three dimensions. Thus, it is possible that an entirely different set of coordinates could define a similar or identical shape. Moreover, slight variations in the individual coordinates will have little effect on overall shape.

The variations in coordinates may be generated due to mathematical manipulations of the structure coordinates. For example, the structure coordinates set forth in Appendix I could be manipulated by crystallographic permutations of the structure coordinates, fractionalisation of the structure coordinates, integer additions or subtractions to sets of the structure coordinates, inversion of the structure coordinates, or any combination thereof.

Alternatively, modification in the crystal structure due to mutations, additions, substitutions, and/or deletions of amino acids, or other changes in any of the components that make up the crystal could also account for variations in structure coordinates.

Various computational analyses are used to determine whether a molecular complex or a portion thereof is sufficiently similar to all or parts of the structure of the venom insulin described above. Such analyses may be carried out using software known to the person skilled in the art, for example PDBeFOLD (Krissinel and Henrick, 2004), DALI (Holm and Rosenström, 2010), LSQMAN (Kleywegt and Jones, 1994) and CHIMERA (Pettersen et al. 2004).

Comparisons typically involve calculation of the optimum translations and rotations required such that the root mean square difference of the fit over the specified pairs of equivalent atoms is an absolute minimum. This number is given in angstroms. Accordingly, structural coordinates of venom insulin within the scope of the present invention include structural coordinates related to the atomic coordinates listed in Appendix I by whole body translations and/or rotations. Accordingly, RMSD values listed above assume that at least the backbone atoms of the structures are optimally superimposed which may require translation and/or rotation to achieve the required optimal fit from which to calculate the RMSD value.

In some embodiments, there is also provided subsets of said atomic coordinates listed in Appendix I and subsets that conform substantially thereto. Preferred subsets define one or more regions of the venom insulin, for example, (i) the A chain, (ii) the B chain, (iii) the hydrophobic core (for example in Con-Ins G1 the hydrophobic core comprises the side chains of residues ValA2, CysA6, CysA11, PheA16, TyrA19, ArgB6, IleB11, TyrB15 and LeuB18), (iv) the PTM and residues interacting with the PTM, (v) the receptor binding surface (for example, the IR binding surface of Con-Ins G1); (vi) TyrB15 and residues interacting with TyrB15; (vii) TyrB20 and residues interacting with TyrB20; (viii) PheA16 and residues interacting with PheA16. (ix) subsets of residues in the immediate vicinity the respective A-chain termini.

A three dimensional structure of a venom insulin or region thereof which substantially conforms to a specified set of atomic coordinates can be modelled by a suitable modelling computer program such as MODELER (Sali and Blundell, 1993), as implemented in the Insight II Homology software package (Insight II (97.0), MSI, San Diego), using information, for example, derived from the following data: (1) the amino acid sequence of the venom insulin; (2) the amino acid sequence of the related portion(s) of the protein represented by the specified set of atomic coordinates having a three dimensional configuration; and, (3) the atomic coordinates of the specified three dimensional configuration. A three dimensional structure of a venom insulin which substantially conforms to a specified set of atomic coordinates can also be calculated by a method such as molecular replacement, which is described in detail below.

Structure coordinates/atomic coordinates are typically loaded onto a machine readable-medium for subsequent computational manipulation. Thus models and/or atomic coordinates are advantageously stored on machine-readable media, such as magnetic or optical media and random-access or read-only memory, including tapes, diskettes, hard disks, CD-ROMs and DVDs, flash memory cards or chips, servers and the internet. The machine is typically a computer. The present invention also provides a computer readable media having recorded thereon data representing a model and/or the atomic coordinates of Con-Ins G1. Also provided is a computer readable media having recorded thereon coordinate data according to Appendix I, or a subset thereof of either, where said coordinate data define a three dimensional structure of Con-Ins G1 or a region of Con-Ins G1.

The present invention also provides a set of atomic coordinates as shown in Appendix I, or a subset thereof or either, in which said coordinates define a three dimensional structure of a venom insulin. The structure coordinates/atomic coordinates may be used in a computer to generate a representation, e.g. an image, of the three-dimensional structure of the cone snail insulin crystal which can be displayed by the computer and/or represented in an electronic file.

The structure coordinates/atomic coordinates and models derived therefrom may also be used for a variety of purposes such as drug discovery, biological reagent (binding protein) selection and X-ray crystallographic analysis of other protein crystals. In one aspect, the use of the structure of Con-Ins G1 as a structural model is provided. In some embodiments, the structural model may be used for identification of insulin analogs. The present invention also encompasses insulin analogs identified using the structure of Con-Ins G1 as a structural model.

The three-dimensional structure of Con-Ins G1 or a region thereof may be used to develop models useful for drug design and in silico screening of candidate compounds that interact with and/or modulate IR. Other physicochemical characteristics may also be used in developing the model, e.g. bonding, electrostatics etc.

Generally the term "in silico" refers to the creation in a computer memory, i.e., on a silicon or other like chip. Unless stated otherwise "in silico" means "virtual." When used herein the term "in silico" is intended to refer to screening methods based on the use of computer models rather than in vitro or in vivo experiments.

Molecular Replacement

The crystal structure of Con-Ins G1 provided herein may also be used to model/solve the structure of a new crystal using molecular replacement.

In some aspects, the present invention also provides the use of the structure of venom insulin, or a subset thereof, as a structural model.

In some embodiments, the atomic coordinates of venom insulin, such as those set forth in Appendix I, or a region of venom insulin can be used for determining at least a portion of the three-dimensional structure of a molecular complex which contains at least some structural features similar to the venom insulin. In particular, structural information about another crystallised venom insulin or insulin analog may be obtained. This may be achieved by any of a number of well-known techniques, including molecular replacement.

Methods of molecular replacement are generally known by those of skill in the art, for example PHASER (McCoy et al. 2007). Methods of molecular replacement are generally described in Brunger, 1997; Navaza and Saludjian, 1997; Tong and Rossmann, 1997; Bentley, 1997; Lattman, 1985; Rossmann, 1972.

Generally, X-ray diffraction data are collected from the crystal of a crystallised target structure. The X-ray diffraction data is transformed to calculate a Patterson function. The Patterson function of the crystallised target structure is compared with a Patterson function calculated from a known structure (referred to herein as a search structure). The Patterson function of the crystallised target structure is rotated on the search structure Patterson function to determine the correct orientation of the crystallised target structure in the crystal. The translation function is then calculated to determine the location of the target structure with respect to the crystal axes. Once the crystallised target structure has been correctly positioned in the unit cell, initial phases for the experimental data can be calculated. These phases are necessary for calculation of an electron density map from which structural differences can be observed and for refinement of the structure. Preferably, the structural features (e.g., amino acid sequence, conserved di-sulphide bonds, and beta-strands or beta-sheets) of the search molecule are related to the crystallised target structure.

The electron density map can, in turn, be subjected to any well-known model building and structure refinement techniques to provide a final, accurate structure of the unknown crystallised molecular complex (e.g. see Jones et al. 1991; Brunger et al. 1998).

Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure. By using molecular replacement, all or part of the structure coordinates of venom insulin provided herein (and set forth in Appendix I) can be used to determine the structure of a crystallised molecule/molecular complex whose structure is unknown more rapidly and efficiently than attempting to determine such information ab initio.

The structure of any portion of any crystallised molecule/molecular complex that is sufficiently homologous to any portion of the venom insulin may be solved by this method. This method is especially useful in determining the structure of insulin analogs that were designed using the methods described herein.

All of the molecules/molecular complexes referred to herein may be studied using well-known X-ray diffraction techniques and may be refined versus 1.5-3.5 Å resolution X-ray data to an R value of about 0.25 or less using computer software, such as X-PLOR (Yale University, distributed by Molecular Simulations, Inc.; see Brunger, 1996), REFMAC (Murshudov et al. 1997), PHENIX (Adams et al. 2010) and BUSTER (distributed by Global Phasing Ltd, Bricogne et al. 2011). This information may thus be used to optimize known insulin analogs, and more importantly, to design new or improved insulin analogs.

Methods for Crystallising Venom Insulin

The present invention also provides a method for producing crystals comprising venom insulin. Crystal forms of venom insulin disclosed herein can be obtained by the following crystallization methods.

In one aspect, the present invention provides a method for crystallizing venom insulin comprising the steps:

(a) providing an aqueous solution of venom insulin;

(b) optionally, concentrating the solution of step (a); and (c) diluting the solution of step (a) or step (b) with a precipitant solution so that the final concentration of the venom insulin is in the range of 0.5 mg/mL to 10 mg/mL.

The aqueous solution of venom insulin provided in step (a) may be buffered or unbuffered. Any suitable buffer known to a person skilled in the art may be used. Non-limiting examples for the venom insulin solutions include Tris-HCl, sodium phosphate, and triethanolamine buffer. In case the desired pH value is not obtained, adjusting the pH by addition of a base or acid such as ammonium chloride, sodium acetate, sodium hydroxide, potassium hydroxide, or hydrochloric acid can be performed. Preferably, the solution of step (a) contains 10 mM HCl.

Optionally, the solution may optionally then be concentrated. In some embodiments, the solution is concentrated by centrifugal filtration. However, any suitable technique known to a person skilled in the art may be used. After the concentration step (b) the concentration of the venom insulin should be in the range of 1.0 mg/mL to 20 mg/mL. Preferably, the concentration of the venom insulin is approximately 4.0 mg/mL. This is the concentration of the venom insulin at the end of step (b) before dilution with the buffered precipitant solution of step (c). The concentration of the venom insulin in the concentrated solution of step (b) or during the concentration in step (b) or after the concentration of step (b) could be determined, for instance, by the Bradford protein assay or by other routine methods including UV absorbance spectroscopy.

In step (c) a precipitant solution is added to the solution of step (b). Preferably the solution of step (b) is diluted with the precipitant solution at a ratio of between 1:4 to 4:1 (solution of step (b):buffered precipitant solution), most preferably at a ratio of 1:1.

The precipitant solution may comprise at least one small organic amphiphilic molecule and/or at least one inorganic salt. In some embodiments, the small organic amphiphilic molecule may be selected from the group comprising or consisting of glycerol, ethylene glycol, butyl ether, benzamidine, dioxane, ethanol, isopropanol, butanol, pentanol, methyl pentanediol, pentanediol, hexanediol, heptanetriol, dithiothreitol, MES, Tris, Tris-HCl, Bis-Tris, imidazole, bicine, trimethylamine N-oxide, succinic acid, DL-malate, CHES, CAPS, glycine, CAPSO, ADA, MOPS, Bis-Tris propane, SPG, MIB, PCB, MMT, N-[2-hydroxyethyl]piperazine-N'-[2-ethanesulfonic acid] (HEPES), TRIS, sucrose and combinations thereof. In a preferred embodiment, the small organic amphiphilic molecule comprises DL-malate, TRIS and MES. In some embodiments, the small organic amphiphilic molecules may act as a buffer. In some embodiments, the pH of the small organic amphiphilic molecules in solution may be adjusted to between about 2.0 and about 11.0 and any pH in between, for example 2.0, 2.5, 3.0, 3.5, 4.0, 4.5, 5.0, 5.5, 6.0, 6.5, 7.0, 7.5, 8.0, 8.5, 9.0, 9.5, 10.0, 10.5 and 11.0. In some embodiments, the pH is between about 8.0 and about 10.0. In a preferred embodiment, the pH is 9.0.

In some embodiments, the amount of all small organic amphiphilic molecules in the precipitant solution is between 1% weight/volume and 50% weight/volume, preferably between 5% weight/volume and 20% weight/volume, and more preferably between 8% weight/volume and 12% weight/volume of the small organic amphiphilic molecule in regard to the total weight of the buffered precipitant solution. In a preferred embodiment, the buffered precipitant solution comprises 10% weight/volume of the small organic amphiphilic molecule.

The term "at least one small organic amphiphilic molecule" means that mixtures of the afore-mentioned small organic amphiphilic molecules may be used. In case mixtures of small organic amphiphilic molecules are used, the amount used refers to the total amount of all small organic amphiphilic molecules together.

The precipitant solution may also comprise an inorganic salt. In some embodiments, the inorganic salts is selected from the group comprising or consisting of ammonium chloride, ammonium sulphate, ammonium acetate, ammonium fluoride, ammonium bromide, ammonium iodide, ammonium nitride, cadmium chloride, cadmium sulphate, calcium chloride, calcium acetate, cesium chloride, cesium sulphate, cobalt chloride, ferric chloride, lithium acetate, lithium chloride, lithium nitrate, lithium sulphate, magnesium acetate, magnesium formate, magnesium nitrate, nickel chloride, potassium acetate, potassium bromide, potassium fluoride, potassium formate, potassium iodide, potassium nitrate, potassium thiocyanate, potassium/sodium tartrate, sodium acetate, sodium bromide, sodium fluoride, sodium iodide, sodium nitrate, sodium phosphate, sodium sulphate, sodium thiocyanate, zinc chloride, zinc sulphate, zinc acetate, magnesium chloride, sodium chloride, sodium cacodylate, sodium hydroxide, potassium chloride, potassium hydroxide, potassium sulphate, sodium acetate, sodium tartrate, ammonium formate, di-ammonium tartrate, sodium malonate, di-sodium tartrate, sodium succinate, and sodium succinate and combinations thereof. In a preferred embodiment, the inorganic salt is ammonium sulphate.

In some embodiments, the amount of the at least one inorganic salt in the precipitant solution is between about 50 mM and about 4000 mM, between about 1000 mM and about 3000 mM, between about 1500 mM and about 2500 mM or about 2000 mM. In case more than one inorganic salt is used, the afore-mentioned concentration refers to the concentration of all inorganic salts together and not to the concentration of each single salt used in the mixture of inorganic salts.

In some embodiments, the precipitant solution may be buffered. Any buffer known to a person may be used. In some embodiments, the buffer comprises or consists of citric acid, sodium acetate, sodium citrate, sodium cacodylate, HEPES sodium, TRIS HCl, CAPSO, CAPS, sodium malate, sodium MES and the like and combinations thereof. In some embodiments, the precipitant solution may have a pH between about 2.0 and about 11.0 and any pH in between, for example 2.0, 2.5, 3.0, 3.5, 4.0, 4.5, 5.0, 5.5, 6.0, 6.5, 7.0, 7.5, 8.0, 8.5, 9.0, 9.5, 10.0, 10.5 and 11.0. In some embodiments, the precipitant solution may have a pH between about 8.0 and about 10.0. In a preferred embodiment, the precipitant solution may have a pH of 9.0.

In some embodiments, the buffered precipitant solution contains more than 1 M of at least one inorganic salt and/or between 5% by weight and 20% by weight of at least one small organic amphiphilic molecule. In a preferred embodiment, the precipitant solution comprises 2.0M ammonium sulphate and 10% DL-malate-MES-Tris (pH 9.0).

In theory, at least one precipitating agent in the diluted solution of step (c) competes with the protein molecules for water, thus leading to supersaturation of the protein. Crystals can normally only grow from supersaturated states, and thus they can grow from precipitates. Salts, polymers, and organic solvents are suitable precipitating agents. In addition to the components of the buffered precipitant solution listed above, the solution of step (c) may contain further precipitating agents.

In some embodiments, the hanging drop or the sitting drop methods are used for crystallization. The "hanging drop vapor diffusion" technique is the most popular method for the crystallization of macromolecules. By this method, a drop composed of a mixture of sample and reagent is placed in vapor equilibration with a liquid reservoir of reagent. Typically the drop contains a lower reagent concentration than the reservoir. To achieve equilibrium, water vapor leaves the drop and eventually ends up in the reservoir. As water leaves the drop, the sample undergoes an increase in relative supersaturation. Both the sample and reagent increase in concentration as water leaves the drop for the reservoir. Equilibration is reached when the reagent concentration in the drop is approximately the same as that in the reservoir.

Insulin Analogs

Wild type insulin comprises an A chain peptide and a B chain peptide. Wild type human insulin A chain is represented by the sequence GIVEQCCTSICSLYQLENYCN (SEQ ID NO: 24). Wild type human insulin B chain is represented by the sequence (SEQ ID NO: 25)
FVNQHLCGSHLVEALYLVCGERGFFYTPKT.

The present inventors have determined the three-dimensional structure of Con-G1 Ins, a monomeric insulin that lacks an equivalent to the aromatic triplet PheB24-PheB25-TyrB26 of human insulin. Without wishing to be bound by theory it is thought that the side chain of TyrB15 may compensate for the absence of the critical human insulin PheB24 in terms of IR engagement. It is also thought that the side chain of Con-Ins G1 TyrB20 may be involved in compensating for the lack of an equivalent to human insulin PheB24. The potential importance of these residues could not be predicted based on sequence analysis. The structural findings provided herein provide a platform for the design of a novel class of therapeutic human insulin analogues that are intrinsically monomeric and rapid-acting.

In one aspect, the present invention provides an insulin analog comprising an A chain peptide and a B chain peptide, wherein the B chain comprises an aromatic or large aliphatic residue at a position corresponding to amino acid number 15 of the B chain of human insulin and/or an aromatic or large aliphatic residue at a position corresponding to amino acid number 20 of the B chain of human insulin, wherein the analog comprises at least one amino acid found in human insulin but lacking in the corresponding position of *Conus geographus* insulin, and wherein the A chain peptide and the B chain peptide are bonded together across at least one pair of cysteine residues. In some embodiments, the aromatic residue or large aliphatic residue can be a natural or a non-natural amino acid.

The co-crystal structure of an insulin-IR complex revealed that the side chain of PheB24 plays a unique role as an "anchor" within a nonpolar pocket (referred to as the B24 related binding pocket) defined by the IR and insulin B chain (Menting et al. 2014). Without wishing to be bound by theory, the present invention envisions that the large aliphatic or aromatic substitutions at position 15 and/or position 20 of the B chain of human insulin may compensate for the lack of PheB24 by inserting in the B24 related binding pocket. It is contemplated that the side-chains of large aliphatic or aromatic residues may be physical and chemically compatable with B24 related binding pocket.

In some embodiments, the aromatic or large aliphatic residue at a position corresponding to amino acid number 15 of the B chain of human insulin is selected from the group consisting of tyrosine, phenylalanine, 4-methylphenylalanine, histidine, tryptophan, methionine, cyclopentylalanine and cyclohexylalanine. In some embodiments, the aromatic or large aliphatic residue at a position corresponding to amino acid number 20 of the B chain of human insulin is selected from the group consisting of tyrosine, phenylalanine, 4-methylphenylalanine, histidine, tryptophan, methionine, cyclopentylalanine and cyclohexylalanine. The aromatic residue or large aliphatic may be a natural or non-natural amino acid.

In some embodiments, the B chain comprises an aromatic residue at a position corresponding to amino acid number 15 of the B chain of human insulin and/or an aromatic residue at a position corresponding to amino acid number 20 of the B chain of human insulin. The aromatic residue may be a natural or non-natural amino acid. For example, the aromatic amino acid can be tyrosine, phenylalanine, tryptophan, histidine, 4-acetylphenylalanine and the like.

In some embodiments, the insulin analog has a tyrosine at a position corresponding to amino acid number 15 of the B chain of human insulin. In some embodiments, the insulin analog has a tyrosine at a position corresponding to amino acid number 20 of the B chain of human insulin. In some embodiments, the insulin analog has a tyrosine at a position corresponding to amino acid number 15 of the B chain of human insulin and/or a tyrosine at a position corresponding to amino acid number 20 of the B chain of human insulin. In some embodiments, the insulin analog has a phenylalanine at a position corresponding to amino acid number 15 of the B chain of human insulin and/or a phenylalanine at a position corresponding to amino acid number 20 of the B chain of human insulin. In some embodiments, the insulin analog has a tryptophan at a position corresponding to amino acid number 15 of the B chain of human insulin and/or a tryptophan at a position corresponding to amino acid number 20 of the B chain of human insulin. In some embodiments, the insulin analog has a 4-acetylphenylalanine at a position corresponding to amino acid number 15 of the B chain of human insulin and/or a 4-acetylphenylalanine at a position corresponding to amino acid number 20 of the B chain of human insulin.

In some embodiments, the B chain comprises a large aliphatic residue at a position corresponding to amino acid number 15 of the B chain of human insulin and/or a large aliphatic residue at a position corresponding to amino acid number 20 of the B chain of human insulin. As used herein, a "large aliphatic" residue has a side-chain that is larger than the leucine (naturally occurring in human insulin at position 15 and 20) side-chain. For example, in some embodiments the side-chain of large aliphatic residue may have the same number or more non-hydrogen atoms compared to leucine. In some embodiments the side-chain of the large aliphatic residue has a greater side-chain volume when compared to leucine. In some embodiments, the side-chain of large aliphatic residue has a greater molecular weight when compared to leucine. In some embodiments, the side-chain of the large aliphatic residue has more conformational flexibility when compared to leucine. The large aliphatic" residue may be may be a natural or non-natural amino acid. For example, the large aliphatic residue may methionine, isoleucine, cyclopentylalanine or cyclohexylalanine and the like.

In some embodiments, the insulin analog has a methionine at a position corresponding to amino acid number 15 of the B chain of human insulin. In some embodiments, the insulin analog has a methionine at a position corresponding to amino acid number 20 of the B chain of human insulin. In some embodiments, the insulin analog has a cyclohexylalanine at a position corresponding to amino acid number 15 of the B chain of human insulin and/or a cyclohexylalanine at a position corresponding to amino acid number of the B chain of human insulin. In some embodiments, the insulin analog has a cyclopentylalanine at a position corresponding to amino acid number 15 of the B chain of human insulin and/or a cyclopentylalanine at a position corresponding to position 20 of the B chain of human insulin.

In some embodiments, the insulin analogs have modified B chains which lack the aromatic triplet PheB24-PheB25-TyrB26 thought essential for IR binding, and have, in most cases, shorter B-chains compared to human insulin. In some embodiments, the B chain is truncated at the C-terminal end when compared to human insulin. In some embodiments, the B chain is lacking one or more of the nine C-terminal amino acids of human insulin, for example, the B chain is lacking one, two, three, four, five, six, seven, eight or nine C-terminal amino acids of human insulin. In some embodiments, the B chain is at least lacking PheB24 of human insulin. In some embodiments, the B chain is at least lacking the human B chain aromatic triplet (amino acids PheB24-PheB25-TyrB26 of human insulin). These residues may be absent or may be substituted such that the amino acids at a position corresponding to amino acid number 24, 25 and/or 26 of the B chain of human insulin are not phenylalanine, phenylalanine or tyrosine, respectively.

In some embodiments, the insulin analog comprises an A chain peptide comprising the sequence Gly-$X_{A2}$-$X_{A3}$-$X_{A4}$-$X_{A5}$-Cys$_{A6}$-Cys$_{A7}$-$X_{A8}$-$X_{A9}$-$X_{A10}$-Cys$_{A11}$-$X_{A12}$-$X_{A13}$-$X_{A14}$-$X_{A15}$-$X_{A16}$-$X_{A17}$-$X_{A18}$-$X_{A19}$-Cys$_{A20}$-$X_{A21}$-$X_{A22}$-$X_{A23}$-$X_{A24}$-$X_{A25}$-$X_{A26}$-$X_{A27}$-$X_{A28}$-$X_{A29}$-$X_{A30}$-$X_{A31}$-$X_{A32}$-$X_{A33}$-$X_{A34}$, wherein $X_{A2}$=Val or Ile; $X_{A3}$=Val or Ala; $X_{A4}$=Glu, Asp, gamma carboxyglutamate or Cys; $X_{A5}$=Gln, Glu, gamma carboxyglutamate, His or Val; Cys$_{A6}$, Cys$_{A7}$, and Cys$_{A11}$ are independently Cys or selenocysteine; $X_{A8}$=Thr, His, Asp, Gln, Tyr, Lys, Ala or Val; $X_{A9}$=Ser, Arg, Asn, Gly, His or Lys; $X_{A10}$=Ile, Pro, Tyr, Ala, Ser, Val, Phe, His or Thr; $X_{A12}$=Ser or Thr; $X_{A13}$=Leu, Asn, Val, Arg or Asp; $X_{A14}$=Tyr, Ala, Gln, His, Asp or Glu; $X_{A15}$=Gln, Glu or Thr; $X_{A16}$=Phe, Leu, or Ala; $X_{A17}$=Glu, Gln, Lys, Arg, Ile, Met, Thr or Ser; $X_{A18}$=Lys, Ser, Thr, Asn, Gln or Glu; $X_{A19}$=Tyr or Phe; Cys$_{A20}$=Cys, selenocysteine, amidated Cys or amidated selenocysteine; $X_{A21}$=Asn, Pro, His, Ser, Gly, Ala, or is absent; $X_{A22}$=Pro, Asn, Thr, Leu, Ser or is absent; $X_{A23}$=Thr, Leu, Val, Ser or is absent; $X_{A24}$=Arg, Thr, Met, Gln, Leu or is absent; $X_{A25}$=Glu, Gly or is absent; from $X_{A26}$=Ser, Leu or is absent; $X_{A27}$ to $X_{A31}$ are independently Ser or are absent; $X_{A32}$=Ala, Ser or is absent; $X_{A33}$=Ala, Val or is absent; and $X_{A34}$=Ala or is absent (SEQ ID NO: 1); and a B chain peptide comprising the sequence $X_{B1}$-$X_{B2}$-$X_{B3}$-$X_{B4}$-$X_{B5}$-$X_{B6}$-$X_{B7}$-$X_{B8}$-Cys$_{B9}$-$X_{B10}$-$X_{B11}$-$X_{B12}$-$X_{B13}$-$X_{B14}$-$X_{B15}$-$X_{B16}$-$X_{B17}$-$X_{B18}$-$X_{B19}$-$X_{B20}$-Cys$_{B21}$-$X_{B22}$-$X_{B23}$-$X_{B24}$-$X_{B25}$-$X_{B26}$-$X_{B27}$-$X_{B28}$-$X_{B29}$-$X_{B30}$-$X_{B31}$-$X_{B32}$-$X_{B33}$-$X_{B34}$-$X_{B35}$-$X_{B36}$-$X_{B37}$-$X_{B38}$-$X_{B39}$, wherein $X_{B1}$=Thr, Asn, Ser or is absent; $X_{B2}$=Phe, Ser, Asn, Thr, Gln or is absent; $X_{B3}$=Ala, Asp, Gly, Pro, Leu, Phe, or His; $X_{B4}$=Ala, Thr, Pro, Asp, Val or Gly; $X_{B5}$=Asn, Pro, His, Thr, Arg, Lys, Ser or hydroxyproline; $X_{B6}$=Lys, Glu, Asn, Asp, Arg, Gln or Gly; $X_{B7}$=His, Tyr, Arg or Ile; $X_{B8}$=Arg, Thr, Ile, Ser, Leu, Tyr or Lys; Cys$_{B9}$=Cys or selenocysteine; $X_{B10}$=Gly, Gln or Asp; $X_{B11}$=Ser, Leu, Gly or Pro; $X_{B12}$=His, Glu, gamma carboxyglutamate, Asp, or Asn; $X_{B13}$=Ile, Leu, Asp, Val or Ala; $X_{B14}$=Thr, Ala, Pro, Val or Arg; $X_{B15}$=Asn, Asp, Ala, Val, Thr, Pro or Glu; $X_{B16}$=Ala, Ser, Gln, His, Thr, Tyr, Arg or Gly; $X_{B17}$=Thr, Tyr, Pro, Leu or Gly; $X_{B18}$=Tyr, Met, Val, Gln, Ile, Asp, Gly, Asn or Leu; $X_{B19}$=Leu, Asp, Gln, Gly, Lys, Glu, Arg, Ser or Thr; $X_{B20}$=Val, Leu or Lys; C$_{B21}$=Cys, amidated Cys, selenocysteine or amidated selenocysteine; $X_{B22}$=Val, Tyr, Phe, His, Gly, Gln, Leu, amidated His, amidated Val or is absent; $X_{B23}$=Glu, Asp, Arg, Ser, Gly or is absent; $X_{B24}$=Arg, Asp, Val or is absent; $X_{B25}$=Gly, Leu, Val or is absent; $X_{B26}$=Phe, Val, Ile or is absent; $X_{B27}$=Phe, Asn, Pro, Glu or is absent; $X_{B28}$=Tyr, Cys, His or is absent; $X_{B29}$=Thr, His, Ile, Leu, Ser, Tyr or is absent; $X_{B30}$=Pro, Glu, Leu, Ile, Arg or is absent; $X_{B31}$=Ile, Lys or is absent; $X_{B32}$=Ala, Asp, Ser, Thr, Lys, Leu, Gln or is absent; $X_{B333}$=Cys or is absent; $X_{B34}$=Glu, Pro, Val or is absent; $X_{B35}$=Glu, Gly or is absent; $X_{B36}$=Glu, Gly or is absent; $X_{B37}$=Glu, Val or is absent; $X_{B38}$=Ala, Asp or is absent; and $X_{B39}$=Ala or is absent (SEQ ID NO: 2).

In some embodiments, the insulin analog comprises a the B chain peptide comprises the sequence $X_{B1}$-$X_{B2}$-$X_{B3}$-$X_{B4}$-$X_{B5}$-$X_{B6}$-$X_{B7}$-$X_{B8}$-Cys$_{B9}$-$X_{B10}$-$X_{B11}$-$X_{B12}$-$X_{B13}$-$X_{B14}$-$X_{B15}$-$X_{B16}$-$X_{B17}$-$X_{B18}$-$X_{B19}$-$X_{B20}$-Cys$_{B21}$-$X_{B22}$-$X_{B23}$-$X_{B24}$-$X_{B25}$-$X_{B26}$-$X_{B27}$-$X_{B28}$-$X_{B29}$-$X_{B30}$-$X_{B31}$-$X_{B32}$-$X_{B33}$-$X_{B34}$-$X_{B35}$-$X_{B36}$-$X_{B37}$-$X_{B38}$-$X_{B39}$, wherein $X_{B1}$=Thr, Asn, Ser or is absent; $X_{B2}$=Phe, Ser, Asn, Thr, Gln or is absent; $X_{B3}$=Asp, Gly, Pro, Leu, Phe, or His; $X_{B4}$=Thr, Pro, Asp, Val or Gly; $X_{B5}$=Asn, Pro, His, Thr, Arg, Ser or hydroxyproline; $X_{B6}$=Lys, Glu, Asn, Asp, Arg, Gln or Gly; $X_{B7}$=His, Tyr, Arg or Ile; $X_{B8}$=Arg, Thr, Ile, Ser, Leu, Tyr or Lys; Cys$_{B9}$=Cys or selenocysteine; $X_{B10}$=Gly, Gln or Asp; $X_{B11}$=Ser, Leu, Gly or Pro; $X_{B12}$=His, Glu, gamma carboxyglutamate, Asp, or Asn; $X_{B13}$=Ile, Leu, Asp, Val or Ala; $X_{B14}$=Thr, Ala, Pro, Val or Arg; $X_{B15}$=Asn, Asp, Ala, Val, Thr, Pro or Glu; $X_{B16}$=Ala, Ser, Gln, His, Tyr, Arg or Gly; $X_{B17}$=Tyr or Leu; $X_{B18}$=Tyr, Met, Val, Gln, Ile, Asp, Gly, Asn or Leu; $X_{B19}$=Leu, Asp, Gln, Gly, Lys, Glu, Arg or Thr; $X_{B20}$=Val, Leu or Lys; C$_{B21}$=Cys, amidated Cys, selenocysteine or amidated selenocysteine; $X_{B22}$=Tyr, Phe or His; $X_{B23}$=Glu, Arg, Ser, Gly or is absent; $X_{B24}$=Arg, Asp, Val or is absent; $X_{B25}$=Gly, Leu, Val or is absent; $X_{B26}$=Phe, Val, Ile or is absent; $X_{B27}$=Phe, Asn, Pro, Glu or is absent; $X_{B28}$=Tyr, Cys, His or is absent; $X_{B29}$=Thr, His, Leu, Tyr or is absent; $X_{B30}$=Pro, Glu, Leu, Ile, Arg or is absent; $X_{B31}$=Ile, Lys or is absent; $X_{B32}$=Thr, Lys, Leu, Gln or is absent; $X_{B333}$=Cys or is absent; $X_{B34}$=Glu, Pro, Val or is absent; $X_{B35}$=Glu, Gly or is absent; $X_{B36}$=Glu, Gly or is absent; $X_{B37}$=Glu, Val or is absent; $X_{B38}$=Ala, Asp or is absent; and $X_{B39}$=Ala or is absent (SEQ ID NO: 3).

In some embodiments, the insulin analog comprises a B chain peptide comprises the sequence $X_{B1}$-$X_{B2}$-$X_{B3}$-$X_{B4}$-$X_{B5}$-$X_{B6}$-$X_{B7}$-$X_{B8}$-Cys$_{B9}$-$X_{B10}$-$X_{B11}$-$X_{B12}$-$X_{B13}$-$X_{B14}$-$X_{B15}$-$X_{B16}$-$X_{B17}$-$X_{B18}$-$X_{B19}$-$X_{B20}$-Cys$_{B21}$-$X_{B22}$-$X_{B23}$-$X_{B24}$-$X_{B25}$-$X_{B26}$-$X_{B27}$-$X_{B28}$-$X_{B29}$-$X_{B30}$-$X_{B31}$-$X_{B32}$-$X_{B33}$-$X_{B34}$-$X_{B35}$-$X_{B36}$-$X_{B37}$-$X_{B38}$-$X_{B39}$, Wherein $X_{B1}$=Thr, Asn, Ser or is absent; $X_{B2}$=Phe, Ser, Asn, Thr, Gln or is absent; $X_{B3}$=Asp, Gly, Pro, Leu, Phe, or His; $X_{B4}$=Thr, Pro, Asp, Val or Gly; $X_{B5}$=Asn, Pro, His, Thr, Arg, Ser or hydroxyproline; $X_{B6}$=Lys, Glu, Asn, Asp, Arg, Gln or Gly; $X_{B7}$=His, Tyr, Arg or Ile; $X_{B8}$=Arg, Thr, Ile, Ser, Leu, Tyr or Lys; Cys$_{B9}$=Cys or selenocysteine; $X_{B10}$=Gly, Gln or Asp; $X_{B11}$=Ser, Leu, Gly or Pro; $X_{B12}$=His, Glu, gamma carboxyglutamate, Asp, or Asn; $X_{B13}$=Ile, Leu, Asp, Val or Ala; $X_{B14}$=Thr, Ala, Pro, Val or Arg; $X_{B15}$=Asn, Asp, Ala, Val, Thr, Pro or Glu; $X_{B16}$=Ala, Ser, Gln, His, Tyr, Arg or Gly; $X_{B17}$=Tyr or Leu; $X_{B18}$=Tyr, Met, Val, Gln, Ile, Asp, Gly, Asn or Leu; $X_{B19}$=Leu, Asp, Gln, Gly, Lys, Glu, Arg or Thr; $X_{B20}$=Val, Leu or Lys; $C_{B21}$=Cys, amidated Cys, selenocysteine or amidated selenocysteine; $X_{B22}$=Tyr, Phe or His; $X_{B23}$=Glu, Arg, Ser, Gly or is absent; and $X_{B24}$, $X_{B25}$, $X_{B26}$, $X_{B27}$, $X_{B28}$, $X_{B29}$, $X_{B30}$, $X_{B31}$, $X_{B32}$, $X_{B33}$, $X_{B34}$, $X_{B35}$, $X_{B36}$, $X_{B37}$, $X_{B38}$ and $X_{B39}$ are absent (SEQ ID NO: 4).

In some embodiments, the insulin analog comprises a B chain peptide comprises the sequence $X_{B1}$-$X_{B2}$-$X_{B3}$-$X_{B4}$-$X_{B5}$-$X_{B6}$-$X_{B7}$-$X_{B8}$-Cys$_{B9}$-Gly-Ser-$X_{B12}$-$X_{B13}$-$X_{B14}$-$X_{B15}$-$X_{B16}$-$X_{B17}$-$X_{B18}$-$X_{B19}$-$X_{B20}$-Cys$_{B21}$-$X_{B22}$-$X_{B23}$-$X_{B24}$-$X_{B25}$-$X_{B26}$-$X_{B27}$-$X_{B28}$-$X_{B29}$-$X_{B30}$-$X_{B31}$-$X_{B32}$-$X_{B33}$-$X_{B34}$-$X_{B35}$-$X_{B36}$-$X_{B37}$-$X_{B38}$-$X_{B39}$, where $X_{B1}$=Thr, Asn, Ser or is absent; $X_{B2}$=Phe, Ser, Asn, Thr, Gln or is absent; $X_{B3}$=Asp, Gly, Pro, Leu, Phe, or His; $X_{B4}$=Thr, Pro, Asp, Val or Gly; $X_{B5}$=Asn, Pro, His, Thr, Arg, Ser or hydroxyproline; $X_{B6}$=Lys, Glu, Asn, Asp, Arg, Gln or Gly; $X_{B7}$=His, Tyr, Arg or Ile; $X_{B8}$=Arg, Thr, Ile, Ser, Leu, Tyr or Lys; Cys$_{B9}$=Cys or selenocysteine; $X_{B12}$=His, Glu, gamma carboxyglutamate, Asp, or Asn; $X_{B13}$=Ile, Leu, Asp, Val or Ala; $X_{B14}$=Thr, Ala, Pro, Val or Arg; $X_{B15}$=Asn, Asp, Ala, Val, Thr, Pro or Glu; $X_{B16}$=Ala, Ser, Gln, His, Tyr, Arg or Gly; $X_{B17}$=Tyr or Leu; $X_{B18}$=Tyr, Met, Val, Gln, Ile, Asp, Gly, Asn or Leu; $X_{B19}$=Leu, Asp, Gln, Gly, Lys, Glu, Arg or Thr; $X_{B20}$=Val, Leu or Lys; $C_{B21}$=Cys, amidated Cys, selenocysteine or amidated selenocysteine; $X_{B22}$=Tyr, Phe or His; $X_{B23}$=Glu, Arg, Ser, Gly or is absent; $X_{B24}$=Arg, Asp, Val or is absent; $X_{B25}$=Gly, Leu, Val or is absent; $X_{B26}$=Phe, Val, Ile or is absent; $X_{B27}$=Phe, Asn, Pro, Glu or is absent; $X_{B28}$=Tyr, Cys, His or is absent; $X_{B29}$=Thr, His, Leu, Tyr or is absent; $X_{B30}$ Pro, Glu, Leu, Ile, Arg or is absent; $X_{B31}$=Ile, Lys or is absent; $X_{B32}$=Thr, Lys, Leu, Gln or is absent; $X_{B33}$=Cys or is absent; $X_{B34}$=Glu, Pro, Val or is absent; $X_{B35}$=Glu, Gly or is absent; $X_{B36}$=Glu, Gly or is absent; $X_{B37}$=Glu, Val or is absent; $X_{B38}$=Ala, Asp or is absent; and $X_{B39}$=Ala or is absent (SEQ ID NO: 5).

In some embodiments, the insulin analog comprises a B chain peptide comprises the sequence $X_{B1}$-$X_{B2}$-$X_{B3}$-$X_{B4}$-$X_{B5}$-$X_{B6}$-$X_{B7}$-$X_{B8}$-Cys$_{B9}$-Gly-Ser-$X_{B12}$-$X_{B13}$-$X_{B14}$-$X_{B15}$-$X_{B16}$-$X_{B17}$-$X_{B18}$-$X_{B19}$-$X_{B20}$-Cys$_{B21}$-$X_{B22}$-$X_{B23}$-$X_{B24}$-$X_{B25}$-$X_{B26}$-$X_{B27}$-$X_{B28}$-$X_{B29}$-$X_{B30}$-$X_{B31}$-$X_{B32}$-$X_{B33}$-$X_{B34}$-$X_{B35}$-$X_{B36}$-$X_{B37}$-$X_{B38}$-$X_{B39}$, where $X_{B1}$=Thr, Asn, Ser or is absent; $X_{B2}$=Phe, Ser, Asn, Thr, Gln or is absent; $X_{B3}$=Asp, Gly, Pro, Leu, Phe, or His; $X_{B4}$=Thr, Pro, Asp, Val or Gly; $X_{B5}$=Asn, Pro, His, Thr, Arg, Ser or hydroxyproline; $X_{B6}$=Lys, Glu, Asn, Asp, Arg, Gln or Gly; $X_{B7}$=His or Tyr; $X_{B8}$=Arg, Thr, Ile, Ser, Leu, Tyr or Lys; Cys$_{B9}$=Cys or selenocysteine; $X_{B12}$=His, Glu, gamma carboxyglutamate, Asp, or Asn; $X_{B13}$=Ile, Leu, Asp, Val or Ala; $X_{B14}$=Thr, Ala, Pro, Val or Arg; $X_{B15}$=Asn, Asp, Ala, Val, Thr, Pro or Glu; $X_{B16}$=Ala, Ser, Gln, His, Tyr, Arg or Gly; $X_{B17}$=Tyr or Leu; $X_{B18}$=Tyr, Met, Val, Gln, Ile, Asp, Gly, Asn or Leu; $X_{B19}$=Leu, Asp, Gln, Gly, Lys, Glu, Arg or Thr; $X_{B20}$=Val or Leu; $C_{B21}$=Cys, amidated Cys, selenocysteine or amidated selenocysteine; $X_{B22}$=Tyr, Phe or His; $X_{B23}$=Glu, Arg, Ser, Gly or is absent; $X_{B24}$=Arg, Asp, Val or is absent; $X_{B25}$=Gly, Leu, Val or is absent; $X_{B26}$=Phe, Val, Ile or is absent; $X_{B27}$=Phe, Asn, Pro, Glu or is absent; $X_{B28}$=Tyr, Cys, His or is absent; $X_{B29}$=Thr, His, Leu, Tyr or is absent; $X_{B30}$=Pro, Glu, Leu, Ile, Arg or is absent; $X_{B31}$=Ile, Lys or is absent; $X_{B32}$=Thr, Lys, Leu, Gln or is absent; $X_{B33}$=Cys or is absent; $X_{B34}$=Glu, Pro, Val or is absent; $X_{B35}$=Glu, Gly or is absent; $X_{B36}$=Glu, Gly or is absent; $X_{B37}$=Glu, Val or is absent; $X_{B38}$=Ala, Asp or is absent; and $X_{B39}$=Ala or is absent (SEQ ID NO: 6).

In some embodiments, the insulin analog comprises a B chain peptide comprises the sequence $X_{B1}$-$X_{B2}$-$X_{B3}$-$X_{B4}$-$X_{B5}$-$X_{B6}$-$X_{B7}$-$X_{B8}$-Cys$_{B9}$-Gly-Ser-$X_{B12}$-$X_{B13}$-$X_{B14}$-$X_{B15}$-$X_{B16}$-$X_{B17}$-$X_{B18}$-$X_{B19}$-$X_{B20}$-Cys$_{B21}$-$X_{B22}$-$X_{B23}$, wherein $X_{B1}$=Thr, Asn or is absent; $X_{B2}$=Phe, Ser or is absent; $X_{B3}$=Phe or Asp; $X_{B4}$=Thr or Val; $X_{B5}$=Pro, Asn or hydroxyproline; $X_{B6}$=Lys, Asn or Gln; $X_{B7}$=His or Tyr; $X_{B8}$=Arg, Ile or Leu; $X_{B12}$=His, Asp, Glu or gamma carboxyglutamate; Cys$_{B9}$=Cys or selenocysteine; $X_{B13}$=Val, Ile or Leu; $X_{B14}$=Thr, Ala, Pro, or Val; $X_{B15}$=Glu, Val, Asn or Asp; $X_{B16}$=Ser, Gln, Tyr or Ala; $X_{B17}$=Tyr or Leu; $X_{B18}$=Tyr, Asp, Met or Val; $X_{B19}$=Leu, Asp, Gln or Lys; $X_{B20}$=Leu or Val; Cys$_{B21}$=Cys, amidated Cys, selenocysteine or amidated selenocysteine; $X_{B22}$=Tyr or Gly; and $X_{B23}$=Glu, Arg, Gly or is absent (SEQ ID NO: 7).

In some embodiments, the insulin analog comprises a the B chain peptide comprises the sequence $X_{B1}$-$X_{B2}$-$X_{B3}$-$X_{B4}$-$X_{B5}$-$X_{B6}$-His-$X_{B8}$-Cys$_{B9}$-Gly-Ser-$X_{B12}$-$X_{B13}$-$X_{B14}$-$X_{B15}$-$X_{B16}$-$X_{B17}$-$X_{B18}$-$X_{B19}$-$X_{B20}$-Cys$_{B21}$-$X_{B22}$-$X_{B23}$, wherein $X_{B1}$=Thr or is absent; $X_{B2}$=Phe or is absent; $X_{B3}$=Phe or Asp; $X_{B4}$=Thr or Val; $X_{B5}$=Pro, Asn or hydroxyproline; $X_{B6}$=Lys or Gln; $X_{B8}$=Arg or Leu; $X_{B12}$=His, Glu or gamma carboxyglutamate; $X_{B13}$=Ile or Leu; $X_{B14}$=Thr, or Val; $X_{B15}$=Glu, or Asn; $X_{B16}$=Ser or Ala; $X_{B17}$=Tyr or Leu, $X_{B18}$=Tyr or Met; $X_{B19}$=Leu or Asp, $X_{B20}$=Leu or Val; $X_{B22}$=Tyr; and $X_{B23}$=Glu or Arg (SEQ ID NO: 8).

In some embodiments, the residue at position $X_{B17}$ and $X_{B22}$ are tyrosine. In some embodiments, $X_{B22}$ is Tyr. In some embodiments, $X_{B17}$ is Tyr.

In some embodiments, the insulin analog comprises an A chain peptide comprising the sequence Gly-$X_2$-$X_3$-$X_4$-$X_{A5}$-Cys$_{A6}$-Cys$_{A7}$-$X_{A8}$-$X_{A9}$-$X_{A10}$-Cys$_{A11}$-$X_{A12}$-$X_{A13}$-$X_{A14}$-$X_{A15}$-Phe-$X_{A17}$-$X_{A18}$-$X_{A19}$-Cys$_{A20}$-$X_{A21}$-$X_{A22}$-$X_{A23}$-$X_{A24}$-$X_{A2}$-$X_{A26}$-$X_{A27}$-$X_{A28}$-$X_{A29}$-$X_{A30}$-$X_{A31}$-$X_{A32}$-$X_{A33}$-$X_{A34}$, wherein $X_{A2}$=Val or Ile; $X_{A3}$=Val or Ala; $X_{A4}$=Glu, gamma carboxyglutamate or Cys; $X_{A5}$=Gln, Glu, gamma carboxyglutamate, His or Val; Cys$_{A6}$, Cys$_{A7}$, and Cys$_{A11}$ are independently Cys or selenocysteine; $X_{A8}$=Thr, His, Asp, Gln, Tyr, Lys or Val; $X_{A9}$=Ser, Arg, Asn, His or Lys; $X_{A10}$=Ile, Pro, Tyr, Ala, Ser, Phe, His or Thr; $X_{A12}$=Ser or Thr; $X_{A13}$=Leu, Asn, Val or Asp; $X_{A14}$=Tyr, Ala, Gln, Asp or Glu; $X_{A15}$=Gln, Glu or Thr; or Ala; $X_{A17}$=Glu, Lys, Arg, Ile, Met, Thr or Ser; $X_{A18}$=Lys, Thr, Asn, Gln or Glu; $X_{A19}$=Tyr or Phe; Cys$_{A20}$=Cys, selenocysteine, amidated Cys, or amidated selenocysteine; $X_{A21}$=Asn, Pro, His, Ser, Gly, Ala, or is absent; $X_{A22}$=Pro, Asn, Thr, Leu, Ser or is absent;

$X_{A23}$=Thr, Leu, Val, Ser or is absent; $X_{A24}$=Arg, Thr, Met, Gln, Leu or is absent; $X_{A25}$=Glu, Gly or is absent; from $X_{A26}$=Ser, Leu or is absent; $X_{A27}$ to $X_{A31}$ are independently Ser or are absent; $X_{A32}$=Ala, Ser or is absent; $X_{A33}$=Ala, Val or is absent; and $X_{A34}$=Ala or is absent (SEQ ID NO: 9).

In some embodiments, the insulin analog comprises an A chain peptide comprising a sequence Gly-$X_{A2}$-Val-$X_{A4}$-$X_{A5}$-Cys$_{A6}$-Cys$_{A7}$-$X_{A8}$-$X_{A9}$-$X_{A10}$-Cys$_{A11}$-Ser-$X_{A13}$-$X_{A14}$-$X_{A15}$-$X_{A16}$-$X_{A17}$-$X_{A18}$-Tyr-Cys$_{A20}$-$X_{A21}$, wherein $X_{A2}$ is Val or Ile, $X_{A4}$ is Glu or gamma carboxyglutamate, $X_{A5}$ is His or Gln, $X_{A8}$ is His or Thr, $X_{A9}$ is Arg or Ser, $X_{A10}$ is Pro or Ile, $X_{A13}$ is Asn or Leu, $X_{A14}$ is Ala or Tyr, $X_{A15}$ is Glu or Gln, $X_{A16}$ is Phe or Leu, $X_{A17}$ is Lys or Glu, $X_{A18}$ is Lys or Asn and $X_{A21}$ is Asn or absent (SEQ ID NO: 10); and an B chain peptide comprising the sequence $X_{B1}$-$X_{B2}$-$X_{B3}$-$X_{B4}$-$X_{B5}$-$X_{B6}$-His-$X_{B8}$-Cys$_{B9}$-Gly-Ser-$X_{B12}$-$X_{B13}$-$X_{B14}$-$X_{B15}$-$X_{B16}$-$X_{B17}$-$X_{B18}$-$X_{B19}$-$X_{B20}$-Cys$_{B21}$-$X_{B22}$-$X_{B23}$, wherein $X_{B1}$=Thr or is absent; $X_{B2}$=Phe or is absent; $X_{B3}$=Phe or Asp; $X_{B4}$=Thr or Val; $X_{B5}$=Pro, Asn or hydroxyproline; $X_{B6}$=Lys or Gln; $X_{B8}$=Arg or Leu; $X_{B12}$=His, Glu or gamma carboxyglutamate; $X_{B13}$=Ile or Leu; $X_{B14}$=Thr, or Val; $X_{B15}$=Glu, or Asn; $X_{B16}$=Ser or Ala; $X_{B17}$=Tyr or Leu; $X_{B18}$=Tyr or Met; $X_{B19}$=Leu or Asp, $X_{B20}$=Leu or Val; $X_{B22}$=Gly or Tyr; and $X_{B23}$=Glu or Arg (SEQ ID NO: 11).

In some embodiments, the insulin analog comprises an A chain peptide comprising a sequence Gly-$X_{A2}$-Val-$X_{A4}$-$X_{A5}$-Cys$_{A6}$-Cys$_{A7}$-$X_{A8}$-$X_{A9}$-$X_{A10}$-Cys$_{A11}$-Ser-$X_{A13}$-$X_{A14}$-$X_{A15}$-Phe-$X_{A17}$-$X_{A1}$-Tyr-Cys$_{A2}$n-$X_{A21}$, wherein $X_{A2}$ is Val or Ile, $X_{A4}$ is Glu or gamma carboxyglutamate, $X_{A5}$ is His or Gln, $X_{A8}$ is His or Thr, $X_{A9}$ is Arg or Ser, $X_{A10}$ is Pro or Ile, $X_{A13}$ is Asn or Leu, $X_{A14}$ is Ala or Tyr, $X_{A15}$ is Glu or Gln, $X_{A17}$ is Lys or Glu, $X_{A18}$ is Lys or Asn and $X_{A21}$ is Asn or absent (SEQ ID NO: 12); and a B chain peptide comprising the sequence $X_{B1}$-$X_{B2}$-$X_{B3}$-$X_{B4}$-$X_{B5}$-$X_{B6}$-His-$X_{B8}$-Cys$_{B9}$-Gly-Ser-$X_{B12}$-$X_{B13}$-$X_{B14}$-$X_{B15}$-$X_{B16}$-$X_{B17}$-$X_{B18}$-$X_{B19}$-$X_{B20}$-Cys$_{B21}$-Tyr-$X_{B23}$, wherein $X_{B1}$=Thr or is absent; $X_{B2}$=Phe or is absent; $X_{B3}$=Phe or Asp; $X_{B4}$=Thr or Val; $X_{B5}$=Pro, Asn or hydroxyproline; $X_{B6}$=Lys or Gln; $X_{B8}$=Arg or Leu; $X_{B12}$=His, Glu or gamma carboxyglutamate; $X_{B13}$=Ile or Leu; $X_{B14}$=Thr, or Val; $X_{B15}$=Glu, or Asn; $X_{B16}$=Ser or Ala; $X_{B17}$=Tyr or Leu; $X_{B18}$=Tyr or Met; $X_{B19}$=Leu or Asp, $X_{B20}$=Leu or Val; and $X_{B23}$=Glu or Arg (SEQ ID NO: 13).

In some embodiments, the insulin analog comprises an A chain peptide comprising a sequence Gly-Val-Val-$X_{A4}$-$X_{A5}$-Cys$_{A6}$-Cys$_{A7}$-$X_{A8}$-$X_{A9}$-$X_{A10}$-Cys$_{A11}$-Ser-$X_{A13}$-$X_{A14}$-$X_{A15}$-Phe-$X_{A17}$-$X_{A18}$-Tyr-Cys$_{A20}$-$X_{A21}$, wherein $X_{A4}$ is Glu or gamma carboxyglutamate, $X_{A5}$ is His or Gln, $X_{A8}$ is His or Thr, $X_{A9}$ is Arg or Ser, $X_{A10}$ is Pro or Ile, $X_{A13}$ is Asn or Leu, $X_{A14}$ is Ala or Tyr, $X_{A15}$ is Glu or Gln, $X_{A17}$ is Lys or Glu, $X_{A18}$ is Lys or Asn and $X_{A21}$ is Asn or absent (SEQ ID NO: 14); and a B chain peptide comprising the sequence $X_{B1}$-$X_{B2}$-$X_{B3}$-$X_{B4}$-$X_{B5}$-$X_{B6}$-His-Arg-Cys$_{B9}$-Gly-Ser-$X_{B12}$-Ile-$X_{B14}$-$X_{B15}$-$X_{B16}$-$X_{B17}$-$X_{B18}$-$X_{B19}$-Leu-Cys$_{B21}$-Tyr-$X_{B23}$, wherein $X_{B1}$=Thr or is absent; $X_{B2}$=Phe or is absent; $X_{B3}$=Phe or Asp; $X_{B4}$=Thr or Val; $X_{B5}$=Pro, Asn or hydroxyproline; $X_{B6}$=Lys or Gln; $X_{B12}$=His, Glu or gamma carboxyglutamate; $X_{B14}$=Thr, or Val; $X_{B15}$=Glu, or Asn; $X_{B16}$=Ser or Ala; $X_{B17}$=Tyr or Leu; $X_{B18}$=Tyr or Met; $X_{B19}$=Leu or Asp, and $X_{B23}$=Glu or Arg (SEQ ID NO: 15).

In some embodiments, the insulin analog comprises an A chain peptide comprising a sequence Gly-$X_{A2}$-Val-$X_{A4}$-$X_{A5}$-Cys$_{A6}$-Cys$_{A7}$-$X_{A8}$-$X_{A9}$-$X_{A10}$-Cys$_{A11}$-Ser-$X_{A13}$-$X_{A14}$-$X_{A15}$-Phe-$X_{A17}$-$X_{A18}$-Tyr-Cys$_{A20}$-$X_{A21}$, wherein $X_{A2}$ is Val or Ile, $X_{A4}$ is Glu or gamma carboxyglutamate, $X_{A5}$ is His or Gln, $X_{A8}$ is His or Thr, $X_{A9}$ is Arg or Ser, $X_{A10}$ is Pro or Ile, $X_{A13}$ is Asn or Leu, $X_{A14}$ is Ala or Tyr, $X_{A15}$ is Glu or Gln, $X_{A17}$ is Lys or Glu, $X_{A18}$ is Lys or Asn and $X_{A21}$ is Asn or absent (SEQ ID NO: 26); and a B chain peptide comprising the sequence $X_{B1}$-$X_{B2}$-$X_{B3}$-$X_{B4}$-$X_{B5}$-$X_{B6}$-His-$X_{B8}$-Cys$_{B9}$-Gly-Ser-$X_{B12}$-$X_{B13}$-$X_{B14}$-$X_{B15}$-$X_{B16}$-Tyr-$X_{B18}$-$X_{B19}$-$X_{B20}$-Cys$_{B21}$-$X_{B22}$-$X_{B23}$, wherein $X_{B1}$=Thr or is absent; $X_{B2}$=Phe or is absent; $X_{B3}$=Phe or Asp; $X_{B4}$=Thr or Val; $X_{B5}$=Pro, Asn or hydroxyproline; $X_{B6}$=Lys or Gln; $X_{B8}$=Arg or Leu; $X_{B12}$=His, Glu or gamma carboxyglutamate; $X_{B13}$=Ile or Leu; $X_{B14}$=Thr, or Val; $X_{B15}$=Glu, or Asn; $X_{B16}$=Ser or Ala; $X_{B18}$=Tyr or Met; $X_{B19}$=Leu or Asp, $X_{B20}$=Leu or Val; $X_{B22}$=Gly or Tyr; and $X_{B23}$=Glu or Arg (SEQ ID NO: 27).

In some embodiments, the insulin analog comprises an A chain peptide comprising a sequence Gly-Val-Val-$X_{A4}$-$X_{A5}$-Cys$_{A6}$-Cys$_{A7}$-$X_{A8}$-$X_{A9}$-$X_{A10}$-Cys$_{A11}$-Ser-$X_{A13}$-$X_{A14}$-$X_{A15}$-Phe-$X_{A17}$-$X_{A18}$-Tyr-Cys$_{A20}$-$X_{A21}$, wherein $X_{A4}$ is Glu or gamma carboxyglutamate, $X_{A5}$ is His or Gln, $X_{A8}$ is His or Thr, $X_{A9}$ is Arg or Ser, $X_{A10}$ is Pro or Ile, $X_{A13}$ is Asn or Leu, $X_{A14}$ is Ala or Tyr, $X_{A15}$ is Glu or Gln, $X_{A17}$ is Lys or Glu, $X_{A18}$ is Lys or Asn and $X_{A21}$ is Asn or absent (SEQ ID NO: 28); and a B chain peptide comprising the sequence $X_{B1}$-$X_{B2}$-$X_{B3}$-$X_{B4}$-$X_{B5}$-$X_{B6}$-His-Arg-Cys$_{B9}$-Gly-Ser-$X_{B12}$-Ile-$X_{B14}$-$X_{B15}$-$X_{B16}$-Tyr-$X_{B18}$-$X_{B19}$-Leu-Cys$_{B21}$-$X_{B22}$-$X_{B23}$, wherein $X_{B1}$=Thr or is absent; $X_{B2}$=Phe or is absent; $X_{B3}$=Phe or Asp; $X_{B4}$=Thr or Val; $X_{B5}$=Pro, Asn or hydroxyproline; $X_{B6}$=Lys or Gln; $X_{B12}$=His, Glu or gamma carboxyglutamate; $X_{B14}$=Thr, or Val; $X_{B15}$=Glu, or Asn; $X_{B16}$=Ser or Ala; $X_{B18}$=Tyr or Met; $X_{B19}$=Leu or Asp, $X_{B22}$=Gly or Tyr; and $X_{B23}$=Glu or Arg (SEQ ID NO: 29).

In some embodiments, the insulin analog comprises an A chain peptide comprising the sequence Gly-Ile-Val-Glu-Gln-Cys-Cys-Thr-Ser-Ile-Cys-Ser-Leu-Tyr-Gln-Leu-Glu-Asn-Tyr-Cys-Asn (SEQ ID NO: 16); and a B chain peptide comprising the sequence Phe-Val-Asn-Gln-His-Leu-Cys-Gly-Ser-His-Leu-Val-Glu-Ala-Xaa-Tyr-Leu-Val-Cys-Gly-Glu, where Xaa is an aromatic residue or large aliphatic residue (SEQ ID NO: 17).

In some embodiments, the insulin analog comprises an A chain peptide comprising the sequence Gly-Ile-Val-Glu-Gln-Cys-Cys-Thr-Ser-Ile-Cys-Ser-Leu-Tyr-Gln-Leu-Glu-Asn-Tyr-Cys-Asn (SEQ ID NO: 18); and a B chain peptide comprising the sequence Phe-Val-Asn-Gln-His-Leu-Cys-Gly-Ser-His-Leu-Val-Glu-Ala-Leu-Tyr-Leu-Val-Cys-Xaa-Glu, where Xaa is an aromatic residue or large aliphatic residue (SEQ ID NO: 19).

In some embodiments, the insulin analog comprises an A chain peptide comprising the sequence Gly-Ile-Val-Glu-Gln-Cys-Cys-Thr-Ser-Ile-Cys-Ser-Leu-Tyr-Gln-Leu-Glu-Asn-Tyr-Cys-Asn (SEQ ID NO: 20); and a B chain peptide comprising the sequence Phe-Val-Asn-Gln-His-Leu-Cys-Gly-Ser-His-Leu-Val-Glu-Ala-Xaa-Tyr-Leu-Val-Cys-Xaa-Glu, where Xaa is an aromatic residue or large aliphatic residue (SEQ ID NO: 21). A number of modifications of human insulin have previously been identified which increase the affinity of the analog for IR. For example, replacing ThrA8 of human insulin with histidine leads to a three fold increase in affinity for IR (Glendorf et al. (2011). In some embodiments, the insulin analog has a histidine residue at the position corresponding to ThrA8 of human insulin.

The insulin analogs may comprise one or more unnatural amino acids, modified amino acids or synthetic amino acid analogues, some of which are indicated with the sequences herein. For example, such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, gamma carboxyglutamate, hydroxyproline, homocitrulline, cysteic acid, t-butylglycine, t-butylalanine, phenylglycine, cyclohexylalanine, cyclopentylalanine, selenocysteine, amidated cysteine, amidated selenocysteine, β-alanine, fluoro-amino acids, designer amino acids such as β-methyl amino acids, Cα-methyl amino acids, Nα-methyl amino acids, and amino acid analogues in general. Also included within the scope are peptides which are differentially modified during or after synthesis, for example, by biotinylation, benzylation, glycosylation, acetylation, phosphorylation, amidation, derivatization by known protecting/blocking groups, proteolytic cleavage, linkage to an antibody molecule or other cellular ligand, etc.

As disclosed herein, a synthetic analogue of Con-Ins G1 containing PTMs was four times more active against the human IR-B than a PTM-free analogue (see examples). In some embodiments, one or more Glu residues can be replaced with gamma-carboxyglutamate (Gla), for example at the $X_{A4}$ or $X_{A5}$ Glu positions of various A chains, or at the $X_{B12}$ Glu position of some B chains. In some embodiments, one or more Pro residues can be replaced with hydroxyproline (Hyp), for example at the $X_{B5}$ Pro position of certain B chains. In some embodiments, the C-terminal ends can be amidated, such as an amidated Cys (*) at the terminal end of various A chains, among others. In some embodiments, the insulin analog comprises one or more of the following (i) $X_{A4}$ is gamma carboxyglutamate, ii) $X_{B5}$=hydroxyproline; and iii) $X_{B12}$=gamma carboxyglutamate. The present inventors have found that at least some of these PTM contribute to Con-Ins G1 binding to the IR.

The insulin analogs have an A chain peptide and the B chain peptide that are bonded together across at least one pair of cysteine residues. In some embodiments, $Cys_{B9}$ of the B chain peptide is bonded to $Cys_{A6}$ of the A chain peptide, $Cys_{B21}$ of the B chain peptide is bonded to $Cys_{A20}$ of the A chain peptide and/or $Cys_{A7}$ is bonded to $Cys_{A11}$.

In some embodiments, the A chain peptide and the B chain peptide can be linked together at one or more terminal ends. In some embodiments the A chain peptide and the B chain peptide are linked together at a terminal end. For example, the N-terminus of the A chain peptide can be linked to the N- or C-terminus of the B chain peptide, the C-terminus of the A chain peptide can be linked to the N- or C-terminus of the B chain peptide, the C-terminus of the A chain peptide can be linked to the N-terminus of the A chain peptide or the C-terminus of the B chain peptide can be linked to the N-terminus of the B chain peptide. In some embodiments, the A chain peptide and the B chain peptide are linked together at both terminal ends. Thus, while in some embodiments the insulin analog is acyclic, in other cases the insulin analogs may be cyclic, while retaining the Cys-bonding pattern described. In such embodiments, the insulin analog has cyclized backbone such that the A and B chains have no free N- or C-terminus (for the embodiment whereby both terminal ends are linked). The linkage at the one or more terminal ends can be directly between amino acids of the A and B chain peptide backbones, or there can be a linker of one or more amino acids or other linker molecules bonded therebetween.

In some embodiments, chemical groups, residues or groups of residues known to the person skilled in the art to improve stability can be added to the C-terminus and/or N-terminus. In some embodiments, chemical groups, residues or groups of residues known to the person skilled in the art to improve bioavailability can be added to the C-terminus and/or N-terminus. In some embodiments, such residues or groups that can be added to the N-terminus can also replace Gly within the insulin analogs. In some embodiments, fluorescent tags are may be attached to either the C- or N-terminus.

Insulin analog peptides as disclosed herein can be made by any technique or method known to the person skilled in the art, and any of such techniques or methods are considered to be within the present scope. For example, techniques include, but are not limited to, chemical synthesis, solid phase peptide synthesis, recombinant expression, a combination of peptide synthesis and recombinant expression, and the like. Example techniques are described further in the Examples section. The insulin analog may be prepared in various forms, for example native, fusions, glycosylated, lipidated, etc.

The insulin analogs are preferably prepared in substantially pure form (i.e. substantially free from host cell proteins or other contaminants). Typically, the insulin analog is substantially pure when it is at least 60%, by weight, of total protein present. For example, the insulin analog is at least 75%, at least about 80%, at least about 85%, at least about 90%, at least about 91%, at least about 92%, at least about 93%, at least about 94%, at least about 95%, at least about 96%, at least about 97%, at least about 98%, at least about 99%, more preferably at least 90%, by weight, of total protein present.

The present disclosure also provides salts or derivatives of the insulin analogs, The term "salt", as used herein, denotes acidic and/or basic salts, formed with inorganic or organic acids and/or bases, preferably basic salts. While pharmaceutically acceptable salts are generally preferred, particularly when employing the insulin analogs as medicaments, other salts find utility, for example, in processing these compounds, or where non-medicament-type uses are contemplated. Salts of these compounds may be prepared by any technique know to a person skilled in the art.

The term "pharmaceutically acceptable salt" as used herein, refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "derivative" as used herein includes alpha amino acids wherein one or more side groups found in the naturally occurring alpha-amino acids have been modified. Thus, for example the naturally-occurring amino acids may be replaced with a variety of uncoded or modified amino acids such as the corresponding D-amino acid or N-methyl amino acid. Other modifications are known to the person skilled in the art and include substitution of hydroxyl, thiol, amino and carboxyl functional groups with chemically similar groups, for example substitution of —SH with —SeH in cysteine.

In some embodiments, the insulin analog, salt or derivative thereof is able to bind the IR. Preferably, the IR is the human IR-B receptor. In some embodiments, the $IC_{50}$ or affinity ($K_d$) against the human IR-B receptor of less than $10^{-4}$ M, $10^{-5}$ M, $10^{-6}$ M $10^{-7}$ M, $10^{-8}$ M, $10^{-9}$ M or $10^{-10}$ M. Preferably, the $IC_{50}$ against the human IR-B receptor of less than $10^{-6}$ M.

In some embodiments, the insulin analog, salt or derivative thereof does not bind IGF-IR or binds the IGF-IR weakly. As used herein, "weakly" refers to an insulin analog that does not bind with sufficient affinity to the IGF-IR to result in activation of the IGF-IR and/or cause signal transduction via IGF-IR. In some embodiments, the insulin analog has an $IC_{50}$ or $K_d$ for IGF-IR of weaker than $10^{-9}$ M, $10^{-8}$ M, $10^{-7}$ M, $10^{-6}$ M, $10^{-5}$ M or $10^{-4}$ M, preferably, the insulin analog has an affinity ($K_d$) for IGF-IR of weaker than 100 nM.

In some embodiments, the insulin analog, salt or derivative thereof is predominantly monomeric in solution. In some embodiments, at least 50% of the insulin analog is a monomer, at least 60% of the insulin analog is a monomer, at least 70% of the insulin analog is a monomer, at least 75% of the insulin analog is a monomer, at least 80% of the insulin analog is a monomer, at least 85% of the insulin analog is a monomer, at least 90% of the insulin analog is a monomer, at least 95% of the insulin analog is a monomer, at least 98% of the insulin analog is a monomer, at least 99% of the insulin analog is a monomer or approximately 100% of the insulin analog is a monomer. In some embodiments, the insulin analog is monomeric. In some embodiments, the insulin analog may be at least partially monomeric and dissociate into monomeric form upon administration to a subject. In some embodiments, the insulin analog is monomeric or dissociates into a monomeric form in a subjects blood stream.

In some embodiments, the insulin analog, salt or derivative thereof is a rapid acting insulin analog. In some embodiments, has increased bioavailability when administered to a human when compared human insulin. In some embodiments, the insulin analog, salt or derivative thereof has a peak bioavailability within 10 minutes to 6 hours of administration to a human. In some embodiments, the maximum plasma concentration of the insulin analog after administration occurs earlier than the maximum plasma concentration of human insulin after administration. For example, the peak availability of the insulin analog, salt or derivative thereof occurs within 10 minutes to 4 hours of administration, within 15 minutes to 3 hours of administration, within 30 minutes to 1 hour of administration or within 40 to 55 minutes of administration. In some embodiments, the insulin analog, salt or derivative thereof has an onset of activity within 2 min, 5 min, 10 minute, 15 minute, 20 minute or 30 minutes of administration. Preferably, the onset of activity is within 10 to 30 minutes of administration.

Insulin analogs of the present invention also include those designed or identified using a method of the invention and those which are capable of recognising and binding to a target binding site.

Target binding sites include physiological binding partners of insulin, such as the IR, as well as regions of physiological binding partners. For example, a target binding site may be a short polypeptide defining an epitope (e.g. corresponding to a loop structure identified below as a target binding site) or a mimetic, e.g. a peptidomimetic, mimicking a loop structure.

In some embodiments, the target binding site is the insulin receptor, preferably human insulin receptor. In some embodiments, the target binding site is a region of IR involved in insulin docking to the receptor. In some embodiments, the region of the IR includes low affinity target binding sites comprising one or more of the following: the L1 domain, the CT peptide and the CR domain of IR ectodomain. With regards to the L1 domain, the target binding site preferably comprises portions of the molecular surface of the central R-sheet of L1 and portions of the molecular surface of the second LRR which contain Phe39 or the loop in the fourth LRR rung of L1, or preferably both. With regards the CR domain, the target binding site preferably comprises module 6 of the CR domain.

In some embodiments, the low affinity target binding site may comprise one or more amino acids from one or more of the following amino acid sequences: (i) amino acids 1-156; (ii) amino acids 704-719; and (iii) amino acids 157-310.

With regards to amino acids 1-156, the target binding site preferably comprises at least one amino acid from the amino acid sequence 1-68, preferably 1-55, and more preferably amino acid sequence 27-55. The target binding site preferably comprises at least one amino acid selected from Arg14, Asn15, Gln34, Leu36, Leu37, Phe39, Pro43-Phe46, Phe64, Leu87, Phe88, Asn90 and Phe89, more preferably at least one amino acid selected from Arg14, Asn15, Gln34, Leu37, Phe39, Pro43-Phe46, Phe64, yet more preferably at least one amino acid selected from Phe39 and Pro43-Phe46, and most preferably at least Phe39.

With regards to amino acids 157-310, the target binding site preferably comprises at least one amino acid from the amino acid sequence 192-310, more preferably at least one amino acid from the sequence 227-303, yet more preferably least one amino acid selected from the sequence 259-284.

In another aspect, the present invention also provides peptides comprising an insulin A chain peptide and an insulin B chain peptide, wherein the B chain peptide comprises a substitution at amino acid 10 and amino acid 20. Disclosed are peptides comprising an A chain peptide and a B chain peptide, wherein the B chain peptide comprises a substitution at amino acid 10 and amino acid 20 compared to wild type human insulin. In some instances, any conservative amino acid substitution can be present at positions 10, 20, or both positions. For example, another hydrophilic amino acid, polar amino acid, or aliphatic amino acid could be substituted at one or both positions.

In some instances of the disclosed peptides, the substitution at amino acid 20 of the B chain peptide can be G20Y, G20F, or G20P. In some instances, the substitution at amino acid 20 is G20Y. In some instances, the substitution at amino acid 20 can be G20P and the peptide further comprises a substitution at amino acid 21, wherein the substitution at amino acid 21 can be G21H. In some instances, the amino acid substitution can be any conservative substitution from glycine.

In some instances of the disclosed peptides, the substitution at amino acid 10 of the B chain peptide can be H10E, H10D or H10Q. In some instances, the substitution at amino acid 10 is H10E. In some instances, the amino acid substitution can be any conservative substitution from histidine.

In some instances, both the insulin A chain peptide and the B chain peptide can contain substitutions compared to wild type insulin. Disclosed are peptides comprising an insulin A chain peptide and an insulin B chain peptide, wherein the B chain peptide comprises a substitution at amino acid 10 and amino acid 20 and further comprising at least one substitution in the A chain peptide. In some instances, the at least one substitution can be found at position 8 or 9. In some instances, the at least one substitution in the A chain peptide can be T8H, T8Y, T8K, or S9R. In some instances, any conservative amino acid substitution can be present at position 8 or 9 or both positions. For example, another hydrophilic amino acid could be substituted or other polar amino acids could be substituted.

Disclosed are peptides comprising an insulin A chain peptide and an insulin B chain peptide, wherein the B chain peptide comprises a substitution at amino acid 10 and amino acid 20 and further comprising at least two substitutions in the A chain peptide. In some instances, the at least two substitutions can be found at positions 8 and 9. In some instances, the at least two substitutions in the A chain peptide can be selected from: T8H, T8Y, T8K, and S9R. In some instances, any conservative amino acid substitution can be present at position 8 or 9 or both positions. For example, another hydrophilic amino acid could be substituted or other polar amino acids could be substituted at one or both positions.

In some instances, the B chain peptide is lacking one or more, up to eight, of the C-terminal amino acids compared to wild type. Thus, the disclosed peptides can be des-octapeptide insulin peptides (missing the last 8 amino acids of the C-terminus of the hlcgshlvealylvca B chain peptide that comprises the sequence of:

FVNQHLCGSELVEALYLVCYER, (SEQ ID NO: 30)

FVNQHLCGSELVEALYLVCFER, (SEQ ID NO: 31)

FVNQHLCGSELVEALYLVCPER, (SEQ ID NO: 32)

FVNQHLCGSDLVEALYLVCYER, (SEQ ID NO: 33)

FVNQHLCGSDLVEALYLVCFER, (SEQ ID NO: 34)

FVNQHLCGSDLVEALYLVCPER, (SEQ ID NO: 35)

FVNQHLCGSQLVEALYLVCYER, (SEQ ID NO: 36)

FVNQHLCGSQLVEALYLVCFER, (SEQ ID NO: 37)
or

FVNQHLCGSQLVEALYLVCPER. (SEQ ID NO: 38)

In some instances, the disclosed peptides can have an A chain comprising the sequence of GIVEQCCHRICS-LYQLENYCN (SEQ ID NO: 39), GIVEQCCYRICS-LYQLENYCN (SEQ ID NO: 40), or GIVEQCCKRICS-LYQLENYCN (SEQ ID NO: 41).

In some instances of the disclosed peptides, the A chain peptide and B chain peptide can be bonded via at least one disulfide bond. In some instances, the A chain peptide and B chain peptide can be bonded via at least two disulfide bonds.

In some instances, the disclosed peptides are monomers. In other words, in some instances, the disclosed peptides are less likely to form dimers, tetramers, hexamers, etc.

In some instances of the disclosed peptides, the insulin A chain peptide can be at least 70% identical to wild type human insulin A chain peptide. In some instances, the insulin A chain peptide can be at least 60, 65, 70, 75, 80, 85, 90, 95, 99% identical to wild type human insulin A chain peptide. In some instances, the percent identity can be reached by the deletion of one or more amino acids from the N-terminus or C-terminus end of the disclosed peptides.

In some instances of the disclosed peptides, the insulin B chain peptide can be at least 70% identical to wild type human insulin B chain peptide. In some instances, the insulin B chain peptide can be at least 60, 65, 70, 75, 80, 85, 90, 95, 99% identical to wild type human insulin B chain peptide. In some instances, the percent identity can be reached by the deletion of one or more amino acids from the N-terminus or C-terminus end of the disclosed peptides.

In some instances, the disclosed peptides can comprise one or more unnatural amino acids, modified amino acids or synthetic amino acid analogues. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, cyclopentylalanine, β-alanine, fluoro-amino acids, designer amino acids such as β-methyl amino acids, Cα-methyl amino acids, Nα-methyl amino acids, and amino acid analogues in general. Also included within the scope are peptides which are differentially modified during or after synthesis, for example, by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the peptide.

In further instances of the disclosed peptides, provided are therapeutic proteins having an A chain peptide bonded to a B chain peptide via at least one disulfide bond, wherein the A chain comprises the sequence of GIVEQCCHRICS-LYQLENYCN (SEQ ID NO: 39), and wherein the B chain peptide comprises the sequence of

FVNQHLCGSELVEALYLVCYER. (SEQ ID NO: 30)

It is appreciated that the disclosed therapeutic proteins can be employed in pharmaceutical compositions and used in connection with treatment of disorders including diabetes.

Methods for the Design of Insulin Analogs

The three-dimensional structure of venom insulin provided by the present invention may be used to design insulin analogs (also referred to herein as JR agonists, molecules and compounds), particularly rapid acting insulin analogs. In one aspect, there is provided the use of the structure of Con-Ins G1 as defined by the atomic coordinates of Appendix I as a structural model. In some embodiments, the structural model is used for identification of insulin analogs.

In some embodiments, a method of identifying, designing or screening for a compound that can potentially interact with IR is provided. The method comprises performing structure-based identification, design or screening of a compound based on the compound's interactions with an IR structure defined by the three-dimensional structure of Con-Ins G1, or a subset thereof.

The present invention is also useful for improving the properties of known IR binding molecules. For example, known IR binding molecules can be screened against the 3D structure of Con-Ins G1 defined by the atomic coordinates of Appendix I or a portion thereof, and an assessment made of the ability to self-associate and the potential to interact with IR.

In view of this assessment the known IR binding molecule could be redesigned (i.e. chemically modified) so as to impart one or more of the following properties: (i) reduce self-association, (ii) improve its affinity for the low affinity binding site of IR (i.e. the binding site governing selectivity), (iii) improve its affinity for the high affinity binding site for IR (i.e. the binding site governing signal transduction) and (iv) lower its affinity for binding to IGF-1R.

In some embodiments, a method of redesigning or modifying a polypeptide which is known to bind to IR, or a region of the IR, is provided. The method comprises performing structure-based evaluation of a structure defined by the atomic coordinates of Appendix I or a subset thereof, and redesigning or chemically modifying the polypeptide as a result of the evaluation. In some embodiments, structure-based evaluation comprises comparison of the structure defined by the atomic coordinates of Appendix I or a subset thereof, with the atomic coordinates of insulin or a subset thereof. In some embodiments, structure-based evaluation further comprises molecular modelling of a complex formed between the structure defined by the atomic coordinates of Appendix I or a subset thereof with the atomic coordinates of an insulin receptor or a subset thereof. In some embodiments, the model is defined by the atomic coordinates of Appendix II or a subset thereof.

In some embodiments, the method further comprises synthesising or obtaining the redesigned or chemically modified polypeptide and testing for its ability to bind IR. In some embodiments, the ability of the redesigned or chemically modified polypeptide to modulate IR activation is determined. In some embodiments, the ability of the redesigned or chemically modified polypeptide to lower blood glucose levels may be determined.

In some embodiments, the polypeptide which is known to bind to IR is an insulin-like growth factor (IGF). Suitable IGFs include those from humans, pigs, cattle, birds, mice and the like. In some embodiments the IGF is human IGF-I or IGF-II.

In a preferred embodiment, the polypeptide which is known to bind to IR is insulin. Suitable insulin includes human insulin, porcine insulin bovine insulin, ovine insulin, murine insulin, guinea pig insulin and the like. In some embodiments, the insulin is human insulin.

As used herein, the term "modelling" includes the quantitative and qualitative analysis of molecular structure and/or function based on atomic structural information and interaction models. The term "modelling" includes conventional numeric-based molecular dynamic and energy minimisation models, interactive computer graphic models, modified molecular mechanics models, distance geometry and other structure-based constraint models.

Molecular modelling techniques can be applied to the atomic coordinates of Con-Ins G1 or a region thereof to derive a range of 3D models and to investigate the structure of binding sites, such as the binding site of IR and other protein targets.

A region of Con-Ins G1 as referred to herein may be defined by a single amino acid (or side-chain thereof), by a continuous amino acid sequence or by two or more separate amino acids and/or stretches of amino acids. Such separate amino acids and/or stretches of amino acids may exist in close spatial proximity to one another in the three dimensional structure or may have the potential to be brought into close spatial proximity, for example, upon the binding of a suitable ligand. Suitably, regions of Con-Jns G1 comprise amino acid sequences involved in the binding of IR, both the initial selective low affinity binding and the subsequent high affinity binding to the other monomer in the IR dimer.

These techniques may also be used to screen for or design small and large chemical entities which are capable of binding IR and modulating the activity of IR. The screen may employ a solid 3D screening system or a computational screening system.

In some embodiments, such modelling methods are to design or select chemical entities (for example a polypeptide, peptide, peptidomimetic, compound and the like) that possess stereochemical complementary to particular regions of IR. By "stereochemical complementarity" we mean that the compound or a portion thereof makes a sufficient number of energetically favourable contacts with the receptor as to have a net reduction of free energy on binding to the receptor.

It will be appreciated that it is not necessary that the complementarity between chemical entities and the receptor site extend over all residues of the receptor site in order to inhibit binding of a molecule or complex that naturally interacts with IR ectodomain.

A number of methods may be used to identify chemical entities possessing stereo-complementarity to a region of the IR. For instance, the process may begin by visual inspection of Con-Ins G1 structure on a computer screen based on the atomic coordinates of Con-Ins G1, or region thereof, in Appendix I generated from the machine-readable storage medium. In some embodiments, the process may begin by molecular modelling of a complex formed between the structure defined by the atomic coordinates of Appendix I or a subset thereof with the atomic coordinates of an insulin receptor or a subset thereof. Modelling software that is well known and available in the art may be used, for example MODELLER (v9.15) (Webb and Sali, (2014). This modelling step may be followed by energy minimization with standard molecular mechanics force fields such as CHARMM (Guvench et al. 2011; Best et al. 2012). Modelling and energy minimization may be followed by molecular dynamics simulations using software known in the art, for example NAMD (Phillips et al. 2005). In addition, there are a number of more specialized computer programs to assist in the process of selecting the binding moieties of this invention.

There is also provided a polypeptide or salt or analog thereof which has been redesigned or modified by the method of redesigning or modifying a polypeptide defined herein. Preferably, the redesigned or modified polypeptide is monomeric, or dissociates to a monomer when administered to a subject.

Preferred regions of the IR are those governing specificity, for example those described as target binding sites above.

In another aspect, there is provided an isolated molecule which is an IR agonist wherein the molecule is identified and/or designed based on the 3D structure of Con-Ins G1 defined by the atomic coordinates of Appendix I or a subset thereof. Suitable molecules include peptides, polypeptides or peptidomimetics.

The term "peptidomimetic", as used herein is a molecule that mimics the biological activity of a peptide but is no longer completely peptidic in chemical nature. By strict definition, a peptidomimetic is a molecule that no longer contains any peptide bonds (that is, amide bonds between amino acids). However, the term peptide mimetic can be used to describe molecules that are no longer completely peptidic in nature, such as pseudo-peptides, semi-peptides and peptoids. Whether completely or partially non-peptide, peptidomimetics of the invention provide a spatial arrangement of reactive chemical moieties that closely resembles the three-dimensional arrangement of active groups in the peptide on which the peptidomimetic is based. As a result of this similar active-site geometry, the peptidomimetic has effects on biological systems which are similar to the biological activity of the peptide.

Suitable peptidomimetics based on venom insulin can be developed using readily available techniques and/or the methods described herein. Thus, for example, peptide bonds can be replaced by non-peptide bonds that allow the peptidomimetic to adopt a similar structure, and therefore biological activity, to the original peptide. Further modifications can also be made by replacing chemical groups of the amino acids with other chemical groups of similar structure. The development of peptidomimetics derived from venom insulin can be aided by reference to the three dimensional structure of these residues as provided in Appendix I or a subset thereof. This structural information can be used to search three-dimensional databases to identify molecules having a similar structure, using programs such as MACCS-3D and ISIS/3D (Molecular Design Ltd., San Leandro, CA), ChemDBS-3D (Chemical Design Ltd., Oxford, U.K.), and Sybyl/3DB Unity (Tripos Associates, St. Louis, MO).

Those skilled in the art will recognize that the design of a peptidomimetic may require slight structural alteration or adjustment of a chemical structure designed or identified using the methods of the invention. In general, mimetics identified or designed using the methods of the invention can be synthesized chemically and then tested for ability to modulate insulin receptor activity using any of the methods described herein. The methods of the invention are particularly useful because they can be used to greatly decrease the number of potential mimetics which must be screened for their ability to modulate insulin receptor activity.

In some embodiments, the isolated molecule is able to bind the IR. Preferably, the IR is the human IR-B receptor. In some embodiments, the $IC_{50}$ or $K_d$ against the human IR-B receptor is stronger than $10^{-4}$ M, $10^{-5}$ M, $10^{-6}$ M $10^{-7}$ M, $10^{-8}$ M, $10^{-9}$ M or $10^{-10}$ M. Preferably, the $IC_{50}$ or $K_d$ against the human IR-B receptor is stronger than $10^{-6}$ M. In some embodiments, the isolated molecule does not bind IGF-IR or binds IGF-IR weakly. Preferably, the isolated molecule has an affinity ($K_d$) for IGF-IR of weaker than 100 nM.

In some embodiments, the isolated molecule is predominantly monomeric in solution. In some embodiments, at least 50% of the isolated molecule is a monomer, at least 60% of the isolated molecule is a monomer, at least 70% of the isolated molecule is a monomer, at least 75% of the isolated molecule is a monomer, at least 80% of the isolated molecule is a monomer, at least 85% of the isolated molecule is a monomer, at least 90% of the isolated molecule is a monomer, at least 95% of the isolated molecule is a monomer, at least 98% of the isolated molecule is a monomer, at least 99% of the isolated molecule is a monomer or approximately 100% of the isolated molecule is a monomer. In some embodiments, the isolated molecule may be at least partially monomeric and dissociate into monomeric form upon administration to a subject. In some embodiments, the isolated molecule is monomeric or dissociates into a monomeric form in a subjects blood stream.

The present invention is also useful in the identification and/or design of insulin analogs which do not bind or only bind weakly to IGF-1R. For example, insulin analogs identified using the methods of this invention can be screened in silico, in vitro and/or in vivo for their ability to bind the IGF-IR. Any insulin analogs found or suspected to bind to IGF-IR can be redesigned so as to be more selective for IR.

In some embodiments, an insulin analog (which includes an isolated molecule, compound or IR agonist) identified by the methods herein does not bind IGF-IR or binds the IGF-IR weakly. In some embodiments, the insulin analog has an $IC_{50}$ or $K_d$ for IGF-IR of weaker than $10^{-9}$ M, $10^{-8}$ M, $10^{-7}$ M, $10^{-6}$ M, $10^{-5}$ M or $10^{-4}$ M, preferably, the insulin analog has an affinity ($K_d$) for IGF-IR of weaker than 100 nM.

The present disclosure also provides a method of identifying a compound which binds IR, the method comprising:

- i) generating a three-dimensional structure model of a polypeptide having
  - a) a structure defined by the atomic coordinates of Appendix I or a subset thereof, or
  - b) a structure having a root mean square deviation less than about 2.0 Å when superimposed on the corresponding backbone atoms of a), and
- ii) designing or screening for a compound which potentially binds the IR.

In some embodiments, generating a three-dimensional structure model comprises generating a model of the polypeptide bound to IR or regions thereof. Preferred regions of the IR are those governing specificity, for example those described as target binding sites above. In some embodiments, the model is defined by the atomic coordinates of Appendix II or a subset thereof.

The model may be adaptive in a sense that it allows for slight surface changes to improve the fit between the candidate compound and the protein, e.g. by small movements in side chains or main chain.

In some embodiments, the methods further comprise synthesising the compound which potentially binds the IR. In some embodiments, compound modulates at least one biological activity of IR. In some embodiments, the method may further comprise testing the compound designed or screened for in ii) for its ability to modulate at least one biological activity of JR. For example, the method may further comprise testing the compound designed or screened for in ii) for its ability to modulate blood glucose levels. In some embodiments, steps i) and ii) are performed in silico.

The present invention also provides a computer-based method of identifying a compound which mimics insulin activity, the method comprising

- i) generating a three-dimensional structure model of a polypeptide having
  - a) a structure defined by the atomic coordinates of Appendix I or a subset thereof, or
  - b) a structure having a root mean square deviation less than about 2.0 Å when superimposed on the corresponding backbone atoms of a), and
- ii) designing or screening for a compound which mimics insulin activity.

In some embodiments, generating a three-dimensional structure model comprises generating a model of the polypeptide bound to IR or regions thereof. In some embodiments, the model is defined by the atomic coordinates of Appendix II or a subset thereof. Preferred regions of the IR are those governing specificity, for example those described as target binding sites above.

In some embodiments, the methods further comprise synthesising the compound which potentially binds the IR. In some embodiments, compound modulates at least one biological activity of IR. In some embodiments, the method may further comprise testing the compound designed or screened for in ii) for its ability to modulate at least one biological activity of IR. For example, the method may further comprise testing the compound designed or screened for in ii) for its ability to modulate blood glucose levels. In some embodiments, steps i) and ii) are performed in silico.

In some embodiments, the compounds identified by the methods of the present invention are able to bind the IR. Preferably, the IR is the human IR-B receptor. In some embodiments, the $IC_{50}$ against the human IR-B receptor of less than $10^{-4}$ M, $10^{-5}$ M, $10^{-6}$ M $10^{-7}$ M, $10^{-8}$ M, $10^{-9}$ M or $10^{-10}$ M. Preferably, the $IC_{50}$ against the human IR-B receptor of less than $10^{-6}$ M.

In some embodiments, the compounds identified by the methods of the present invention do not bind IGF-JR or binds the IGF-JR weakly. In some embodiments, the insulin analog has an $IC_{50}$ or $K_d$ for IGF-IR of weaker than $10^{-9}$ M, $10^{-8}$ M, $10^{-7}$ M, $10^{-6}$ M, $10^{-5}$ M or $10^{-4}$ M, preferably, the insulin analog has an affinity ($K_d$) for IGF-IR of weaker than 100 nM.

In some embodiments, the compounds identified by the methods of the present invention are predominantly monomeric in solution. In some embodiments, at least 50% of the compound is a monomer, at least 60% of the compound is a monomer, at least 70% of the compound is a monomer, at least 75% of the compound is a monomer, at least 80% of the compound is a monomer, at least 85% of the compound is a monomer, at least 90% of the compound is a monomer, at least 95% of the compound is a monomer, at least 98% of the compound is a monomer, at least 99% of the compound is a monomer or approximately 100% of the compound is a monomer. In some embodiments, the compound may be at least partially monomeric and dissociate into monomeric form upon administration to a subject. In some embodiments, the compound is monomeric or dissociates into a monomeric form in a subjects blood stream.

As will be readily understood by those skilled in this field the methods of the present invention provide a rational method for designing and selecting insulin analog proteins which interact with the insulin receptor. In the some cases these proteins may require further development in order to increase activity. Such further development is routine in this field and will be assisted by the structural information provided in this application. It is intended that in particular embodiments the methods of the present invention includes such further developmental steps.

Once an insulin analog has been designed or selected by the above methods, the efficiency with which that insulin analog may bind to a target such as the IR can be tested and optimised by computational evaluation. For example, an insulin analog that has been designed or selected to bind the IR must also preferably traverse a volume not overlapping that occupied by the binding site when it is bound to the native IR. An insulin analog designed or selected as binding to IR may be further computationally optimised so that in its bound state it would preferably lack repulsive electrostatic interaction with the target protein. Such non-complementary (e.g., electrostatic) interactions include repulsive charge-charge, dipole-dipole and charge-dipole interactions. Specifically, the sum of all electrostatic interactions between the compound and the insulin analog when the insulin analog is bound to IR, preferably make a neutral or favourable contribution to the enthalpy of binding.

Once an insulin analog has been optimally selected or designed, as described above, substitutions may then be made in some of its atoms or side groups to improve or modify its binding properties. Generally, initial substitutions are conservative, i.e., the replacement group will have approximately the same size, shape, hydrophobicity and charge as the original group. It should, of course, be understood that components known in the art to alter conformation should be avoided. Such substituted insulin analogs may then be analysed for efficiency of fit to IR by the same computer methods described in detail above.

Specific computer software is available in the art to evaluate compound deformation energy and electrostatic interaction. Examples of programs designed for such uses include: Gaussian 92, revision C (Frisch, Gaussian, Inc., Pittsburgh, PA); AMBER, version 4.0 (Kollman, University of California at San Francisco); QUANTA/CHARMM (Molecular Simulations, Inc., Burlington, MA); and Insight II/Discover (Biosysm Technologies Inc., San Diego, CA).

The present invention encompasses insulin analogs (including IR agonists, molecules, compounds and the like) identified using a method described herein. Some embodiments, also relate pharmaceutical compositions comprising the insulin analogs (including IR agonists, molecules, compounds and the like) identified using a method described herein.

Screening Assays and Confirmation of Binding and Biological Activity

Insulin analogs (which includes compounds and molecules identified using the methods of the present disclosure) of the present invention are preferably assessed by a number of in vitro and in vivo assays of IR and/or IGF-1R function to confirm their ability to interact with and modulate JR and/or IGF-1R activity. For example, compounds may be tested for their ability to bind to IR and/or IGF-1R and/or for their ability to modulate e.g. activate or disrupt IR and/or IGF-1R signal transduction.

Where the screening assay is a binding assay, IR or IGF-1R may be joined to a label, where the label can directly or indirectly provide a detectable signal. Various labels include radioisotopes, fluorescent molecules, chemiluminescent molecules, enzymes, specific binding molecules, particles, e.g., magnetic particles, and the like. Specific binding molecules include pairs, such as biotin and streptavidin, digoxin and antidigoxin, etc. For the specific binding members, the complementary member would normally be labelled with a molecule that provides for detection, in accordance with known procedures.

A variety of other reagents may be included in the screening assay. These include reagents like salts, neutral proteins, e.g., albumin, detergents, etc., which are used to facilitate optimal protein-protein binding and/or reduce nonspecific or background interactions. Reagents that improve the efficiency of the assay, such as protease inhibitors, nuclease inhibitors, antimicrobial agents, etc., may be used. The components are added in any order that produces the requisite binding. Incubations are performed at any temperature that facilitates optimal activity, typically between 4 and 40° C.

Direct binding of compounds to IR or IGF-1R can also be done by Surface Plasmon Resonance (BIAcore) (reviewed in Morton and Myszka, 1998). Here the receptor is immobilized on a CM5 or other sensor chip by either direct chemical coupling using amine or thiol-disulphide exchange coupling (Nice and Catimel, 1999) or by capturing the receptor ectodomain as an Fc fusion protein to an appropriately derivatised sensor surface (Morten and Myszka, 1998). The potential insulin analog (called an analyte) is passed over the sensor surface at an appropriate flow rate and a range of concentrations. The classical method of analysis is to collect responses for a wide range of analyte concentrations. A range of concentrations provides sufficient information about the reaction, and by using a fitting algorithm such as CLAMP (see Morton and Myszka, 1998), rate constants can be determined (Morton and Myszka, 1998; Nice and Catimel, 1999). Normally, the ligand surface is regenerated at the end of each analyte binding cycle. Surface regeneration ensures that the same number of ligand binding sites is accessible to the analyte at the beginning of each cycle.

Incubation periods are selected for optimum activity, but may also be optimized to facilitate rapid high-throughput screening. Normally, between 0.1 and 1 hour will be sufficient. In general, a plurality of assay mixtures is run in parallel with different test agent concentrations to obtain a differential response to these concentrations. Typically, one of these concentrations serves as a negative control, i.e. at zero concentration or below the level of detection.

The basic format of an in vitro competitive receptor binding assay as the basis of a heterogeneous screen for insulin analog replacements for native insulin may be as follows: occupation of the active site of IR or IGF-1R is quantified by time-resolved fluorometric detection (TRFD) as described by Denley et al. (2004). R$^-$IR-A, R$^-$IR-B and P6 cells are used as sources of IR-A, IR-B and IGF-1R respectively. Cells are lysed with lysis buffer (20 mM HEPES, 150 mM NaCl, 1.5 mM $MgCl_2$, 10% (v/v) glycerol, 1% (v/v) Triton X-100, 1 mM EGTA pH 7.5) for 1 hour at 4° C. Lysates are centrifuged for 10 minutes at 3500 rpm and then 100 μl is added per well to a white Greiner Lumitrac 600 plate previously coated with anti-insulin receptor antibody 83-7 or anti-IGF-1R antibody 24-31. Neither capture antibody interferes with receptor binding by insulin, IGF-I or IGF-II. Approximately 100,000 fluorescent counts of europium-labelled insulin or europium-labelled IGF-I are added to each well along with various amounts of unlabelled competitor insulin analog and incubated for 16 hours at 4° C. Wells are washed with 20 mM Tris, 150 mM NaCl, 0.05% (v/v) Tween 20 (TBST) and DELFIA enhancement solution (100 μl/well) is added. Time-resolved fluorescence is measured using 340 nm excitation and 612 nm emission filters with a BMG Lab Technologies Polarstar™ Fluorimeter or a Wallac Victor II (EG & G Wallac, Inc.).

Examples of other suitable assays which may be employed to assess the binding and biological activity of compounds to and on IR are well known in the art. For example, suitable assays may be found in PCT International Publication Number WO 03/027246. Examples of suitable assays include the following:

(i) Receptor autophosphorylation (as described by Denley et al. (2004). R$^-$ IR-A, R$^-$ IR-B cells or P6 cells are plated in a Falcon 96 well flat bottom plate at $2.5 \times 10^4$ cells/well and grown overnight at 37° C., 5% $CO_2$. Cells are washed for 4 hours in serum-free medium before treating with one of either insulin, IGF-I or IGF-II in 100 μl DMEM with 1% BSA for 10 minutes at 37° C., 5% $CO_2$. Lysis buffer containing 2 mM $Na_3VO_4$ and 1 mg/ml NaF is added to cells and receptors from lysates are captured on 96 well plates precoated with antibody 83-7 or 24-31 and blocked with 1×TBST/0.5% BSA. After overnight incubation at 4° C., the plates are washed with 1×TBST. Phosphorylated receptor is detected with europium-labelled antiphosphotyrosine antibody PY20 (130 ng/well, room temperature, 2 hours). DELFIA enhancement solution (100 μl/well) is added and time resolved fluorescence detected as described above.

(ii) Glucose uptake using 2-deoxy-[U-$^{14}$C] glucose (as described by Olefsky, 1978). Adipocytes between days 8-12 post-differentiation in 24-well plates are washed twice in Krebs-Ringer Bicarbonate Buffer (25 mM Hepes, pH 7.4 containing 130 mM NaCl, 5 mM KCl, $KH_2PO_4$, 1.3 mM $MgSO_4·7H_2O$, 25 mM $NaHCO_3$ and 1.15 mM $CaCl_2$)) supplemented with 1% (w/v) RIA-grade BSA and 2 mM sodium pyruvate. Adipocytes are equilibrated for 90 min at 37° C. prior to insulin addition, or for 30 min prior to agonist or antagonist addition. Insulin (Actrapid, Novogen) is added over a concentration range of 0.7 to 70 nM for 30 min at 37° C. Agonist or antagonist (0 to 500 mM) is added to adipocytes for 90 min followed by the addition of native insulin in the case of antagonists. Uptake of 50 mM 2-deoxy glucose and 0.5 mCi 2-deoxy-[U-$^{14}$C] glucose (NEN, PerkinElmer Life Sciences) per well is measured over the final 10 min of agonist stimulation by scintillation counting.

(iii) Glucose transporter GLUT4 translocation using plasma membrane lawns (as described by Robinson and James (1992) and Marsh et al. (1995)).

(iv) GLUT4 translocation using plasma membrane lawns (as described by Marsh et al. 1995). 3T3-L1 fibroblasts are grown on glass coverslips in 6-well plates and differentiated into adipocytes. After 8-12 days post-differentiation, adipocytes are serum-starved for 18 hrs in DMEM containing 0.5% FBS. Cells are washed twice in Krebs-Ringer Bicarbonate Buffer, pH 7.4 and equilibrated for 90 min at 37° C. prior to insulin (100 nM) addition, or for 30 min prior to compound (100 μM) addition. After treatments, adipocytes are washed in 0.5 mg/ml poly-L-lysine in PBS, shocked hypotonically by three washes in 1:3 (v/v) membrane buffer (30 mM Hepes, pH 7.2 containing 70 mM KCl, 5 mM $MgCl_2$, 3 mM EGTA and freshly added 1 mM DTT and 2 mM PMSF) on ice. The washed cells are then sonicated using a probe sonicator (Microson) at setting 0 in 1:1 (v/v) membrane buffer on ice, to generate a lawn of plasma membrane fragments that remain attached to the coverslip. The fragments are fixed in 2% (w/v) paraformaldehyde in membrane buffer for 20 min at 22° C. and the fixative quenched by 100 mM glycine in PBS. The plasma membrane fragments are then blocked in 1% (w/v) Blotto in membrane buffer for 60 min at 22° C. and immunolabelled with an in-house rabbit affinity purified anti-GLUT4 polyclonal antibody (clone R10, generated against a peptide encompassing the C-terminal 19 amino acids of GLUT4) and Alexa 488 goat anti-rabbit secondary antibody (Molecular Probes; 1:200). Coverslips are mounted onto slides using FluoroSave reagent (Calbiochem), and imaged using an OptiScan confocal laser scanning immunofluoroscence microscope (Optiscan, VIC., Australia). Data are analysed using ImageJ (NIH) imaging software. At least six fields are examined within each experiment for each condition, and the confocal microscope gain settings over the period of experiments are maintained to minimise between-experiment variability.

Insulin analog activity may be determined using an adipocyte assay. Insulin increases uptake of $^3H$ glucose into adipocytes and its conversion into lipid. Incorporation of $^3H$ into a lipid phase is determined by partitioning of lipid phase into a scintillant mixture, which excludes water-soluble $^3H$ products. The effect of insulin analogs on the incorporation of $^3H$ glucose at a sub-maximal insulin dose is determined. The method is adapted from Moody et al. (1974). Mouse epididymal fat pads are dissected out, minced into digestion buffer (Krebs-Ringer 25 mM HEPES, 4% HSA, 1.1 mM glucose, 0.4 mg/ml Collagenase Type 1, pH 7.4), and digested for up to 1.5 hours at 36.5 C. After filtration, washing (Krebs-Ringer HEPES, 1% HSA) and resuspension in assay buffer (Krebs-Ringer HEPES, 1% HSA), free fat cells are pipetted into 96-well Picoplates containing test solution.

The assay is started by addition of $^3H$ glucose (e.g. ex. Amersham TRK 239), in a final concentration of 0.45 mM glucose. The assay is incubated for 2 hours at 36.5° C., in a Labshaker incubation tower, 400 rpm, then terminated by the addition of Permablend/Toluene scintillant (or equivalent), and the plates sealed before standing for at least 1 hour and detection in a Packard Top Counter or equivalent. A full native insulin standard curve (8 dose) is run as control on each plate.

Data are presented graphically, as the effect of the insulin analog on $^3H$ glucose uptake, with data compared to a native insulin response. The assay can also be run at basal or maximal insulin concentration.

To test the in vivo activity of an insulin analog, an intravenous blood glucose test may be carried out on Wistar rats as follows. Male Mol:Wistar rats, weighing about 300 g, are divided into two groups. A 10 µl sample of blood is taken from the tail vein for determination of blood glucose concentration. The rats are then anaesthetized (e.g. with Hypnorm/Dormicum) at t=30 min and blood glucose measured again at t=−20 min and at t=0 min. After the t=0 sample is taken, the rats are injected into the tail vein with vehicle or test substance in an isotonic aqueous buffer at a concentration corresponding to a 1 ml/kg volume of injection. Blood glucose is measured at times 5, 10, 20, 30, 40, 60, 80, 120, and 180 min. The anaesthetic administration is repeated at 20 min intervals.

Insulin analogs, compounds and/or molecules designed or selected according to the methods of the present invention may also be assessed by a number of biophysical methods. Suitable methods include x-ray crystallography, analytical ultracentrifugation, size exclusion chromatography, isothermal calorimetry and the like. For example, insulin analogs (which includes compounds and molecules identified using the methods of the present disclosure) may be subjected to further confirmation by crystallization of the analog and structural determination, as described herein. For example, the multimerisation state in solution may be determined by analytical ultracentrifugation. Analytical ultracentrifugation is carried out at 20° C. using a Beckman XLI analytical centrifuge in 12 mm path-length cells. The sample containing the compound is diluted in 10 mM HCl into 10 mM Tris, 50 mM NaCl, pH 7.4 to a final concentration of 100 µg/mL. The person skilled in the art will appreciate that other buffers, salts and the like may be used. For example, samples may also be prepared that contain 0.2 mM $ZnCl_2$, 2 mM $CaCl_2$), 1 mM sodium phosphate (pH 7.4) or 0.1 M ammonium sulfate. An equal volume of 10 mM NaOH is added to neutralize any pH change. A total sample volume of 100 µL is used.

Radial concentration distributions are measured by absorbance at 220 nm. Sedimentation equilibrium was established at 30,000 and 45,000 rpm, as assessed by sequential absorbance scans 1 h apart. Data at both speeds are jointly fitted to a single ideal sedimenting species in SEDPHAT (Houtman et al. 2007) using values of solution density and solvent partial specific volume estimated from composition using SEDNTERP (Laue et al. 1992). With the exception of the disulfides, all post-translational modifications are neglected in the estimation of compound partial specific volume.

Clinical Indications, Routes of Administration, Dosages and Pharmaceutical Compositions The insulin analogs, compounds and molecules with which the present disclosure is concerned are of value in the treatment of conditions which are responsive to activation and/or modulation of IR. These conditions include those for which regulation of glucose metabolism and/or blood glucose levels is indicated.

Conditions which are responsive to activation and/or modulation of IR include, but are not limited to, diabetes myelitis (e.g. type 1 diabetes, type 2 diabetes, gestational diabetes), hyperglycemia, insulin resistance, impaired glucose tolerance and the like. In some embodiments, the condition is an insulin-related condition. Insulin related conditions, include but are not limited to, hyperglycemia, insulin resistance, type-1 diabetes, gestational diabetes or type-2 diabetes.

The insulin analogs of the present invention are suitable for use in a subject, such as a mammal including a human, in order to regulate glucose metabolism. Accordingly, there is provided methods for regulating glucose metabolism. Some embodiments relate to a method for regulating glucose metabolism by administering to a subject in need thereof a therapeutically effective amount of such an insulin analog. Some embodiments relate to a method for treating an insulin-related condition, comprising administering a therapeutically effective amount of the insulin analog as defined herein to a subject in need thereof. Some embodiments relate to a method for treating diabetes by administering to a subject in need thereof a therapeutically effective amount of an insulin analog. Diabetes, includes but is not limited to, type 1 diabetes, type 2 diabetes or gestational diabetes. Some embodiments relate to a method for treating hyperglycemia by administering to a subject in need thereof a therapeutically effective amount of such an insulin analog. Some embodiments relate to a method for treating insulin resistance by administering to a subject in need thereof a therapeutically effective amount of such an insulin analog. Some embodiments relate to a method for treating impaired glucose tolerance by administering to a subject in need thereof a therapeutically effective amount of such an insulin analog. Some embodiments relate to a method for decreasing blood glucose levels in a subject by administering to a subject in need thereof a therapeutically effective amount of such an insulin analog.

For example, disclosed are methods of treating type 1 diabetes in a subject comprising administering a therapeutically effective amount of a peptide comprising an insulin A chain peptide and an insulin B chain peptide, wherein the B chain peptide comprises a substitution at amino acid 10 and amino acid 20 to a subject in need thereof. In some instances, the substitution at amino acid 20 of the B chain peptide can be G20Y, G20F, or G20P. In some instances of the disclosed peptides, the substitution at amino acid 10 of the B chain peptide can be H10E, H10D or H10Q. In some instances, any combination of the B chain substitutions at amino acid 10 and 20 can be present. In some instance, the A chain of the administered peptide can also comprise at least one substitution. For example, in some instances, the at least one substitution in the A chain peptide can be T8H, T8Y, T8K, or S9R. In some instances, the amino acid substitution can be present at position 8 or 9 or both positions. Thus, in some instances, any combination of the disclosed B chain peptide substitutions and A chain peptide substitutions can be present. Also disclosed herein are methods of treating type 1 diabetes in a subject comprising administering a therapeutically effective amount of an insulin analog as defined herein. In some instances, the subject has been diagnosed with type 1 diabetes prior to administering the peptide. In some instances, the subject has been diagnosed with being at risk for developing type 1 diabetes prior to administering the peptide.

Use of an insulin analog, compound or molecule as defined herein in the manufacture of a medicament is also provided. Some embodiments relate to the use of the insulin analog as defined herein in the manufacture of a medicament for regulating glucose metabolism in a subject. Some embodiments relate to the use of the insulin analog as defined herein in the manufacture of a medicament for treating and/or preventing an insulin-related condition in a subject. Some embodiments relate to the use of the insulin analog as defined herein in the manufacture of a medicament for treating and/or preventing an diabetes in a subject. Some embodiments relate to the use of the insulin analog as defined herein in the manufacture of a medicament for treating and/or preventing an hyperglycemia in a subject. Some embodiments relate to the use of the insulin analog as defined herein in the manufacture of a medicament for treating and/or preventing insulin resistance in a subject. Some embodiments relate to the use of the insulin analog as defined herein in the manufacture of a medicament for treating and/or preventing impaired glucose tolerance in a subject. Some embodiments relate to the use of the insulin analog as defined herein in the manufacture of a medicament for decreasing blood glucose levels in a subject.

Some embodiments also relate to an insulin analog as defined herein for use in regulating glucose metabolism in a subject. Some embodiments relate to an insulin analog as defined herein for use in treating and/or preventing an insulin-related condition in a subject. Some embodiments relate to an insulin analog as defined herein for use in treating and/or preventing diabetes in a subject. Some embodiments relate to an insulin analog as defined herein for use in treating and/or preventing hyperglycemia in a subject. Some embodiments relate to an insulin analog as defined herein for use in treating and/or preventing insulin resistance in a subject. Some embodiments relate to an insulin analog as defined herein for use in treating and/or preventing impaired glucose tolerance in a subject. Some embodiments relate to an insulin analog as defined herein for use in decreasing blood glucose levels in a subject.

In some embodiments, administration of the insulin analog results in a decrease in blood glucose levels. Preferably, the insulin analog is a rapid acting insulin analog such that administration of the insulin analog results in a decrease in blood glucose levels within 60 minutes of administration. In some embodiments, administration of the insulin analog results in a decrease in blood glucose levels within minutes, 40 minutes, 30 minutes, 20 minutes, 10 minutes or 5 minutes of administration. In some embodiments, administration of the insulin analog results in a decrease in blood glucose levels for 1 hour, 2 hours, 3 hours, 4 hours, 5 hours, 6 hours, 7 hours, 8 hours, 9 hours, 10 hours, 11 hours, or 12 hours. In any of the methods disclosed herein, the preferred compounds that have been discussed in details herein could be administered. Blood glucose levels can be measured by any means known to one of skill in the art.

Methods of Increasing Insulin Receptor Activation

Disclosed are methods of increasing insulin receptor activation in a subject comprising administering a therapeutically effective amount of any one of the disclosed insulin analog, peptide, compound, molecule or pharmaceutical compositions to a subject in need thereof. In some instances, a subject in need thereof can be a subject known to have decreased insulin receptor activation compared to a standard activation level. In some instances, a standard activation level of insulin receptor activation can be based on established levels in healthy individuals. In some instances, a standard activation level of insulin receptor activation can be based on established levels in the subject being treated prior to the determination of a need for increased insulin receptor activation.

For example, disclosed are methods of increasing insulin receptor activation in a subject comprising administering a therapeutically effective amount of a peptide comprising an insulin A chain peptide and an insulin B chain peptide, wherein the B chain peptide comprises a substitution at amino acid 10 and amino acid 20 to a subject in need thereof. In some instances, the substitution at amino acid 20 of the B chain peptide can be G20Y, G20F, or G20P. In some instances of the disclosed peptides, the substitution at amino acid 10 of the B chain peptide can be H10E, H10D or H10Q. In some instances, any combination of the B chain substitutions at amino acid 10 and 20 can be present. In some instance, the A chain of the administered peptide can also comprise at least one substitution. For example, in some instances, the at least one substitution in the A chain peptide can be T8H, T8Y, T8K, or S9R. In some instances, the amino acid substitution can be present at position 8 or 9 or both positions. Thus, in some instances, any combination of the disclosed B chain peptide substitutions and A chain peptide substitutions can be present. Also disclosed are methods of increasing insulin receptor activation in a subject comprising administering a therapeutically effective amount of an insulin analog as defined herein.

Methods of Lowering Blood Sugar

Disclosed are methods of lowering the blood sugar in a subject comprising administering a therapeutically effective amount of any one of the disclosed insulin analogs, peptides, compounds or pharmaceutical compositions to a subject in need thereof.

In some instances, a subject in need thereof can be a subject known to have increased blood sugar compared to a standard blood sugar level. In some instances, a standard activation level of insulin receptor activation can be based on established levels in healthy individuals. In some instances, a standard activation level of insulin receptor activation can be based on established levels in the subject being treated prior to the determination of a need for increased insulin receptor activation.

For example, disclosed are methods of lowering the blood sugar in a subject comprising administering a therapeutically effective amount of a peptide comprising an insulin A chain peptide and an insulin B chain peptide, wherein the B chain peptide comprises a substitution at amino acid 10 and amino acid 20 to a subject in need thereof. In some instances, the substitution at amino acid 20 of the B chain peptide can be G20Y, G20F, or G20P. In some instances of the disclosed peptides, the substitution at amino acid 10 of the B chain peptide can be H10E, H10D or H10Q. In some instances, any combination of the B chain substitutions at amino acid 10 and 20 can be present. In some instance, the A chain of the administered peptide can also comprise at least one substitution. For example, in some instances, the at least one substitution in the A chain peptide can be T8H, T8Y, T8K, or S9R. In some instances, the amino acid substitution can be present at position 8 or 9 or both positions. Thus, in some instances, any combination of the disclosed B chain peptide substitutions and A chain peptide substitutions can be present. Also disclosed are methods of lowering the blood sugar in a subject comprising administering a therapeutically effective amount of an insulin analog as defined herein.

Administration and Dosages

The routes of administration and dosages described are intended only as a guide. The person skilled in the art will understand, based on the disclosure set forth herein, that specific dosage regimens for compositions, formulations, methods and uses encompassed herein may be determined empirically through clinical and/or pharmacokinetic experimentation, and that such dosages may be adjusted according to prespecified effectiveness and/or toxicity criteria. It will also be understood that a specific dosage and treatment regimen for any particular patient will depend upon a variety of factors, including the activity and concentration of the specific compounds employed, the characteristics of the patient such as age, weight and response of the particular patient, active combination, the judgment of the treating physician and the nature and severity of the condition being treated. The below dosages are exemplary of the average case. There can, of course, be individual instances where higher or lower dosage ranges are merited, and such are within the scope of this invention.

In accordance with the methods and uses as described herein, a subject may receive a therapeutically effective amount of an insulin analog in one or more doses. The actual amount administered, and the rate and time-course of administration, will vary with the route of administration, the nature of the benefit required, the nature and severity of the condition being treated, the condition of the subject being treated and will ultimately be at the discretion of the attendant veterinarian or medical professional. Prescription of treatment, e.g. decisions on dosage, timing, etc., is within the responsibility of the attendant veterinarian or medical professional and typically takes account of the nature of the disorder, the condition of the individual patient, the site of delivery, the method of administration and other factors known to practitioners.

A person skilled in the art will understand that one or more analog(s) together or separately can be administered on any appropriate schedule, e.g., from one or more times per day to one or more times per week; including once every other day, for any number of days or weeks, or any variation thereon. Normally, the insulin analog is administered one, two, three, four or more times daily. However, the insulin analog can also be administered on an as needs basis, for example when blood glucose levels are above the normal range or when blood glucose levels need to be reduced. Generally the compound or composition of the present invention is administered with, before or after ingesting food. Preferably, the insulin analog is administered prior to every meal, for example breakfast, lunch and dinner. In some embodiments, the compound or composition is administered 5, 10, 20, 30, 40, 50 or 60 minutes before ingesting food. In some embodiments, the compound or composition is administered immediately before ingesting food.

The insulin analog, as well as pharmaceutical compositions as described herein, can be administered by any route known to one of skill in the art, the parenteral being of most interest. Accordingly, in one embodiment of the invention the insulin analogs are administered by the parenteral route, such as by injection or infusion. Other suitable administration routes, for example enteral (e.g. oral administration), are within the scope of the present invention. In a specific embodiment, the parenteral route is preferred and includes intravenous, intraarticular, intraperitoneal, subcutaneous, intramuscular, intrastemal injection and infusion as well as administration by the sublingual, transdermal, topical, transmucosal including nasal route, or by inhalation such as, e.g., pulmonary inhalation.

The insulin analogs can be administered in a suitable vehicle or they can be administered in the form of a suitable pharmaceutical composition. Such compositions are also within the scope of the invention. In the following are described suitable pharmaceutical compositions.

Pharmaceutical Compositions

A person skilled in the art will appreciate that the insulin analogs described herein may be formulated in pharmaceutical compositions. Such compositions may include the insulin analog and one or more pharmaceutically acceptable carriers.

As used herein, the term "pharmaceutically acceptable carrier" includes any and all solids or solvents (such as phosphate buffered saline buffers, water, saline) dispersion media, coatings, antibacterial and antifungal agents, isotonic and absorption delaying agents, and the like, compatible with pharmaceutical administration. The pharmaceutically acceptable carriers must be 'acceptable' in the sense of being compatible with the other ingredients of the composition and not deleterious to the recipient thereof. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, 20th Edition, (Lippincott, Williams and Wilkins), 2000; Liberman, et al. Eds., Pharmaceutical Dosage Forms, Marcel Decker, New York, N.Y., 1980; and Kibbe, et al. Eds., Handbook of Pharmaceutical Excipients (3rd Ed.), American Pharmaceutical Association, Washington, 1999. Generally, suitable pharmaceutically acceptable carriers are known in the art and are selected based on the end use application. For example, pharmaceutically acceptable carriers that may be used in the present invention include, but are not limited to, those suitable for injectable or infusion compositions. Supplementary active compounds can also be incorporated into the compositions. The use of such media and agents for pharmaceutically active substances is well known in the art. Pharmaceutical compositions are described in a number of sources that are well known and readily available to those skilled in the art, for example, Remington's Pharmaceutical Sciences (Martin E. W., Easton Pa., Mack Publishing Company, 19th ed., 1995).

The amount of pharmaceutically acceptable carrier will depend upon the level of the compound and any other optional ingredients that a person skilled in the art would classify as distinct from the carrier (e.g., other active agents). The formulations of the present invention may comprise, for example, from about 5% to 99.99%, or 25% to about 99.9% or from 30% to 90% by weight of the composition, of a pharmaceutically acceptable carrier. The pharmaceutically acceptable carrier can, in the absence of other adjuncts, form the balance of the composition.

Optionally, the pharmaceutical composition of the present disclosure further comprises other additional components, for example therapeutic and/or prophylactic ingredients. The invention thus relates in a further aspect to pharmaceutical composition comprising the compound of the present invention, one or more pharmaceutically acceptable carriers together with one or more other active agents. Generally, the amount of other active agent present in the pharmaceutical composition is sufficient to provide an additional benefit either alone or in combination with the other ingredients in the composition.

It will be understood by the person skilled in the art that these optional components may be categorized by their therapeutic or aesthetic benefit or their postulated mode of action. However, it is also understood that these optional components may, in some instances, provide more than one therapeutic or aesthetic benefit or operate via more than one mode of action. Therefore, classifications herein are made for the sake of convenience and are not intended to limit the component to that particular application or applications listed. Also, when applicable, the pharmaceutically-acceptable salts of the components are useful herein.

When other active agents are present in the pharmaceutical formulation of the present invention, the dose of the compound may either be the same as or differ from that employed when the other additional components are not present. Appropriate doses will be readily appreciated by those skilled in the art.

A pharmaceutical composition is formulated to be compatible with its intended route of administration, e.g., local or systemic. Examples of routes of administration include parenteral, e.g., intravenous, intradermal, subcutaneous, oral, nasal, topical, transdermal, transmucosal, and rectal administration. Oral and nasal administration include administration via inhalation. Solutions or suspensions used for parenteral, intradermal, or subcutaneous application can include the following components: a sterile diluent, such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions, non-aqueous solutions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringability exists. It should be stable under the conditions of manufacture and storage and be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. Isotonic agents, for example, sugars, polyalcohols such as manitol, sorbitol, sodium chloride can also be included in the composition. Prolonged absorption of the injectable compositions can be brought about by including in the composition an agent that delays absorption, such as aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the polynucleotide into a sterile vehicle, which contains a basic dispersion medium and the required other ingredients from those enumerated above. In the case of sterile powders for the preparation of sterile injectable solutions, suitable methods of preparation include vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL, or corn starch; a lubricant such as magnesium stearate or sterotes; a glidant such as colloidal silicon dioxide; a sweetening agent such as sucrose or saccharin; or a flavouring agent such as peppermint, methyl salicylate, or orange flavouring.

Formulations suitable for administration by nasal inhalation include where the carrier is a solid, include a coarse powder having a particle size, for example, in the range of about to about 500 microns, which is administered in the manner in which snuff is taken, i.e., by rapid inhalation through the nasal passage from a container of the powder held close up to the nose. Suitable formulations wherein the carrier is a liquid for administration by nebulizer, include aqueous or oily solutions of the agent. For administration by inhalation, the agent(s) can also be delivered in the form of drops or an aerosol spray from a pressured container or dispenser that contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays, drops, or suppositories. For transdermal administration, the active compound (e.g., polynucleotides of the invention) are formulated into ointments, salves, gels, or creams, as generally known in the art.

The pharmaceutical compositions may be prepared by any of the method well known to a person skilled in pharmaceutical formulation. Generally, the compositions are prepared by contacting the insulin analog, molecule or compound uniformly and intimately with liquid carriers or finely divided solid carriers or both. Then, if necessary, the product is shaped into the desired formulation. For parenteral administration, in one embodiment the insulin analogs, compounds or molecules of the invention can be formulated by mixing it at the desired degree of purity, in a unit dosage injectable form (solution, suspension, or emulsion), with a pharmaceutically acceptable carrier.

In some embodiments, the pharmaceutical composition comprises a therapeutically effective amount of an insulin analog, peptide, compound or molecule according to the invention. The content of the insulin analog, peptide, compound or molecule of the invention in a pharmaceutical composition of the invention is e.g. from about 0.1 to about 100% w/w of the pharmaceutical composition.

Kits

The materials described above as well as other materials can be packaged together in any suitable combination as a kit useful for performing, or aiding in the performance of, the disclosed method. It is useful if the kit components in a given kit are designed and adapted for use together in the disclosed method. Disclosed are kits comprising one or more of the disclosed insulin analogs. For example disclosed are kits comprising one or more of the disclosed insulin analogs, peptides, compounds or pharmaceutical compositions.

The present invention will now be described further with reference to the following examples, which are illustrative only and non-limiting. The examples refer to the figures.

EXAMPLES

Example 1—Peptide Synthesis of Con-Ins G1

Solid Phase Peptide Synthesis of Con-Ins G1 Chain a and Chain B.

Both A and B chains of Con-Ins G1 were synthesized with Fmoc (9-fluorenmethyloxycarbonyl) chemistry on a CEM Liberty 1 automated microwave peptide synthesizer (CEM Corporation, Matthews, NC). For the synthesis of A chain pre-loaded Fmoc-Cys(Trt)-Rink Amide MBHA resin (0.21 mmol/g) (Peptides International, Louisville, KY) and for the synthesis of B chain pre-loaded Fmoc-Arg(Pbf)-Wang resin (0.4 mmol/g) (AnaSpec, EGT., Freemont, CA) were used. Fmoc-$N^\alpha$-protected amino acids with side chain protection were from commercial sources: Bachem Inc. (Torrance, CA), Chem-Impex International (Wood Dale, IL), Genzyme (Cambridge, MA), Novabiochem (San Diego, CA), P3 Biosystem (Louisville, KY) and Reanal (Budapest, Hungary). Fmoc-γ-carboxy-L-glutamic acid γ,γ-di-t-butyl ester (Fmoc-Gla(OtBu)$_2$-OH) was synthesized in house (Rivier et al. 1987). Side-chain protection for the amino acids was as follows: Lys, tert-butyloxycarbonyl (Boc); Hyp, Ser, Thr and Tyr, tert-butyl ether (tBu); Asn, Cys, and His trityl (Trt); Arg 2,2,4,6,7-pentamethyl-dihydroxybenzofuran-5-sulfonyl (Pbf); Glu, Gla, and Asp tert-butyl ester (OtBu); Cys, acetamidomethyl (Acm); Cys, 4-methoxytrityl (Mmt); Cys, S-tert-butylthionyl (S-t-Bu).

To be able make the correct intra- and intermolecular disulfide bonds, the side chain protecting group of CysA7 and CysB7 was Acm, the side chain protecting group of CysA20 and CysB19 was Trt, the side chain of CysA11 was Mmt protected, and the side chain of CysA6 was S-t-Bu protected. Both chains were synthesized on a 0.1 mmol scale. Coupling reactions were performed on the resin in the presence of 5-fold molar excess of Fmoc-protected amino acids dissolved in DMF (except His in NMP) with activation by HATU [2-(1H-9-(Azabenzotriazol-1-yl)-1,1,3,3-tetramethyl-aminium hexafluorophosphate]:DIEA [N,N-diisopropylethylamine]:AA [protected amino acids] (0.9:2:1) at 0 W for 2 min then at 35 W with a maximum temperature of 60° C. for 10 min. Arg was always double-coupled at room temperature for 25 min then at 15 W with a maximum temperature of 50° C. for 12 min. Cys, His, and Gla were coupled at 40 W with a maximum temperature of 50° C. for 6 min. Deprotection of the Fmoc group was performed with 20% piperidine containing 0.1 M HOBt in DMF in two stages (using a fresh reagent each time): with an initial deprotection of 2 min at 35 W followed by 5 min deprotection at 35 W with a maximum temperature of 60° C.

Con-Ins G1 Chain A: Intramolecular Disulfide Bond Formation, Cleavage and Purification.

The intramolecular disulfide bridge between CysA6 and CysA11 was formed on the resin using a non-oxidative method (Galande et al. 2005). In the first step, S-t-Bu of CysA6 was removed by reduction to liberate free thiol by treating the resin (760 mg) with 20% mercaptoethanol (ME) (Fluka) and 1% N-Methylmorpholine (NMM) in dimethylformamide (DMF) 8 mL overnight at room temperature. The resin was washed with DMF and dried. The resin was then reacted with a 10-fold excess of 2,2'-dithiobis(5-nitropyridine) (DTNB) ~1 mmol (Sigma-Aldrich, St Louis, MO) in dichloromethane (DCM) 8 mL for 1 h to form the S-5-nitropyridin-sufenyl (5-Npys) protected CysA6. After washing out the excess of the reagents with DCM, the resin was treated with 1% trifluoroacetic acid (TFA) in dichloromethane (DCM) 8 mL in the presence of 2 μL triisopropylsilane (TIS) as a scavenger for 20 min to deprotect CysA11(Mmt) and to form the disulfide bridge between CysA6 and CysA11 at the same time.

Cleavage from the resin (720 mg) and simultaneous deprotection of chain A were performed by stirring the resin with 10 mL of a reagent containing (TFA/water/TIS: 95/2.5/2.5) for 2 h. This was followed by precipitation of the peptide using ice-cold anhydrous ethyl ether, then extraction with 0.1% TFA/40% water/60% acetonitrile and lyophilization. The peptide was purified by preparative Waters HPLC (Milford, MA) on Waters PrepPak cartridge (2.5×10 cm) packed with Bondapak $C_{18}$ (15-20 μm particle size, 300 Å) in solvent system A: 0.1% TFA/water, B: 0.1% TFA/40% water/60% ACN with a linear gradient ranging from 5% to 65% solvent B in 60 min at a flow rate 20 mL/min. 18.7 mg (7.7 μmol) of chain A was obtained. The mass of the peptide was confirmed by electrospray ionization (ESI)-MS measured on a ThermoScientific LTQ Orbitrap XL (Waltham, MA) instrument (calculated monoisotopic $MH^{+1}$: 2422.03 Da; determined monoisotopic $MH^{+1}$ value 2422.01 Da).

Con-Ins G1 Chain B: Cleavage and Purification.

Cleavage from the resin and simultaneous deprotection of chain B were performed by stirring 500 mg resin with 10 mL reagent containing (TFA/thioanisol/3,6-Dioxa-1,8-octanedithol (DODT, TCI America, Portland, OR)/water: 87.5/5/2.5/5) for 2 h, followed by precipitation of the peptide using ice-cold anhydrous ethyl ether, then extraction with 0.1% TFA/40% water/60% ACN and lyophilization. The peptide was purified by preparative HPLC (as described for purification of chain A, except that the gradient ranged from 20 to 80% solvent B in 60 min) 25.9 mg (9 μmol) of chain B was obtained. The mass of the peptide was confirmed by ESI-MS (calculated monoisotopic $MH^{+1}$ value 2868.24 Da; determined monoisotopic $MH^{+1}$ value 2868.22 Da).

DMSO-Assisted Chain a and Chain B Ligation to Form Partially Folded Con-Ins G1 (Containing One Disulfide Bond).

Chain A and chain B (7 μmol each) were dissolved together in 0.1% TFA/water solution (7.1 mL) and added to a mixture of 14.5 mL DMSO, 14.25 mL water, 35.6 mL 0.2 M Tris containing 2 mM EDTA, pH 7.5. The oxidation was monitored by analytical HPLC. After 25 h at room temperature, the reaction was quenched with 8% formic acid (1 mL), diluted with 0.1% TFA to a total volume of 225 mL and purified by preparative HPLC with a gradient ranged from 15 to 75% B in 60 min. 4.5 mg (0.85 μmol, 12.1% yield based on the starting amount of 7 μmol) of heterodimer was obtained. The identity of the peptide was confirmed by ESI-MS (calculated monoisotopic MH$^{+1}$: 5287.25 Da; determined monoisotopic MH$^{+1}$: 5287.19 Da).

$I_2$-Assisted Oxidation to Form Fully-Oxidized Con-Ins G1.

4.5 mg (0.85 μmol) of Con-Ins G1 (partially folded) was dissolved in 6.2 mL of 2.5% TFA/water solution and 55 μL of $I_2$ solution (50 mg $I_2$ in 5 mL MeOH) was added and stirred for 60 min. It was quenched by adding 1M ascorbic acid solution until the yellow colour of the solution became clear. The reaction was diluted with 60 mL water and loaded on preparative RP-HPLC column. 1.5 mg (0.29 μmol) of fully-oxidized Con-Ins G1 was obtained (yield 35% based on the starting amount of the partially folded product containing one interchain disulfide bond and 4% based on the starting amount of purified chain A). The identity of the peptide was confirmed by ESI-MS on a ThermoScientific LTQ Orbitrap XL (Waltham, MA) mass spectrometer (calculated monoisotopic MH$^{+1}$: 5143.16 Da; determined monoisotopic MH$^{+1}$: 5143.16 Da).

Purity of the peptide was assessed by RP-HPLC and capillary electrophoresis. Quantitative RP-HPLC was performed using a GE Healthcare AKTApurifier 10 (Pittsburgh, PA) and a Phenomenex (Torrance, CA) Kinetex XB-C18 column (4.6×100 mm, 5.0 μm particle size, 100 Å pore size). The solvent system comprised solvent A=0.1% TFA in water and solvent B=60% ACN, 40% A. A gradient was performed from 20 to 80% B in 30 min at a flow rate of 1.0 mL/min. Detection was at 214 and 280 nm. The purity of the peptide was determined to be 89%. Capillary electrophoresis (CE) was performed using a Groton Biosystems GPA 100 instrument. (Boxborough, MA) The electrophoresis buffer was 0.1 M sodium phosphate (15% acetonitrile), pH 2.5. Separation was accomplished by application of 20 kV to the capillary (0.75 μm×100 cm). Detection was at 214 nm. The assessed purity of the peptide was 80%.

Synthesis and Purification of sCon-Ins G1.

Con-Ins G1 containing CysA6, A11 to SecA6, A11 modifications in the A chain (referred to as sCon-Ins G1; Sec=selenocysteine) was chemically synthesized, purified and oxidized as described by Safavi-Hemami et al. (2015), with the exception that corrected extinction coefficients were used for quantification of the B chain (2,980 M-1·cm-1) and fully oxidized sCon-Ins G1 (4,470 M-1·cm-1). Synthesis of sCon-Ins G1[GluA4, ProB3, GluB10] was performed as described for sCon-Ins G1 (Safavi-Hemami et al. (2015)). The stepwise formation of disulfide bonds of sCon-Ins G1[GluA4, ProB3, GluB10] is described in detail below.

sCon-Ins G1[GluA4] Chain A: Cleavage, DTT Reduction and Purification.

The peptide was cleaved from 125 mg of resin for 1.5 h using 1 mL of enriched Reagent K (TFA/water/phenol/thioanisole/1,2-ethanedithiol, 82.5/5.0/5.0/5.0/2.5 by volume), which was prepared using 2 mL TFA (Fisher Scientific, Fair Lawn, NJ), 66 μL $H_2O$, 12 mg 2,2-dithiobis(5-nitropyridine) (DTNP; Aldrich; Saint Louis, MO), and 150 mg phenol, followed by addition of 25 μL thioanisole. The cleavage mixture was filtered and precipitated with 10 mL of cold methyl-tert-butyl ether (MTBE; Fisher Scientific, Fair Lawn, NJ). The crude peptide was precipitated by centrifugation at 7,000×g for 6 min and washed once with 10 mL cold MTBE. To induce intramolecular diselenide bond formation (SecA6 to SecA10), the washed peptide pellet was dissolved in 50% ACN (Fisher Scientific; Fair Lawn, NJ) (vol/vol) in water and 2 mL of 100 mM dithiotreitol (DTT, EMD Chemicals, Gibbstown, NJ) in 1 mL 0.2 M Tris-HCl (Sigma, St Louis, MO) containing 2 mM EDTA (Mallinckrodt, St. Louis, MO), pH 7.5, 1 mL of water was added and vortexed gently, and the reaction was allowed to proceed for 2 h. It was then quenched with 8% formic acid (vol/vol) (Fisher Scientific, Fair Lawn, NJ), diluted with 0.1% TFA (vol/vol) in water, and purified by reversed-phase (RP) HPLC using a semi-preparative C18 Vydac column (218TP510, 250×10 mm, 5-μm particle size; Grace, Columbia, MD) eluted with a linear gradient ranging from 10 to 40% solvent B in 30 min at a flow rate 4 mL/min. The HPLC solvents were 0.1% (vol/vol) TFA in water (solvent A) and 0.1% TFA (vol/vol) in 90% aqueous ACN (vol/vol) (solvent B). UV absorbance was measured at 220 and 280 nm to monitor the eluent. Purity of the peptide was assessed by analytical RP-HPLC on a C18 Vydac column (218TP54, 250×4.6 mm, 5 m particle size, Grace, Columbia, MD) using a linear gradient ranging from 10 to 40% of solvent B in 30 min with a flow rate 1 mL/min. The peptide was quantified by UV absorbance at 280 nm using an extinction coefficient (F) of 1,490 $M^{-1} \cdot cm^{-1}$. From 135 mg of the resin, 3.8 mg of chain A was obtained. The mass of the peptide was confirmed by electrospray ionization (ESI)-MS (calculated monoisotopic MH$^{+1}$: 2,473.674, determined monoisotopic: MH$^{+1}$ 2,472.924). Molecular masses were calculated using ProteinProspector (version 5.12.1).

sCon-Ins G1[ProB3, GluB10] chain B: cleavage and purification.

The peptide was cleaved from 94 mg resin by a 3 h treatment with 1 mL of Reagent K and subsequently filtered, precipitated, and washed as described above. The washed peptide pellet was purified as described above with the exception that the gradient ranged from 15 to 45% solvent B. The same gradient was used to assess the purity of the linear peptide as described above, and peptide quantitation was carried out using F value of 2,980 $M^{-1} \cdot cm^{-1}$. From 94 mg of the cleaved resin, 2.37 mg of chain B was obtained. The mass of the peptide was confirmed by ESI-MS (calculated monoisotopic MH$^{+1}$: 2,808.24, determined monoisotopic MH$^{+1}$: 2,808.25).

Copper-Assisted Chain a and Chain B Ligation to Form sCon-Ins G1[GluA4, ProB3, GluB10].

A total of 100 nmol of each chain was combined and dried using a SpeedVac. The peptide mixture was dissolved in 100 μL of 0.1% TFA (vol/vol) and added to a mixture of 800 μL $CuCl_2 \cdot H_2O$ (J. T. Baker, Phillipsburg, NJ) 100 μL 1M Tris-HCl containing 10 nM EDTA, pH 7.5. The final peptide concentration was 100 μM. The reaction was left for 24 h at room temperature and then quenched with 8% formic acid (vol/vol), diluted with 0.1% TFA and purified by RP-HPLC using a preparative C18 Vydac column eluted with a linear gradient ranging from 15 to 45% of solvent B in 30 min at a flow rate 4 mL/min. The purity of sCon-Ins G1 was assessed by analytical RP-HPLC using the same gradient as for the semi-preparative purification, at a flow rate 1 mL/min. sCon-Ins G1[GluA4, ProB3, GluB10] was quantified at 280 nm using an E value of 4,470 $M^{-1} \cdot cm^{-1}$. The yield of the reaction was 28%. From 900 nmol of the 1:1 mixture of chain A and B, 1.36 mg of the desired product was obtained. The identity of the peptide was confirmed by ESI-MS (calculated monoisotopic MH$^{+1}$: 5,278.15; determined monoisotopic MH$^{+1}$: 5278.15).

Iodine (I$_2$)-Assisted Formation of Fully Folded sCon-Ins G1[GluA4, ProB3, GluB10].

A solution of I$_2$ (Acros Organics, Geel, Belgium) was prepared as follows: 10 mg of 12 was added to 5 mL of ACN. After 20 min of stirring, the 12 was completely dissolved, and 15 mL of water and 600 µL of TFA were added. A total of 300 µL of the 12 mixture was added to 149 nmol (90% purity) and 106 nmol (72% purity) of partially folded sCon-Ins G1[GluA4, Cys(Acm)7, ProB3, C(Acm) B7, GluB10] dissolved in 300 µL of 0.1% TFA each. Reactions were incubated for 5 min, quenched with 10 µL of 1 M L-ascorbic acid (Sigma, St. Louis, MO), diluted with 0.1% TFA in water to a total volume of 4.5 mL and purified as described for partially folded sCon-Ins G1[GluA4, ProB3, GluB10]. The purity of the final product (fully-folded sCon-Ins G1[GluA4, ProB3, GluB10]) was assessed by analytical RP-HPLC on C18 Vydac column (218TP54, 250×4.6 mm, 5 m particle size) using the same gradient as for the semi-preparative purification, at a flow rate 1 mL/min, and was determined to be 97%. sCon-Ins G1[GluA4, ProB3, GluB10] was quantified as described for the partially folded product. The yield of the reaction was 14%, with 0.18 mg of the desired product being obtained. The identity of the peptide was confirmed by ESI-MS (calculated monoisotopic MH$^{+1}$: 5,134.84; determined monoisotopic MH$^{+1}$: 5,134.07).

Synthesis and Purification of hIns[DOI] and hIns[TyrB15, TyrB20, DOI]

hIns [DOI] is a monomeric analogue lacking residues 23 to 30 of the B chain of human insulin. hIns[DOI] and hIns[TyrB15, TyrB20, DOI] were chemically synthesized, purified and oxidized following standard procedures.

Example 2—Con-Ins G1 Human Insulin Receptor Binding and Signalling Activation

Insulin Receptor Binding.

The ability of Con-Ins G1 to bind to the human insulin receptor (hIR) was measured by a binding competition assay. Competition binding assays were performed using solubilised immuno-captured human IR (isoform B) with europium-labelled human insulin and increasing concentrations of venom insulin as previously described (Denley et al. 2004). Time-resolved fluorescence was measured using 340-nm excitation and 612-nm emission filters with a Polarstar Fluorimeter (BMGLab Technologies, Mornington, Australia). $IC_{50}$ values were calculated, using Prism 6, by curve-fitting with a non-linear regression (one-site) analysis. At least three assays were performed with three replicates per data point.

The *C. geographus* venom insulin sCon-Ins G1 was found to be only thirty-fold less active against the human IR-B receptor than hIns (sCon-Ins G1: log [$IC_{50}$ (nM)]=1.24±0.06; hIns: log [$IC_{50}$ (nM)]=−0.26±0.02) despite lacking any equivalent to ArgB23 through to ThrB30 of hIns (FIGS. 1 and 2).

Insulin Signalling Activation Assay.

The ability of Con-Ins G1 to induce insulin signalling was assessed by Akt phosphorylation analysis. Briefly, pAkt Ser473 levels were measured in a mouse fibroblast cell line, NIH 3T3, overexpressing human IR-B. The cell line was cultured in DMEM with 10% fetal bovine serum (FBS), 100 U/mL penicillin-streptomycin and 2 μg/mL puromycin. For the assay, 40,000 cells per well were plated in a 96-well plates with culture media containing 1% FBS. 24 h later, 50 μL of insulin solution was pipetted into each well after the removal of the original media. After a 30-min treatment, the insulin solution was removed and the HTRF pAkt Ser473 kit (Cisbio, Massachusetts, USA) was used to measure the intracellular level of pAkt Ser473. Briefly, the cells were first treated with cell lysis buffer (50 μL per well) for 1 h under mild shaking. 16 μL of cell lysate was then added to 4 μL of detecting reagent in a white 384-well plate. After 4-h incubation, the plate was read in a Synergy Neo plate reader (BioTek, Vermont, USA) and the data processed according to the manufacturer's protocol. The assays were repeated for a total of four times. $EC_{50}$ values were calculated (using Prism 6) by curve-fitting with a non-linear regression (one-site) analysis.

It was found that Con-Ins G1 is only ca ten-fold less active than hIns in an Akt phosphorylation assay (sCon-Ins G1: log [$EC_{50}$ (nM)]=0.90±0.05; Con-Ins G1: log [$EC_{50}$ (nM)]=0.78±0.15; hIns: log [$EC_{50}$ (nM)]=−0.20±0.20; FIG. 3). Our results highlight the existence within Con-Ins G1 of structural motifs that enable potent activity despite the venom protein's lack of an equivalent to either the canonical aromatic triplet or the B-chain C-terminal segment as a whole.

Example 3—Crystal Structure of Con-Ins G1

Crystallisation and Data Collection.

Con-Ins G1 was synthesised as described above. Con-Ins G1 was prepared for crystallization in 10 mM HCl at a concentration of 4 mg/mL.

Initial crystallization trials employed a robotic 192-condition sparse-matrix hanging-drop screen conducted at the CSIRO Collaborative Crystallisation Centre (Parkville, Australia). A single crystal was extracted from a condition comprising 2.0 M ammonium sulphate plus 10% DL-malate-MES-Tris (pH 9.0) and then mounted directly (without cryo-protective agent) in a cryo-loop for diffraction data collection at 100K on the MX2 beamline at the Australian Synchrotron (λ=0.9537 Å). Data were processed to a resolution of 1.95 Å using XDS (Kabsch (2010)). The space group is P432 with unit cell dimensions a=b=c=74.91 Å. From the apparent molecular mass of 5143 Da per monomer and 1 molecule per asymmetric unit, the solvent content is estimated as 64%.

Structure Solution and Refinement

The structure was solved by molecular replacement using as starting model an insulin monomer from PDB entry 3I3Z and using the PHASER software (McCoy et al, 2007). Crystallographic refinement employed PHENIX (Adams et al. 2010) iterated with model building within COOT (Emsley and Cowtan, 2004). The single sulphate ion observed close to the four-fold axis was modelled without restraint upon its orientation or position, effected in PHENIX by setting its occupancy to unity rather than 0.25. Data processing and refinement statistics are presented in Table 1. The final model had a $R_{work}/R_{free}$ of 0.208/0.217. All residues in the final model lay in the favoured region of the Ramachandran plot.

TABLE 1

| X-ray data processing and refinement statistics | |
|---|---|
| X-ray data processing | |
| Space group | P432 |
| Cell dimensions | |
| a, b, c (Å) | 74.91, 74.91, 74.91 |
| α, β, γ(°) | 90, 90, 90 |

TABLE 1-continued

X-ray data processing and refinement statistics

| | |
|---|---|
| Resolution (Å) | 33.5-1.95 (2.02-1.95)[a] |
| $R_{merge}$ | 0.368 (2.67) |
| <I/σ(I)> | 6.46 (0.90) |
| $CC_{1/2}$ | 0.99 (0.20)[b] |
| Completeness (%) | 99.5 (95.8) |
| Redundancy | 8.9 (8.2) |
| X-ray refinement | |
| Resolution | 33.5-1.95 (2.04-1.95) |
| No. reflections | 5645 (635) |
| $R_{work}/R_{free}$ | 0.211/0.233 |
| No. atoms | |
| protein | 349 |
| sulfate ion | 1 |
| water | 35 |
| B factors (Å$^2$) | |
| protein | 35 |
| sulfate ion | 25 |
| water | 38 |
| r.m.s. deviations | |
| Bond lengths (Å) | 0.013 |
| Bond angles (°) | 1.39 |
| Ramachandran plot (%) | 100.0/0.0/0.0 |

[a]Numbers in parentheses refer to the outer resolution shell.
[b]Data were included to the maximum resolution at which the $CC_{1/2}$ correlation statistic remained significant at the p = 0.001 level of significance.

Example 4—Con-Ins G1 Structure

Figure 4A:
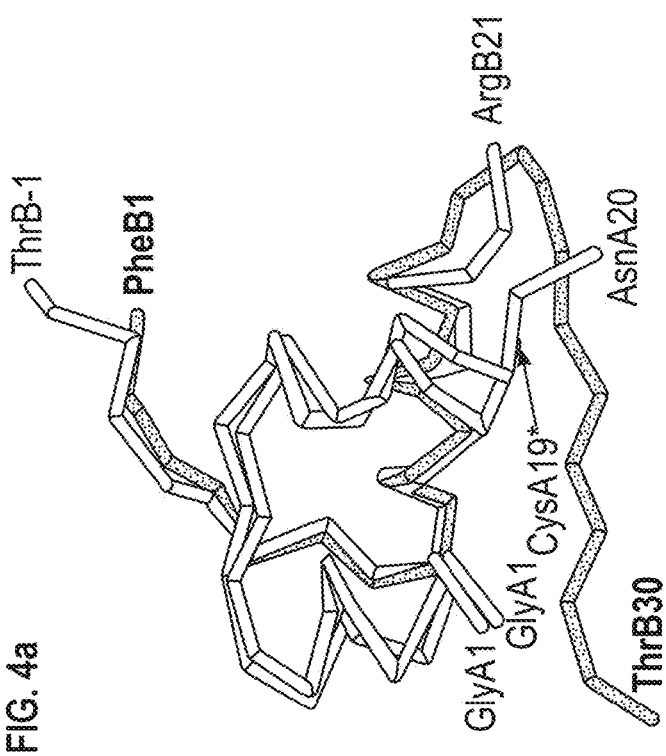
Figure 5:
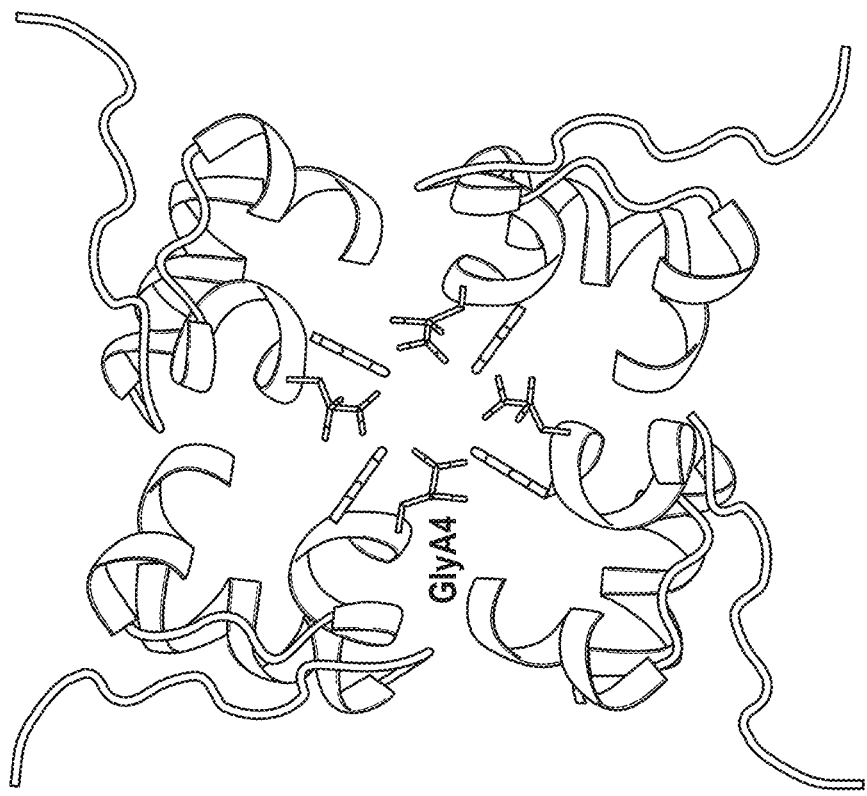
Figure 5:
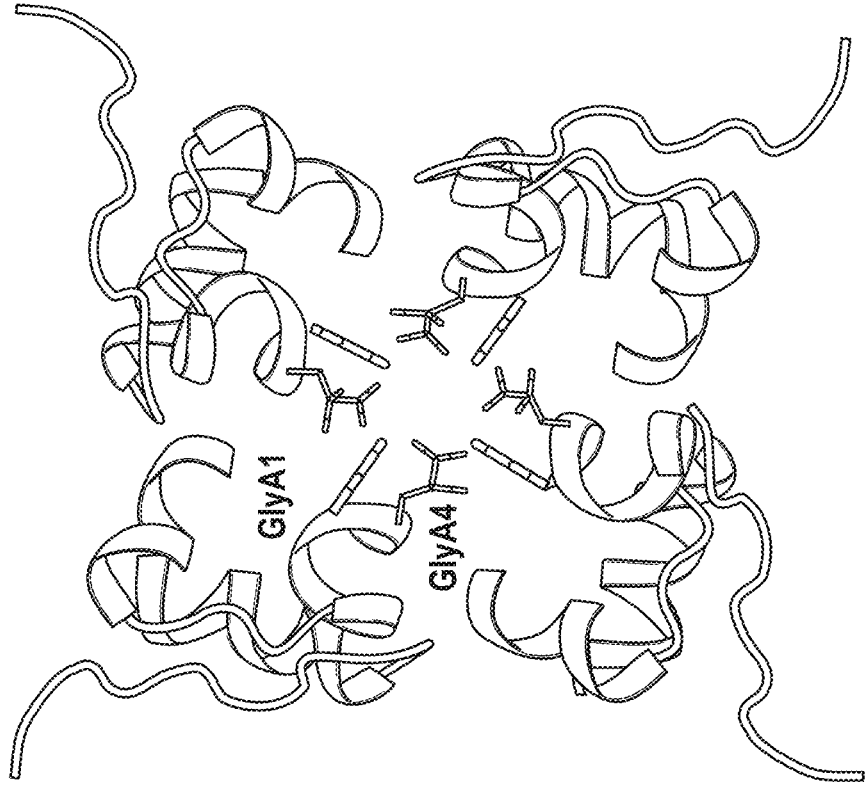

The structure reveals that the overall Con-Ins G1 secondary structure is similar to that of hIns, with the N-terminal residues of the B-chain following an extended path similar to that of the classical T-state hIns (FIG. 4a) (the T-state is characterized by residues B1-B8 being in an extended conformation, folded back against the A-chain helical assembly). As anticipated from the absence of residues equivalent to hIns B22-B30, there is no interface within the crystallographic unit cell resembling the hIns dimer interface. All monomer-monomer interfaces within the crystal are sparse, bar those formed between Con-Ins G1 monomers packed around the four-fold axis, each of which buries ~440 Å$^2$ of molecular surface. The four monomers coordinate an apparent sulphate ion lying close to the four-fold axis, which forms part of a charged-compensated cluster with the amides of GlyA1 and a single side-chain carboxylate group of each GlaA4 (FIG. 5). Based on sedimentation equilibrium data below the inventors conclude that this association is an artefact of crystallization.

Figure 4B:
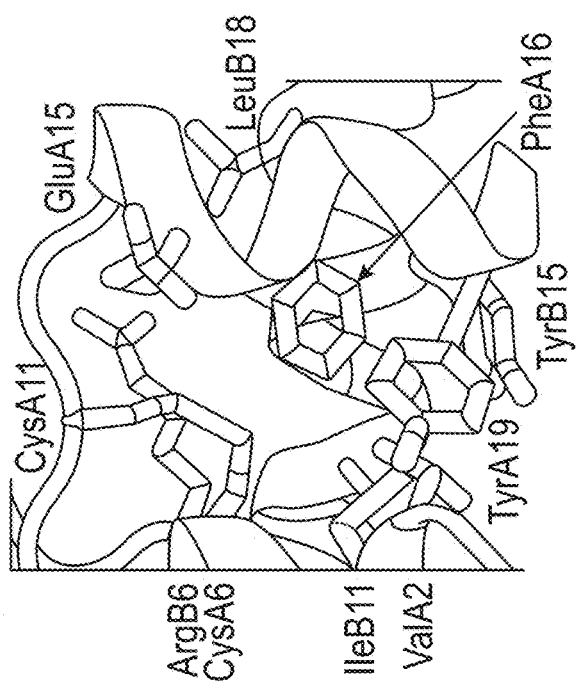

The hydrophobic core of Con-Ins G1 involves the side chains of residues ValA2, CysA6, CysA11, PheA16, TyrA19, ArgB6, IleB11, TyrB15 and LeuB18 (FIG. 4b). Of these, three are identical in human insulin (CysA6, CysA11 and TyrA19), three differ conservatively (ValA2→Ile, IleB11→Leu and LeuB18→Val) and three are markedly different (ArgB6→Leu, PheA16→Leu and TyrB15→Leu). In hIns, the LeuB15 equivalent of TyrB15 in Con-Ins G1 packs in part against the core and in part against the side chain of hIns PheB24; substitution by Tyr reduces somewhat the exposed hydrophobic surface of the Con-Ins G1 monomer in the absence of an equivalent to hIns B24. The bulkier side chain of Cons-Ins G1 PheA16 (compared to that of hIns LeuA16) appears to be associated with the change at TyrB15: the side chain of TyrB15 is further away from the core of the protein compared to its hIns counterpart, with the (larger) PheA16 aromatic ring compensating for this in terms of packing (FIG. 4b).

Example 5—Homology Modelling and Molecular Dynamics

To gain insight into the structural principles that enable Con-Ins G1 activity against the vertebrate insulin receptor in the absence of an equivalent of the key receptor-engaging residue hIns PheB24, the inventors created a model of Con-Ins G1 bound to the elements of the human insulin receptor (hIR) that form the primary binding site for the hormone. Models of Con-Ins G1 in complex with the IR L1-CR module (residues Gly5 to Lys310) and the IR αCT segment (residues Phe705 to Ser719 of the IR-A isoform) were created using MODELLER (v9.15) (Webb and Sali, (2014)) with the templates being the above crystal structure of Con-Ins G1, the crystal structure of the IR site 1 components in complex with hIns (PDB entry 4OGA; Menting et al. 2014), and the NMR structure of the A-chain of insulin (PDB entry 2HIU; Hua et al. 1995). All models included the post-translation modifications of Con-Ins G1 and a single N-linked N-acetyl-D-glucosamine residue at each of the IR residues Asn16, Asn25, Asn111, Asn215 and Asn255 (Sparrow et al. 2008).

Molecular dynamics (MD) simulations employed GROMACS (v5.0.4) (Pronk et al. 2013) with the CHARMM36 force field (Guvench et al. 2011; Best et al. 2012) and were initiated with the model of the Con-Ins G1/IR complex that had the lowest modeler objective function. Ionizable residues, including the carboxy-glutamic acids, were assumed to be in their charged state. Each system was solvated using the TIP3P water model in a cubic box extending 10 Å beyond all atoms. Sodium and chloride ions were added to neutralize the system and provide a final ionic strength of 0.1 M. The protein and solvent (including ions) were coupled separately with velocity rescaling to a thermal bath at 300 K applied with a coupling time of 0.1 ps. All simulations were performed with a single non-bonded cut-off of 10 Å and applying the Verlet neighbour searching cut-off scheme with a neighbour-list update frequency of 25 steps (50 fs); the time step used in all the simulations was 2 fs.

Periodic boundary conditions were used with the particle-mesh Ewald method used to account for long-range electrostatics, applying a grid width of 1.2 Å and a sixth-order spline interpolation. All bond lengths were constrained using the β-LINCS algorithm. Simulations consisted of an initial minimization, followed by 50 ps of MD with all protein atoms restrained. Following positionally-restrained MD, MD simulations were continued for a further 10 ns applying positional restraints on the Cα atoms of the IR excluding the C-terminal residues of αCT (residues Val715 to Ser719). Following the Cα atom-restrained MD, the simulations were continued without restraints for a further 50 ns. The coordinates of the final model are provided in Appendix II.

TyrB15

Figure 6:
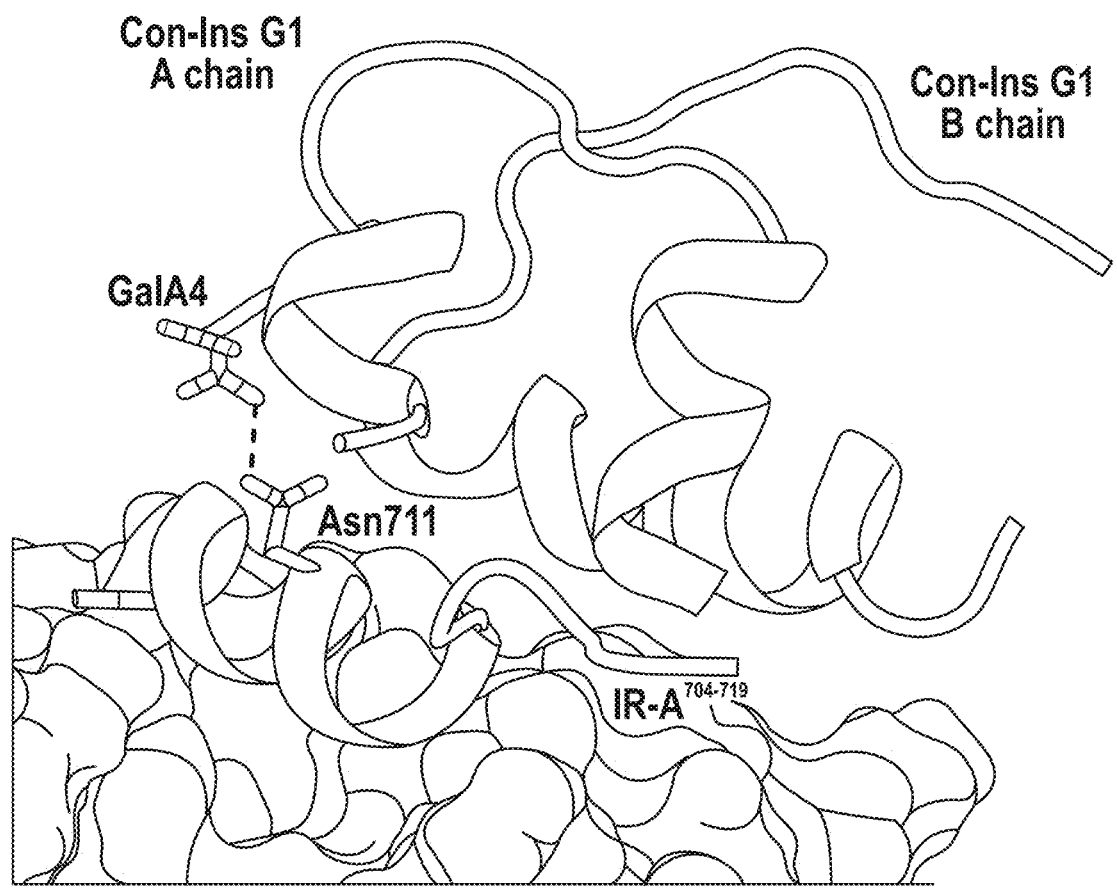

A salient feature that emerges from the model is that the side chain of Con-Ins G1 TyrB15 is rotated with respect to its conformation in our crystal structure in order to avoid steric clash with the hIR αCT residue Phe714. The rotation directs the side chain of Con-Ins G1 TyrB15 into the pocket occupied by hIns PheB24 in the receptor complex, suggesting that Con-Ins G1 TyrB15 is thus a surrogate for hIns PheB24 in terms of receptor engagement (FIG. 6). Such rotation of the TyrB15 side chain also permits the key hIR αCT residue Phe714 to engage the venom protein core (FIG.

6). By contrast, vertebrate insulins have leucine at position B15, which is strictly conserved.

TyrB20

Figure 7:
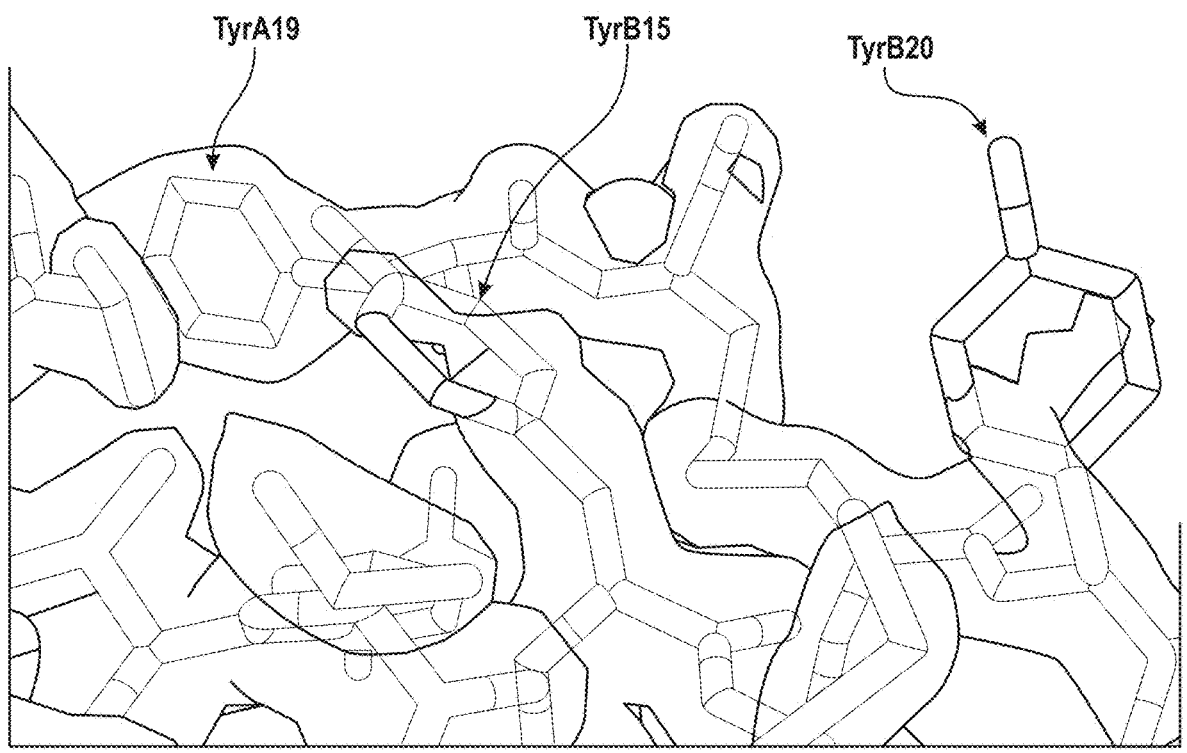

The side chain of Con-Ins G1 TyrB20 is adjacent to that of Con-Ins G1 TyrB15 and may also be involved in compensating for the lack of an equivalent to hInsPheB24. We note that the crystallographic difference electron density associated with the TyrB15 side chain is somewhat poorly defined, compatible with such mobility (FIG. 7). By contrast, vertebrate insulins have a glycine at position B20, which is strictly conserved.

The PTM

Figure 3:
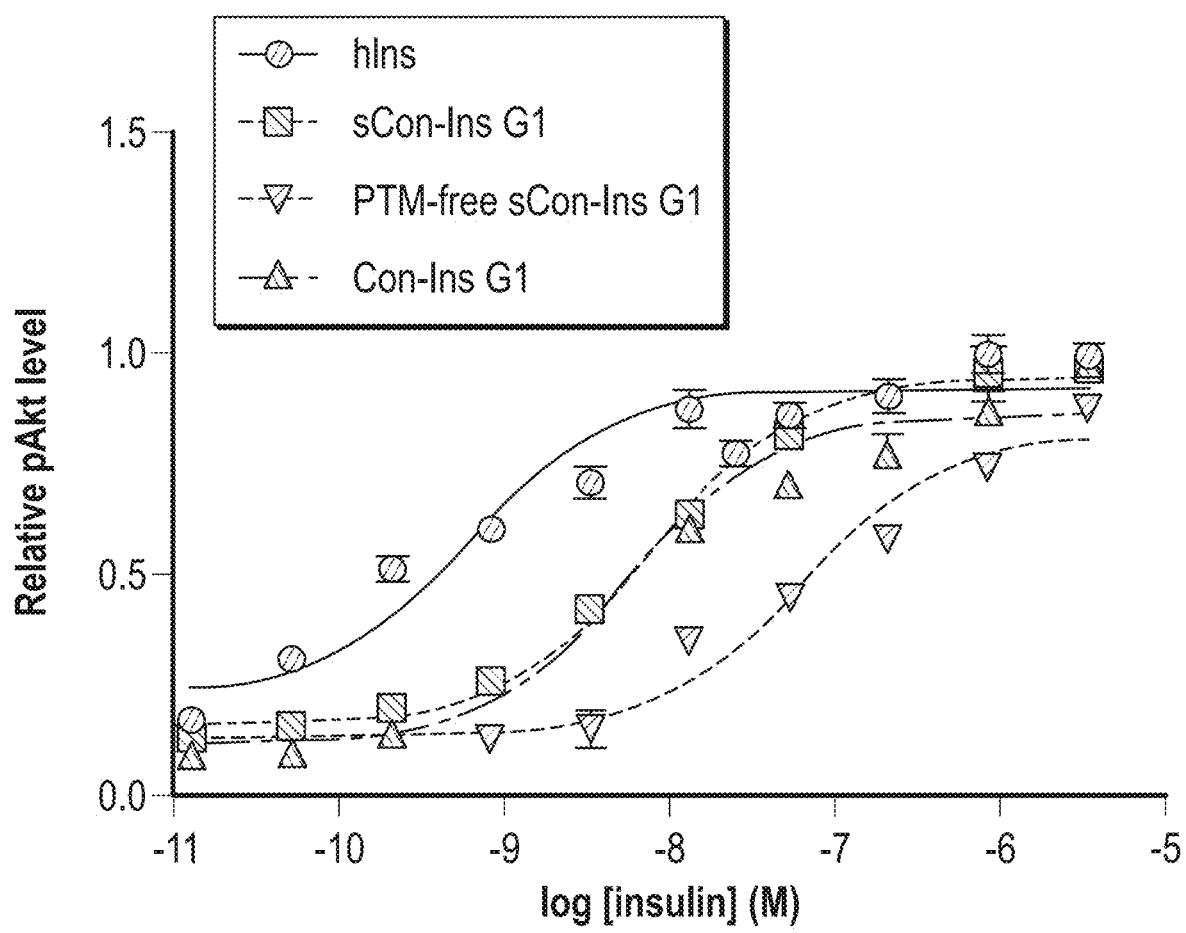

Con-Ins G1 contains the following four post-translational modifications (PTMs): residues A4 and B10 are γ-carboxy-glutamates (Gla) as opposed to Glu and His (respectively) in hIns, residue B3 is hydroxyproline (Hyp) as opposed to Asn in hIns, and the A-chain C-terminal residue CysA20 is amidated (FIG. 1); note that the Con-Ins G1 B-chain numbering begins at −1 to allow comparison with hIns). Such modifications are commonly observed in conotoxins but have not been detected previously in insulins (Safavi-Hemami et al. 2015). A synthetic analogue of Con-Ins G1 containing PTMs was four times more active against the human IR-B than a PTM-free analogue (FIG. 2) and induced Akt phosphorylation at eight-fold greater efficiency than the PTM-free analogue (FIG. 3).

Figure 4D:
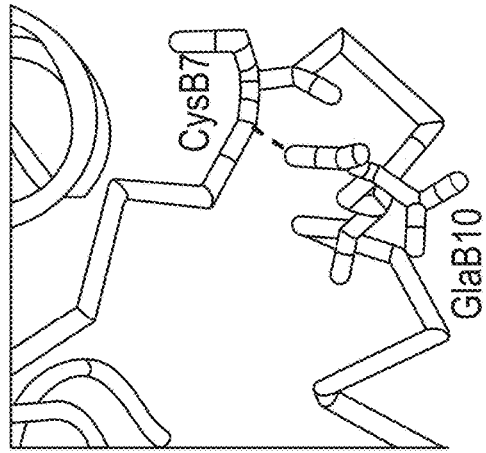
Figure 4C:
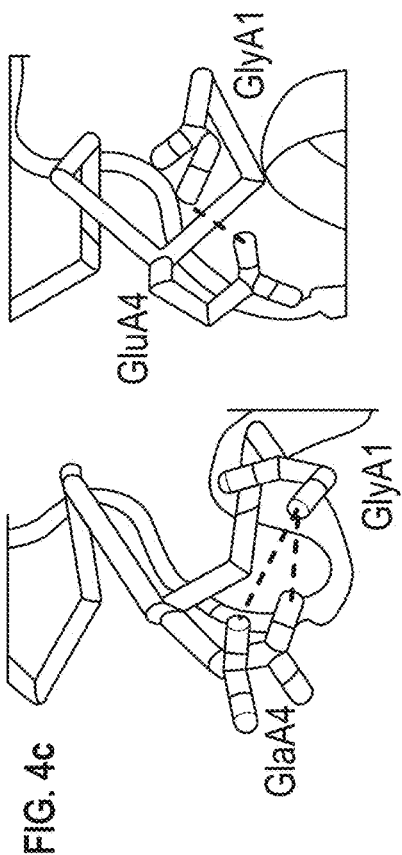
Figure 4E:
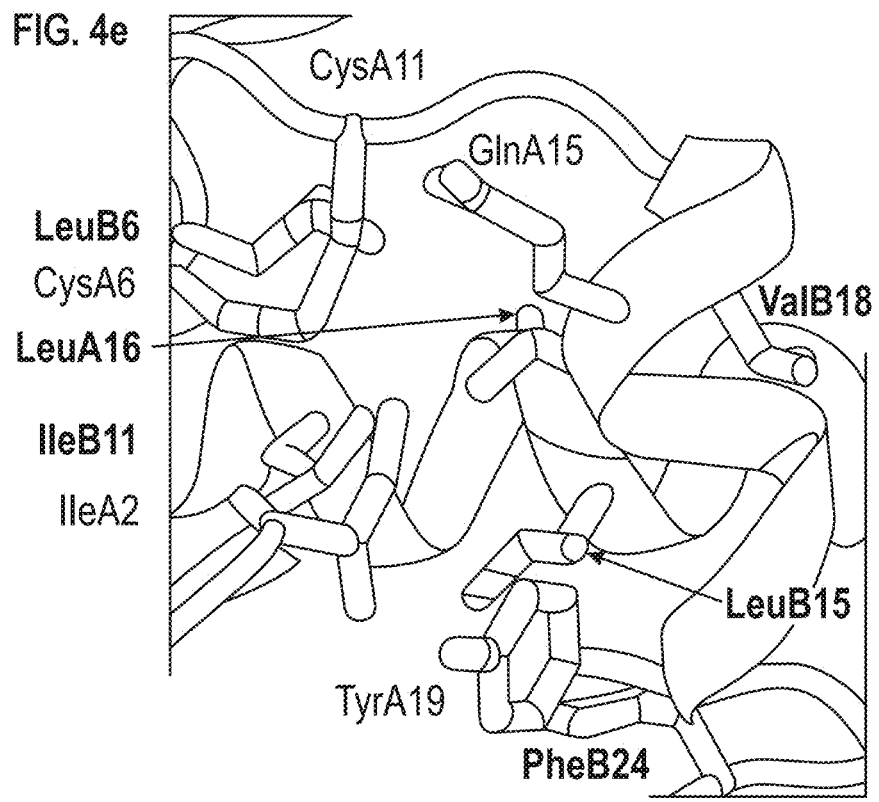
Figure 4F:
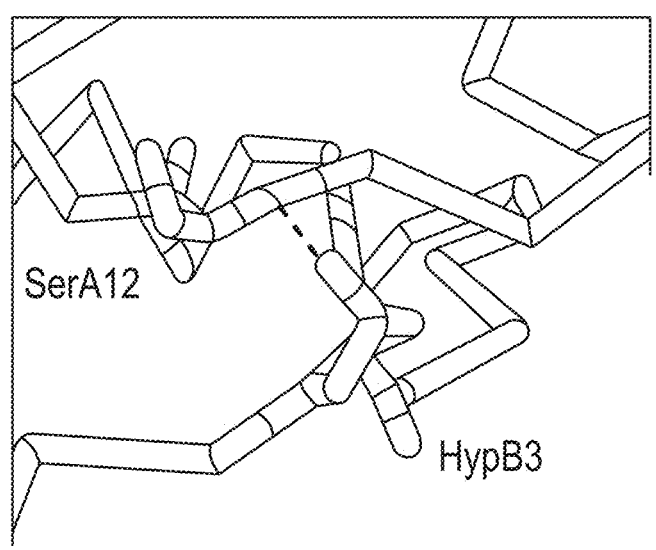

Examination of the four PTMs within the Con-Ins structure reveals that all—with the exception of amidation of CysA20—are likely to play a role in stabilizing the structure of Con-Ins G1. Both side-chain carboxylates of GlaA4 are in polar interactions with the N-terminal amino group of GlyA1, as is the single side-chain carboxylate of hIns GluA4 (FIG. 4c). These additional interactions in Con-Ins G1 may assist in stabilizing the short A-chain N-terminal helix. One side-chain carboxylate group of GlaB10 forms a hydrogen bond to the backbone amide of CysB7 and may play a role in stabilizing the B-chain N-terminal region; there is no equivalent interaction within hIns, hIns HisB10 being involved in hexamer formation (FIG. 4d). The side-chain hydroxyl group of HypB3 is equivalently located to the side-chain amide oxygen of hIns AsnB3 and may be able to form a (long) H-bond to the backbone amide of SerA12 (FIG. 4f). The C-terminal amide of CysA20 makes no interaction with the remainder of the venom protein.

Figure 8:
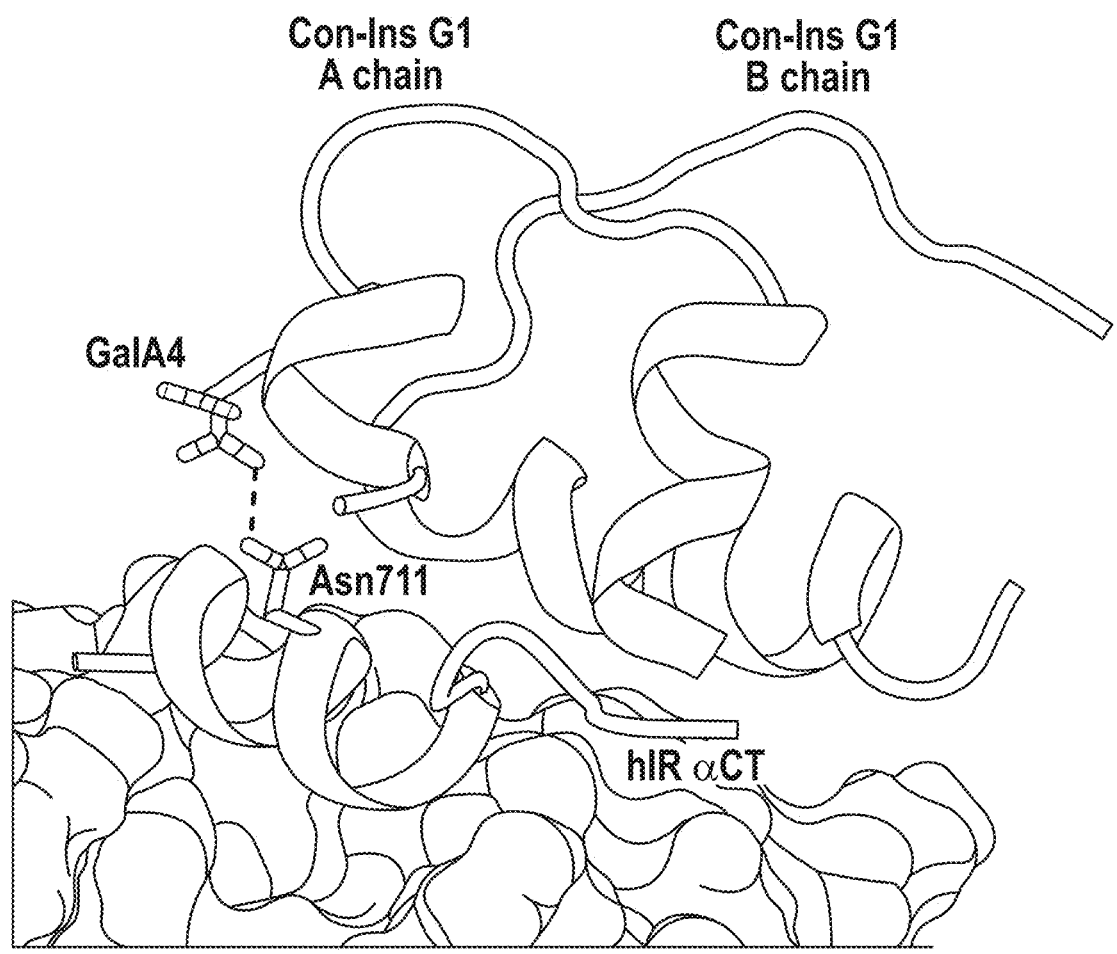

Within the model presented at example 5, the only PTM residue interacting with the receptor is GlaB4, its interaction being equivalent to that between hIns GluB4 and αCT Asn711 (FIG. 8).

Example 6—hIns G1 DOI L15Y.G20Y Signalling Activation

The ability of hIns[DOI] and hIns[TyrB15, TyrB20, DOI] to induce insulin signalling was assessed by Akt phosphorylation analysis as described above. Briefly, pAkt Ser473 levels were measured in a mouse fibroblast cell line, NIH 3T3, overexpressing human IR-B. The cell line was cultured in DMEM with 10% fetal bovine serum (FBS), 100 U/mL penicillin-streptomycin and 2 µg/mL puromycin. For the assay, 40,000 cells per well were plated in a 96-well plates with culture media containing 1% FBS. 24 h later, 50 µL of insulin solution was pipetted into each well after the removal of the original media. After a 30-min treatment, the insulin solution was removed and the HTRF pAkt Ser473 kit (Cisbio, Massachusetts, USA) was used to measure the intracellular level of pAkt Ser473. Briefly, the cells were first treated with cell lysis buffer (50 µL per well) for 1 h under mild shaking. 16 µL of cell lysate was then added to 4 µL of detecting reagent in a white 384-well plate. After 4-h incubation, the plate was read in a Synergy Neo plate reader (BioTek, Vermont, USA) and the data processed according to the manufacturer's protocol. The assays were repeated for a total of four times. $EC_{50}$ values were calculated (using Prism 6) by curve-fitting with a non-linear regression (one-site) analysis.

Figure 9:
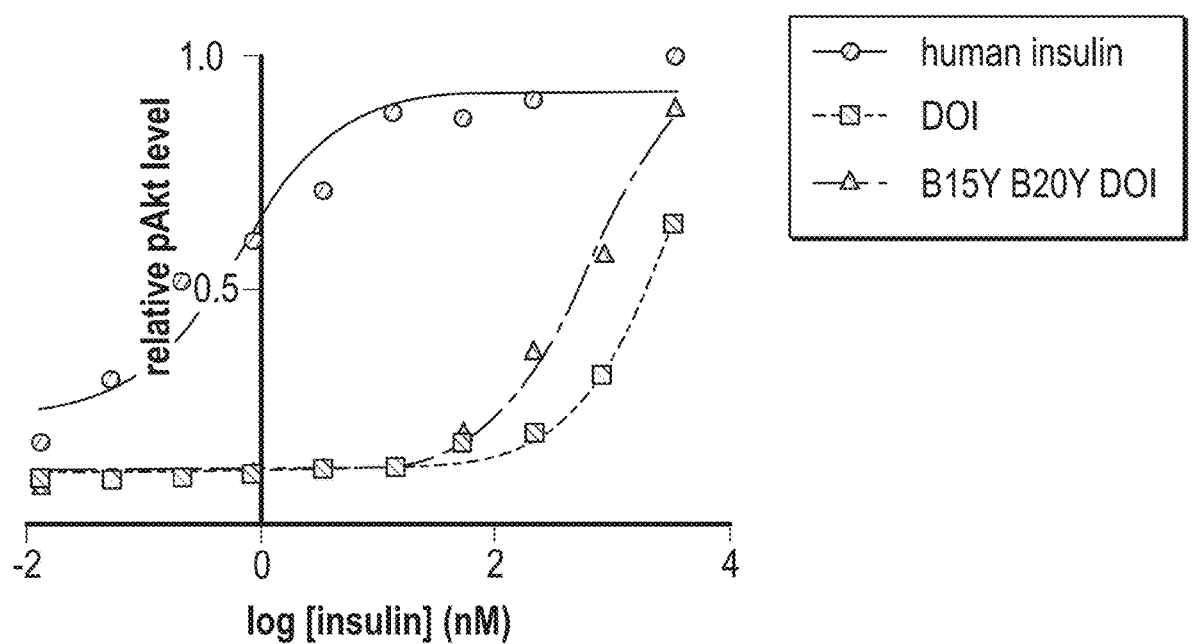

It was found that hIns[TyrB15, TyrB20, DOI] was ca five-fold more active than hIns[DOI] in an Akt phosphorylation assay (FIG. 9). Our results highlight the ability of mutations at position 15 and 20 of the human insulin B chain to at least partially compensate for the lack 8 C-terminal residues.

Example 7—Solution Properties of Con-Ins G1

The self-association state of Con-Ins G1 in solution at 100 µg/mL was analysed using sedimentation equilibrium analysis. Briefly, analytical ultracentrifugation was conducted at 20° C. using a Beckman XLI analytical centrifuge in 12 mm path-length cells. Con-Ins G1 was diluted from a 10 mg/mL stock in 10 mM HCl into 10 mM Tris, 50 mM NaCl, pH 7.4 to a final concentration of 100 µg/mL. An equal volume of 10 mM NaOH was added to neutralize any pH change. A total sample volume of 100 µL was used. Identical samples were prepared also containing 0.2 mM $ZnCl_2$, 2 mM $CaCl_2$), 1 mM sodium phosphate (pH 7.4) or 0.1 M ammonium sulfate. Radial concentration distributions were measured by absorbance at 220 nm. Sedimentation equilibrium was established at 30,000 and 45,000 rpm, as assessed by sequential absorbance scans 1 h apart. Data at both speeds were jointly fitted to a single ideal sedimenting species in SEDPHAT (Houtman et al. 2007) using values of solution density and solvent partial specific volume estimated from composition using SEDNTERP (Laue et al. 1992). With the exception of the disulfides, all post-translational modifications were neglected in the estimation of Con-Ins G1 partial specific volume. Reported errors describe the precision of the fit at 0.68 confidence level, estimated from Monte Carlo simulations as implemented in SEDPHAT.

Figure 10:
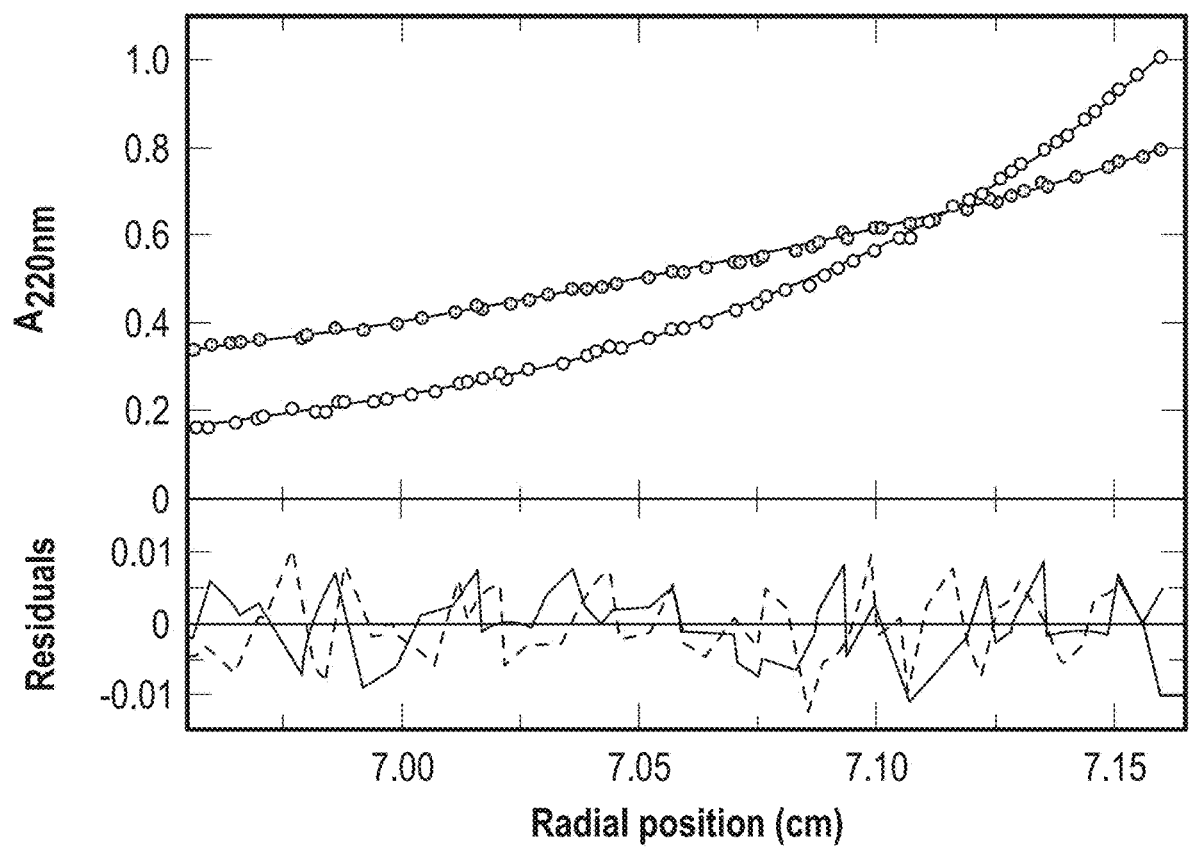

The data (obtained at 30,000 and 45,000 rpm) are well described by Con-Ins G1 being a single sedimenting species of apparent MW 5380±55 g/mol (FIG. 10). Although the fit is excellent (reduced $X$=0.95), the best-fit mass is slightly higher than expected. It is likely that this reflects an inaccurate estimate of the protein partial specific volume, which the inventors have determined from amino acid composition, neglecting the post-translational modifications present. It is possible however that this increase in predicted mass is the result of a small amount of higher molecular weight species present. At most this would equate to the presence of 5% dimeric Con-Ins G1. Based on a calculated theoretical mass of 5143, the inventors conclude that Con-Ins G1 is predominantly monomeric in solution. The monomeric nature of Con-Ins G1 is therefore in agreement with its lack of an equivalent to C-terminal part of human insulin chain B (amino acids B22-B30), which have been shown to be critical for the oligomerisation of insulin.

The inventors also tested whether $Zn^{2+}$, $Ca^{2+}$, $SO_4^{2-}$ or $PO_4^{3-}$ altered the aggregation state of Con-Ins G1; in particular, in the case of $Zn^{2+}$ to test whether the ion might mediate Con-Ins G1 multimerization as it does for hIns, and in the case of $SO_4^{2-}$ to test whether the ion might be involved in mediating the tetrameric arrangement observed in the crystal. In the presence of each of these respective ions similar sedimentation equilibrium profiles were observed, equally well described by single sedimenting species and with no significant change in apparent MW (data not shown). Accordingly, the inventors conclude that Con-Ins G1 remains predominantly monomeric in the presence of each of these ions, at least at concentrations up to 100 µg/mL.

Example 8—Crystal Structure of Con-Ins G1 in Complex with Human Insulin Receptor Fragments that Reconstitute the Primary Hormone Binding Site of the Receptor Crystallisation and Data Collection.

The primary insulin binding site ("Site 1") of the human insulin receptor (hIR) can be re-created in a domain minimized and suitable for crystallographic analysis of the interaction of insulin or insulin analogues with Site 1 (Menting et al. 2013) (Lawrence et al. 2016). Integral to this process is the further attachment of fragments of the monoclonal antibody 83-7 (Soos et al. 1986) to the CR domain of the receptor fragment to assist crystallization. This technique was used to generate crystals of Con-Ins G1 in co-complex with the elements that re-create hIR Site 1.

Con-Ins G1 was synthesised as described in Example 1. Con-Ins G1 was resuspended in 10 mM HCl.

hIR construct IR310.T (i.e., residues 1-310 of hIR followed by the N-terminal remnant Leu-Val-Pro-Arg of a thrombin cleavage site and inclusive of the population variant Tyr144His) was produced and purified as described in Menting et al. 2013. Fv83-7, the variable domain module of the monoclonal antibody 83-7 (Soos et al. 1986), was produced and purified as described in (Lawrence et al. 2016). IR310.T was then complexed with Fv83-7 and the complex purified as described in Lawrence et al. 2016. The Fv83-7.IR310.T complex was then subject to endoglycosidase H treatment as described in Lawrence et al. 2016.

Peptide IR-A$^{704-719}$ of the A isoform of hIR was synthesized under contract by Genscript (USA).

Con-Ins G1 in complex with human insulin receptor fragments that reconstitute the primary hormone binding site of the receptor was prepared by combining EndoH-treated Fv83.7.IR310.T, IR-A$^{704-719}$ and Con-Ins G1 as shown in Table 2.

TABLE 2

Preparation of Con-Ins G1 in complex with human insulin receptor fragments

| Component | Buffer and concentration | Mol equivalent (relative to EndoH-treated Fv83.7.IR310.T) |
|---|---|---|
| EndoH-treated Fv83.7.IR310.T | 3 mg/ml in 10 mM HEPES-NaOH buffer pH 7.5 plus 0.02% sodium azide | 1 |
| IR-A$^{704-719}$ | 10 mM HCl | 3 |
| Con-Ins G1 | 10 mM HCl | 3 |

Initial crystallization trials employed a robotic 576-condition sparse-matrix sitting-drop screen conducted at the CSIRO Collaborative Crystallisation Centre (Parkville, Australia). Each drop contained a 1:1 well:complex volume ratio. Crystal growth was observed using 1.8 to 2.0 M ammonium sulfate or 1.8 to 2.0 M ammonium sulfate with any one of 0.1 M Tris-HCl, pH 7.5; MOPS-NaOH pH 7.0 and MES-NaOH, pH 6.5.

Crystallisation conditions were optimised and single crystals of the same protein:peptide:Con-Ins G1 mixture were grown using hanging drop format in Linbro 24 plates and a reservoir buffer consisting of 1.8 to 2.0 M ammonium sulfate or 1.8 to 2.0 M ammonium sulfate, 0.1 M Tris-HCl, pH 7.5. Other buffers (e.g. MOPS-NaOH pH 7.0 and MES-NaOH, pH 6.5) were also trialed and produced similarly diffracting crystals. A single crystal grown in a solution of 1.7 M ammonium sulphate, 50 mM MOPS-NaOH pH 7.0 gave the best diffraction data, The single crystal of Con-Ins G1 in co-complex with IR-A$^{704-719}$ and the EndoH-treated Fv83.7.IR310.T complex was cryo-protected by transfer to a solution consisting of reservoir buffer plus 30% glycerol and extraction into a cryo-loop. The loop was then plunged directly into a bath of liquid nitrogen. Diffraction data to 3.25 Å resolution were collected at beamline MX2 at the Australian Synchrotron (Melbourne, Australia). Data were integrated and merged using the XDS package (Kabsch, 2010); Data processing statistics are presented in Table 3. The space group is I222 with unit cell dimensions a=106.16, b=227.12 and c=228.70 Å. From the apparent molecular mass of 63440 Da per complex and 2 complexes per asymmetric unit, the solvent content is estimated as 77%.

Structure Solution and Refinement

The structure was solved by molecular replacement using PHASER (McCoy et al. 2007), employing as search model the a single Fv83-7.IR310.T component of PDB entry 4OGA (Menting et al. 2014). Two copies were located in the asymmetric unit. Electron density corresponding to two copies of Con-InsG1 (bound separately to the two respective L1+IR-A$^{704-709}$ fragments of IR) were visible in the difference electron density map. Residues of Con-Ins G1 were then built objectively into the electron density. X-ray crystallographic refinement employed PHENIX (Adams et al. 2010). Final stages of refinement included TLS refinement, restrained individual B-factor refinement and torsional NCS restraints. Final refinement statistics are presented in Table 3. The final model included the residues detailed in Table 4.

TABLE 3

X-ray data processing and refinement statistics

| X-ray data processing | |
|---|---|
| Space group | I222 |
| a, b, c (Å) | 106.16, 227.12, 228.70 |
| Resolution (Å) | 50-3.25 (3.35-3.25) |
| $R_{merge}$ | 0.259 (2.748) |
| I/σ(I) | 6.44 (0.59) |
| $CC_{1/2}$ | 0.992 (0.163) |
| Completeness (%) | 99.8 (99.9) |
| Redundancy | 5.8 (6.0) |
| X-ray refinement | |
| Resolution (Å) | 50-3.25 |
| No. reflections | 43845 |
| $R_{work}/R_{free}$ | 0.2285/0.2786 |
| No. atoms: | |
| Protein | 8969 |
| Carbohydrate | 282 |
| Solvent | 20 |
| <B> (Å$^2$): | |
| Protein | 124.9 |
| Carbohydrate | 153.9 |
| Solvent | 127.4 |
| Root-mean-square deviations: | |
| Bond lengths (Å) | 0.002 |
| Bond angles (°) | 0.5 |

TABLE 3-continued

X-ray data processing and refinement statistics

Ramachandran plot:

| | |
|---|---|
| Allowed (%) | 92.0 |
| Favoured (%) | 7.6 |
| Outlier (%) | 0.4 |

[a] Numbers in parentheses refer to the outer resolution shell.
[b] Data were included to the maximum resolution at which the $CC_{1/2}$ correlation statistic remained significant at the p = 0.001 level of significance.

TABLE 4

Residues included in the final model of Con-Ins G1 in complex with Fv83-7.IR310.T and IR-A$^{704-719}$ The final model contain two copies (Complex 1 and complex 2) of the complex in the asymmetric unit.

| | Complex 1 | Complex 2 |
|---|---|---|
| Con-Ins G1 A chain | 1-20 | 1-20 |
| Con-Ins G1 B chain | 4-19 | 4-19 |
| IR310.T | 5-159, 168-265, 276-309 | 5-159, 168-265, 276-309 |
| IR-A$^{704-719}$ | 705-719 | 705-715 |
| Fv83-7 Heavy chain | 1-118 | 1-117 |
| Fv83-7 Light chain | 1-114 | 1-111 |
| No. of N-linked glycan residues | 11 | 11 |
| No. of ions | 4 sulfate ions | |

Example 9—Con-Ins G1 in Complex with Human Insulin Receptor Fragments

Figure 11:
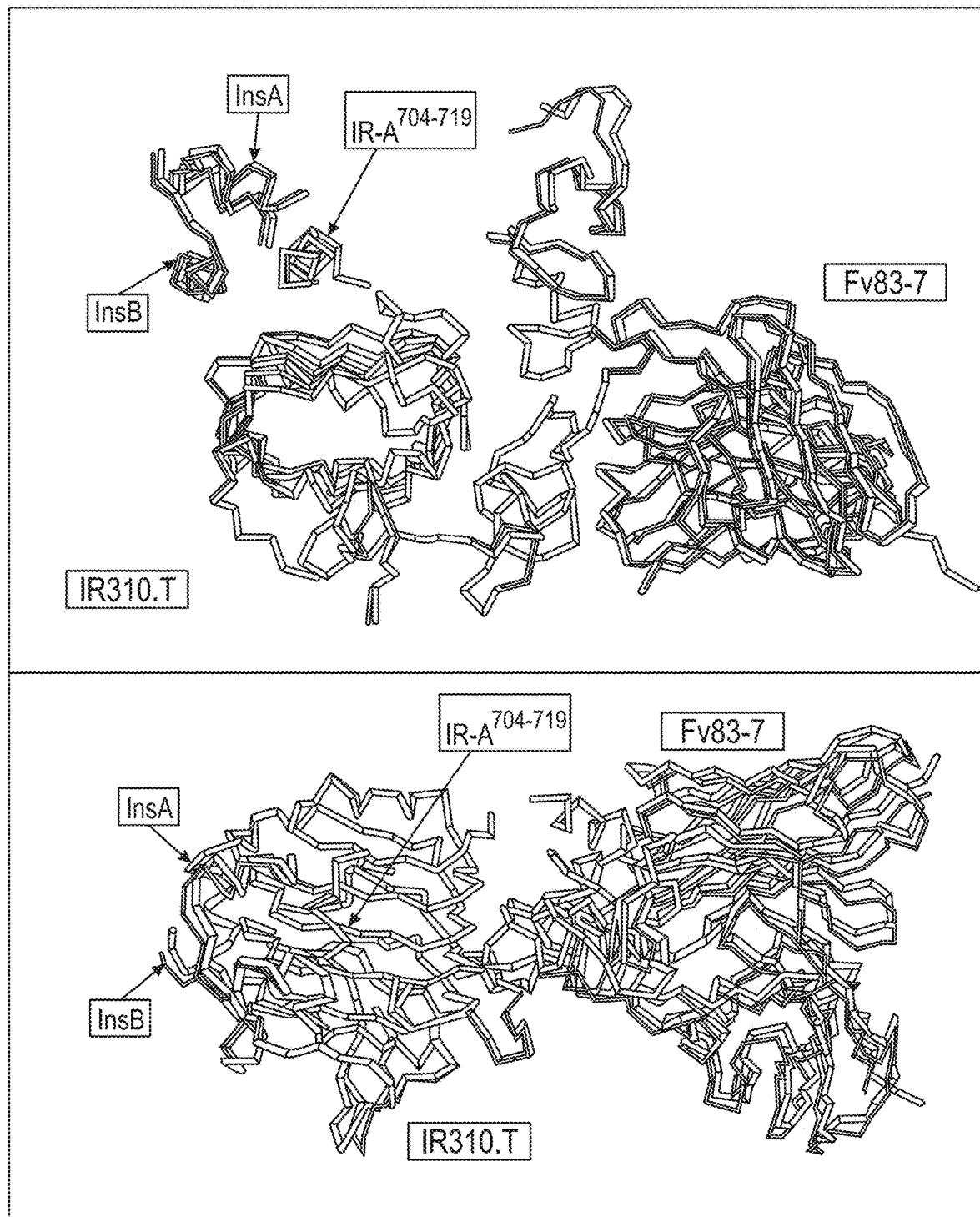

The two copies of the complex within the crystallographic asymmetric unit showed only limited differences in overall structure (FIG. 11) and description here will thus be restricted to the Complex 1.

An overlay of crystal structure of the Con-InsG1 complex with the crystal structure of hIns in co-complex with Fab83-7.IR310.T and IR-A$^{704-719}$ (PDB entry 4OGA; Menting et al. 2014) is provided in FIG. 12. The overall structure of Con-Ins G1 in complex with human insulin receptor fragments is similar to that of equivalent sub-structure within the structure of hIns complexed with IR310.T, IR-A$^{704-719}$ and Fab 83-7. A salient difference is that for the Con-InsG1 complex interpretable electron density was apparent for three residues N-terminal to Con-Ins G1 B7. The final model thus includes Con-Ins G1 residues B4, B5 and B6. In contrast, in the human insulin co-complex structure, the B chain of hIns could be modelled only from residue B7 onwards in the C-terminal direction.

FIG. 13 shows an overlay of the structure of the Con-Ins G1 complex determined here with that of human insulin complexed with IR310.T, IR-A$^{704-719}$ and Fab 83-7, focusing on residue TyrB15 of Con-Ins G1. As is evident, the side-chain of TyrB15 is rotated from its receptor-free position to be positioned in the same location that is occupied by that of hIns PheB24 in the human insulin complex. The complex structure supports the conclusion from Example 5 that TyrB15 helps compensate for the lack of PheB24. No interpretable electron density is present for Con-Ins G1 TyrB20.

Example 10—Molecular Modelling of hIns[DOI], hIns[TyrB15, DOI] and hIns[TyrB20, DOI] with the Components that Comprise the Primary Binding Site (Site 1) of the Human Insulin Receptor Models of des-octa-insulin (hIns[DOI]: a human insulin that lacks the eight C-terminal residues of the B chain) in complex with the IR L1 domain (residues Gly5 to Cys155) and IR-A$^{705-714}$ were created with MODELLER (v9.16) (Webb & Sali, 2014) using the crystal structure of the IR site 1 components in complex with human insulin (hIns) (PDB entry 4OGA; Menting et al. 2014) and the NMR structure of the A chain of insulin (PDB entry 2KJJ). All models included the post-translational modifications of a single respective N-linked N-acetyl-D-glucosamine residue at each of the IR residues Asn16, Asn25 and Asn111.

Molecular dynamics (MD) simulations were conducted using the GROMACS (v5.1.2) (Abraham et al. 2015) suite of programs and a modified version of the CHARMM36 (Guvench et al. 2011; Best et al. 2012) force field initiated with the model of the hIns[DOI]-IR complex that had the lowest MODELLER objective function. Each system was placed in a TIP3P single point water model solvated cubic box extending 10 Å beyond all atoms with periodic boundary conditions used along all axes. Ionizable residues were assumed to be in their charged state and a final ionic strength of 0.1 M was obtained by neutralizing the system and adding sufficient sodium and chloride ions. Temperature coupling was conducted in 2 groups with the protein and solvent coupled independently to a velocity rescaling (Bussi et al. 2007), thermostat at 300 K, both groups utilising a time constant of 0.1 ps. Isotropic pressure coupling was implemented with the Berendsen (Berendsen et al. 1984) technique using a reference pressure of 1 bar and a time constant of 0.5 ps. All simulations were performed with a universal 12 Å non-bonded interactions cut-off, with long-range electrostatics accounted for using the particle-mesh Ewald method (Essmann et al. 1995) with a grid width of 1.0 Å and a sixth-order spline interpolation. The Verlet neighbour searching cut-off scheme was applied with a neighbour-list update frequency of 25 steps (50 fs); the time step used in all the simulations was 2 fs. All bond lengths were constrained with the β-LINCS algorithm (Hess, 2008). Simulations underwent an initial steepest decent minimization followed by 50 ps of MD with all protein atoms restrained. Following positionally restrained MD, MD simulations were continued for a further 100 ns Analysis of the insulin analogue interaction with the receptor was made using the FoldX suite of programs (Schymkowitz, et al. 2005) after 100 ns MD. The FoldX RepairPDB utility was used to ensure the structures had no unreasonable torsion angles or van der Waals' clashes before the position scan was conducted, indicating the resultant mutational ΔΔG contribution at each site of the hIns[DOI].

Des-Octa-Insulin (hIns[DOI])

The interactions made by hIns[DOI] conserves similar interactions at the interface between insulin and the receptor observed in the X-ray crystal structure of native hIns with the receptor (PDB entry 4OGA), particularly interactions made within the hydrophobic pocket generated by B domain residues ValB12, LeuB15 and receptor residues Asn15, Leu37, Phe39, and Phe714. The absence of B-chain C-terminal residues results in the B-chain helix no longer unwinding, resulting in a transient salt bridge between ArgB22 and GluA17. This also allows the B chain helix to shift closer to IR-L1, resulting in π-π parallel displaced stacking between TyrB16 and IR-L1 Tyr67. The final model is shown in FIG. 14.

Des-Octa-Insulin-TyrB15 (hIns[TyrB15, DOI])

Over a 100 ns time period the interactions observed by hIns[TyrB15, DOI] are similar to those made by hIns[DOI]. The B-chain helix mirrors the shift closer to the IR L1 domain with similar π-π stacking between TyrB16 and IR-L1 Tyr67. The flexibility of C-terminal B-chain residues similarly allows the transient salt bridge between ArgB22 and GluA17. The presence of a Tyr at the B15 position projects into the hydrophobic core of the DOI-(IR-A$^{704-719}$)-L1 interface occupying space otherwise occupied by hIns LeuB15. The final model is shown in FIG. 15.

Des-Octa-Insulin-TyrB20 (hIns[TyrB20, DOI])

The initial comparative model included a restraint to ensure TyrB20 occupied the hInsB24 binding site. Following 100 ns of MD TyrB20 remained in the hIns B24 binding site, with all other interactions with the receptor appearing native-like. Unlike hIns[DOI], the native π-π parallel displaced stacking between TyrB16 and IR L1 Phe39 was maintained, however, the salt bridge caused by the lack of B-chain C-terminal residues between ArgB22 and GluA17 was the same as that observed with hIns[DOI]. The final model is shown in FIG. 16.

FoldX Mutational Position Scan Analysis

The FoldX position scan utility provides a qualitative interpretation as to the positions within hIns[DOI] that can accommodate mutations, and those that cannot (FIGS. 17, 18 and 19). Within hIns[DOJ] and hIns[TyrB20, DOJ] the solvent-exposed residues within the A chain, particularly residues GluA4, GlnA5 and ThrA8 indicate a little net positive or negative effect to most mutations. This is dissimilar to that of the hIns[TyrB15, DOI] analogue which instead proposed a positive impact on mutation of these residues. Mutations occurring within the hydrophobic core at the interaction face not-surprisingly appeared to suggest a greater effect with all models, and all models suggested disulfide bonded cysteines could undergo significant ΔΔG advantages however this data was removed due to the importance the disulfide interactions have on the overall structure of the analogues. Mutations at residues TyrA14, AsnA18, HisB5 and GluB21 indicated that in the DOI-TyrB20 analogue mutations at these positions were advantageous, where they were not in the DOI analogue; indicating a more favourable interaction. The DOI-TyrB15 analogue however provided results analogous to an amalgam of the results of DOI and DOI-TyrB20, suggesting only minor differences at all sites, with the exception of HisB5. Mutations at positions AsnB3 and GlnB4 indicated the inverse, however this is presumably due to the orientation of the B chain in proximity to the B chain helix at this frame, and is therefore an artefact of the sampling technique.

Conclusions

The MD simulations of the hIns analogues, hIns[DOI], hIns[TyrB15, DOI] and hIns[TyrB20, DOI], in complex with the IR L1 domain and IR-$A^{705-719}$ and subsequent mutational analysis provide insight as to the method hIns[DOI] binds despite the lack of key receptor engagement residues, particularly PheB24. The simulations indicate that the tyrosine substitution at position B20 can act as a substitute for PheB24 in hIns, occupying approximately the same location, and is stable over the simulated time. The simulation of hIns[DOI] (which lacks PheB24 and any attempt to replace it by mutation at B15 or B20) in interaction with the insulin receptor fragments shows that its engagement is holistically similar to that of hIns with IR L1 and IR-$A^{705-719}$ but with subtle differences at sites between the IR L1 domain and the analogue B chain. The shift of the B chain towards the IR L1 domain is not observed in the hIns[TyrB20, DOI] complex due to the steric clash that would occur, however it is observed in hIns[TyrB15, DOT], suggesting the impact of substitution at B20 is different to that at B15. The mutational FoldX calculations suggest that similarly favourable mutations exist at sites unaffected by the resultant change in binding pose upon B20 mutation, with these differences localized distal to the hydrophobic core.

Example 11—Development of Monomeric Human Insulin Analogs

Research Strategy for New Insulin Analogs

As described herein, the recent discovery of a monomeric insulin variant (Con-Ins-G1) in the venom of a predatory snail has helped propel the research behind the disclosed peptides. Methods have been developed and data has been obtained that explain how Con-Ins-G1 both avoids dimerization and maintains receptor binding and insulin signaling, and thereby acts very quickly. Furthermore, insights from fundamental discoveries have been used to develop a protein that only differs from the sequence of human insulin at four amino acid positions yet is monomeric, fast acting, and displays potency comparable to that of authentic human insulin.

The insights gained from study of Con-Ins-G1 were used to develop a monomeric human insulin that displays only four amino acid substitutions from the human "shortened" protein.

To circumvent the constraints of human insulin's structure, solutions were taken from nature: fish-hunting cone snails, *Conus geographus*, have evolved the use of specialized insulin from their venom that induces paralyzing hypoglycemic shock in fish within seconds. The sequence of venomous insulin, Con-Ins-G1, was elucidated using a combination of genome sequencing and mass spectrometry (FIG. 1). Notably, four post-translational modifications were observed: A4 Glu and B10 Glu to gammacarboxyglutamic acid, Gla; B3 Pro to 2-hydroxylproline, and a C-terminal amide on the A-chain. Due to the low abundance of this venomous insulin, it cannot be isolated from the animal. Instead, a synthetic analogue (sCon-Ins-G1) was obtained in which, for ease of synthesis, a diselenium-bond replaced the intra-molecular disulfide bond in the A chain. sCon-Ins-G1 induces hypoglycemic shock when it is injected into fish, and it slows fish motility when it is present in the water. Other than its effects on fish, the most special feature of Con-Ins-G1 is that it is the shortest insulin molecule reported to date with a "shortened" B chain. Because a shortened human insulin (des-octapeptide insulin, DOI) is monomeric, it indicated that Con-Ins-G1 is monomeric and can be used as an UFI (ultra-fast acting insulin). Con-Ins-G1 lacks two segments that in human insulin are involved in binding to with the human insulin receptor (hIR): First, A21 Asn of human insulin contacts hIR binding site 1 and its removal causes a 100-fold reduction in binding affinity. Second, the aromatic triplet (B24-B26) is one element for human insulin to bind hIR binding through contacts at hIR binding site 1. Removal of these residues leads to a 1,000-fold reduction in affinity.

Despite these concerns, Con-Ins-G1 (instead of the selenium analogue) was chemically synthesized and it was found that it binds to hIR with only 30-fold less affinity than human insulin. This surprising result raised a key question: how does Con-Ins-G1 bind to hIR without the key aromatic residues used by human insulin? The structure of Con-Ins-G1 was found to display a nearly identical backbone as human insulin. By fitting the Con-Ins-G1 structure into a published human insulin-hIR co-structure, it was inferred that Con-Ins-G1 B15 Tyr and B20 Tyr (Leu and Gly in human insulin) interact with human IR to substitute for the role played by human B24 Phe. These strong results provide a rational basis to develop a human monomeric UFI based on the snail insulin structure.

Develop Human Monomeric Insulin Analogs as Therapeutic Leads.

The development of ultra-fast acting insulin (UFI) represents the next major advance in insulin analogue development. The fundamental challenge in redesigning human insulin is that the same residues involved in receptor binding also mediate dimer formation. Thus, the discovery of the venomous insulin Con-Ins-G1 represents an important step forward in the creation of a monomeric, ultrafast-acting insulin because it lacks these residues (and thus does not dimerize) but retains the ability to bind and activate the insulin receptor. There is concern, however, that the low sequence identity between Con-Ins-G1 and human insulin could give rise to an immune response, especially given that diabetes is a chronic disease that requires daily insulin injections. Therefore, instead of developing an UFI based on the venomous insulin, one can start with the scaffold of human DOI (Des-octapeptide (B23-30) human insulin) because it is monomeric and because close analogs of this truncated human insulin are likely to be tolerated by the human immune system, as indicated by the current clinical use of insulin analogues displaying two or three mutations. The challenge, however, is that DOI is nearly inactive (1,000-fold weaker than human insulin). Data indicate that Con-Ins-G1 uses the B15 Tyr and/or B20 Tyr to compensate for the loss of B24 Phe, and further indicate additional modifications that enhance the affinity of Con-Ins-G1. Leveraging these insights, DOI can be developed into an active UFI analogue as a therapeutic lead for diabetes treatment.

Develop Human DOI into a Bioactive Monomeric Insulin

Traditionally, DOI was synthesized enzymatically by trypsin cleavage of human insulin, which is not suitable for analogue synthesis. Therefore, a modular synthetic route to access DOI has been developed. The primary challenge for the synthesis of human insulin is the hydrophobic character of the A chain. By using an isoacyl peptide pair on the A8-A9 Thr-Ser, an extra charged residue (amine) was introduced to the A chain to increase its solubility (FIG. 21). After disulfide bond formation, the isoacyl peptide underwent an O-to-N acyl shift at pH 8 to yield the DOI sequence. This synthetic DOI has the same molecular weight (from MALDI) and hIR activation activity as the enzymatically synthetic DOI, which proves the reliability of the developed method.

It has been demonstrated that the two Tyr on B15 and B20 of Con-Ins-G1 are important for hIR activation. To test the hypothesis that mutations on these two sites will increase the potency of hIR activation, three DOI analogues with B15 Leu and/or B20 Gly mutated to Tyr were synthesized. As shown in FIG. 22, the two analogues with B20 Tyr have 5-fold increased potency in hIR activation while the B15 Tyr DOI analogue is similar to DOI. This demonstrates that B20 Tyr alone can increase the potency of DOI, likely due to compensation for loss of B24 Phe. To further increase potency, a DOI analogue that additionally displays B10 Glu was synthesized, which is the B10 substitution that gives the strongest hIR binding. This provided another 5-fold increase in potency compared to B20 Tyr alone, and has a similar potency as Con-Ins-G1 (FIG. 23). This demonstrates that mutations from the venomous insulin can be grafted onto human DOI to develop bioactive analogues.

The crystal structures of Con-Ins-G1 and of ConIns G1 in complex with the site 1 fragments of the human insulin receptor lack clear electron density for the B20 residue, which indicates that it may be flexible. It is also possible that the side chain of a tyrosine substituent at this position may not optimally engage the insulin receptor. Therefore, the hypothesis that substitutions other than Tyr can further increase potency were tested by synthesizing a series of B10E, B20X DOI analogues with X being aromatic amino acids (FIG. 24A). Interestingly, large substituents such as indole (Trp) and biphenyl group lead to higher potency in hIR activation (FIG. 24B). The biphenyl analogue is 10% of the potency of human insulin (3-fold higher than N10E, B20Y DOI). This demonstrates the power of the interdisciplinary approach using both protein engineering and structural biology. The potency of DOI has been increased by 100-fold by mutating two positions. Halogen-substituted naphthyl and biphenyl groups on B20 can be used to further optimize DOI analogue potency.

Because the A8 position is important for interacting with hIR binding site 2, the A8 His mutation can be introduced into the current lead analogue and assay for hIR activation. Both A8 His and A9 Arg (original residues on Con-Ins-G1) were introduced to the DOI analogue with B10 Glu and B20 Tyr, the lead analogue (FIG. 23). This quadruple DOI mutant has potency for hIR activation that is comparable to that of human insulin (FIG. 25). The mutations on Con-Ins-G1 promote binding to IR site 2. X-ray crystallography can be used to study the interaction between insulin and binding site 2. Protein engineering efforts can be expanded to the A8-A10 triplet to further optimize interaction with hIR binding site 2 by using a medicinal chemistry approach similar to the work on B20. Currently, the best DOI analog varies from the parent human insulin sequence at only 4 residues, so it is likely that the immunogenicity of the monomeric DOI analogues will be similar to that of the FDA-approved insulin analogues that are in clinical use.

It was demonstrated that each mutation on A8, A9, B10 and B20 has individual effects in affect hIR activation (FIG. 26).

Evaluate Monomeric Insulin Leads in STZ Treated Diabetic Mouse Models.

After potent monomeric insulin analogues are identified, the in vivo properties can be evaluated. An insulin tolerance test can be performed in STZ-treated mice to confirm the in vivo glucose-lowering ability. The two key features for an UFI analogue are fast onset and short duration of action. UFI analogue serum levels will be measured using HPLC coupled with mass spectrometry (LC/MS/MS) in diabetic mice after subcutaneous injections to measure its absorption rate (using insulin lispro as a control). For monomeric insulins, a faster absorption rate can be seen compared to the dimeric insulin lispro. Furthermore, glycemic clamp experiments can be used to quantify the onset and duration of UFI analogues in vivo by determining the amount of glucose infusion required to maintain a targeted glucose level. The glucose clamp study can show that UFI analogues have a shorter onset and duration of action due to their reduced depot effects in subcutaneous tissue. The combination of these properties can greatly reduce the risk of hypoglycemia.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive. Those skilled in the art will recognize, or be able to ascertain using no more than routine experimentation, many equivalents to the specific embodiments of the method and compositions described herein. Such equivalents are intended to be encompassed by the following claims.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abraham et al. (2015) SoftwareX 1-2, 19-25.
Adams et al. (1969) Nature 224, 491-495.
Adams. et al. (2010) D. Biol. Crystallogr. 66, 213-221.
Bao et al. (1997) Proc. Natl. Acad. Sci. USA 94, 2975-2980.
Bentley (1997) Meth. Enzym., 276, 611-619.
Berendsen et al. (1984) J. Chem. Phys. 81, 3684-3690.
Best et al. (2012) J. Chem. Theory Comput. 8, 3257-3273.
Bricogne et al. (2011) BUSTER version 2.10, Cambridge, United Kingdom: Global Phasing Ltd.
Brunger (1996). X-PLOR reference manual 3.851 (Yale Univ., New Haven, CT).
Brunger (1997) Meth. Enzym., 276, 558-580,
Brunger et al. (1998) D. Biol. Crystallogr., 54, 905-921.
Bussi et al. (2007). J. Chem. Phys. 126: 014101.
Chen et al. (1998) J. Biol. Chem. 273, 16248-16258.
Cnudde et al. (2011) J. Biol. Inorg. Chem. 16, 257-266.
Dai et al. (2011) J. Inorg. Biochem. 105, 52-57.
Denley et al. (2004) Mol. Endocrinol. 18, 2502-2512.
Dodson and Steiner (1998) Curr. Opin. Struct. Biol. 8, 189-194.
Emsley and Cowtan (2004) D. Biol. Crystallogr. 60, 2126-2132.
Essmann et al. (1995) J Chem Phys 103, 8577-8593.
Galande et al. (2005) J. Comb. Chem. 7, 174-177.
Glendorf et al. (2011) PLoS One. 6, e20288.
Guvench et al. (2011) J. Chem. Theory Comput. 7, 3162-3180.
Heni et al. (2015) Nat. Rev. Endocrinol. 11, 701-711.
Hess (2008) J. Chem. Theory Comput. 4, 116-122.
Holm and Rosenström (2010) Nucl. Acids Res. 38, W545-549.
Houtman et al. (2007) Protein Sci. 16, 30-42.
Hua et al. (1995) Nat. Struct. Biol. 2, 129-138.
Jones et al. (1991) Acta Crystallogr., A 47, 110-119).
Kabsch (2010) Biol. Crystallogr. 66, 133-144.
Kleywegt and Jones (1994). CCP4/ESF-EACBM Newsletter on Protein Crystallography, 31 Nov. 1994, 9-14. [http://xray.bmc.uu.se/usf/factory_4.html]
Krissinel and Henrick (2004) Acta Cryst. D60, 2256-2268.
King (2011) Expert Opin. Biol. Ther. 11, 1469-1484.
Lattman (1985) Meth. Enzymol., 115, 55-77.
Laue et al. (1992) in Analytical Ultracentrifugation in Biochemistry and Polymer Science 90-125.
Lawrence et al. (2016). J. Biol. Chem. 291, 15473-15481.
McCoy et al. (2007) J. Appl. Crystallogr. 40, 658-674.
Marsh et al. (1995) J. Cell Biol., 130, 1081-1091.
Menting et al. (2013) Nature 493, 241-245.
Menting et al. (2014) Proc. Natl. Acad. Sci. USA 111, E3395-E3404.
Moody et al. (1974) Horm. Metab. Res. 6(1), 12-6,
Morton and Myszka (1998) Methods Enzymol., 295, 268-294.
Murshudov et al. (1997) Acta Crystallogr. D. Biol. Crystallogr. 53, 240-255.
Muttenthaler et al. (2010) Biopolymers 94, 423-432.
Navaza and Saludjian (1997) Meth. Enzym. 276, 581-594.
Nice and Catimel (1999) Bioessays, 21, 339-352,
Olefsky (1978) Biochem. J., 172, 137-145.
Owens (2002) Nat. Rev. Drug Discov. 1, 529-540.
Pettersen et al. (2004) J Comput Chem. 25, 1605-12.
Phillips et al. (2005) J Comput Chem. 26, 1781-1802.
Pronk et al. (2013) Bioinformatics 29, 845-854.
Rivier et al. (1987) Biochemistry 26, 8508-8512.
Robinson and James (1992) Am. J. Physiol., 263, E383-E393.
Rossmann (1972) Int. Sci. Rev. Ser., No. 13, Gordon & Breach, New York.
Sambrook et al. (2001) Molecular Cloning: A Laboratory Manual, 3rd ed. Cold Spring Harbor Laboratory Press.
Safavi-Hemami et al. (2015) Proc. Natl. Acad. Sci. USA 112, 1743-1748.
Schymkowitz et al. (2005) Nucleic Acids Res. 33, W382-8.
Smith et al. (2003) D. Biol. Crystallogr. 59, 474-482.
Soos et al. (1986). Biochem. J. 235, 199-208.
Sparrow et al. (2008) Struct. Funct. Bioinform. 71, 426-439.
Tong and Rossmann (1997) Meth. Enzym. 276:594-611.
Walewska et al. (2009) Angew. Chem. Int. Ed. Engl. 48, 2221-2224.
Webb and Sali (2014) Curr. Protoc. Bioinformatics 47, 5.6.1-5.6.32.
Weiss (2009) Vitam. Horm. 80, 33-49.
Zambelli et al. (2016) Pharmacol. Res., epub ahead of print.

APPENDIX I

ATOMIC COORDINATES FOR CON-INS G1 INSULIN (CHAIN A AND CHAIN B)
Format comprises the following colon-separated fields: (1) atom name,
(2) residue type, (3) chain name, (4) residue number,
(5-7) xyz coordinates, (8) thermal B-factor.

| | |
|---|---|
| N:GLY:A:1:15.439:38.785:34.309:26.76 | CD1:CGU:A:4:16.419:42.187:35.88:25.08 |
| CA:GLY:A:1:14.11:39.14:33.733:22.21 | OE12:CGU:A:4:16.135:42.812:36.937:28.6 |
| C:GLY:A:1:14.251:39.976:32.492:21.3 | OE11:CGU:A:4:15.531:41.542:35.211:22.71 |
| O:GLY:A:1:15.353:40.312:32.093:22.73 | CD2:CGU:A:4:18.45:40.98:36.25:48.38 |
| H1:GLY:A:1:15.395:38.813:35.197:32.11 | OE21:CGU:A:4:18.448:39.819:35.754:54.62 |
| H2:GLY:A:1:15.666:37.965:34.049:32.11 | OE22:CGU:A:4:18.871:41.181:37.42:85.42 |
| H3:GLY:A:1:16.051:39.366:34.024:32.11 | C:CGU:A:4:18.255:43.089:31.618:20.98 |
| HA2:GLY:A:1:13.625:38.331:33.508:26.65 | O:CGU:A:4:19.303:43.691:31.269:21.08 |
| HA3:GLY:A:1:13.595:39.639:34.386:26.65 | HG:CGU:A:4:18.338:43.105:35.863:33.4 |
| N:VAL:A:2:13.113:40.325:31.895:21.05 | HB3:CGU:A:4:17.661:41.115:33.568:26.58 |
| CA:VAL:A:2:13.122:41.169:30.72:22.11 | HB2:CGU:A:4:19.22:41.867:33.754:26.58 |
| C:VAL:A:2:13.696:42.561:31.01:20.41 | HA:CGU:A:4:18.079:44.185:33.551:25.82 |
| O:VAL:A:2:14.274:43.187:30.116:20.06 | N:HIS:A:5:17.548:42.333:30.786:21.02 |

APPENDIX I-continued

ATOMIC COORDINATES FOR CON-INS G1 INSULIN (CHAIN A AND CHAIN B)
Format comprises the following colon-separated fields: (1) atom name,
(2) residue type, (3) chain name, (4) residue number,
(5-7) xyz coordinates, (8) thermal B-factor.

CB:VAL:A:2:11.698:41.225:30.132:25.46
CG1:VAL:A:2:10.72:41.927:31.074:21.3
CG2:VAL:A:2:11.725:41.902:28.839:27.88
H:VAL:A:2:12.33:40.084:32.154:25.26
HA:VAL:A:2:13.693:40.756:30.053:26.54
HB:VAL:A:2:11.38:40.32:29.989:30.55
HG11:VAL:A:2:9.841:41.939:30.665:25.56
HG12:VAL:A:2:10.688:41.442:31.914:25.56
HG13:VAL:A:2:11.026:42.835:31.227:25.56
HG21:VAL:A:2:10.824:41.931:28.48:33.45
HG22:VAL:A:2:12.061:42.804:28.963:33.45
HG23:VAL:A:2:12.306:41.412:28.238:33.45
N:VAL:A:3:13.604:43.056:32.249:26.31
CA:VAL:A:3:14.092:44.414:32.525:22.38
C:VAL:A:3:15.618:44.365:32.529:26.64
O:VAL:A:3:16.283:45.246:31.982:21.94
CB:VAL:A:3:13.517:44.989:33.842:28.85
CG1:VAL:A:3:14.192:46.325:34.21:23.35
CG2:VAL:A:3:11.967:45.154:33.731:22.25
H:VAL:A:3:13.276:42.642:32.928:31.58
HA:VAL:A:3:13.816:44.998:31.802:26.85
HB:VAL:A:3:13.695:44.361:34.559:34.62
HG11:VAL:A:3:13.808:46.654:35.037:28.02
HG12:VAL:A:3:15.144:46.176:34.323:28.02
HG13:VAL:A:3:14.039:46.963:33.496:28.02
HG21:VAL:A:3:11.628:45.515:34.565:26.7
HG22:VAL:A:3:11.767:45.762:33.001:26.7
HG23:VAL:A:3:11.569:44.287:33.558:26.7
N:CGU:A:4:16.193:43.318:33.099:21.34
CA:CGU:A:4:17.68:43.233:33.107:21.52
CB:CGU:A:4:18.136:42.041:33.939:22.15
CG:CGU:A:4:17.867:42.164:35.47:27.83
H:CYS:A:7:16.14:45.864:29.941:25.26
HA:CYS:A:7:16.016:48.446:29.103:26.09
HB2:CYS:A:7:14.229:48.033:30.465:25.71
HB3:CYS:A:7:15.165:47.394:31.576:25.71
N:HIS:A:8:18.157:47.348:31.264:28.49
CA:HIS:A:8:19.509:47.657:31.747:25.02
C:HIS:A:8:20.564:47.453:30.657:30.05
O:HIS:A:8:21.558:48.179:30.604:34.16
CB:HIS:A:8:19.847:46.811:32.972:27.96
CG:HIS:A:8:18.916:47.03:34.125:33.4
ND1:HIS:A:8:18.619:46.043:35.044:34.99
CD2:HIS:A:8:18.234:48.129:34.521:27.24
CE1:HIS:A:8:17.767:46.516:35.936:33.7
NE2:HIS:A:8:17.527:47.782:35.648:38.53
H:HIS:A:8:17.818:46.619:31.57:34.19
HA:HIS:A:8:19.538:48.589:32.014:30.03
HB2:HIS:A:8:19.802:45.874:32.728:33.55
HB3:HIS:A:8:20.744:47.033:33.268:33.55
HD2:HIS:A:8:18.233:48.959:34.103:32.68
HE1:HIS:A:8:17.417:46.045:36.658:40.44
HE2:HIS:A:8:17.009:48.305:36.092:46.23
N:ARG:A:9:20.377:46.477:29.813:32.17
CA:ARG:A:9:21.026:46.221:28.542:24.61
C:ARG:A:9:19.985:46.413:27.464:24.55
O:ARG:A:9:18.838:46.063:27.712:22.58
CB:ARG:A:9:21.524:44.776:28.434:42.6
CG:ARG:A:9:22.966:44.545:28.786:89.14
CD:ARG:A:9:23.608:43.537:27.831:118.62
NE:ARG:A:9:25.059:43.702:27.796:137.92
CZ:ARG:A:9:25.928:42.745:27.485:154.54
NH1:ARG:A:9:25.517:41.519:27.184:170.53
NH2:ARG:A:9:27.224:43.02:27.49:152.73
H:ARG:A:9:19.797:45.864:29.977:38.61
HA:ARG:A:9:21.763:46.836:28.4:29.53
HB2:ARG:A:9:20.99:44.224:29.027:51.12
HB3:ARG:A:9:21.399:44.478:27.519:51.12
HG2:ARG:A:9:23.451:45.382:28.719:106.97
HG3:ARG:A:9:23.024:44.192:29.688:106.97
HD2:ARG:A:9:23.41:42.637:28.132:142.34
HD3:ARG:A:9:23.263:43.677:26.935:142.34
HE:ARG:A:9:25.375:44.477:27.991:165.51
HH11:ARG:A:9:24.676:41.336:27.181:204.63
HH12:ARG:A:9:26.09:40.909:26.987:204.63

CA:HIS:A:5:18.007:41.966:29.443:20.65
C:HIS:A:5:17.659:43.013:28.373:19.86
O:HIS:A:5:18.285:43.07:27.334:23.44
CB:HIS:A:5:17.391:40.584:29.071:20.16
CG:HIS:A:5:18.115:39.864:27.981:47.58
ND1:HIS:A:5:19.277:39.15:28.201:43.05
CD2:HIS:A:5:17.832:39.734:26.661:45.41
CE1:HIS:A:5:19.678:38.617:27.058:50.46
NE2:HIS:A:5:18.82:38.957:26.111:52.67
HA:HIS:A:5:18.972:41.867:29.458:24.79
HB2:HIS:A:5:17.402:40.017:29.858:24.19
HB3:HIS:A:5:16.476:40.72:28.778:24.19
HD2:HIS:A:5:17.106:40.104:26.213:54.49
HD:HIS:A:5:20.437:38.093:26.94:60.55
HE2:HIS:A:5:18.873:38.729:25.284:63.2
H:HIS:A:5:16.775:42.01:30.98:25.23
N:CYS:A:6:16.641:43.84:28.616:19.88
CA:CYS:A:6:16.113:44.731:27.591:19.76
C:CYS:A:6:16.063:46.184:28.028:21.58
O:CYS:A:6:15.909:47.06:27.165:20.58
CB:CYS:A:6:14.695:44.308:27.194:21.07
SG:CYS:A:6:14.678:42.722:26.317:26
H:CYS:A:6:16.238:43.902:29.373:23.85
HA:CYS:A:6:16.676:44.674:26.803:23.71
HB2:CYS:A:6:14.154:44.217:27.994:25.29
HB3:CYS:A:6:14.315:44.981:26.608:25.29
N:CYS:A:7:16.128:46.463:29.323:21.05
CA:CYS:A:7:16.186:47.837:29.839:21.74
C:CYS:A:7:17.553:48.188:30.41:23.78
O:CYS:A:7:18.103:49.215:30.042:30.88
CB:CYS:A:7:15.098:48.081:30.895:21.43
SG:CYS:A:7:15.221:49.718:31.732:27.59
HA:PRO:A:10:18.468:47.268:25.508:27.06
HB2:PRO:A:10:19.65:47.726:23.299:25.72
HB3:PRO:A:10:19.633:48.849:24.439:25.72
HG2:PRO:A:10:21.703:47.018:23.883:28.7
HG3:PRO:A:10:21.853:48.59:24.112:28.7
HD2:PRO:A:10:22.324:46.948:26.013:31.28
HD3:PRO:A:10:21.706:48.395:26.32:31.28
N:CYS:A:11:17.965:45.34:23.974:20.27
CA:CYS:A:11:17.735:44.077:23.278:20.11
C:CYS:A:11:17.021:44.299:21.95:20.29
O:CYS:A:11:16.249:45.24:21.766:20.43
CB:CYS:A:11:16.959:43.053:24.166:20.58
SG:CYS:A:11:15.186:43.358:24.401:23.25
H:CYS:A:11:17.296:45.881:23.98:24.33
HA:CYS:A:11:18.598:43.683:23.076:24.13
HB2:CYS:A:11:17.048:42.175:23.763:24.7
HB3:CYS:A:11:17.368:43.045:25.045:24.7
N:SER:A:12:17.349:43.443:21.002:19.95
CA:SER:A:12:16.64:43.374:19.734:20.24
C:SER:A:12:15.198:42.876:19.921:19.9
O:SER:A:12:14.82:42.314:20.95:19.48
CB:SER:A:12:17.365:42.442:18.794:20.66
OG:SER:A:12:17.226:41.115:19.254:20.36
H:SER:A:12:17.993:42.877:21.068:23.94
HA:SER:A:12:16.611:44.256:19.332:24.29
HB2:SER:A:12:16.978:42.517:17.908:24.79
HB3:SER:A:12:18.306:42.677:18.772:24.79
HG:SER:A:12:17.626:40.589:18.736:24.43
N:ASN:A:13:14.386:43.089:18.896:20.29
CA:ASN:A:13:13.05:42.486:18.857:20.21
C:ASN:A:13:13.113:40.969:18.999:19.99
O:ASN:A:13:12.303:40.375:19.72:19.76
CB:ASN:A:13:12.338:42.827:17.571:20.89
CG:ASN:A:13:11.993:44.254:17.455:21.34
OD1:ASN:A:13:12.063:45.022:18.425:21.1
ND2:ASN:A:13:11.561:44.637:16.254:22.2
H:ASN:A:13:14.577:43.575:18.213:24.35
HA:ASN:A:13:12.523:42.835:19.593:24.25
HB2:ASN:A:13:12.913:42.598:16.823:25.07
HB3:ASN:A:13:11.515:42.316:17.522:25.07
HD21:ASN:A:13:11.343:45.457:16.116:26.64
HD22:ASN:A:13:11.502:44.063:15.616:26.64
N:ALA:A:14:14.073:40.323:18.327:20.53

APPENDIX I-continued

ATOMIC COORDINATES FOR CON-INS G1 INSULIN (CHAIN A AND CHAIN B)
Format comprises the following colon-separated fields: (1) atom name,
(2) residue type, (3) chain name, (4) residue number,
(5-7) xyz coordinates, (8) thermal B-factor.

HH21:ARG:A:9:27.495:43.812:27.686:183.27
HH22:ARG:A:9:27.794:42.407:27.293:183.27
N:PRO:A:10:20.315:46.922:26.273:21.04
CA:PRO:A:10:19.325:46.947:25.186:22.55
C:PRO:A:10:19.153:45.573:24.54:20.8
O:PRO:A:10:20.049:44.721:24.565:22.83
CB:PRO:A:10:19.914:47.951:24.205:21.44
CG:PRO:A:10:21.394:47.783:24.393:23.92
CD:PRO:A:10:21.581:47.551:25.858:26.07
N:GLU:A:15:15.393:39.048:20.418:19.99
CA:GLU:A:15:15.674:38.714:21.807:20.64
C:GLU:A:15:14.459:38.979:22.702:20.25
O:GLU:A:15:14.126:38.165:23.56:19.51
CB:GLU:A:15:16.886:39.507:22.306:24.27
CG:GLU:A:15:18.221:38.954:21.864:52.08
CD:GLU:A:15:18.481:37.555:22.399:68.3
OE1:GLU:A:15:18.414:37.354:23.638:37.34
OE2:GLU:A:15:18.75:36.655:21.573:92.14
H:GLU:A:15:15.838:39.719:20.116:23.99
HA:GLU:A:15:15.889:37.77:21.867:24.77
HB2:GLU:A:15:16.82:40.416:21.974:29.12
HB3:GLU:A:15:16.876:39.513:23.276:29.12
HG2:GLU:A:15:18.242:38.914:20.895:62.5
HG3:GLU:A:15:18.927:39.535:22.188:62.5
N:PHE:A:16:13.813:40.136:22.56:19.08
CA:PHE:A:16:12.627:40.394:23.379:19.01
C:PHE:A:16:11.58:39.275:23.258:19.21
O:PHE:A:16:10.937:38.891:24.259:19.32
CB:PHE:A:16:12:41.738:23.008:19.12
CG:PHE:A:16:10.869:42.118:23.896:19.26
CD2:PHE:A:16:11.086:42.876:25.025:19.26
CD1:PHE:A:16:9.575:41.712:23.603:19.56
CE2:PHE:A:16:10.018:43.216:25.879:19.59
CE1:PHE:A:16:8.496:42.075:24.429:19.92
CZ:PHE:A:16:8.717:42.809:25.564:19.95
H:PHE:A:16:14.029:40.767:22.018:22.9
HA:PHE:A:16:12.898:40.443:24.309:22.81
HB2:PHE:A:16:12.677:42.43:23.073:22.95
HB3:PHE:A:16:11.663:41.689:22.1:22.95
HD2:PHE:A:16:11.95:43.143:25.241:23.11
HD1:PHE:A:16:9.416:41.209:22.837:23.48
HE2:PHE:A:16:10.173:43.731:26.637:23.51
HE1:PHE:A:16:7.635:41.79:24.221:23.9
HZ:PHE:A:16:8.006:43.046:26.114:23.93
N:LYS:A:17:11.394:38.736:22.051:19.63
CA:LYS:A:17:10.38:37.7:21.84:19.97
C:LYS:A:17:10.614:36.46:22.684:20.12
O:LYS:A:17:9.672:35.685:22.893:20.5
CB:LYS:A:17:10.329:37.289:20.362:20.31
CG:LYS:A:17:9.504:38.28:19.498:20.56
CD:LYS:A:17:9.689:38.041:18.044:21.03
CE:LYS:A:17:9.094:39.21:17.228:23.58
NZ:LYS:A:17:9.222:39.104:15.74:26.95
H:LYS:A:17:11.837:38.95:21.346:23.56
HA:LYS:A:17:9.512:38.061:22.078:23.96
HB2:LYS:A:17:11.232:37.262:20.009:24.37
HB3:LYS:A:17:9.917:36.413:20.291:24.37
HG2:LYS:A:17:8.562:38.173:19.703:24.67
HG3:LYS:A:17:9.788:39.186:19.694:24.67
HD2:LYS:A:17:10.636:37.977:17.845:25.23
HD3:LYS:A:17:9.232:37.224:17.789:25.23
N:CY3:A:20:8.084:36.362:25.53:22.5
CB:CY3:A:20:6.382:35.984:23.834:33.52
SG:CY3:A:20:6.832:37.458:22.767:39.89
H:CY3:A:20:8.534:36.217:24.812:27
HA:CY3:A:20:6.252:37.151:25.536:26.25
HB2:CY3:A:20:5.439:35.782:23.725:40.22
HB3:CY3:A:20:6.908:35.214:23.567:40.22
HN11:CY3:A:20:4.569:36.191:27.039:51.9
HN12:CY3:A:20:4.467:34.738:27.347:51.9
O:THR:B:-1:16.056:46.908:9.868:60.34
N:THR:B:-1:16.406:48.652:7.605:78.37
CA:THR:B:-1:17.132:48.822:8.897:76.87
C:THR:B:-1:17.109:47.519:9.689:64.38
CB:THR:B:-1:16.526:49.975:9.74:82.36

CA:ALA:A:14:14.136:38.865:18.34:20.59
C:ALA:A:14:14.514:38.344:19.713:20.2
O:ALA:A:14:13.966:37.34:20.17:20.42
CB:ALA:A:14:15.122:38.388:17.293:21.21
H:ALA:A:14:14.689:40.704:17.863:24.64
HA:ALA:A:14:13.262:38.509:18.115:24.71
HB1:ALA:A:14:15.156:37.419:17.311:25.45
HB2:ALA:A:14:14.827:38.694:16.421:25.45
HB3:ALA:A:14:15.997:38.755:17.494:25.45
HE2:LYS:A:17:8.148:39.275:17.433:28.3
HE3:LYS:A:17:9.539:40.028:17.499:28.3
HZ1:LYS:A:17:8.855:39.816:15.352:32.34
HZ2:LYS:A:17:10.081:39.061:15.511:32.34
HZ3:LYS:A:17:8.808:38.371:15.451:32.34
N:LYS:A:18:11.856:36.224:23.113:20.04
CA:LYS:A:18:12.144:35.116:24.033:21.82
C:LYS:A:18:11.301:35.19:25.294:20.55
O:LYS:A:18:11.071:34.163:25.936:21.12
CB:LYS:A:18:13.624:35.111:24.441:20.42
CG:LYS:A:18:14.518:34.782:23.279:20.61
CD:LYS:A:18:16.015:34.803:23.664:30.84
CE:LYS:A:18:16.866:34.3:22.484:38.22
NZ:LYS:A:18:18.269:33.984:22.906:62
H:LYS:A:18:12.546:36.685:22.889:24.05
HA:LYS:A:18:11.951:34.276:23.589:26.19
HB2:LYS:A:18:13.867:35.989:24.772:24.51
HB3:LYS:A:18:13.763:34.442:25.13:24.51
HG2:LYS:A:18:14.303:33.894:22.954:24.73
HG3:LYS:A:18:14.379:35.436:22.576:24.73
HD2:LYS:A:18:16.284:35.711:23.875:37
HD3:LYS:A:18:16.163:34.218:24.424:37
HE2:LYS:A:18:16.468:33.491:22.125:45.86
HE3:LYS:A:18:16.902:34.987:21.8:45.86
HZ1:LYS:A:18:18.739:33.696:22.207:74.4
HZ2:LYS:A:18:18.658:34.713:23.236:74.4
HZ3:LYS:A:18:18.263:33.351:23.531:74.4
N:TYR:A:19:10.88:36.384:25.687:25.2
CA:TYR:A:19:10.118:36.604:26.923:20.68
C:TYR:A:19:8.575:36.613:26.737:31.44
O:TYR:A:19:7.832:36.875:27.687:29.68
CB:TYR:A:19:10.538:37.943:27.555:20.37
CG:TYR:A:19:11.901:37.935:28.109:23.44
CD1:TYR:A:19:13:38.247:27.323:19.93
CD2:TYR:A:19:12.117:37.579:29.428:23.18
CE1:TYR:A:19:14.278:38.224:27.859:26.81
CE2:TYR:A:19:13.379:37.562:29.96:25.73
CZ:TYR:A:19:14.444:37.864:29.184:22.56
OH:TYR:A:19:15.682:37.826:29.75:22.36
H:TYR:A:19:11.025:37.107:25.245:30.24
HA:TYR:A:19:10.335:35.898:27.552:24.82
HB2:TYR:A:19:10.498:38.635:26.876:24.45
HB3:TYR:A:19:9.926:38.154:28.276:24.45
HD2:TYR:A:19:11.39:37.364:29.968:27.82
HD1:TYR:A:19:12.877:38.483:26.431:23.92
HE2:TYR:A:19:13.505:37.32:30.849:30.88
HE1:TYR:A:19:15.015:38.436:27.332:32.17
HH:TYR:A:19:16.265:38.03:29.18:26.83
O:CY3:A:20:6.334:34.016:25.918:46.46
C:CY3:A:20:5.968:35.121:26.067:39.6
N1:CY3:A:20:4.848:35.386:26.929:43.25
CA:CY3:A:20:6.666:36.307:25.294:21.87
OD2:ASP:B:1:15.36:41.913:16.004:22.1
H:ASP:B:1:17.404:44.028:12.384:30.65
HA:ASP:B:1:16.014:45.456:14.145:29.15
HB2:ASP:B:1:15.068:43.46:13.639:37.19
HB3:ASP:B:1:16.427:42.677:13.894:37.19
O:THR:B:2:17.54:46.872:18.038:27.96
N:THR:B:2:18.026:46.134:15.452:24.07
CA:THR:B:2:19.15:46.377:16.357:23.86
C:THR:B:2:18.686:46.539:17.782:24.18
CB:THR:B:2:19.911:47.632:15.99:31.47
OG1:THR:B:2:18.958:48.664:15.749:33.31
CG2:THR:B:2:20.815:47.367:14.758:33.17
H:THR:B:2:17.631:46.838:15.155:28.88
HA:THR:B:2:19.762:45.626:16.318:28.64

APPENDIX I-continued

ATOMIC COORDINATES FOR CON-INS G1 INSULIN (CHAIN A AND CHAIN B)
Format comprises the following colon-separated fields: (1) atom name,
(2) residue type, (3) chain name, (4) residue number,
(5-7) xyz coordinates, (8) thermal B-factor.

OG1:THR:B:-1:17.021:51.231:9.25:103.8
CG2:THR:B:-1:16.88:49.85:11.228:68.98
H1:THR:B:-1:16.283:49.449:7.227:94.05
H2:THR:B:-1:16.886:48.137:7.061:94.05
H3:THR:B:-1:15.617:48.27:7.756:94.05
HA:THR:B:-1:18.058:49.042:8.712:92.25
HB:THR:B:-1:15.56:49.958:9.656:98.83
HG1:THR:B:-1:16.698:51.862:9.7:124.55
HG21:THR:B:-1:16.486:50.584:11.725:82.78
HG22:THR:B:-1:16.538:49.013:11.58:82.78
HG23:THR:B:-1:17.843:49.871:11.343:82.78
O:PHE:B:0:17.693:47.018:12.852:32.11
N:PHE:B:0:18.285:47.117:10.17:47.49
CA:PHE:B:0:18.434:45.859:10.88:33.82
C:PHE:B:0:17.777:45.945:12.258:30.41
CB:PHE:B:0:19.916:45.528:11.007:28.4
CG:PHE:B:0:20.185:44.138:11.419:27.64
CD2:PHE:B:0:20.443:43.17:10.471:29.44
CD1:PHE:B:0:20.187:43.786:12.753:26.31
CE2:PHE:B:0:20.706:41.883:10.832:27.99
CE1:PHE:B:0:20.454:42.477:13.135:27.97
CZ:PHE:B:0:20.702:41.517:12.166:27.51
H:PHE:B:0:19.016:47.564:10.094:56.99
HA:PHE:B:0:18.003:45.151:10.377:40.59
HB2:PHE:B:0:20.342:45.669:10.147:34.08
HB3:PHE:B:0:20.311:46.115:11.67:34.08
HD1:PHE:B:0:20.017:44.431:13.402:31.58
HD2:PHE:B:0:20.445:43.402:9.571:35.33
HE1:PHE:B:0:20.45:42.243:14.035:33.57
HE2:PHE:B:0:20.874:41.244:10.177:33.58
HZ:PHE:B:0:20.881:40.638:12.411:33.01
O:ASP:B:1:18.276:43.923:15.696:23.3
N:ASP:B:1:17.325:44.791:12.774:25.54
CA:ASP:B:1:16.642:44.721:14.072:24.29
C:ASP:B:1:17.702:44.882:15.159:25.42
CB:ASP:B:1:15.863:43.408:14.192:30.99
CG:ASP:B:1:15.425:43.112:15.613:33.34
OD1:ASP:B:1:15.172:44.1:16.35:26.15
HE3:LYS:B:4:14.763:49.424:17.062:130.99
HZ1:LYS:B:4:12.937:50.469:16.185:126.28
HZ2:LYS:B:4:12.482:49.435:17.093:126.28
HZ3:LYS:B:4:12.449:50.825:17.502:126.28
O:HIS:B:5:14.227:50.871:24.963:32.55
N:HIS:B:5:16.734:50.025:24.109:21.79
CA:HIS:B:5:16.363:50.01:25.519:21.56
C:HIS:B:5:14.857:50.045:25.607:22.3
CB:HIS:B:5:16.937:51.202:26.275:22.18
CG:HIS:B:5:18.423:51.204:26.337:22.64
ND1:HIS:B:5:19.131:50.545:27.328:28.27
CD2:HIS:B:5:19.345:51.765:25.516:25.48
CE1:HIS:B:5:20.428:50.699:27.11:22.51
NE2:HIS:B:5:20.585:51.441:26.022:28.72
H:HIS:B:5:17.013:50.786:23.824:26.15
HA:HIS:B:5:16.682:49.193:25.934:25.87
HB2:HIS:B:5:16.657:52.018:25.832:26.62
HB3:HIS:B:5:16.601:51.188:27.185:26.62
HD1:HIS:B:5:18.784:50.097:27.975:33.93
HD2:HIS:B:5:19.173:52.273:24.756:30.58
HD:HIS:B:5:21.112:50.36:27.64:27.01
N:ARG:B:6:14.278:49.126:26.37:20.97
CA:ARG:B:6:12.838:49.07:26.561:24.52
C:ARG:B:6:12.608:49.07:28.058:21.26
O:ARG:B:6:12.884:48.066:28.727:23.78
CB:ARG:B:6:12.238:47.832:25.893:20.69
CG:ARG:B:6:12.796:47.582:24.53:26.83
CD:ARG:B:6:12.576:46.115:24.096:33.07
NE:ARG:B:6:13.308:45.832:22.86:31.36
CZ:ARG:B:6:12.807:45.919:21.638:20.49
NH1:ARG:B:6:11.527:46.276:21.431:28.98
NH2:ARG:B:6:13.594:45.629:20.612:25.07
H:ARG:B:6:14.707:48.515:26.795:25.17
HA:ARG:B:6:12.425:49.861:26.181:29.42
HB2:ARG:B:6:12.426:47.054:26.441:24.83
HB3:ARG:B:6:11.279:47.953:25.806:24.83
HG2:ARG:B:6:12.352:48.159:23.89:32.19
HB:THR:B:2:20.479:47.889:16.733:37.77
HG1:THR:B:2:19.352:49.376:15.542:39.98
HG21:THR:B:2:21.302:48.173:14.525:39.81
HG22:THR:B:2:21.45:46.662:14.959:39.81
HG23:THR:B:2:20.272:47.097:14.001:39.81
C:HYP:B:3:18.617:47.825:20.609:37.46
O:HYP:B:3:19.172:48.867:20.197:33.28
CA:HYP:B:3:19.208:46.443:20.27:30.06
CB:HYP:B:3:20.366:46.23:20.929:46.37
CG:HYP:B:3:21.21:45.388:19.961:34.65
OD1:HYP:B:3:20.787:44.116:19.901:37.02
CD:HYP:B:3:20.889:46.065:18.606:30.67
N:HYP:B:3:19.59:46.315:18.708:25.2
HD23:HYP:B:3:21.065:45.458:17.869:36.81
HD22:HYP:B:3:21.39:46.89:18.507:36.81
HG:HYP:B:3:22.156:45.447:20.171:41.58
HD1:HYP:B:3:21.078:43.754:19.188:44.43
HB3:HYP:B:3:20.807:47.074:21.115:55.65
HB2:HYP:B:3:20.201:45.739:21.749:55.65
HA:HYP:B:3:18.572:45.748:20.503:36.08
O:LYS:B:4:16.271:47.848:23.837:25.52
N:LYS:B:4:17.521:47.837:21.368:29.31
CA:LYS:B:4:16.899:49.058:21.865:26.28
C:LYS:B:4:16.634:48.93:23.365:21.83
CB:LYS:B:4:15.558:49.322:21.159:37.68
CG:LYS:B:4:15.666:49.595:19.675:65.23
CD:LYS:B:4:14.269:49.657:19.051:94.75
CE:LYS:B:4:14.289:50.089:17.586:109.16
NZ:LYS:B:4:12.904:50.217:17.038:105.24
H:LYS:B:4:17.109:47.124:21.616:35.17
HA:LYS:B:4:17.488:49.813:21.713:31.53
HB2:LYS:B:4:14.99:48.544:21.273:45.21
HB3:LYS:B:4:15.139:50.094:21.569:45.21
HG2:LYS:B:4:16.106:50.447:19.533:78.28
HG3:LYS:B:4:16.163:48.879:19.248:78.28
HD2:LYS:B:4:13.864:48.777:19.098:113.71
HD3:LYS:B:4:13.732:50.296:19.544:113.71
HE2:LYS:B:4:14.727:50.951:17.511:130.99
HA:CYS:B:7:12.223:49.551:30.477:29.3
HB2:CYS:B:7:12.791:52.292:30.093:30.73
HB3:CYS:B:7:12.874:51.551:31.492:30.73
N:GLY:B:8:10.246:50.438:31.636:23.3
CA:GLY:B:8:8.941:50.832:32.13:24.26
C:GLY:B:8:7.848:50.372:31.198:27.94
O:GLY:B:8:7.783:49.176:30.882:23.54
H:GLY:B:8:10.721:49.975:32.183:27.96
HA2:GLY:B:8:8.79:50.442:33.005:29.11
HA3:GLY:B:8:8.898:51.798:32.208:29.11
N:SER:B:9:7.045:51.325:30.7:25.43
CA:SER:B:9:5.825:51.05:29.947:28.83
C:SER:B:9:6.127:50.664:28.495:33.52
O:SER:B:9:5.335:49.988:27.841:31.13
CB:SER:B:9:4.914:52.281:29.986:36.62
OG:SER:B:9:5.573:53.396:29.4:36.38
H:SER:B:9:7.199:52.166:30.793:30.51
HA:SER:B:9:5.353:50.312:30.364:34.6
HB2:SER:B:9:4.104:52.092:29.487:43.94
HB3:SER:B:9:4.698:52.488:30.908:43.94
HG:SER:B:9:6.279:53.567:29.822:43.65
N:CGU:B:10:7.28:51.095:27.998:28.76
CA:CGU:B:10:7.81:50.596:26.686:28.05
CB:CGU:B:10:9.239:51.112:26.411:26.61
CG:CGU:B:10:9.333:52.622:26.497:48.2
CD1:CGU:B:10:10.796:53.099:26.309:43.27
OE12:CGU:B:10:10.997:54.252:25.818:32.43
OE11:CGU:B:10:11.775:52.332:26.659:28.59
CD2:CGU:B:10:8.34:53.322:25.507:61.07
OE21:CGU:B:10:8.191:52.877:24.334:60.62
OE22:CGU:B:10:7.665:54.311:25.914:71.45
C:CGU:B:10:7.888:49.082:26.653:29.41
O:CGU:B:10:7.883:48.518:25.527:30.26
HG:CGU:B:10:9.037:52.937:27.534:57.84
HB3:CGU:B:10:9.957:50.658:27.117:31.93
HB2:CGU:B:10:9.575:50.754:25.412:31.93
HA:CGU:B:10:7.113:50.935:25.873:33.66

APPENDIX I-continued

ATOMIC COORDINATES FOR CON-INS G1 INSULIN (CHAIN A AND CHAIN B)
Format comprises the following colon-separated fields: (1) atom name,
(2) residue type, (3) chain name, (4) residue number,
(5-7) xyz coordinates, (8) thermal B-factor.

HG3:ARG:B:6:13.75:47.758:24.537:32.19
HD2:ARG:B:6:12.903:45.519:24.789:39.68
HD3:ARG:B:6:11.632:45.963:23.935:39.68
HE:ARG:B:6:14.13:45.591:22.934:37.64
HH11:ARG:B:6:11.019:46.461:22.1:34.78
HH12:ARG:B:6:11.218:46.324:20.63:34.78
HH21:ARG:B:6:14.411:45.398:20.748:30.08
HH22:ARG:B:6:13.289:45.676:19.809:30.08
N:CYS:B:7:12.125:50.193:28.588:22.09
CA:CYS:B:7:12.018:50.387:30.028:24.41
C:CYS:B:7:10.61:50.801:30.421:28.77
O:CYS:B:7:9.878:51.453:29.662:23.73
CB:CYS:B:7:12.995:51.452:30.534:25.61
SG:CYS:B:7:14.735:51.095:30.241:32.01
H:CYS:B:7:11.851:50.864:28.126:26.51
HG23:ILE:B:11:8.781:44.443:28.517:27.8
HD11:ILE:B:11:11.603:46.651:30.649:41.53
HD12:ILE:B:11:10.194:47.009:31.291:41.53
HD13:ILE:B:11:10.522:45.509:30.881:41.53
N:THR:B:12:5.642:47.089:28.133:23.69
CA:THR:B:12:4.264:46.785:27.759:27.8
C:THR:B:12:4.051:46.987:26.269:32.55
O:THR:B:12:3.511:46.106:25.58:24.04
CB:THR:B:12:3.292:47.642:28.58:33.52
OG1:THR:B:12:3.502:47.358:29.965:32.74
CG2:THR:B:12:1.803:47.355:28.223:26.3
H:THR:B:12:5.726:47.666:28.765:28.42
HA:THR:B:12:4.082:45.854:27.961:33.36
HB:THR:B:12:3.471:48.581:28.413:40.23
HG1:THR:B:12:2.979:47.818:30.435:39.29
HG21:THR:B:12:1.22:47.914:28.761:31.56
HG22:THR:B:12:1.644:47.545:27.285:31.56
HG23:THR:B:12:1.594:46.424:28.396:31.56
N:ASN:B:13:4.453:48.15:25.751:24.48
CA:ASN:B:13:4.301:48.421:24.321:25.34
C:ASN:B:13:4.974:47.353:23.491:24.13
O:ASN:B:13:4.462:46.938:22.439:24.08
CB:ASN:B:13:4.909:49.776:23.943:28.08
CG:ASN:B:13:4.169:50.958:24.563:43.36
OD1:ASN:B:13:3.038:50.826:25.036:39.56
ND2:ASN:B:13:4.82:52.121:24.575:47.85
H:ASN:B:13:4.812:48.79:26.2:29.38
HA:ASN:B:13:3.358:48.435:24.096:30.41
HB2:ASN:B:13:5.829:49.805:24.249:33.69
HB3:ASN:B:13:4.877:49.876:22.978:33.69
HD21:ASN:B:13:4.449:52.819:24.913:57.42
HD22:ASN:B:13:5.612:52.174:24.244:57.42
N:SER:B:14:6.155:46.925:23.918:22.66
CA:SER:B:14:6.85:45.888:23.173:21.94
C:SER:B:14:6.098:44.563:23.22:21.87
O:SER:B:14:5.951:43.898:22.193:22.01
CB:SER:B:14:8.269:45.758:23.696:25.08
OG:SER:B:14:9.033:46.775:23.091:24.01
H:SER:B:14:6.565:47.209:24.618:27.19
HA:SER:B:14:6.904:46.16:22.243:26.33
HB2:SER:B:14:8.274:45.874:24.659:30.1
HB3:SER:B:14:8.63:44.891:23.453:30.1
HG:SER:B:14:9.828:46.735:23.358:28.81
N:TYR:B:15:5.629:44.144:24.4:21.89
CA:TYR:B:15:4.768:42.964:24.454:22.13
C:TYR:B:15:3.609:43.089:23.478:22.94
O:TYR:B:15:3.283:42.128:22.771:23.01
CB:TYR:B:15:4.193:42.718:25.852:22.53
CG:TYR:B:15:5.115:42.148:26.893:22.01
CD1:TYR:B:15:5.679:40.889:26.759:37.65
CD2:TYR:B:15:5.351:42.85:28.079:48.14
CE1:TYR:B:15:6.507:40.375:27.747:62.89
HB3:LEU:B:18:7.823:41.055:19.704:27.14
HG:LEU:B:18:7.407:43.85:19.787:25.75
HD11:LEU:B:18:9.717:44.053:19.841:29.4
HD12:LEU:B:18:9.192:43.267:21.118:29.4
HD13:LEU:B:18:9.848:42.471:19.91:29.4
HD21:LEU:B:18:8.494:43.959:17.702:33.72
HD22:LEU:B:18:8.607:42.375:17.675:33.72
HD23:LEU:B:18:7.183:43.071:17.578:33.72

N:ILE:B:11:8.048:48.421:27.803:25.25
CA:ILE:B:11:8.061:46.962:27.816:21.79
C:ILE:B:11:6.652:46.486:27.505:22.28
O:ILE:B:11:6.473:45.595:26.699:22.22
CB:ILE:B:11:8.584:46.402:29.14:29.42
CG1:ILE:B:11:10.089:46.697:29.267:30.34
CG2:ILE:B:11:8.328:44.893:29.247:23.17
CD1:ILE:B:11:10.655:46.443:30.653:34.61
H:ILE:B:11:8.15:48.789:28.574:30.3
HA:ILE:B:11:8.645:46.647:27.108:26.14
HB:ILE:B:11:8.12:46.846:29.867:35.31
HG12:ILE:B:11:10.571:46.133:28.643:36.41
HG13:ILE:B:11:10.243:47.63:29.052:36.41
HG21:ILE:B:11:8.671:44.574:30.097:27.8
HG22:ILE:B:11:7.373:44.731:29.195:27.8
CE2:TYR:B:15:6.165:42.337:29.078:52.81
CZ:TYR:B:15:6.748:41.113:28.908:60.82
OH:TYR:B:15:7.558:40.637:29.929:54.81
H:TYR:B:15:5.789:44.514:25.16:26.27
HA:TYR:B:15:5.287:42.185:24.203:26.56
HB2:TYR:B:15:3.868:43.565:26.195:27.03
HB3:TYR:B:15:3.448:42.104:25.765:27.03
HD1:TYR:B:15:5.53:40.399:25.982:45.19
HD2:TYR:B:15:4.966:43.688:28.195:57.77
HE1:TYR:B:15:6.897:39.537:27.638:75.46
HE2:TYR:B:15:6.328:42.83:29.85:63.37
HH:TYR:B:15:7.597:41.201:30.551:65.77
N:MET:B:16:2.967:44.255:23.427:23.8
CA:MET:B:16:1.803:44.423:22.544:28.09
C:MET:B:16:2.197:44.329:21.083:26.65
O:MET:B:16:1.471:43.748:20.275:36.43
CB:MET:B:16:1.118:45.775:22.768:30.99
CG:MET:B:16:0.499:45.977:24.148:42.33
SD:MET:B:16:-0.954:44.949:24.404:68.25
CE:MET:B:16:-0.206:43.67:25.426:42.42
H:MET:B:16:3.177:44.953:23.883:28.56
HA:MET:B:16:1.157:43.726:22.74:33.71
HB2:MET:B:16:1.775:46.477:22.639:37.19
HB3:MET:B:16:0.409:45.872:22.114:37.19
HG2:MET:B:16:1.153:45.748:24.826:50.79
HG3:MET:B:16:0.232:46.905:24.243:50.79
HE1:MET:B:16:-0.883:43.016:25.657:50.9
HE2:MET:B:16:0.508:43.245:24.926:50.9
HE3:MET:B:16:0.15:44.078:26.231:50.9
N:ASP:B:17:3.344:44.897:20.719:29.89
CA:ASP:B:17:3.758:44.849:19.322:34.2
C:ASP:B:17:4.362:43.503:18.931:30.46
O:ASP:B:17:4.224:43.095:17.781:28.87
CB:ASP:B:17:4.769:45.957:19.002:41.66
CG:ASP:B:17:4.239:47.347:19.307:78.78
OD1:ASP:B:17:3:47.511:19.374:89.35
OD2:ASP:B:17:5.064:48.277:19.478:72.64
H:ASP:B:17:3.887:45.306:21.246:35.87
HA:ASP:B:17:2.978:44.994:18.764:41.04
HB2:ASP:B:17:5.569:45.818:19.534:49.99
HB3:ASP:B:17:4.989:45.92:18.058:49.99
N:LEU:B:18:5.062:42.822:19.831:22.66
CA:LEU:B:18:5.868:41.669:19.444:22.1
C:LEU:B:18:5.314:40.329:19.885:22.41
O:LEU:B:18:5.69:39.304:19.308:24.4
CB:LEU:B:18:7.286:41.806:20.002:22.61
CG:LEU:B:18:7.948:43.093:19.512:21.46
CD1:LEU:B:18:9.302:43.234:20.155:24.5
CD2:LEU:B:18:8.07:43.128:17.966:28.1
H:LEU:B:18:5.088:43.006:20.671:27.19
HA:LEU:B:18:5.935:41.652:18.476:26.53
HB2:LEU:B:18:7.249:41.832:20.971:27.14
HB3:TYR:B:20:-1.312:40.768:21.254:35.48
HD1:TYR:B:20:-2.106:38.797:22.644:85.58
HD2:TYR:B:20:0.735:41.274:23.956:71.73
HE1:TYR:B:20:-2.44:38.024:24.782:87.33
HE2:TYR:B:20:0.409:40.506:26.11:88.2
HH:TYR:B:20:-0.786:39.058:27.486:73.93
O:ARG:B:21:-2.375:41.115:18.001:73.56
N:ARG:B:21:-0.904:38.888:18.851:48.09

APPENDIX I-continued

ATOMIC COORDINATES FOR CON-INS G1 INSULIN (CHAIN A AND CHAIN B)
Format comprises the following colon-separated fields: (1) atom name,
(2) residue type, (3) chain name, (4) residue number,
(5-7) xyz coordinates, (8) thermal B-factor.

N:CYS:B:19:4.481:40.285:20.912:26.31
CA:CYS:B:19:4.018:39.001:21.403:23.2
C:CYS:B:19:2.573:38.743:21.045:29.55
O:CYS:B:19:2.204:37.602:20.812:27.61
CB:CYS:B:19:4.199:38.915:22.923:25.28
SG:CYS:B:19:5.942:39.114:23.454:33.59
H:CYS:B:19:4.174:40.968:21.334:31.58
HA:CYS:B:19:4.553:38.3:21:27.84
HB2:CYS:B:19:3.677:39.617:23.342:30.34
HB3:CYS:B:19:3.891:38.047:23.227:30.34
O:TYR:B:20:0.453:40.693:18.643:58.94
N:TYR:B:20:1.763:39.78:20.969:30.88
CA:TYR:B:20:0.33:39.624:20.788:36.15
C:TYR:B:20:−0.046:39.793:19.324:48.21
CB:TYR:B:20:−0.44:40.615:21.651:29.56
CG:TYR:B:20:−0.651:40.122:23.065:55.92
CD1:TYR:B:20:−1.597:39.145:23.34:71.32
CD2:TYR:B:20:0.094:40.621:24.118:59.77
CE1:TYR:B:20:−1.8:38.679:24.621:72.77
CE2:TYR:B:20:−0.098:40.161:25.411:73.5
CZ:TYR:B:20:−1.058:39.185:25.659:74.33
OH:TYR:B:20:−1.29:38.681:26.931:61.61
H:TYR:B:20:2.02:40.599:21.019:37.06
HA:TYR:B:20:0.074:38.728:21.06:43.38
HB2:TYR:B:20:0.055:41.447:21.695:35.48

CA:ARG:B:21:−1.505:38.926:17.518:54.86
C:ARG:B:21:−2.02:40.306:17.132:67.04
CB:ARG:B:21:−2.675:37.949:17.448:56.88
CG:ARG:B:21:−2.44:36.661:16.704:66.58
CD:ARG:B:21:−3.714:36.364:15.961:87.2
NE:ARG:B:21:−3.936:34.955:15.663:104.85
CZ:ARG:B:21:−5.147:34.397:15.619:123.5
NH1:ARG:B:21:−6.239:35.129:15.88:136.71
NH2:ARG:B:21:−5.27:33.101:15.333:115.82
OXT:ARG:B:21:−2.121:40.62:15.939:68.47
H:ARG:B:21:−1.164:38.209:19.309:57.7
HA:ARG:B:21:−0.844:38.656:16.862:65.83
HB2:ARG:B:21:−2.926:37.714:18.355:68.25
HB3:ARG:B:21:−3.418:38.398:17.016:68.25
HG2:ARG:B:21:−1.716:36.768:16.067:79.9
HG3:ARG:B:21:−2.258:35.94:17.327:79.9
HD2:ARG:B:21:−4.462:36.672:16.495:104.64
HD3:ARG:B:21:−3.698:36.842:15.117:104.64
HE:ARG:B:21:−3.252:34.434:15.65:125.82
HH11:ARG:B:21:−6.162:35.965:16.065:164.05
HH12:ARG:B:21:−7.017:34.764:15.855:164.05
HH21:ARG:B:21:−4.571:32.628:15.17:138.98
HH22:ARG:B:21:−6.049:32.738:15.311:138.98

APPENDIX II

ATOMIC COORDINATES FOR MODEL OF CON-INS G1 INSULIN
(CHAINS A AND B) BOUND TO INSULIN RECEPTOR (CHAINS E, F AND X)
Format comprises the following colon-separated fields: (1) atom name, (2)
residue type, (3) chain name, (4) residue number, (5-7) xyz coordinates.

N:GLY:A:1:50.25:62.37:57.42
CA:GLY:A:1:50.21:62.09:55.93
C:GLY:A:1:50.37:63.37:55.13
O:GLY:A:1:50.44:64.47:55.71
N:VAL:A:2:50.36:63.33:53.84
CA:VAL:A:2:50.39:64.45:52.97
CB:VAL:A:2:50.68:64.02:51.52
CG1:VAL:A:2:49.47:63.39:50.84
HG11:VAL:A:2:49.15:62.42:51.28
HG12:VAL:A:2:48.57:64.02:50.95
HG13:VAL:A:2:49.67:63.37:49.74
CG2:VAL:A:2:51.09:65.27:50.71
HG21:VAL:A:2:51.18:64.92:49.66
HG22:VAL:A:2:50.29:66.03:50.8
HG23:VAL:A:2:52.02:65.72:51.11
C:VAL:A:2:49.28:65.39:53.13
O:VAL:A:2:49.47:66.66:53.13
N:VAL:A:3:48.03:64.83:53.43
CA:VAL:A:3:46.92:65.71:53.69
CB:VAL:A:3:45.62:64.98:53.83
CG1:VAL:A:3:44.49:66.01:54.29
HG11:VAL:A:3:43.5:65.55:54.43
HG12:VAL:A:3:44.78:66.38:55.31
HG13:VAL:A:3:44.46:66.82:53.53
CG2:VAL:A:3:45.4:64.44:52.42
HG21:VAL:A:3:45.44:65.23:51.65
HG22:VAL:A:3:46.13:63.62:52.26
HG23:VAL:A:3:44.4:63.97:52.44
C:VAL:A:3:47.13:66.53:54.97
O:VAL:A:3:47.09:67.77:54.94
N:CGU:A:4:47.56:65.91:56.11
CA:CGU:A:4:47.83:66.64:57.38
CB:CGU:A:4:48.2:65.74:58.59
CG:CGU:A:4:47.15:64.64:59.01
CD1:CGU:A:4:46.83:63.56:58.09
OE11:CGU:A:4:45.67:63.06:58.15
OE12:CGU:A:4:47.69:63.15:57.27
CD2:CGU:A:4:47.66:63.83:60.16
OE21:CGU:A:4:48.79:63.44:60.04

C:CGU:A:4:48.94:67.66:57.17
O:CGU:A:4:48.88:68.76:57.7
N:HSP:A:5:49.99:67.35:56.35
CA:HSP:A:5:51.16:68.26:56.32
CB:HSP:A:5:52.31:67.31:55.81
CD2:HSP:A:5:54.53:67.05:57.13
CG:HSP:A:5:53.68:67.72:56.33
NE2:HSP:A:5:55.52:67.95:57.54
ND1:HSP:A:5:54.12:69.02:56.28
CE1:HSP:A:5:55.24:69.11:57.01
C:HSP:A:5:50.95:69.36:55.26
O:HSP:A:5:51.53:70.39:55.44
N:CYS:A:6:50.13:69.07:54.23
CA:CYS:A:6:50.12:70.02:53.1
CB:CYS:A:6:50.43:69.37:51.79
SG:CYS:A:6:52.15:68.87:51.77
C:CYS:A:6:48.76:70.68:52.84
O:CYS:A:6:48.67:71.65:52.16
N:CYS:A:7:47.63:70.09:53.34
CA:CYS:A:7:46.24:70.54:53.04
CB:CYS:A:7:45.1:69.69:53.59
SG:CYS:A:7:43.48:69.8:52.7
C:CYS:A:7:45.9:71.97:53.55
O:CYS:A:7:45.19:72.7:52.82
N:HIS:A:8:46.4:72.37:54.71
CA:HIS:A:8:45.79:73.56:55.37
CB:HIS:A:8:45.46:73.16:56.86
ND1:HIS:A:8:43.21:72.06:57
CG:HIS:A:8:44.57:71.94:56.89
CE1:HIS:A:8:42.72:70.85:57.06
NE2:HIS:A:8:43.69:69.92:56.99
CD2:HIS:A:8:44.85:70.62:56.98
C:HIS:A:8:46.71:74.82:55.23
O:HIS:A:8:46.22:75.95:55.27
N:ARG:A:9:48:74.57:55.05
CA:ARG:A:9:49.01:75.52:54.99
CB:ARG:A:9:49.72:75.72:56.41
CG:ARG:A:9:48.86:76.27:57.56
CD:ARG:A:9:48.32:77.67:57.25

APPENDIX II-continued

ATOMIC COORDINATES FOR MODEL OF CON-INS G1 INSULIN
(CHAINS A AND B) BOUND TO INSULIN RECEPTOR (CHAINS E, F AND X)
Format comprises the following colon-separated fields: (1) atom name, (2)
residue type, (3) chain name, (4) residue number, (5-7) xyz coordinates.

OE22:CGU:A:4:47.02:63.74:61.23
CZ:ARG:A:9:49.65:79.62:56.2
NH1:ARG:A:9:48.56:80.19:55.69
NH2:ARG:A:9:50.8:80.13:55.88
C:ARG:A:9:50.08:74.83:54.07
O:ARG:A:9:50.03:73.62:54.02
N:PRO:A:10:50.96:75.61:53.49
CD:PRO:A:10:50.86:77.07:53.54
CA:PRO:A:10:51.91:75.19:52.5
CB:PRO:A:10:52.56:76.52:52.07
CG:PRO:A:10:51.54:77.6:52.31
C:PRO:A:10:52.88:74.29:53.1
O:PRO:A:10:53.1:74.37:54.31
N:CYS:A:11:53.41:73.39:52.3
CA:CYS:A:11:54.53:72.61:52.57
CB:CYS:A:11:54.09:71.06:52.69
SG:CYS:A:11:53.26:70.5:51.18
C:CYS:A:11:55.53:72.94:51.45
O:CYS:A:11:55.12:73.21:50.35
N:SER:A:12:56.8:72.88:51.78
CA:SER:A:12:57.88:73.04:50.78
CB:SER:A:12:59.21:73.42:51.47
OG:SER:A:12:59.57:72.46:52.46
C:SER:A:12:58.11:71.8:49.87
O:SER:A:12:57.59:70.71:50.1
N:ASN:A:13:58.93:71.94:48.84
CA:ASN:A:13:59.38:70.76:48.15
CB:ASN:A:13:60.35:71.19:46.96
CG:ASN:A:13:59.8:71.95:45.78
OD1:ASN:A:13:60.32:72.95:45.28
ND2:ASN:A:13:58.63:71.47:45.27
C:ASN:A:13:60.16:69.73:49.01
O:ASN:A:13:60.08:68.53:48.85
N:ALA:A:14:61.02:70.12:49.92
CA:ALA:A:14:61.68:69.29:50.94
CB:ALA:A:14:62.6:70.18:51.71
C:ALA:A:14:60.74:68.46:51.87
O:ALA:A:14:61.02:67.28:52.14
N:GLU:A:15:59.62:69.04:52.35
CA:GLU:A:15:58.47:68.37:52.89
CB:GLU:A:15:57.49:69.39:53.57
CG:GLU:A:15:58.09:70.2:54.8
CD:GLU:A:15:57.33:71.55:54.96
OE1:GLU:A:15:57.68:72.55:54.29
OE2:GLU:A:15:56.54:71.67:55.93
C:GLU:A:15:57.71:67.43:51.92
O:GLU:A:15:57.42:66.29:52.27
N:PHE:A:16:57.55:67.8:50.61
CA:PHE:A:16:56.93:66.92:49.6
CB:THR:B:−1:66.52:74.1:41.37
OG1:THR:B:−1:67.48:74.53:40.42
CG2:THR:B:−1:67.16:72.85:42.06
HG21:THR:B:−1:67.99:73.25:42.68
HG22:THR:B:−1:66.33:72.49:42.7
HG23:THR:B:−1:67.4:72.02:41.37
C:THR:B:−1:64.12:73.54:41.84
O:THR:B:−1:63.46:72.51:41.95
N:PHE:B:0:63.74:74.7:42.52
CA:PHE:B:0:62.74:74.78:43.62
CB:PHE:B:0:63.39:75.47:44.88
CG:PHE:B:0:64.56:74.7:45.18
CD1:PHE:B:0:65.84:75.3:45.05
CE1:PHE:B:0:67:74.52:45.26
CZ:PHE:B:0:66.87:73.25:45.9
CD2:PHE:B:0:64.44:73.34:45.64
CE2:PHE:B:0:65.63:72.67:46.03
C:PHE:B:0:61.59:75.64:43.29
O:PHE:B:0:61.64:76.7:42.61
N:ASP:B:1:60.4:75.21:43.77
CA:ASP:B:1:59.15:75.98:43.64
CB:ASP:B:1:58.08:74.84:43.54
CG:ASP:B:1:58.26:73.88:42.4
OD1:ASP:B:1:58.25:74.2:41.23
OD2:ASP:B:1:58.29:72.65:42.73
C:ASP:B:1:59.76.84:44.9

NE:ARG:A:9:49.56:78.48:56.93
CB:PHE:A:16:56.65:67.71:48.26
CG:PHE:A:16:55.52:67.12:47.54
CD1:PHE:A:16:54.3:67.71:47.66
CE1:PHE:A:16:53.2:67.06:47.12
CZ:PHE:A:16:53.35:65.96:46.22
CD2:PHE:A:16:55.72:66.01:46.68
CE2:PHE:A:16:54.6:65.4:46.07
C:PHE:A:16:57.92:65.77:49.39
O:PHE:A:16:57.51:64.65:48.97
N:LYS:A:17:59.2:66.01:49.58
CA:LYS:A:17:60.17:65.1:49.09
CB:LYS:A:17:61.57:65.7:49.13
CG:LYS:A:17:62.75:64.81:48.61
CD:LYS:A:17:62.61:64.47:47.08
CE:LYS:A:17:63.89:63.73:46.59
NZ:LYS:A:17:63.71:63.37:45.1
C:LYS:A:17:60.1:63.81:49.85
O:LYS:A:17:60.47:62.72:49.41
N:LYS:A:18:59.51:63.87:51.09
CA:LYS:A:18:59.36:62.7:51.98
CB:LYS:A:18:58.96:63.08:53.42
CG:LYS:A:18:60.02:64.01:54.14
CD:LYS:A:18:61.31:63.29:54.45
CE:LYS:A:18:62.48:64.29:54.85
NZ:LYS:A:18:63.76:63.61:54.99
C:LYS:A:18:58.23:61.74:51.51
O:LYS:A:18:58.08:60.61:51.89
N:TYR:A:19:57.3:62.26:50.64
CA:TYR:A:19:56.22:61.46:50.05
CB:TYR:A:19:54.96:62.33:49.8
CG:TYR:A:19:54.68:63.01:51.05
CD1:TYR:A:19:54.62:64.38:51.09
CE1:TYR:A:19:54.43:65.14:52.32
CZ:TYR:A:19:54.13:64.37:53.45
OH:TYR:A:19:53.83:65.03:54.66
CD2:TYR:A:19:54.35:62.29:52.2
CE2:TYR:A:19:54.07:62.94:53.42
C:TYR:A:19:56.57:60.84:48.73
O:TYR:A:19:55.82:60.08:48.13
N:CYS:A:20:57.76:61.14:48.23
CA:CYS:A:20:58.16:60.66:46.93
CB:CYS:A:20:59.26:61.58:46.16
SG:CYS:A:20:58.71:63.23:45.66
C:CYS:A:20:58.91:59.31:47.13
NT:CYS:A:20:58.67:58.33:46.22
O:CYS:A:20:59.61:59.11:48.11
N:THR:B:−1:64.69:74.65:39.71
CA:THR:B:−1:65.2:73.71:40.76
CG:LYS:B:4:52.23:76.3:45.71
CD:LYS:B:4:51.28:77.47:45.48
CE:LYS:B:4:51.75:78.6:44.56
NZ:LYS:B:4:51.76:78.34:43.11
C:LYS:B:4:51.33:74.75:49.05
O:LYS:B:4:51.97:73.79:49.52
N:HIS:B:5:50.05:74.91:49.33
CA:HIS:B:5:49.21:73.89:49.97
CB:HIS:B:5:48.13:74.62:50.83
ND1:HIS:B:5:47.21:76.49:49.4
CG:HIS:B:5:47.02:75.21:49.99
CE1:HIS:B:5:46.03:76.76:48.79
NE2:HIS:B:5:45.14:75.76:48.88
CD2:HIS:B:5:45.71:74.81:49.71
C:HIS:B:5:48.62:72.89:49.05
O:HIS:B:5:47.89:73.33:48.15
N:ARG:B:6:49.14:71.68:49.06
CA:ARG:B:6:48.7:70.67:48.09
CB:ARG:B:6:49.87:69.72:47.69
CG:ARG:B:6:51.23:70.54:47.59
CD:ARG:B:6:51.26:71.53:46.5
NE:ARG:B:6:52.72:71.85:46.15
CZ:ARG:B:6:53.08:72.5:45.03
NH1:ARG:B:6:52.31:72.87:44
NH2:ARG:B:6:54.36:72.88:44.97
C:ARG:B:6:47.65:69.78:48.71

APPENDIX II-continued

ATOMIC COORDINATES FOR MODEL OF CON-INS G1 INSULIN
(CHAINS A AND B) BOUND TO INSULIN RECEPTOR (CHAINS E, F AND X)
Format comprises the following colon-separated fields: (1) atom name, (2)
residue type, (3) chain name, (4) residue number, (5-7) xyz coordinates.

O:ASP:B:1:59.69:76.66:45.91
N:THR:B:2:57.96:77.74:44.9
CA:THR:B:2:57.54:78.49:46.12
CB:THR:B:2:56.98:79.95:45.82
OG1:THR:B:2:55.81:80.02:44.98
CG2:THR:B:2:58.1:80.75:45.16
HG21:THR:B:2:59:80.68:45.8
HG22:THR:B:2:58.33:80.32:44.16
HG23:THR:B:2:57.63:81.75:45.05
C:THR:B:2:56.44:77.62:46.85
O:THR:B:2:55.58:77.05:46.16
N:HYP:B:3:56.41:77.52:48.18
CA:HYP:B:3:55.62:76.6:48.99
CB:HYP:B:3:56:76.88:50.44
CG:HYP:B:3:57.39:77.4:50.38
OD1:HYP:B:3:58.2:76.26:50.04
CD:HYP:B:3:57.32:78.25:49.04
C:HYP:B:3:54.14:76.75:48.68
O:HYP:B:3:53.65:77.85:48.47
N:LYS:B:4:53.39:75.63:48.59
CA:LYS:B:4:51.96:75.7:48.3
CB:LYS:B:4:51.68:75.31:46.8
OE11:CGU:B:10:46.6:73.47:44.54
OE12:CGU:B:10:45.19:73.92:42.89
CD2:CGU:B:10:47.12:72.03:41.77
OE21:CGU:B:10:48.28:72.52:41.89
OE22:CGU:B:10:46.68:71.76:40.62
C:CGU:B:10:48.15:68.65:43.91
O:CGU:B:10:49.32:68.74:43.58
N:ILE:B:11:47.8:67.7:44.92
CA:ILE:B:11:48.8:66.72:45.33
CB:ILE:B:11:48.41:65.79:46.46
CG2:ILE:B:11:49.6:65.08:47
HG21:ILE:B:11:50.09:64.42:46.24
HG22:ILE:B:11:50.34:65.69:47.54
HG23:ILE:B:11:49.29:64.33:47.77
CG1:ILE:B:11:47.56:66.48:47.58
HG11:ILE:B:11:48.27:67.03:48.23
HG12:ILE:B:11:46.86:67.21:47.12
CD:ILE:B:11:46.86:65.41:48.35
C:ILE:B:11:49.34:65.88:44.19
O:ILE:B:11:50.56:65.65:44.14
N:THR:B:12:48.53:65.33:43.22
CA:THR:B:12:48.88:64.49:42.06
CB:THR:B:12:47.73:63.83:41.3
OG1:THR:B:12:47.03:62.84:42.01
CG2:THR:B:12:48.36:63.09:40.05
HG21:THR:B:12:48.85:63.73:39.29
HG22:THR:B:12:49.04:62.32:40.48
HG23:THR:B:12:47.63:62.42:39.55
C:THR:B:12:49.79:65.29:41.11
O:THR:B:12:50.84:64.87:40.6
N:ASN:B:13:49.45:66.58:40.89
CA:ASN:B:13:50.11:67.48:39.98
CB:ASN:B:13:49.2:68.71:39.88
CG:ASN:B:13:47.88:68.42:39.08
OD1:ASN:B:13:47.81:67.41:38.44
ND2:ASN:B:13:46.85:69.37:39.23
C:ASN:B:13:51.5:67.78:40.54
O:ASN:B:13:52.46:67.76:39.78
N:SER:B:14:51.66:68:41.88
CA:SER:B:14:53.01:68.18:42.46
CB:SER:B:14:52.89:68.82:43.85
OG:SER:B:14:54.2:69.12:44.45
C:SER:B:14:53.68:66.9:42.61
O:SER:B:14:54.89:66.86:42.55
N:TYR:B:15:52.99:65.72:42.68
CA:TYR:B:15:53.58:64.41:42.53
CB:TYR:B:15:52.71:63.21:43.15
CG:TYR:B:15:53.26:61.84:42.94
C:TYR:B:20:61.19:64.32:38.26
O:TYR:B:20:61.74:64.35:37.15
N:ARG:B:21:61.42:65.28:39.1
CA:ARG:B:21:62.44:66.31:39.01
CB:ARG:B:21:62:67.59:39.64

O:ARG:B:6:47.82:69.06:49.68
N:CYS:B:7:46.44:69.85:48.2
CA:CYS:B:7:45.34:69.09:48.69
CB:CYS:B:7:44.48:69.99:49.69
SG:CYS:B:7:43.61:68.9:50.86
C:CYS:B:7:44.51:68.71:47.4
O:CYS:B:7:44.7:69.41:46.41
N:GLY:B:8:43.6:67.71:47.42
CA:GLY:B:8:42.92:67.32:46.24
C:GLY:B:8:43.79:66.93:45.05
O:GLY:B:8:44.82:66.24:45.2
N:SER:B:9:43.35:67.38:43.85
CA:SER:B:9:44.03:67.09:42.55
CB:SER:B:9:43.2:67.82:41.43
OG:SER:B:9:43.07:69.22:41.72
C:SER:B:9:45.53:67.5:42.52
O:SER:B:9:46.42:66.82:41.94
N:CGU:B:10:45.83:68.72:43.12
CA:CGU:B:10:47.09:69.37:43.2
CB:CGU:B:10:46.95:70.75:43.85
CG:CGU:B:10:46.26:71.75:42.93
CD1:CGU:B:10:46:73.11:43.47
CD1:TYR:B:15:53.92:61.2:44.03
CE1:TYR:B:15:54.48:59.89:43.86
CZ:TYR:B:15:54.47:59.29:42.59
OH:TYR:B:15:54.87:57.98:42.46
CD2:TYR:B:15:53.16:61.18:41.71
CE2:TYR:B:15:53.74:59.87:41.56
C:TYR:B:15:54.27:64.21:41.11
O:TYR:B:15:55.36:63.71:41
N:MET:B:16:53.69:64.59:39.93
CA:MET:B:16:54.25:64.42:38.62
CB:MET:B:16:53.21:64.31:37.49
CG:MET:B:16:52.44:62.94:37.6
SD:MET:B:16:51.33:62.6:36.24
CE:MET:B:16:50.3:64.09:36.2
C:MET:B:16:55.3:65.43:38.3
O:MET:B:16:56.12:65.26:37.42
N:ASP:B:17:55.4:66.49:39.16
CA:ASP:B:17:56.33:67.56:39.06
CB:ASP:B:17:55.67:68.84:39.59
CG:ASP:B:17:56.3:70.13:39.08
OD1:ASP:B:17:57.42:70.07:38.45
OD2:ASP:B:17:55.79:71.18:39.46
C:ASP:B:17:57.53:67.26:39.91
O:ASP:B:17:58.57:66.88:39.4
N:LEU:B:18:57.42:67.34:41.25
CA:LEU:B:18:58.6:67.29:42.17
CB:LEU:B:18:58.13:67.79:43.54
CG:LEU:B:18:59.29:67.99:44.61
CD1:LEU:B:18:59.8:66.71:45.38
CD2:LEU:B:18:60.5:68.79:44.05
C:LEU:B:18:59.26:65.87:42.26
O:LEU:B:18:60.49:65.71:42.29
N:CYS:B:19:58.41:64.8:42.21
CA:CYS:B:19:58.9:63.42:42.29
CB:CYS:B:19:57.92:62.32:42.81
SG:CYS:B:19:57.19:62.86:44.35
C:CYS:B:19:59.72:62.92:41.1
O:CYS:B:19:60.62:62.13:41.22
N:TYR:B:20:59.48:63.5:39.89
CA:TYR:B:20:60.21:63.21:38.64
CB:TYR:B:20:59.23:63.06:37.55
CG:TYR:B:20:58.26:61.89:37.68
CD1:TYR:B:20:58.46:60.68:36.92
CE1:TYR:B:20:57.53:59.62:37.09
CZ:TYR:B:20:56.54:59.69:38.03
OH:TYR:B:20:55.4:58.82:37.99
CD2:TYR:B:20:57.1:61.98:38.49
CE2:TYR:B:20:56.33:60.85:38.81
CA:PRO:E:9:49.99:38.5:44.1
CB:PRO:E:9:51.47:38.6:44.53
CG:PRO:E:9:51.97:37.17:44.28
C:PRO:E:9:49.37:39.91:43.73
O:PRO:E:9:49.23:40.18:42.53

APPENDIX II-continued

ATOMIC COORDINATES FOR MODEL OF CON-INS G1 INSULIN
(CHAINS A AND B) BOUND TO INSULIN RECEPTOR (CHAINS E, F AND X)
Format comprises the following colon-separated fields: (1) atom name, (2)
residue type, (3) chain name, (4) residue number, (5-7) xyz coordinates.

CG:ARG:B:21:62.87:68.85:39.35
CD:ARG:B:21:62.45:70.08:40.08
NE:ARG:B:21:60.98:70.45:39.88
CZ:ARG:B:21:60.21:71.04:40.75
NH1:ARG:B:21:60.62:71.6:41.81
NH2:ARG:B:21:58.96:71.22:40.38
C:ARG:B:21:63.71:65.92:39.82
OT1:ARG:B:21:64.84:66.14:39.3
OT2:ARG:B:21:63.54:65.45:40.89
N:GLY:E:5:44.17:26.88:38.71
CA:GLY:E:5:44.62:28.14:37.98
C:GLY:E:5:45.67:29.03:38.58
O:GLY:E:5:45.77:29.25:39.8
N:GLU:E:6:46.45:29.68:37.73
CA:GLU:E:6:47.55:30.45:38.02
CB:GLU:E:6:48.31:30.93:36.77
CG:GLU:E:6:49.65:31.81:36.96
CD:GLU:E:6:50.72:31.2:37.82
OE1:GLU:E:6:51.83:30.94:37.18
OE2:GLU:E:6:50.53:31.06:39.04
C:GLU:E:6:47.17:31.63:38.85
O:GLU:E:6:46.05:32.15:38.64
N:VAL:E:7:48.05:32.06:39.79
CA:VAL:E:7:47.92:33.11:40.79
CB:VAL:E:7:47.8:32.46:42.09
CG1:VAL:E:7:47.47:33.5:43.22
HG11:VAL:E:7:48.36:34.16:43.27
HG12:VAL:E:7:46.54:34.06:43.01
HG13:VAL:E:7:47.38:32.94:44.19
CG2:VAL:E:7:46.75:31.33:42.07
HG21:VAL:E:7:45.89:31.45:41.38
HG22:VAL:E:7:47.19:30.36:41.76
HG23:VAL:E:7:46.37:31.24:43.11
C:VAL:E:7:48.91:34.21:40.76
O:VAL:E:7:50.05:33.9:40.88
N:CYS:E:8:48.39:35.44:40.73
CA:CYS:E:8:49.15:36.68:40.85
CB:CYS:E:8:48.55:37.79:39.98
SG:CYS:E:8:49.07:37.75:38.31
C:CYS:E:8:48.97:37.14:42.3
O:CYS:E:8:47.85:37.24:42.79
N:PRO:E:9:50.03:37.49:43.04
CD:PRO:E:9:51.35:36.96:42.94
O:ARG:E:14:52.07:54.1:37.32
N:ASN:E:15:50.33:55.33:36.91
CA:ASN:E:15:50.95:56.14:35.79
CB:ASN:E:15:52.03:57.17:36.14
CG:ASN:E:15:51.71:58.12:37.33
OD1:ASN:E:15:52.48:58.06:38.3
ND2:ASN:E:15:50.61:58.92:37.34
C:ASN:E:15:51.35:55.45:34.52
O:ASN:E:15:51.35:56.07:33.48
N:NLG:E:16:51.7:54.11:34.56
CA:NLG:E:16:52.14:53.31:33.41
CB:NLG:E:16:53.74:53.04:33.52
CG:NLG:E:16:54.55:54.25:33.28
OD1:NLG:E:16:55.23:54.79:34.16
ND2:NLG:E:16:54.62:54.59:32.04
C:NLG:E:16:51.47:52.01:33.48
O:NLG:E:16:51.17:51.47:34.52
N:LEU:E:17:51.28:51.34:32.29
CA:LEU:E:17:50.62:50.03:32.18
CB:LEU:E:17:49.62:49.98:30.99
CG:LEU:E:17:48.56:51.12:30.98
CD1:LEU:E:17:47.88:51.34:29.61
CD2:LEU:E:17:47.53:50.89:32.13
C:LEU:E:17:51.6:48.76:32.2
O:LEU:E:17:51.17:47.65:32.24
N:THR:E:18:52.92:49.03:32.35
CA:THR:E:18:54.03:48.06:32.4
CB:THR:E:18:55.22:48.91:32.71
OG1:THR:E:18:55.32:50.07:31.91
CG2:THR:E:18:56.54:48.09:32.6
HG21:THR:E:18:56.48:47.27:33.33
HG22:THR:E:18:56.75:47.76:31.56

N:GLY:E:10:49.09:40.77:44.74
CA:GLY:E:10:48.48:42.11:44.71
C:GLY:E:10:49.18:43.08:43.72
O:GLY:E:10:50.4:43.08:43.54
N:MET:E:11:48.38:43.94:43.11
CA:MET:E:11:48.8:44.79:42.01
CB:MET:E:11:48.14:44.37:40.71
CG:MET:E:11:48.83:43.2:40.06
SD:MET:E:11:48.37:43.08:38.35
CE:MET:E:11:49.73:42.37:37.84
C:MET:E:11:48.45:46.28:42.19
O:MET:E:11:47.32:46.68:41.95
N:ASP:E:12:49.46:47.1:42.5
CA:ASP:E:12:49.39:48.55:42.73
CB:ASP:E:12:50.23:48.78:44.03
CG:ASP:E:12:50.28:50.19:44.51
OD1:ASP:E:12:49.47:51.04:44.03
OD2:ASP:E:12:51.11:50.52:45.4
C:ASP:E:12:49.95:49.27:41.51
O:ASP:E:12:51.17:49.44:41.38
N:ILE:E:13:49.09:49.66:40.55
CA:ILE:E:13:49.46:49.96:39.22
CB:ILE:E:13:48.86:49.13:38.07
CG2:ILE:E:13:49.61:49.46:36.79
HG21:ILE:E:13:50.7:49.22:36.83
HG22:ILE:E:13:49.12:48.94:35.95
HG23:ILE:E:13:49.67:50.56:36.61
CG1:ILE:E:13:48.84:47.63:38.4
HG11:ILE:E:13:48.24:47.55:39.33
HG12:ILE:E:13:48.37:47.12:37.54
CD:ILE:E:13:50.14:46.87:38.62
C:ILE:E:13:49.19:51.48:38.98
O:ILE:E:13:48.05:51.89:39.06
N:ARG:E:14:50.24:52.28:38.72
CA:ARG:E:14:50.15:53.74:38.76
CB:ARG:E:14:50.85:54.26:40.04
CG:ARG:E:14:50.26:53.93:41.42
CD:ARG:E:14:50.99:54.45:42.68
NE:ARG:E:14:50.54:53.62:43.82
CZ:ARG:E:14:50.7:53.9:45.12
NH1:ARG:E:14:51.52:54.77:45.58
NH2:ARG:E:14:50.03:53.14:45.96
C:ARG:E:14:50.92:54.39:37.62
CB:LEU:E:20:48.58:46.44:34.43
CG:LEU:E:20:47.18:45.93:34.02
CD1:LEU:E:20:46.63:44.91:35.12
CD2:LEU:E:20:46.24:47.12:33.76
C:LEU:E:20:49.83:44.33:33.66
O:LEU:E:20:49.04:43.37:33.64
N:HIS:E:21:50.87:44.44:32.8
CA:HIS:E:21:51.26:43.45:31.72
CB:HIS:E:21:52.32:44.01:30.81
ND1:HIS:E:21:50.67:45.42:29.41
CG:HIS:E:21:51.96:45.17:29.95
CE1:HIS:E:21:50.89:46.48:28.7
NE2:HIS:E:21:52.22:46.95:28.74
CD2:HIS:E:21:52.93:46.12:29.56
C:HIS:E:21:51.65:42.03:32.3
O:HIS:E:21:51.79:41.06:31.55
N:GLU:E:22:51.73:41.85:33.65
CA:GLU:E:22:52.40.72:34.5
CB:GLU:E:22:52.77:41.19:35.78
CG:GLU:E:22:54.11:41.96:35.36
CD:GLU:E:22:54.97:42.45:36.46
OE1:GLU:E:22:56.1:42.99:36.1
OE2:GLU:E:22:54.76:42.22:37.65
C:GLU:E:22:50.75:39.98:34.88
O:GLU:E:22:50.92:39.02:35.67
N:LEU:E:23:49.6:40.37:34.4
CA:LEU:E:23:48.38:39.69:34.78
CB:LEU:E:23:47.2:40.71:34.94
CG:LEU:E:23:45.8:40.32:35.37
CD1:LEU:E:23:45.79:39.81:36.85
CD2:LEU:E:23:44.97:41.61:35.39
C:LEU:E:23:47.84:38.71:33.73

APPENDIX II-continued

ATOMIC COORDINATES FOR MODEL OF CON-INS G1 INSULIN
(CHAINS A AND B) BOUND TO INSULIN RECEPTOR (CHAINS E, F AND X)
Format comprises the following colon-separated fields: (1) atom name, (2)
residue type, (3) chain name, (4) residue number, (5-7) xyz coordinates.

HG23:THR:E:18:57.44:48.66:32.89
C:THR:E:18:53.88:46.94:33.43
O:THR:E:18:54.32:45.77:33.15
N:ARG:E:19:53.38:47.24:34.65
CA:ARG:E:19:53.32:46.27:35.73
CB:ARG:E:19:53.84:46.86:37.09
CG:ARG:E:19:55.34:47.16:37.29
CD:ARG:E:19:56.12:45.89:36.99
NE:ARG:E:19:57.58:45.99:37.47
CZ:ARG:E:19:58.34:44.97:37.76
NH1:ARG:E:19:57.93:43.71:37.62
NH2:ARG:E:19:59.58:45.08:38.23
C:ARG:E:19:51.97:45.64:35.83
O:ARG:E:19:51.71:44.7:36.6
N:LEU:E:20:51.01:45.99:34.97
CA:LEU:E:20:49.73:45.38:34.78
C:NLG:E:25:47.58:33.79:33.93
O:NLG:E:25:47.29:32.64:34.1
N:CYS:E:26:47.42:34.76:34.84
CA:CYS:E:26:46.75:34.59:36.12
CB:CYS:E:26:47.08:35.77:37.12
SG:CYS:E:26:48.82:35.84:37.54
C:CYS:E:26:45.25:34.49:36.05
O:CYS:E:26:44.55:35.41:35.59
N:SER:E:27:44.62:33.38:36.47
CA:SER:E:27:43.17:33.16:36.63
CB:SER:E:27:42.77:31.66:36.55
OG:SER:E:27:43.19:31.06:35.33
C:SER:E:27:42.63:33.72:37.92
O:SER:E:27:41.51:34.19:38.03
N:VAL:E:28:43.4:33.87:39
CA:VAL:E:28:42.99:34.56:40.27
CB:VAL:E:28:42.59:33.58:41.43
CG1:VAL:E:28:42.19:34.29:42.71
HG11:VAL:E:28:41.64:33.62:43.4
HG12:VAL:E:28:43.09:34.63:43.24
HG13:VAL:E:28:41.45:35.1:42.51
CG2:VAL:E:28:41.42:32.65:41.01
HG21:VAL:E:28:41.81:32.06:40.14
HG22:VAL:E:28:41.01:31.93:41.75
HG23:VAL:E:28:40.55:33.24:40.67
C:VAL:E:28:44.17:35.51:40.72
O:VAL:E:28:45.31:35.18:40.45
N:ILE:E:29:43.92:36.61:41.42
CA:ILE:E:29:44.82:37.49:42.11
CB:ILE:E:29:44.91:38.98:41.59
CG2:ILE:E:29:43.58:39.47:41.07
HG21:ILE:E:29:43.68:40.56:40.89
HG22:ILE:E:29:43.11:38.88:40.24
HG23:ILE:E:29:42.94:39.48:41.97
CG1:ILE:E:29:45.52:39.99:42.5
HG11:ILE:E:29:44.8:40.41:43.23
HG12:ILE:E:29:46.34:39.49:43.07
CD:ILE:E:29:46.25:41.12:41.69
C:ILE:E:29:44.59:37.51:43.56
O:ILE:E:29:43.43:37.67:43.99
N:GLU:E:30:45.57:37.26:44.46
CA:GLU:E:30:45.35:37.01:45.93
CB:GLU:E:30:46.19:35.77:46.34
CG:GLU:E:30:45.46:34.52:45.94
CD:GLU:E:30:46.09:33.23:46.57
OE1:GLU:E:30:45.52:32.14:46.28
OE2:GLU:E:30:47.19:33.39:47.15
C:GLU:E:30:45.52:38.26:46.78
CG:LEU:E:36:46.11:53.54:41.94
CD1:LEU:E:36:46.86:53.81:43.25
CD2:LEU:E:36:44.71:53.24:42.31
C:LEU:E:36:46.31:55.62:38.62
O:LEU:E:36:47.33:55.34:37.98
N:LEU:E:37:45.75:56.85:38.52
CA:LEU:E:37:46.35:58.08:38.12
CB:LEU:E:37:47.39:58.58:39.17
CG:LEU:E:37:47.05:58.73:40.71
CD1:LEU:E:37:48.2:59.09:41.69
CD2:LEU:E:37:45.9:59.68:40.71
O:LEU:E:23:46.83:38.01:33.9
N:GLU:E:24:48.48:38.62:32.56
CA:GLU:E:24:47.98:37.85:31.44
CB:GLU:E:24:48.88:38.01:30.19
CG:GLU:E:24:48.81:39.38:29.55
CD:GLU:E:24:49.11:39.42:28.07
OE1:GLU:E:24:48.17:39.55:27.25
OE2:GLU:E:24:50.26:39.36:27.66
C:GLU:E:24:47.6:36.38:31.71
O:GLU:E:24:46.56:35.88:31.32
N:NLG:E:25:48.43:35.55:32.37
CA:NLG:E:25:48.16:34.14:32.55
CB:NLG:E:25:49.46:33.4:32.36
CG:NLG:E:25:50.26:33.64:31.05
OD1:NLG:E:25:51.31:34.22:31.07
ND2:NLG:E:25:49.73:33.18:29.93
O:GLU:E:30:45.52:38.2:48.04
N:GLY:E:31:45.67:39.42:46.25
CA:GLY:E:31:45.63:40.68:46.9
C:GLY:E:31:44.64:41.64:46.22
O:GLY:E:31:43.65:41.22:45.63
N:HIS:E:32:44.93:42.94:46.34
CA:HIS:E:32:44.09:43.91:45.6
CB:HIS:E:32:44.29:45.27:46.26
ND1:HIS:E:32:46.29:45.37:47.77
CG:HIS:E:32:45.73:45.58:46.55
CE1:HIS:E:32:47.61:45.65:47.7
NE2:HIS:E:32:47.86:46.15:46.48
CD2:HIS:E:32:46.7:46.09:45.75
C:HIS:E:32:44.48:44.03:44.18
O:HIS:E:32:45.63:43.77:43.9
N:LEU:E:33:43.58:44.46:43.27
CA:LEU:E:33:43.92:44.98:42
CB:LEU:E:33:43.35:44.1:40.84
CG:LEU:E:33:43.46:44.63:39.39
CD1:LEU:E:33:44.89:44.98:39.04
CD2:LEU:E:33:42.84:43.75:38.34
C:LEU:E:33:43.52:46.46:41.99
O:LEU:E:33:42.4:46.94:41.9
N:GLN:E:34:44.52:47.33:42.05
CA:GLN:E:34:44.28:48.79:41.96
CB:GLN:E:34:44.56:49.49:43.32
CG:GLN:E:34:45.98:49.64:43.91
CD:GLN:E:34:46.05:50.31:45.35
OE1:GLN:E:34:45.12:50.12:46.13
NE2:GLN:E:34:47.2:50.89:45.72
C:GLN:E:34:45.01:49.34:40.8
O:GLN:E:34:46.18:49.08:40.59
N:ILE:E:35:44.3:50.27:40.09
CA:ILE:E:35:44.82:50.86:38.85
CB:ILE:E:35:44.1:50.26:37.55
CG2:ILE:E:35:44.72:51.01:36.31
HG21:ILE:E:35:44.6:52.11:36.29
HG22:ILE:E:35:45.79:50.73:36.17
HG23:ILE:E:35:44.18:50.51:35.46
CG1:ILE:E:35:44.27:48.75:37.39
HG11:ILE:E:35:45.23:48.59:36.86
HG12:ILE:E:35:44.42:48.35:38.41
CD:ILE:E:35:43.21:47.93:36.75
C:ILE:E:35:44.57:52.4:39.03
O:ILE:E:35:43.41:52.83:39.05
N:LEU:E:36:45.66:53.2:39.12
CA:LEU:E:36:45.62:54.56:39.52
CB:LEU:E:36:46.28:54.72:40.92
HG23:THR:E:41:47.95:55.79:30.85
C:THR:E:41:46.44:56.94:27.15
O:THR:E:41:45.72:57.92:27.1
N:ARG:E:42:46.58:56.23:26.03
CA:ARG:E:42:45.68:56.36:24.89
CB:ARG:E:42:46.31:55.86:23.54
CG:ARG:E:42:47.27:56.83:22.91
CD:ARG:E:42:48.62:57.03:23.61
NE:ARG:E:42:49.12:55.64:23.9
CZ:ARG:E:42:50.18:55.04:23.35
NH1:ARG:E:42:50.91:55.57:22.42

APPENDIX II-continued

ATOMIC COORDINATES FOR MODEL OF CON-INS G1 INSULIN
(CHAINS A AND B) BOUND TO INSULIN RECEPTOR (CHAINS E, F AND X)
Format comprises the following colon-separated fields: (1) atom name, (2)
residue type, (3) chain name, (4) residue number, (5-7) xyz coordinates.

C:LEU:E:37:46.89:58.12:36.68
O:LEU:E:37:47.99:58.52:36.49
N:MET:E:38:46.21:57.62:35.72
CA:MET:E:38:46.78:57.54:34.36
CB:MET:E:38:46.36:56.19:33.9
CG:MET:E:38:46.72:54.88:34.71
SD:MET:E:38:48.25:54.02:34.16
CE:MET:E:38:48.04:52.91:35.6
C:MET:E:38:46.31:58.64:33.46
O:MET:E:38:45.15:58.79:33.04
N:PHE:E:39:47.22:59.59:33.19
CA:PHE:E:39:46.98:60.86:32.61
CB:PHE:E:39:47.82:61.96:33.33
CG:PHE:E:39:47.17:62.38:34.59
CD1:PHE:E:39:47.56:61.78:35.78
CE1:PHE:E:39:46.78:61.94:36.94
CZ:PHE:E:39:45.65:62.74:36.95
CD2:PHE:E:39:46.1:63.2:34.6
CE2:PHE:E:39:45.37:63.49:35.81
C:PHE:E:39:47.23:60.86:31.04
O:PHE:E:39:46.59:61.52:30.23
N:LYS:E:40:48.32:60.12:30.69
CA:LYS:E:40:48.87:60.12:29.32
CB:LYS:E:40:50.4:60.44:29.23
CG:LYS:E:40:50.82:61.72:29.99
CD:LYS:E:40:50.48:62.98:29.2
CE:LYS:E:40:51.31:63.06:27.97
NZ:LYS:E:40:50.8:64.2:27.2
C:LYS:E:40:48.46:58.86:28.47
O:LYS:E:40:48.81:58.71:27.28
N:THR:E:41:47.7:57.89:29.06
CA:THR:E:41:47.25:56.64:28.41
CB:THR:E:41:46.37:55.75:29.37
OG1:THR:E:41:45.42:56.51:30.07
CG2:THR:E:41:47.34:55.04:30.31
HG21:THR:E:41:46.68:54.58:31.08
HG22:THR:E:41:48.08:54.45:29.72
O:PHE:E:46:41.48:47.97:25.73
N:ARG:E:47:41.62:49.64:24.3
CA:ARG:E:47:40.99:48.99:23.16
CB:ARG:E:47:40.88:49.94:21.95
CG:ARG:E:47:39.82:50.99:22.14
CD:ARG:E:47:39.77:52.09:21.06
NE:ARG:E:47:38.86:53.12:21.64
CZ:ARG:E:47:38.81:54.43:21.31
NH1:ARG:E:47:39.65:55.06:20.49
NH2:ARG:E:47:37.88:55.13:21.88
C:ARG:E:47:41.75:47.7:22.83
O:ARG:E:47:41.02:46.71:22.71
N:ASP:E:48:43.12:47.69:22.82
CA:ASP:E:48:43.87:46.47:22.59
CB:ASP:E:48:45.29:46.7:22
CG:ASP:E:48:45.3:47.4:20.66
OD1:ASP:E:48:44.31:47.58:19.95
OD2:ASP:E:48:46.45:47.75:20.21
C:ASP:E:48:43.85:45.54:23.8
O:ASP:E:48:43.77:44.33:23.54
N:LEU:E:49:43.86:45.99:25.12
CA:LEU:E:49:43.92:45.05:26.31
CB:LEU:E:49:44.12:45.74:27.59
CG:LEU:E:49:45.45:46.44:27.69
CD1:LEU:E:49:45.49:47.5:28.72
CD2:LEU:E:49:46.64:45.5:28.04
C:LEU:E:49:42.76:44.09:26.53
O:LEU:E:49:41.61:44.54:26.45
N:SER:E:50:43.06:42.9:26.96
CA:SER:E:50:42.06:41.9:27.34
CB:SER:E:50:41.35:40.95:26.23
OG:SER:E:50:40.23:40.19:26.79
C:SER:E:50:42.73:41.01:28.28
O:SER:E:50:43.85:40.57:28
N:PHE:E:51:42.15:40.71:29.47
CA:PHE:E:51:42.64:39.68:30.42
CB:PHE:E:51:42.95:40.28:31.87
CG:PHE:E:51:43.94:41.46:31.66
NH2:ARG:E:42:50.62:53.9:23.84
C:ARG:E:42:44.44:55.53:25.2
O:ARG:E:42:44.55:54.67:26.08
N:PRO:E:43:43.22:55.73:24.64
CD:PRO:E:43:42.86:56.97:23.97
CA:PRO:E:43:42.08:54.82:24.8
CB:PRO:E:43:40.88:55.68:24.31
CG:PRO:E:43:41.42:56.78:23.35
C:PRO:E:43:42.3:53.68:23.9
O:PRO:E:43:41.76:52.62:24.17
N:GLU:E:44:43.05:53.82:22.78
CA:GLU:E:44:43.63:52.75:22.01
CB:GLU:E:44:44.58:53.36:20.94
CG:GLU:E:44:43.81:54.33:20.01
CD:GLU:E:44:42.77:53.64:19.09
OE1:GLU:E:44:42.97:52.58:18.47
OE2:GLU:E:44:41.71:54.22:18.94
C:GLU:E:44:44.35:51.73:22.81
O:GLU:E:44:44.31:50.56:22.53
N:ASP:E:45:45.01:52.13:23.96
CA:ASP:E:45:45.76:51.19:24.83
CB:ASP:E:45:46.57:51.97:25.87
CG:ASP:E:45:47.68:52.8:25.2
OD1:ASP:E:45:47.94:53.94:25.66
OD2:ASP:E:45:48.36:52.37:24.25
C:ASP:E:45:44.85:50.17:25.4
O:ASP:E:45:45.05:48.97:25.29
N:PHE:E:46:43.69:50.61:25.95
CA:PHE:E:46:42.72:49.78:26.57
CB:PHE:E:46:41.96:50.49:27.68
CG:PHE:E:46:42.82:50.9:28.82
CD1:PHE:E:46:43.19:50.01:29.84
CE1:PHE:E:46:43.89:50.42:30.98
CZ:PHE:E:46:44.14:51.76:31.13
CD2:PHE:E:46:43.24:52.23:28.88
CE2:PHE:E:46:43.8:52.67:30.13
C:PHE:E:46:41.88:49.09:25.49
CB:PRO:E:52:40.17:36.16:28.29
CG:PRO:E:52:41.62:36.25:27.76
C:PRO:E:52:40.47:35.48:30.75
O:PRO:E:52:39.47:34.8:30.92
N:LYS:E:53:41.63:35.2:31.33
CA:LYS:E:53:41.74:34.15:32.27
CB:LYS:E:53:43.29:33.68:32.32
CG:LYS:E:53:43.82:33.09:31.02
CD:LYS:E:53:43.54:31.63:30.66
CE:LYS:E:53:43.98:30.7:31.81
NZ:LYS:E:53:43.85:29.29:31.42
C:LYS:E:53:41.2:34.55:33.7
O:LYS:E:53:40.57:33.75:34.39
N:LEU:E:54:41.18:35.86:34.07
CA:LEU:E:54:40.73:36.34:35.37
CB:LEU:E:54:40.99:37.86:35.58
CG:LEU:E:54:40.62:38.49:36.93
CD1:LEU:E:54:41.39:37.9:38.13
CD2:LEU:E:54:40.71:40.36:36.85
C:LEU:E:54:39.25:36.1:35.69
O:LEU:E:54:38.35:36.6:35.03
N:ILE:E:55:38.94:35.27:36.69
CA:ILE:E:55:37.59:34.9:37.07
CB:ILE:E:55:37.4:33.38:37.22
CG2:ILE:E:55:36.77:32.88:35.92
HG21:ILE:E:55:35.68:33.1:35.9
HG22:ILE:E:55:37.38:33.15:35.04
HG23:ILE:E:55:36.71:31.78:35.76
CG1:ILE:E:55:38.7:32.66:37.67
HG11:ILE:E:55:39.26:32.45:36.74
HG12:ILE:E:55:39.25:33.39:38.3
CD:ILE:E:55:38.42:31.37:38.43
C:ILE:E:55:37.26:35.64:38.32
O:ILE:E:55:36.06:35.88:38.51
N:MET:E:56:38.26:35.96:39.16
CA:MET:E:56:37.89:36.54:40.46
CB:MET:E:56:37.29:35.56:41.5
CG:MET:E:56:38.34:23:41.78

APPENDIX II-continued

ATOMIC COORDINATES FOR MODEL OF CON-INS G1 INSULIN
(CHAINS A AND B) BOUND TO INSULIN RECEPTOR (CHAINS E, F AND X)
Format comprises the following colon-separated fields: (1) atom name, (2)
residue type, (3) chain name, (4) residue number, (5-7) xyz coordinates.

CD1:PHE:E:51:45.28:41.17:31.53
CE1:PHE:E:51:46.29:42.13:31.31
CZ:PHE:E:51:45.82:43.48:31.21
CD2:PHE:E:51:43.51:42.84:31.61
CE2:PHE:E:51:44.46:43.83:31.4
C:PHE:E:51:41.61:38.55:30.66
O:PHE:E:51:40.94:38.53:31.72
N:PRO:E:52:41.44:37.59:29.72
CD:PRO:E:52:42.29:37.43:28.49
CA:PRO:E:52:40.35:36.64:29.81
HG23:ILE:E:57:40.03:42.81:42.24
CG1:ILE:E:57:39.44:40.97:40.34
HG11:ILE:E:57:40.47:40.72:40.04
HG12:ILE:E:57:38.79:40.26:39.79
CD:ILE:E:57:39.17:42.37:39.86
C:ILE:E:57:39.33:39.28:43.89
O:ILE:E:57:38.25:39.33:44.36
N:THR:E:58:40.4:38.99:44.66
CA:THR:E:58:40.36:38.57:46.09
CB:THR:E:58:41.66:38:46.59
OG1:THR:E:58:41.98:36.72:46.05
CG2:THR:E:58:41.82:37.76:48.14
HG21:THR:E:58:41.77:38.75:48.65
HG22:THR:E:58:40.93:37.13:48.37
HG23:THR:E:58:42.73:37.17:48.36
C:THR:E:58:39.99:39.73:47.04
O:THR:E:58:39.09:39.5:47.86
N:ASP:E:59:40.67:40.86:47
CA:ASP:E:59:40.48:42.03:47.82
CB:ASP:E:59:41.82:42.63:48.34
CG:ASP:E:59:42.59:41.71:49.28
OD1:ASP:E:59:41.93:40.81:49.85
OD2:ASP:E:59:43.83:41.9:49.55
C:ASP:E:59:39.77:43.09:47.01
O:ASP:E:59:38.94:42.77:46.12
N:TYR:E:60:39.97:44.42:47.18
CA:TYR:E:60:39.2:45.41:46.47
CB:TYR:E:60:39.13:46.74:47.25
CG:TYR:E:60:40.48:47.26:47.61
CD1:TYR:E:60:41.07:48.23:46.82
CE1:TYR:E:60:42.35:48.69:47.11
CZ:TYR:E:60:43.06:48.23:48.27
OH:TYR:E:60:44.39:48.57:48.54
CD2:TYR:E:60:41.1:46.91:48.82
CE2:TYR:E:60:42.47:47.29:49.02
C:TYR:E:60:39.71:45.67:44.98
O:TYR:E:60:40.8:45.32:44.63
N:LEU:E:61:38.86:46.14:44.09
CA:LEU:E:61:39.16:46.54:42.71
CB:LEU:E:61:38.38:45.77:41.63
CG:LEU:E:61:38.29:46.56:40.26
CD1:LEU:E:61:39.65:46.6:39.56
CD2:LEU:E:61:37.33:45.79:39.34
C:LEU:E:61:38.93:48.05:42.69
O:LEU:E:61:37.89:48.51:43.05
N:LEU:E:62:39.99:48.75:42.47
CA:LEU:E:62:40.1:50.2:42.71
CB:LEU:E:62:41.04:50.59:43.93
N:TYR:E:67:42.39:57.99:32.26
CA:TYR:E:67:42.06:58.66:31.03
CB:TYR:E:67:42.9:59.97:30.71
CG:TYR:E:67:42.75:61.03:31.76
CD1:TYR:E:67:42.61:62.36:31.25
CE1:TYR:E:67:42.6:63.51:32.1
CZ:TYR:E:67:42.49:63.33:33.48
OH:TYR:E:67:42.38:64.34:34.39
CD2:TYR:E:67:42.66:60.93:33.17
CE2:TYR:E:67:42.62:62.06:33.99
C:TYR:E:67:41.96:57.69:29.82
O:TYR:E:67:43.01:57.21:29.32
N:GLY:E:68:40.72:57.24:29.42
CA:GLY:E:68:40.45:56.3:28.3
C:GLY:E:68:40.26:54.78:28.51
O:GLY:E:68:40.45:54.03:27.57
N:LEU:E:69:39.73:54.45:29.73

SD:MET:E:56:37.21:33.18:43.07
CE:MET:E:56:38.09:34.22:44.4
C:MET:E:56:39:37.4:41.13
O:MET:E:56:40.17:37.09:41.05
N:ILE:E:57:38.64:38.47:41.87
CA:ILE:E:57:39.53:39.44:42.41
CB:ILE:E:57:39.3:40.81:41.91
CG2:ILE:E:57:40.15:41.82:42.72
HG21:ILE:E:57:39.94:41.93:43.81
HG22:ILE:E:57:41.22:41.52:42.61
CG:LEU:E:62:41.6:52.03:44.02
CD1:LEU:E:62:40.47:53.07:43.99
CD2:LEU:E:62:42.43:52.32:45.21
C:LEU:E:62:40.55:50.78:41.4
O:LEU:E:62:41.62:50.58:40.8
N:LEU:E:63:39.75:51.73:40.83
CA:LEU:E:63:40.08:52.48:39.68
CB:LEU:E:63:39.11:52.18:38.48
CG:LEU:E:63:39.13:50.72:37.89
CD1:LEU:E:63:37.78:50.32:37.32
CD2:LEU:E:63:40.26:50.66:36.98
C:LEU:E:63:40.04:53.96:40.01
O:LEU:E:63:38.96:54.4:40.43
N:PHE:E:64:41.2:54.71:39.92
CA:PHE:E:64:41.17:56.08:40.32
CB:PHE:E:64:41.87:56.05:41.7
CG:PHE:E:64:42.42:57.37:42.33
CD1:PHE:E:64:41.59:58.52:42.41
CE1:PHE:E:64:42.06:59.71:43.12
CZ:PHE:E:64:43.39:59.78:43.52
CD2:PHE:E:64:43.69:57.52:42.86
CE2:PHE:E:64:44.21:58.63:43.47
C:PHE:E:64:41.86:56.99:39.35
O:PHE:E:64:43.08:56.91:39.16
N:ARG:E:65:41.06:57.82:38.63
CA:ARG:E:65:41.56:58.79:37.67
CB:ARG:E:65:42.22:60.02:38.43
CG:ARG:E:65:41.15:60.76:39.38
CD:ARG:E:65:41.84:61.77:40.31
NE:ARG:E:65:40.74:62.4:41.07
CZ:ARG:E:65:40.93:63.01:42.23
NH1:ARG:E:65:42.12:63.26:42.75
NH2:ARG:E:65:39.9:63.29:42.95
C:ARG:E:65:42.33:58.29:36.46
O:ARG:E:65:43.42:58.6:36.18
N:VAL:E:66:41.62:57.48:35.62
CA:VAL:E:66:42.09:56.92:34.36
CB:VAL:E:66:42.11:55.42:34.25
CG1:VAL:E:66:42.69:54.84:32.95
HG11:VAL:E:66:43.02:53.78:33.04
HG12:VAL:E:66:41.93:55.01:32.15
HG13:VAL:E:66:43.68:55.23:32.62
CG2:VAL:E:66:42.98:54.94:35.45
HG21:VAL:E:66:43.88:55.56:35.65
HG22:VAL:E:66:42.3:54.87:36.33
HG23:VAL:E:66:43.38:53.91:35.32
C:VAL:E:66:41.47:57.46:33.14
O:VAL:E:66:40.25:57.61:33.05
CA:LYS:E:73:33.63:44.13:29.2
CB:LYS:E:73:32.5:44.45:28.23
CG:LYS:E:73:32.82:45.51:27.22
CD:LYS:E:73:31.45:45.92:26.5
CE:LYS:E:73:31.35:47.41:25.98
NZ:LYS:E:73:32.61:47.79:25.23
C:LYS:E:73:34.63:43.29:28.43
O:LYS:E:73:34.68:42.05:28.5
N:ASP:E:74:35.49:43.94:27.61
CA:ASP:E:74:36.46:43.2:26.93
CB:ASP:E:74:36.67:43.95:25.62
CG:ASP:E:74:35.47:44:24.76
OD1:ASP:E:74:34.43:43.33:24.84
OD2:ASP:E:74:35.57:44.72:23.79
C:ASP:E:74:37.8:43.16:27.68
O:ASP:E:74:38.65:42.34:27.37
N:LEU:E:75:38:44.05:28.65

APPENDIX II-continued

ATOMIC COORDINATES FOR MODEL OF CON-INS G1 INSULIN
(CHAINS A AND B) BOUND TO INSULIN RECEPTOR (CHAINS E, F AND X)
Format comprises the following colon-separated fields: (1) atom name, (2)
residue type, (3) chain name, (4) residue number, (5-7) xyz coordinates.

CA:LEU:E:69:39.15:53.17:30.02
CB:LEU:E:69:39.33:52.71:31.44
CG:LEU:E:69:38.84:51.19:31.68
CD1:LEU:E:69:39.49:50.15:30.71
CD2:LEU:E:69:39.09:50.77:33.14
C:LEU:E:69:37.63:53.29:29.72
O:LEU:E:69:36.87:53.86:30.47
N:GLU:E:70:37.12:52.79:28.61
CA:GLU:E:70:35.79:53.03:28.13
CB:GLU:E:70:35.66:52.99:26.61
CG:GLU:E:70:36.44:54.07:25.8
CD:GLU:E:70:36.57:53.72:24.36
OE1:GLU:E:70:35.83:54.29:23.52
OE2:GLU:E:70:37.51:52.94:23.99
C:GLU:E:70:34.78:52.04:28.64
O:GLU:E:70:33.63:52.37:28.77
N:SER:E:71:35.26:50.86:29.01
CA:SER:E:71:34.37:49.81:29.59
CB:SER:E:71:33.38:49.22:28.48
OG:SER:E:71:32.36:48.38:29.03
C:SER:E:71:35.24:48.7:30.23
O:SER:E:71:36.42:48.61:30.02
N:LEU:E:72:34.6:47.88:31.04
CA:LEU:E:72:35.29:46.69:31.64
CB:LEU:E:72:34.87:46.55:33.13
CG:LEU:E:72:35.19:47.76:34.07
CD1:LEU:E:72:34.75:47.53:35.51
CD2:LEU:E:72:36.75:47.85:34.12
C:LEU:E:72:35.01:45.37:30.93
O:LEU:E:72:35.49:44.29:31.39
N:LYS:E:73:34.12:45.38:29.89
C:ASN:E:78:35.05:36.5:34.32
O:ASN:E:78:34.55:35.7:35.1
N:LEU:E:79:35.34:37.73:34.69
CA:LEU:E:79:35.14:38.24:36.03
CB:LEU:E:79:35.75:39.66:36.1
CG:LEU:E:79:35.62:40.38:37.42
CD1:LEU:E:79:36.23:39.48:38.55
CD2:LEU:E:79:36.47:41.62:37.39
C:LEU:E:79:33.7:38.28:36.64
O:LEU:E:79:32.84:39.08:36.16
N:THR:E:80:33.48:37.49:37.66
CA:THR:E:80:32.2:37.09:38.15
CB:THR:E:80:31.82:35.67:37.61
OG1:THR:E:80:30.49:35.32:38.01
CG2:THR:E:80:32.88:34.65:38.12
HG21:THR:E:80:33.86:34.79:37.61
HG22:THR:E:80:33.03:34.53:39.21
HG23:THR:E:80:32.56:33.66:37.7
C:THR:E:80:32.13:37.11:39.67
O:THR:E:80:31.06:37.47:40.19
N:VAL:E:81:33.21:36.95:40.36
CA:VAL:E:81:33.12:37.09:41.82
CB:VAL:E:81:33.49:35.79:42.55
CG1:VAL:E:81:33.62:36.05:44.1
HG11:VAL:E:81:33.65:35.05:44.58
HG12:VAL:E:81:34.53:36.56:44.44
HG13:VAL:E:81:32.7:36.61:44.37
CG2:VAL:E:81:32.32:34.86:42.34
HG21:VAL:E:81:31.28:35.23:42.5
HG22:VAL:E:81:32.38:34.41:41.32
HG23:VAL:E:81:32.4:33.99:43.04
C:VAL:E:81:34.15:38.13:42.23
O:VAL:E:81:35.25:38.11:41.76
N:ILE:E:82:33.82:39.01:43.12
CA:ILE:E:82:34.8:39.76:43.88
CB:ILE:E:82:34.56:41.23:43.79
CG2:ILE:E:82:35.61:41.98:44.69
HG21:ILE:E:82:35.55:41.71:45.76
HG22:ILE:E:82:36.63:41.79:44.28
HG23:ILE:E:82:35.57:43.07:44.44
CG1:ILE:E:82:34.55:41.71:42.25
HG11:ILE:E:82:35.6:41.75:41.89
HG12:ILE:E:82:33.99:41.03:41.56
CD:ILE:E:82:33.94:43.1:42.07
CA:LEU:E:75:39.13:44.06:29.56
CB:LEU:E:75:39.15:45.4:30.46
CG:LEU:E:75:40.48:45.69:31.21
CD1:LEU:E:75:41.67:45.84:30.19
CD2:LEU:E:75:40.48:46.84:32.22
C:LEU:E:75:39.23:42.9:30.53
O:LEU:E:75:40.21:42.27:30.67
N:PHE:E:76:38.05:42.55:31.13
CA:PHE:E:76:38.04:41.44:32.04
CB:PHE:E:76:37.99:41.88:33.59
CG:PHE:E:76:39.16:42.78:34.09
CD1:PHE:E:76:40.44:42.32:34.11
CE1:PHE:E:76:41.51:43.15:34.52
CZ:PHE:E:76:41.26:44.46:34.98
CD2:PHE:E:76:38.89:44.13:34.53
CE2:PHE:E:76:39.96:44.98:34.94
C:PHE:E:76:36.8:40.59:31.69
O:PHE:E:76:35.75:40.68:32.4
N:PRO:E:77:36.77:39.85:30.55
CD:PRO:E:77:37.84:39.75:29.56
CA:PRO:E:77:35.59:39.03:30.14
CB:PRO:E:77:36.1:38.17:29
CG:PRO:E:77:37.16:39.11:28.4
C:PRO:E:77:34.9:38.19:31.25
O:PRO:E:77:33.71:38.32:31.52
N:ASN:E:78:35.66:37.41:32.03
CA:ASN:E:78:35.12:36.28:32.8
CB:ASN:E:78:36.06:35.1:32.53
CG:ASN:E:78:35.85:34.68:31.09
OD1:ASN:E:78:34.71:34.86:30.55
ND2:ASN:E:78:36.82:34.22:30.3
CB:ARG:E:83:36.67:36.87:47.3
CG:ARG:E:83:37.15:36.64:48.75
CD:ARG:E:83:36.09:36.03:49.7
NE:ARG:E:83:36.67:35.9:51.09
CZ:ARG:E:83:36.49:36.75:52.07
NH1:ARG:E:83:35.76:37.87:51.99
NH2:ARG:E:83:36.99:36.46:53.23
C:ARG:E:83:35.71:39.11:48.34
O:ARG:E:83:35.22:38.95:49.46
N:GLY:E:84:36.38:40.25:48.05
CA:GLY:E:84:36.54:41.41:49.02
C:GLY:E:84:37.07:41.05:50.32
O:GLY:E:84:36.48:41.51:51.33
N:SER:E:85:38.2:40.21:50.45
CA:SER:E:85:38.65:39.69:51.72
CB:SER:E:85:39.74:38.56:51.55
OG:SER:E:85:40.23:38:52.72
C:SER:E:85:39.2:40.76:52.64
O:SER:E:85:38.85:40.68:53.82
N:ARG:E:86:39.9:41.78:52.16
CA:ARG:E:86:40.15:43.03:52.81
CB:ARG:E:86:41.72:43.33:52.98
CG:ARG:E:86:42.51:42.21:53.77
CD:ARG:E:86:43.75:41.57:53.06
NE:ARG:E:86:43.18:40.38:52.39
CZ:ARG:E:86:43.78:39.29:52.1
NH1:ARG:E:86:44.68:38.8:52.95
NH2:ARG:E:86:43.54:38.74:50.9
C:ARG:E:86:39.46:44.02:51.96
O:ARG:E:86:39.76:44.09:50.73
N:LEU:E:87:38.56:44.87:52.54
CA:LEU:E:87:37.88:45.9:51.72
CB:LEU:E:87:36.42:46.11:52.37
CG:LEU:E:87:35.63:44.82:52.42
CD1:LEU:E:87:34.41:44.75:53.37
CD2:LEU:E:87:35.27:44.36:50.94
C:LEU:E:87:38.69:47.22:51.71
O:LEU:E:87:39.64:47.37:52.41
N:PHE:E:88:38.26:48.22:50.9
CA:PHE:E:88:38.8:49.54:51.02
CB:PHE:E:88:39.59:49.99:49.71
CG:PHE:E:88:40.13:51.4:49.85
CD1:PHE:E:88:39.64:52.51:49.11
CE1:PHE:E:88:40.08:53.83:49.36

APPENDIX II-continued

ATOMIC COORDINATES FOR MODEL OF CON-INS G1 INSULIN
(CHAINS A AND B) BOUND TO INSULIN RECEPTOR (CHAINS E, F AND X)
Format comprises the following colon-separated fields: (1) atom name, (2)
residue type, (3) chain name, (4) residue number, (5-7) xyz coordinates.

C:ILE:E:82:34.67:39.31:45.35
O:ILE:E:82:33.61:39.29:45.93
N:ARG:E:83:35.78:38.82:45.97
CA:ARG:E:83:35.64:38.02:47.23
O:PHE:E:88:36.68:50.58:50.81
N:PHE:E:89:37.76:50.79:52.78
CA:PHE:E:89:36.73:51.52:53.48
CB:PHE:E:89:36.79:53.02:53.17
CG:PHE:E:89:36.05:53.9:54.23
CD1:PHE:E:89:36.43:54.03:55.57
CE1:PHE:E:89:35.69:54.8:56.46
CZ:PHE:E:89:34.61:55.64:56.01
CD2:PHE:E:89:34.94:54.67:53.76
CE2:PHE:E:89:34.26:55.46:54.61
C:PHE:E:89:35.35:50.94:53.34
O:PHE:E:89:34.43:51.66:52.92
N:ASN:E:90:35.21:49.67:53.64
CA:ASN:E:90:34.07:48.77:53.57
CB:ASN:E:90:32.88:48.99:54.59
CG:ASN:E:90:33.34:48.86:56.05
OD1:ASN:E:90:34.49:48.51:56.32
ND2:ASN:E:90:32.47:49.27:57.02
C:ASN:E:90:33.63:48.5:52.12
O:ASN:E:90:32.95:47.48:51.94
N:TYR:E:91:33.95:49.34:51.11
CA:TYR:E:91:33.79:49.05:49.71
CB:TYR:E:91:34.09:50.27:48.74
CG:TYR:E:91:33.21:51.46:49.17
CD1:TYR:E:91:31.8:51.49:48.97
CE1:TYR:E:91:31.03:52.61:49.31
CZ:TYR:E:91:31.73:53.74:49.74
OH:TYR:E:91:31.09:54.93:50.23
CD2:TYR:E:91:33.85:52.67:49.42
CE2:TYR:E:91:33.07:53.79:49.73
C:TYR:E:91:34.65:47.94:49.09
O:TYR:E:91:35.85:47.78:49.45
N:ALA:E:92:34.05:47.17:48.19
CA:ALA:E:92:34.86:46.14:47.57
CB:ALA:E:92:33.95:44.94:47.44
C:ALA:E:92:35.27:46.54:46.11
O:ALA:E:92:36.25:46.09:45.55
N:LEU:E:93:34.34:47.3:45.52
CA:LEU:E:93:34.48:47.83:44.19
CB:LEU:E:93:33.33:47.39:43.25
CG:LEU:E:93:33.37:48.12:41.83
CD1:LEU:E:93:34.76:47.99:41.13
CD2:LEU:E:93:32.32:47.48:40.9
C:LEU:E:93:34.46:49.42:44.27
O:LEU:E:93:33.32:49.9:44.54
N:VAL:E:94:35.53:50.12:43.99
CA:VAL:E:94:35.68:51.6:43.92
CB:VAL:E:94:36.81:52.08:44.85
CE:MET:E:98:38.68:53.95:35.25
C:MET:E:98:37.01:59.09:34.39
O:MET:E:98:36.59.81:34.48
N:VAL:E:99:37.8:59.11:33.35
CA:VAL:E:99:37.67:60.13:32.29
CB:VAL:E:99:38.93:61.05:32.24
CG1:VAL:E:99:39.33:61.66:30.87
HG11:VAL:E:99:38.4:61.9:30.31
HG12:VAL:E:99:39.85:62.63:30.94
HG13:VAL:E:99:39.93:60.95:30.26
CG2:VAL:E:99:38.64:62.06:33.35
HG21:VAL:E:99:38.45:61.53:34.29
HG22:VAL:E:99:39.54:62.7:33.53
HG23:VAL:E:99:37.81:62.75:33.11
C:VAL:E:99:37.47:59.45:31.01
O:VAL:E:99:38.34:58.61:30.74
N:HIS:E:100:36.44:59.78:30.16
CA:HIS:E:100:35.85:59:29.05
CB:HIS:E:100:36.77:59.05:27.83
ND1:HIS:E:100:36.36:61.26:26.86
CG:HIS:E:100:37.21:60.42:27.55
CE1:HIS:E:100:37:62.37:26.77
NE2:HIS:E:100:38.24:62.3:27.28

CZ:PHE:E:88:41.16:54.05:50.2
CD2:PHE:E:88:41.22:51.66:50.72
CE2:PHE:E:88:41.68:52.99:50.96
C:PHE:E:88:37.7:50.39:51.45
CG1:VAL:E:94:37.16:53.58:44.6
HG11:VAL:E:94:36.27:54.22:44.74
HG12:VAL:E:94:37.78:53.92:45.46
HG13:VAL:E:94:37.65:53.79:43.62
CG2:VAL:E:94:36.31:51.94:46.3
HG21:VAL:E:94:37.12:52.11:47.04
HG22:VAL:E:94:35.46:52.62:46.51
HG23:VAL:E:94:35.89:50.92:46.33
C:VAL:E:94:36.06:51.94:42.52
O:VAL:E:94:37.07:51.5:41.94
N:ILE:E:95:35.22:52.71:41.84
CA:ILE:E:95:35.54:53.35:40.57
CB:ILE:E:95:34.59:52.91:39.46
CG2:ILE:E:95:35.19:53.55:38.15
HG21:ILE:E:95:36.22:53.19:37.99
HG22:ILE:E:95:34.52:53.34:37.29
HG23:ILE:E:95:35.36:54.64:38.25
CG1:ILE:E:95:34.61:51.41:39.39
HG11:ILE:E:95:35.67:51.11:39.23
HG12:ILE:E:95:34.27:50.94:40.34
CD:ILE:E:95:33.74:50.86:38.24
C:ILE:E:95:35.44:54.83:40.71
O:ILE:E:95:34.28:55.36:40.83
N:PHE:E:96:36.52:55.59:40.69
CA:PHE:E:96:36.46:56.93:41.06
CB:PHE:E:96:37.13:56.93:42.43
CG:PHE:E:96:37.14:58.31:43.09
CD1:PHE:E:96:38.28:58.83:43.7
CE1:PHE:E:96:38.27:60.12:44.23
CZ:PHE:E:96:37.12:60.94:44.1
CD2:PHE:E:96:35.88:59.06:43.24
CE2:PHE:E:96:35.96:60.41:43.53
C:PHE:E:96:37.08:57.95:40.05
O:PHE:E:96:38.25:57.8:39.65
N:GLU:E:97:36.28:58.99:39.69
CA:GLU:E:97:36.58:59.98:38.78
CB:GLU:E:97:37.33:61.19:39.52
CG:GLU:E:97:36.4:62.15:40.25
CD:GLU:E:97:37.04:63.47:40.54
OE1:GLU:E:97:38.16:63.56:41.07
OE2:GLU:E:97:36.38:64.5:40.22
C:GLU:E:97:37.25:59.6:37.41
O:GLU:E:97:38.11:60.32:36.9
N:MET:E:98:36.72:58.59:36.78
CA:MET:E:98:37.33:58.11:35.57
CB:MET:E:98:36.77:56.76:35.34
CG:MET:E:98:37.19:55.77:36.44
SD:MET:E:98:38.95:55.37:36.31
OE1:GLU:E:103:27.62:49.73:26.47
OE2:GLU:E:103:29.25:51.01:25.5
C:GLU:E:103:30.25:50.78:31.11
O:GLU:E:103:31.4:50.39:30.95
N:LEU:E:104:29.6:50.41:32.25
CA:LEU:E:104:30.26:49.67:33.36
CB:LEU:E:104:29.27:49.52:34.53
CG:LEU:E:104:29.63:48.66:35.81
CD1:LEU:E:104:30.93:49.2:36.52
CD2:LEU:E:104:28.35:48.74:36.62
C:LEU:E:104:30.86:48.34:32.95
O:LEU:E:104:31.99:48.02:33.23
N:GLY:E:105:30.14:47.52:32.13
CA:GLY:E:105:30.67:46.42:31.34
C:GLY:E:105:30.82:45.12:32.03
O:GLY:E:105:31.45:44.21:31.47
N:LEU:E:106:30.34:45:33.22
CA:LEU:E:106:30.6:43.86:34.08
CB:LEU:E:106:30.79:44.26:35.55
CG:LEU:E:106:32.09:45.15:35.95
CD1:LEU:E:106:31.95:45.74:37.39
CD2:LEU:E:106:33.35:44.24:35.92
C:LEU:E:106:29.52:42.8:33.9

APPENDIX II-continued

ATOMIC COORDINATES FOR MODEL OF CON-INS G1 INSULIN
(CHAINS A AND B) BOUND TO INSULIN RECEPTOR (CHAINS E, F AND X)
Format comprises the following colon-separated fields: (1) atom name, (2)
residue type, (3) chain name, (4) residue number, (5-7) xyz coordinates.

CD2:HIS:E:100:38.37:61.07:27.73
C:HIS:E:100:35.55:57.52:29.41
O:HIS:E:100:35.97:56.61:28.68
N:LEU:E:101:34.82:57.21:30.47
CA:LEU:E:101:34.39:55.87:30.82
CB:LEU:E:101:34.6:55.73:32.33
CG:LEU:E:101:33.98:54.5:32.95
CD1:LEU:E:101:34.14:53.23:32.16
CD2:LEU:E:101:34.57:54.13:34.36
C:LEU:E:101:32.9:55.87:30.4
O:LEU:E:101:32.29:56.91:30.7
N:LYS:E:102:32.35:54.8:29.73
CA:LYS:E:102:31.1:54.95:28.98
CB:LYS:E:102:31.31:54.55:27.52
CG:LYS:E:102:32.24:55.48:26.72
CD:LYS:E:102:31.71:56.9:26.44
CE:LYS:E:102:30.46:56.98:25.51
NZ:LYS:E:102:30.25:58.39:25
C:LYS:E:102:30.14:53.97:29.54
O:LYS:E:102:29.03:54.37:29.85
N:GLU:E:103:30.5:52.65:29.57
CA:GLU:E:103:29.62:51.6:30.05
CB:GLU:E:103:29.33:50.74:28.75
CG:GLU:E:103:28.55:51.54:27.69
CD:GLU:E:103:28.46:50.66:26.5
CD1:LEU:E:109:31.38:40.93:40.06
CD2:LEU:E:109:29.63:42.69:40.05
C:LEU:E:109:27.99:39.1:38.32
O:LEU:E:109:26.91:39.64:38.17
N:MET:E:110:28.2:38.08:39.17
CA:MET:E:110:27.25:37.46:39.92
CB:MET:E:110:27.4:35.86:39.74
CG:MET:E:110:27.35:35.35:38.29
SD:MET:E:110:25.86:35.86:37.49
CE:MET:E:110:24.69:35:38.5
C:MET:E:110:27.3:37.91:41.34
O:MET:E:110:26.23:37.95:42.04
N:NLG:E:111:28.51:38.16:41.93
CA:NLG:E:111:28.48:38.33:43.36
CB:NLG:E:111:28.63:36.99:44.09
CG:NLG:E:111:28.61:37.13:45.59
OD1:NLG:E:111:29.57:36.9:46.28
ND2:NLG:E:111:27.41:37.5:46.16
C:NLG:E:111:29.64:39.26:43.78
O:NLG:E:111:30.76:39.24:43.3
N:ILE:E:112:29.34:40.12:44.79
CA:ILE:E:112:30.35:40.67:45.62
CB:ILE:E:112:30.43:42.28:45.48
CG2:ILE:E:112:31.63:42.75:46.33
HG21:ILE:E:112:31.28:43.36:47.18
HG22:ILE:E:112:32.25:41.9:46.7
HG23:ILE:E:112:32.33:43.35:45.69
CG1:ILE:E:112:30.59:42.71:44.05
HG11:ILE:E:112:31.54:42.25:43.68
HG12:ILE:E:112:29.82:42.17:43.47
CD:ILE:E:112:30.48:44.24:43.73
C:ILE:E:112:30.40.18:47.02
O:ILE:E:112:28.9:40.26:47.54
N:THR:E:113:30.99:39.59:47.64
CA:THR:E:113:31.02:39.1:48.99
CB:THR:E:113:31.92:37.84:49.18
OG1:THR:E:113:31.48:36.73:48.41
CG2:THR:E:113:32.01:37.34:50.62
HG21:THR:E:113:31.02:37.26:51.13
HG22:THR:E:113:32.56:36.39:50.7
HG23:THR:E:113:32.61:37.97:51.32
C:THR:E:113:31.22:40.16:50.07
O:THR:E:113:32.22:40.85:50.17
N:ARG:E:114:30.05:40.35:50.84
CA:ARG:E:114:29.79:41.25:51.97
CB:ARG:E:114:30.06:40.32:53.25
CG:ARG:E:114:29.25:39.04:53.46
CD:ARG:E:114:27.81:39.29:53.66
HG11:ILE:E:119:31.75:52.2:40.51
HG12:ILE:E:119:30.57:52.02:41.87
O:LEU:E:106:28.73:42.57:34.76
N:TYR:E:107:29.41:42.14:32.71
CA:TYR:E:107:28.22:41.42:32.27
CB:TYR:E:107:28.02:41.55:30.69
CG:TYR:E:107:29.1:40.72:30.07
CD1:TYR:E:107:28.68:39.47:29.51
CE1:TYR:E:107:29.54:38.87:28.64
CZ:TYR:E:107:30.75:39.47:28.21
OH:TYR:E:107:31.57:38.7:27.33
CD2:TYR:E:107:30.37:41.23:29.79
CE2:TYR:E:107:31.19:40.67:28.79
C:TYR:E:107:28.09:40:32.85
O:TYR:E:107:27.05:39.33:32.83
N:ASN:E:108:29.22:39.58:33.43
CA:ASN:E:108:29.3:38.26:34.08
CB:ASN:E:108:30.51:37.49:33.48
CG:ASN:E:108:30.15:37.02:32.08
OD1:ASN:E:108:29.1:36.37:31.96
ND2:ASN:E:108:30.93:37.28:31.03
C:ASN:E:108:29.35:38.39:35.62
O:ASN:E:108:29.52:37.37:36.31
N:LEU:E:109:29.12:39.52:36.18
CA:LEU:E:109:29.23:39.64:37.66
CB:LEU:E:109:29.56:41.06:38.11
CG:LEU:E:109:29.9:41.29:39.63
NE:ARG:E:114:27.21:38.02:54.2
CZ:ARG:E:114:25.96:38.03:54.74
NH1:ARG:E:114:25.12:39.08:54.75
NH2:ARG:E:114:25.45:36.92:55.18
C:ARG:E:114:30.61:42.56:51.93
O:ARG:E:114:31.41:42.86:52.77
N:GLY:E:115:30.41:43.44:50.94
CA:GLY:E:115:31.24:44.64:50.73
C:GLY:E:115:30.74:45.45:49.59
O:GLY:E:115:30.27:44.92:48.59
N:SER:E:116:30.64:46.76:49.82
CA:SER:E:116:29.84:47.64:48.98
CB:SER:E:116:29.15:48.76:49.74
OG:SER:E:116:30.05:49.39:50.66
C:SER:E:116:30.5:48.2:47.7
O:SER:E:116:31.72:47.97:47.47
N:VAL:E:117:29.78:48.97:46.84
CA:VAL:E:117:30.31:49.5:45.65
CB:VAL:E:117:29.34:48.99:44.51
CG1:VAL:E:117:29.66:49.62:43.13
HG11:VAL:E:117:30.71:49.47:42.82
HG12:VAL:E:117:29.03:49.22:42.3
HG13:VAL:E:117:29.35:50.7:43.13
CG2:VAL:E:117:29.15:47.45:44.41
HG21:VAL:E:117:30.09:46.89:44.59
HG22:VAL:E:117:28.42:47.06:45.14
HG23:VAL:E:117:28.72:47.15:43.43
C:VAL:E:117:30.32:50.98:45.79
O:VAL:E:117:29.44:51.49:46.45
N:ARG:E:118:31.34:51.67:45.19
CA:ARG:E:118:31.37:53.13:45
CB:ARG:E:118:32.19:53.77:46.04
CG:ARG:E:118:32.06:55.29:45.98
CD:ARG:E:118:32.71:55.99:47.19
NE:ARG:E:118:32.73:57.51:47.24
CZ:ARG:E:118:32.37:58.17:48.28
NH1:ARG:E:118:32.05:57.64:49.43
NH2:ARG:E:118:32.38:59.5:48.23
C:ARG:E:118:31.75:53.6:43.63
O:ARG:E:118:32.83:53.3:43.15
N:ILE:E:119:30.85:54.36:42.9
CA:ILE:E:119:31.07:54.61:41.49
CB:ILE:E:119:30.31:53.78:40.53
CG2:ILE:E:119:30.63:54.25:39.08
HG21:ILE:E:119:30.25:55.29:38.99
HG22:ILE:E:119:31.7:54.24:38.79
HG23:ILE:E:119:30.01:53.6:38.42
CG1:ILE:E:119:30.69:52.33:40.81
N:LEU:E:125:29.69:58.07:32.32
CA:LEU:E:125:29.37:56.71:32.7

APPENDIX II-continued

ATOMIC COORDINATES FOR MODEL OF CON-INS G1 INSULIN
(CHAINS A AND B) BOUND TO INSULIN RECEPTOR (CHAINS E, F AND X)
Format comprises the following colon-separated fields: (1) atom name, (2)
residue type, (3) chain name, (4) residue number, (5-7) xyz coordinates.

CD:ILE:E:119:29.84:51.26:39.99
C:ILE:E:119:30.66:56.05:41.33
O:ILE:E:119:29.54:56.42:40.89
N:GLU:E:120:31.59:56.94:41.66
CA:GLU:E:120:31.43:58.36:41.87
CB:GLU:E:120:31.89:58.62:43.2
CG:GLU:E:120:32.27:60.05:43.61
CD:GLU:E:120:32.48:60.09:45.12
OE1:GLU:E:120:33.49:59.51:45.6
OE2:GLU:E:120:31.67:60.73:45.79
C:GLU:E:120:32.2:59.25:40.86
O:GLU:E:120:33.41:59.14:40.67
N:LYS:E:121:31.37:60.18:40.34
CA:LYS:E:121:31.78:61.31:39.53
CB:LYS:E:121:32.52:62.31:40.47
CG:LYS:E:121:31.64:63.11:41.53
CD:LYS:E:121:32.28:64.34:42.2
CE:LYS:E:121:33.38:63.85:43.15
NZ:LYS:E:121:34.16:64.9:43.84
C:LYS:E:121:32.52:60.96:38.18
O:LYS:E:121:33.44:61.63:37.77
N:ASN:E:122:32.07:59.99:37.42
CA:ASN:E:122:32.82:59.48:36.27
CB:ASN:E:122:32.65:57.98:36.19
CG:ASN:E:122:33.25:57.28:37.46
OD1:ASN:E:122:34.43:56.97:37.38
ND2:ASN:E:122:32.37:57.07:38.47
C:ASN:E:122:32.19:60.02:35.01
O:ASN:E:122:31.03:59.72:34.58
N:ASN:E:123:33.01:60.78:34.26
CA:ASN:E:123:32.7:61.44:32.96
CB:ASN:E:123:33.95:62.46:32.56
CG:ASN:E:123:33.97:62.98:31.16
OD1:ASN:E:123:34.66:62.37:30.28
ND2:ASN:E:123:33.12:64.01:30.87
C:ASN:E:123:32.17:60.56:31.86
O:ASN:E:123:32.93:59.83:31.26
N:GLU:E:124:30.84:60.63:31.56
CA:GLU:E:124:30.15:59.81:30.49
CB:GLU:E:124:30.82:59.6:29.13
CG:GLU:E:124:31.03:61:28.53
CD:GLU:E:124:29.82:61.37:27.64
OE1:GLU:E:124:29.3:62.53:27.84
OE2:GLU:E:124:29.57:60.62:26.72
C:GLU:E:124:29.58:58.43:31.01
O:GLU:E:124:29.04:57.65:30.21
O:THR:E:130:19.41:47.53:34.44
N:ILE:E:131:21:47.91:36.07
CA:ILE:E:131:21.19:46.59:36.63
CB:ILE:E:131:22.67:46.22:36.79
CG2:ILE:E:131:23.29:46.02:35.37
HG21:ILE:E:131:23.05:45.04:34.92
HG22:ILE:E:131:22.96:46.82:34.69
HG23:ILE:E:131:24.41:46.05:35.34
CG1:ILE:E:131:23.56:47.18:37.66
HG11:ILE:E:131:22.8:47.55:38.38
HG12:ILE:E:131:24.33:46.58:38.19
CD:ILE:E:131:24.32:48.22:36.87
C:ILE:E:131:20.52:46.33:37.93
O:ILE:E:131:20.12:47.27:38.68
N:ASP:E:132:20.35:45.03:38.28
CA:ASP:E:132:19.65:44.67:39.47
CB:ASP:E:132:18.57:43.57:39.35
CG:ASP:E:132:17.72:43.34:40.58
OD1:ASP:E:132:17.94:44.07:41.62
OD2:ASP:E:132:16.79:42.5:40.56
C:ASP:E:132:20.71:44.36:40.56
O:ASP:E:132:21.33:43.3:40.65
N:TRP:E:133:20.88:45.32:41.48
CA:TRP:E:133:21.92:45.2:42.5
CB:TRP:E:133:22.37:46.59:43.05
CG:TRP:E:133:23.07:47.52:42.04
CD1:TRP:E:133:22.53:48.68:41.53
NE1:TRP:E:133:23.49:49.32:40.76
CE2:TRP:E:133:24.67:48.56:40.82

CB:LEU:E:125:30.1:56.27:33.92
CG:LEU:E:125:29.94:54.92:34.61
CD1:LEU:E:125:30.24:53.72:33.66
CD2:LEU:E:125:30.83:54.72:35.87
C:LEU:E:125:27.84:56.5:32.74
O:LEU:E:125:27.21:57.15:33.59
N:CYS:E:126:27.32:55.62:31.84
CA:CYS:E:126:26.02:55.01:31.91
CB:CYS:E:126:25.35:55.12:30.49
SG:CYS:E:126:24.96:56.89:29.98
C:CYS:E:126:26.09:53.59:32.34
O:CYS:E:126:27.13:52.96:32.3
N:TYR:E:127:24.91:53.08:32.75
CA:TYR:E:127:24.69:51.69:32.96
CB:TYR:E:127:25.23:50.68:31.97
CG:TYR:E:127:24.62:50.94:30.57
CD1:TYR:E:127:25.25:51.76:29.61
CE1:TYR:E:127:24.65:52.05:28.39
CZ:TYR:E:127:23.38:51.49:28.03
OH:TYR:E:127:22.85:51.66:26.78
CD2:TYR:E:127:23.36:50.42:30.26
CE2:TYR:E:127:22.75:50.72:29.08
C:TYR:E:127:24.85:51.22:34.37
O:TYR:E:127:25.36:50.12:34.61
N:LEU:E:128:24.49:52.14:35.28
CA:LEU:E:128:24.74:51.95:36.73
CB:LEU:E:128:25.34:53.14:37.47
CG:LEU:E:128:26.6:53.53:36.71
CD1:LEU:E:128:27.1:54.84:37.41
CD2:LEU:E:128:27.64:52.4:36.64
C:LEU:E:128:23.49:51.67:37.56
O:LEU:E:128:23.66:51.02:38.58
N:ALA:E:129:22.32:52.14:37.04
CA:ALA:E:129:21.07:51.82:37.71
CB:ALA:E:129:20.35:53.06:38.04
C:ALA:E:129:20.22:50.96:36.8
O:ALA:E:129:19.17:50.49:37.21
N:THR:E:130:20.84:50.59:35.64
CA:THR:E:130:20.21:49.79:34.66
CB:THR:E:130:20.8:49.84:33.24
OG1:THR:E:130:22.2:49.65:33.33
CG2:THR:E:130:20.69:51.28:32.69
HG21:THR:E:130:21.09:51.32:31.65
HG22:THR:E:130:19.61:51.51:32.78
HG23:THR:E:130:21.11:52.07:33.35
C:THR:E:130:20.17:48.33:35.06
CZ:ARG:E:135:16.02:38.94:40.95
NH1:ARG:E:135:16.32:37.86:40.34
NH2:ARG:E:135:14.76:39.3:40.97
C:ARG:E:135:22.66:39.99:43.07
O:ARG:E:135:23.26:38.94:42.83
N:ILE:E:136:23.42:41.08:43.44
CA:ILE:E:136:24.82:41.1:43.35
CB:ILE:E:136:25.23:42.44:42.6
CG2:ILE:E:136:26.74:42.65:42.66
HG21:ILE:E:136:26.9:43.64:42.19
HG22:ILE:E:136:27.05:42.85:43.72
HG23:ILE:E:136:27.29:41.84:42.15
CG1:ILE:E:136:24.67:42.56:41.11
HG11:ILE:E:136:23.57:42.54:41.15
HG12:ILE:E:136:24.99:43.51:40.62
CD:ILE:E:136:25.15:41.39:40.29
C:ILE:E:136:25.46:41.12:44.7
O:ILE:E:136:26.48:40.42:44.89
N:LEU:E:137:24.83:41.88:45.69
CA:LEU:E:137:25.32:42.11:46.98
CB:LEU:E:137:26.28:43.34:46.97
CG:LEU:E:137:25.74:44.77:46.78
CD1:LEU:E:137:26.79:45.76:47.32
CD2:LEU:E:137:25.54:45.17:45.35
C:LEU:E:137:24.15:42.42:47.88
O:LEU:E:137:23.07:42.79:47.45
N:ASP:E:138:24.4:42.24:49.18
CA:ASP:E:138:23.51:42.4:50.28
CB:ASP:E:138:23.83:41.34:51.37

APPENDIX II-continued

ATOMIC COORDINATES FOR MODEL OF CON-INS G1 INSULIN
(CHAINS A AND B) BOUND TO INSULIN RECEPTOR (CHAINS E, F AND X)
Format comprises the following colon-separated fields: (1) atom name, (2)
residue type, (3) chain name, (4) residue number, (5-7) xyz coordinates.

CD2:TRP:E:133:24.41:47.41:41.62
CE3:TRP:E:133:25.43:46.49:41.86
CZ3:TRP:E:133:26.66:46.63:41.11
CZ2:TRP:E:133:25.96:48.79:40.3
CH2:TRP:E:133:26.89:47.77:40.43
C:TRP:E:133:21.46:44.33:43.67
O:TRP:E:133:22.35:43.85:44.39
N:SER:E:134:20.17:43.98:43.81
CA:SER:E:134:19.73:43.09:44.85
CB:SER:E:134:18.14:43.09:44.95
OG:SER:E:134:17.5:42.68:43.73
C:SER:E:134:20.12:41.6:44.6
O:SER:E:134:19.95:40.79:45.45
N:ARG:E:135:20.63:41.36:43.41
CA:ARG:E:135:21.15:40.07:43.05
CB:ARG:E:135:20.65:39.82:41.61
CG:ARG:E:135:19.22:40.12:41.36
CD:ARG:E:135:18.28:39.24:42.11
NE:ARG:E:135:16.91:39.64:41.73
HG21:VAL:E:140:22.86:45.83:46.43
HG22:VAL:E:140:22.37:45.14:48.02
HG23:VAL:E:140:21.14:45.26:46.74
C:VAL:E:140:22.57:49.28:48.79
O:VAL:E:140:22.98:50.15:48.03
N:GLU:E:141:22.05:49.57:49.96
CA:GLU:E:141:21.71:50.9:50.43
CB:GLU:E:141:20.75:50.76:51.62
CG:GLU:E:141:19.35:50.24:51.14
CD:GLU:E:141:18.49:49.77:52.28
OE1:GLU:E:141:17.4:50.36:52.42
OE2:GLU:E:141:18.9:48.91:53.11
C:GLU:E:141:23.02:51.74:50.81
O:GLU:E:141:23.03:52.97:50.88
N:ASP:E:142:24.1:50.94:51.16
CA:ASP:E:142:25.33:51.53:51.57
CB:ASP:E:142:26.09:50.63:52.56
CG:ASP:E:142:25.52:50.71:53.95
OD1:ASP:E:142:25.11:51.78:54.49
OD2:ASP:E:142:25.6:49.66:54.58
C:ASP:E:142:26.3:51.68:50.37
O:ASP:E:142:27.42:52.13:50.61
N:ASN:E:143:25.86:51.46:49.14
CA:ASN:E:143:26.41:51.91:47.9
CB:ASN:E:143:25.7:51.46:46.6
CG:ASN:E:143:25.94:50.02:46.38
OD1:ASN:E:143:26.82:49.4:46.97
ND2:ASN:E:143:25.01:49.39:45.57
C:ASN:E:143:26.37:53.45:47.81
O:ASN:E:143:25.34:54.08:48.07
N:HIS:E:144:27.5:54.06:47.32
CA:HIS:E:144:27.51:55.43:46.87
CB:HIS:E:144:28.65:56.21:47.66
ND1:HIS:E:144:27.71:58.45:48.23
CG:HIS:E:144:28.61:57.64:47.48
CE1:HIS:E:144:28.1:59.69:47.92
NE2:HIS:E:144:29.19:59.67:47.07
CD2:HIS:E:144:29.49:58.39:46.78
C:HIS:E:144:27.72:55.54:45.35
O:HIS:E:144:28.88:55.37:44.85
N:ILE:E:145:26.63:55.76:44.6
CA:ILE:E:145:26.75:55.76:43.17
CB:ILE:E:145:26.1:54.52:42.41
CG2:ILE:E:145:25.98:54.92:40.94
HG21:ILE:E:145:25.7:54.05:40.32
HG22:ILE:E:145:25.26:55.77:40.84
HG23:ILE:E:145:27.03:55.2:40.68
CG1:ILE:E:145:26.87:53.17:42.63
OD2:ASP:E:150:22.18:54.81:36
C:ASP:E:150:22.57.96:34.46
O:ASP:E:150:20.87:57.57:34.11
N:ASP:E:151:22.24:58.99:35.31
CA:ASP:E:151:21.23:59.71:36.1
CB:ASP:E:151:21.9:60.25:37.42
CG:ASP:E:151:21.99:59.19:38.51
OD1:ASP:E:151:22.49:59.41:39.63
CG:ASP:E:138:25.28:41.29:51.78
OD1:ASP:E:138:25.58:41.41:53.01
OD2:ASP:E:138:26.15:40.94:50.9
C:ASP:E:138:23.52:43.75:50.91
O:ASP:E:138:22.67:43.97:51.76
N:SER:E:139:24.45:44.75:50.54
CA:SER:E:139:24.55:46.03:51.21
CB:SER:E:139:26.04:46.32:51.66
OG:SER:E:139:26.42:45.43:52.67
C:SER:E:139:24.22:47.2:50.3
O:SER:E:139:24.85:48.29:50.34
N:VAL:E:140:23.2:47.01:49.53
CA:VAL:E:140:22.76:47.84:48.43
CB:VAL:E:140:21.6:47.18:47.71
CG1:VAL:E:140:21.17:48.09:46.58
HG11:VAL:E:140:20.56:48.92:47.01
HG12:VAL:E:140:21.99:48.53:45.97
HG13:VAL:E:140:20.45:47.64:45.87
CG2:VAL:E:140:22.02:45.78:47.17
HG11:ILE:E:145:27.91:53.4:42.32
HG12:ILE:E:145:26.84:52.94:43.72
CD:ILE:E:145:26.28:51.97:41.8
C:ILE:E:145:26.19:57.08:42.66
O:ILE:E:145:24.95:57.23:42.68
N:VAL:E:146:26.91:58.08:42.25
CA:VAL:E:146:26.5:59.43:42.16
CB:VAL:E:146:26.79:60.31:43.41
CG1:VAL:E:146:26.04:59.79:44.7
HG11:VAL:E:146:24.95:59.85:44.52
HG12:VAL:E:146:26.31:58.74:44.98
HG13:VAL:E:146:26.24:60.38:45.62
CG2:VAL:E:146:28.33:60.29:43.7
HG21:VAL:E:146:28.93:59.37:43.58
HG22:VAL:E:146:28.79:61.02:43.01
HG23:VAL:E:146:28.49:60.78:44.69
C:VAL:E:146:27.13:60.22:41.03
O:VAL:E:146:28.24:60.14:40.6
N:LEU:E:147:26.21:61.11:40.5
CA:LEU:E:147:26.49:62.11:39.47
CB:LEU:E:147:27.48:63.15:40.02
CG:LEU:E:147:26.92:63.92:41.22
CD1:LEU:E:147:28.13:64.42:42.08
CD2:LEU:E:147:26.07:65.09:40.72
C:LEU:E:147:27.03:61.6:38.15
O:LEU:E:147:27.68:62.26:37.36
N:ASN:E:148:26.75:60.37:37.83
CA:ASN:E:148:26.99:59.86:36.51
CB:ASN:E:148:27.34:58.4:36.55
CG:ASN:E:148:28.38:58.11:37.68
OD1:ASN:E:148:29.6:58.17:37.44
ND2:ASN:E:148:27.92:57.68:38.85
C:ASN:E:148:25.91:60.16:35.47
O:ASN:E:148:24.73:60.38:35.8
N:LYS:E:149:26.25:60.06:34.18
CA:LYS:E:149:25.39:60.22:33.02
CB:LYS:E:149:26.33:60.22:31.8
CG:LYS:E:149:25.65:60.64:30.5
CD:LYS:E:149:26.58:60.99:29.32
CE:LYS:E:149:25.75:61.55:28.19
NZ:LYS:E:149:26.6:61.52:27.03
C:LYS:E:149:24.27:59.28:32.89
O:LYS:E:149:23.23:59.59:32.3
N:ASP:E:150:24.32:58.18:33.66
CA:ASP:E:150:23.23:57.24:33.96
CB:ASP:E:150:23.76:56.22:34.99
CG:ASP:E:150:22.86:55.14:35.01
OD1:ASP:E:150:22.75:54.55:33.9
CA:ASP:E:157:18.64:52.95:29.53
CB:ASP:E:157:17.68:52.77:30.72
CG:ASP:E:157:17.96:53.61:31.95
OD1:ASP:E:157:19.05:54.2:32.06
OD2:ASP:E:157:17.12:53.53:32.91
C:ASP:E:157:18.3:51.93:28.41
O:ASP:E:157:17.55:50.98:28.65
N:ILE:E:158:18.84:52.18:27.21

APPENDIX II-continued

ATOMIC COORDINATES FOR MODEL OF CON-INS G1 INSULIN
(CHAINS A AND B) BOUND TO INSULIN RECEPTOR (CHAINS E, F AND X)
Format comprises the following colon-separated fields: (1) atom name, (2)
residue type, (3) chain name, (4) residue number, (5-7) xyz coordinates.

OD2:ASP:E:151:21.52:58.06:38.24
C:ASP:E:151:20.67:60.94:35.38
O:ASP:E:151:19.77:61.6:35.87
N:ASN:E:152:21.26:61.29:34.17
CA:ASN:E:152:20.87:62.41:33.29
CB:ASN:E:152:22.08:63.2:32.79
CG:ASN:E:152:22.87:63.97:33.85
OD1:ASN:E:152:24.02:63.71:34.17
ND2:ASN:E:152:22.22:64.93:34.53
C:ASN:E:152:20.1:61.87:32.12
O:ASN:E:152:19.7:62.67:31.27
N:GLU:E:153:19.9:60.58:31.96
CA:GLU:E:153:18.94:59.91:31.1
CB:GLU:E:153:17.46:60.35:31.26
CG:GLU:E:153:17.07:60.15:32.68
CD:GLU:E:153:15.72:60.74:32.95
OE1:GLU:E:153:14.67:60.05:33.11
OE2:GLU:E:153:15.68:62.03:33.01
C:GLU:E:153:19.34:59.91:29.65
O:GLU:E:153:18.58:59.56:28.78
N:GLU:E:154:20.61:60.37:29.29
CA:GLU:E:154:21.04:60.53:27.93
CB:GLU:E:154:22.34:61.4:28.06
CG:GLU:E:154:21.97:62.84:28.4
CD:GLU:E:154:23.01:63.77:28.06
OE1:GLU:E:154:23.38:64.05:26.92
OE2:GLU:E:154:23.66:64.3:29
C:GLU:E:154:21.32:59.28:27.14
O:GLU:E:154:21.07:59.3:25.96
N:CYS:E:155:21.67:58.22:27.87
CA:CYS:E:155:21.68:56.89:27.32
CB:CYS:E:155:22.68:56.01:28.1
SG:CYS:E:155:24.37:56.57:27.96
C:CYS:E:155:20.32:56.19:27.37
O:CYS:E:155:20.17:55.12:26.83
N:GLY:E:156:19.35:56.8:27.98
CA:GLY:E:156:17.93:56.33:27.97
C:GLY:E:156:17.64:54.89:28.36
O:GLY:E:156:16.57:54.37:28.04
N:ASP:E:157:18.64:54.32:29.04
CA:ALA:E:163:10.59:43.02:22.82
CB:ALA:E:163:9.91:43.7:24.08
C:ALA:E:163:9.64:42.32:21.83
O:ALA:E:163:9.04:41.28:22.06
N:LYS:E:164:9.42:42.98:20.69
CA:LYS:E:164:8.56:42.52:19.59
CB:LYS:E:164:8.34:43.65:18.49
CG:LYS:E:164:7.83:45.03:18.95
CD:LYS:E:164:6.33:45.01:19.31
CE:LYS:E:164:5.7:46.4:19.57
NZ:LYS:E:164:4.3:46.21:19.95
C:LYS:E:164:9.11:41.27:19.02
O:LYS:E:164:8.38:40.29:18.98
N:GLY:E:165:10.4:41.32:18.68
CA:GLY:E:165:11.11:40.29:17.95
C:GLY:E:165:11.65:39.23:18.85
O:GLY:E:165:12.19:38.23:18.4
N:LYS:E:166:11.55:39.5:20.17
CA:LYS:E:166:11.95:38.61:21.26
CB:LYS:E:166:11.31:37.25:21.17
CG:LYS:E:166:9.77:37.53:21.2
CD:LYS:E:166:8.92:36.23:21.4
CE:LYS:E:166:7.47:36.72:21.43
NZ:LYS:E:166:6.49:35.75:22
C:LYS:E:166:13.4:38.44:21.47
O:LYS:E:166:13.92:37.35:21.71
N:THR:E:167:14.12:39.58:21.27
CA:THR:E:167:15.54:39.65:21.3
CB:THR:E:167:16.1:40.18:19.98
OG1:THR:E:167:15.74:41.51:19.71
CG2:THR:E:167:15.55:39.4:18.81
HG21:THR:E:167:15.68:38.3:18.87
HG22:THR:E:167:14.45:39.43:18.75
HG23:THR:E:167:15.97:39.73:17.84
C:THR:E:167:16.11:40.47:22.41

CA:ILE:E:158:18.64:51.23:26.1
CB:ILE:E:158:18.97:51.87:24.69
CG2:ILE:E:158:18.8:50.81:23.56
HG21:ILE:E:158:19.21:51.38:22.71
HG22:ILE:E:158:19.52:49.96:23.61
HG23:ILE:E:158:17.82:50.34:23.36
CG1:ILE:E:158:18.23:53.21:24.41
HG11:ILE:E:158:17.15:52.96:24.33
HG12:ILE:E:158:18.32:53.97:25.22
CD:ILE:E:158:18.7:53.88:23.13
C:ILE:E:158:19.47:49.99:26.33
O:ILE:E:158:20.7:50.05:26.47
N:CYS:E:159:18.82:48.82:26.27
CA:CYS:E:159:19.42:47.54:26.47
CB:CYS:E:159:18.95:46.86:27.79
SG:CYS:E:159:19.69:47.44:29.33
C:CYS:E:159:19.19:46.58:25.24
O:CYS:E:159:18.24:46.9:24.55
N:PRO:E:160:19.97:45.54:24.93
CD:PRO:E:160:21.21:45.22:25.65
CA:PRO:E:160:19.9:44.72:23.71
CB:PRO:E:160:20.65:43.47:24.12
CG:PRO:E:160:21.85:44.16:24.81
C:PRO:E:160:18.53:44.4:23.16
O:PRO:E:160:17.56:44.21:23.9
N:GLY:E:161:18.31:44.48:21.78
CA:GLY:E:161:17.17:43.94:21.12
C:GLY:E:161:15.86:44.69:21.11
O:GLY:E:161:15.87:45.93:21.18
N:THR:E:162:14.87:43.96:20.95
CA:THR:E:162:13.5:44.43:20.81
CB:THR:E:162:13.07:44.76:19.4
OG1:THR:E:162:11.66:44.86:19.23
CG2:THR:E:162:13.56:43.66:18.35
HG21:THR:E:162:13.16:43.93:17.35
HG22:THR:E:162:14.67:43.69:18.29
HG23:THR:E:162:13.14:42.67:18.62
C:THR:E:162:12.58:43.43:21.48
O:THR:E:162:12.81:42.19:21.31
N:ALA:E:163:11.56:43.92:22.23
C:CYS:E:169:16.26:40.36:28.81
O:CYS:E:169:15.05:40.64:28.79
N:PRO:E:170:16.83:39.42:29.72
CD:PRO:E:170:18.14:38.77:29.53
CA:PRO:E:170:16.3:39.12:31.06
CB:PRO:E:170:17.37:38.45:31.78
CG:PRO:E:170:18.21:37.78:30.73
C:PRO:E:170:15.83:40.27:31.92
O:PRO:E:170:16.57:41.25:32.12
N:ALA:E:171:14.55:40.3:32.45
CA:ALA:E:171:13.86:41.46:32.97
CB:ALA:E:171:12.56:41.73:32.23
C:ALA:E:171:13.66:41.11:34.43
O:ALA:E:171:13.21:40.01:34.76
N:THR:E:172:13.84:42.1:35.34
CA:THR:E:172:13.61:41.76:36.74
CB:THR:E:172:14.85:41.55:37.62
OG1:THR:E:172:15.57:42.75:37.77
CG2:THR:E:172:15.89:40.59:37.05
HG21:THR:E:172:16.65:40.28:37.8
HG22:THR:E:172:15.36:39.67:36.73
HG23:THR:E:172:16.45:41.06:36.23
C:THR:E:172:12.7:42.87:37.37
O:THR:E:172:12.75:44.03:36.93
N:VAL:E:173:11.89:42.49:38.38
CA:VAL:E:173:10.82:43.23:39.02
CB:VAL:E:173:9.77:42.3:39.72
CG1:VAL:E:173:10.41:41.71:40.93
HG11:VAL:E:173:9.63:41.2:41.52
HG12:VAL:E:173:11.23:40.96:40.81
HG13:VAL:E:173:10.77:42.52:41.62
CG2:VAL:E:173:8.49:43.08:40.02
HG21:VAL:E:173:7.77:42.29:40.33
HG22:VAL:E:173:8.72:43.74:40.88
HG23:VAL:E:173:8:43.61:39.17

APPENDIX II-continued

ATOMIC COORDINATES FOR MODEL OF CON-INS G1 INSULIN
(CHAINS A AND B) BOUND TO INSULIN RECEPTOR (CHAINS E, F AND X)
Format comprises the following colon-separated fields: (1) atom name, (2)
residue type, (3) chain name, (4) residue number, (5-7) xyz coordinates.

O:THR:E:167:17.33:40.61:22.56
N:ASN:E:168:15.24:40.94:23.29
CA:ASN:E:168:15.52:41.62:24.52
CB:ASN:E:168:14.34:42.49:24.98
CG:ASN:E:168:13.1:41.69:25.2
OD1:ASN:E:168:12.79:40.66:24.67
ND2:ASN:E:168:12.24:42.22:26.12
C:ASN:E:168:16.06:40.81:25.71
O:ASN:E:168:16.03:39.56:25.76
N:CYS:E:169:16.7:41.57:26.66
CA:CYS:E:169:17.25:41.03:27.81
CB:CYS:E:169:18.05:42.11:28.59
SG:CYS:E:169:19.52:42.8:27.58
C:ILE:E:174:9.65:47.33:41
O:ILE:E:174:9.18:47.99:40.06
N:ASN:E:175:9.04:47.32:42.21
CA:ASN:E:175:7.74:47.97:42.4
CB:ASN:E:175:7.84:49.46:43.04
CG:ASN:E:175:8.63:49.63:44.38
OD1:ASN:E:175:9.43:48.8:44.74
ND2:ASN:E:175:8.29:50.67:45.19
C:ASN:E:175:6.69:47.86:41.22
O:ASN:E:175:6.24:48.85:40.67
N:GLY:E:176:6.26:46.64:40.88
CA:GLY:E:176:5.08:46.51:39.98
C:GLY:E:176:5.44:46.68:38.54
O:GLY:E:176:4.57:46.5:37.6
N:GLN:E:177:6.76:46.9:38.3
CA:GLN:E:177:7.34:47.04:36.96
CB:GLN:E:177:8.09:48.39:36.79
CG:GLN:E:177:7.28:49.67:37.14
CD:GLN:E:177:5.88:49.75:36.48
OE1:GLN:E:177:5.58:49.32:35.4
NE2:GLN:E:177:4.92:50.32:37.27
C:GLN:E:177:8.49:46.05:36.7
O:GLN:E:177:9.22:45.71:37.6
N:PHE:E:178:8.6:45.45:35.48
CA:PHE:E:178:9.72:44.62:35.05
CB:PHE:E:178:9.23:43.39:34.26
CG:PHE:E:178:8.88:42.23:35.14
CD1:PHE:E:178:7.65:42.15:35.83
CE1:PHE:E:178:7.37:41.05:36.66
CZ:PHE:E:178:8.37:40.01:36.82
CD2:PHE:E:178:9.84:41.24:35.42
CE2:PHE:E:178:9.64:40.18:36.3
C:PHE:E:178:10.68:45.45:34.14
O:PHE:E:178:10.24:46.07:33.15
N:VAL:E:179:11.98:45.36:34.47
CA:VAL:E:179:12.97:46.18:33.83
CB:VAL:E:179:13.37:47.25:34.78
CG1:VAL:E:179:14.5:48.04:34.12
HG11:VAL:E:179:14.28:48.28:33.05
HG12:VAL:E:179:14.51:49.08:34.5
HG13:VAL:E:179:15.51:47.59:34.17
CG2:VAL:E:179:12.11:48.12:35.16
HG21:VAL:E:179:11.78:48.65:34.25
HG22:VAL:E:179:11.29:47.47:35.52
HG23:VAL:E:179:12.33:48.86:35.96
C:VAL:E:179:14.04:45.25:33.25
O:VAL:E:179:14.72:44.51:33.94
N:GLU:E:180:14.2:45.41:31.92
O:THR:E:184:24.57:46.56:27.83
N:HIS:E:185:25.51:48.03:26.45
CA:HIS:E:185:24.55:47.71:25.37
CB:HIS:E:185:24.46:48.92:24.43
ND1:HIS:E:185:23.7:49.73:22.27
CG:HIS:E:185:23.5:48.83:23.31
CE1:HIS:E:185:22.72:49.55:21.4
NE2:HIS:E:185:21.84:48.6:21.9
CD2:HIS:E:185:22.34:48.12:23.11
C:HIS:E:185:25.06:46.53:24.63
O:HIS:E:185:24.31:46.23:23.82
N:SER:E:186:26.3:46.08:24.79
CA:SER:E:186:26.74:44.78:24.18
CB:SER:E:186:28.33:44.61:24.37
C:VAL:E:173:11.31:44.32:39.82
O:VAL:E:173:12.39:44.22:40.39
N:ILE:E:174:10.54:45.41:39.96
CA:ILE:E:174:10.89:46.47:40.88
CB:ILE:E:174:12.04:47.32:40.46
CG2:ILE:E:174:11.91:47.95:39.07
HG21:ILE:E:174:12.85:48.4:38.69
HG22:ILE:E:174:11.48:47.23:38.34
HG23:ILE:E:174:11.24:48.84:39.09
CG1:ILE:E:174:12.33:48.31:41.54
HG11:ILE:E:174:13.21:48.86:41.17
HG12:ILE:E:174:11.51:49.06:41.66
CD:ILE:E:174:12.63:47.55:42.85
CA:GLU:E:180:15.22:44.73:31.18
CB:GLU:E:180:15.08:44.8:29.68
CG:GLU:E:180:13.99:43.87:29.13
CD:GLU:E:180:12.61:44.47:29.07
OE1:GLU:E:180:11.77:43.82:28.47
OE2:GLU:E:180:12.37:45.56:29.62
C:GLU:E:180:16.66:45.18:31.67
O:GLU:E:180:16.92:46.37:31.79
N:ARG:E:181:17.52:44.24:32.03
CA:ARG:E:181:18.77:44.46:32.78
CB:ARG:E:181:18.92:43.63:34.09
CG:ARG:E:181:17.76:43.76:35.05
CD:ARG:E:181:17.44:45.21:35.48
NE:ARG:E:181:16.46:45.07:36.57
CZ:ARG:E:181:15.95:46.04:37.34
NH1:ARG:E:181:16.49:47.25:37.38
NH2:ARG:E:181:14.99:45.77:38.24
C:ARG:E:181:20.01:44.19:31.93
O:ARG:E:181:20.15:43.09:31.34
N:CYS:E:182:20.87:45.22:31.82
CA:CYS:E:182:22.09:45.11:31.14
CB:CYS:E:182:21.99:45.43:29.59
SG:CYS:E:182:21.66:47.18:29.08
C:CYS:E:182:23.04:46.12:31.74
O:CYS:E:182:22.64:47.12:32.34
N:TRP:E:183:24.37:45.81:31.57
CA:TRP:E:183:25.58:46.48:32.16
CB:TRP:E:183:26.58:45.5:32.83
CG:TRP:E:183:25.98:44.5:33.74
CD1:TRP:E:183:25.39:43.33:33.43
NE1:TRP:E:183:25.23:42.54:34.53
CE2:TRP:E:183:25.63:43.27:35.63
CD2:TRP:E:183:26.15:44.45:35.15
CE3:TRP:E:183:26.81:45.35:36
CZ3:TRP:E:183:26.99:45.02:37.31
CZ2:TRP:E:183:25.77:42.94:36.97
CH2:TRP:E:183:26.44:43.87:37.85
C:TRP:E:183:26.4:47.27:31.12
O:TRP:E:183:27.49:47.62:31.35
N:THR:E:184:25.83:47.36:29.96
CA:THR:E:184:26.45:47.71:28.67
CB:THR:E:184:27.84:47.1:28.37
OG1:THR:E:184:28.35:47.31:27.04
CG2:THR:E:184:27.77:45.63:28.61
HG21:THR:E:184:28.68:45.2:28.14
HG22:THR:E:184:27.7:45.6:29.72
HG23:THR:E:184:26.85:45.09:28.28
C:THR:E:184:25.45:47.35:27.6
NZ:LYS:E:190:26.46:35.8:30.78
C:LYS:E:190:21.95:37.03:35.05
O:LYS:E:190:22.29:37.17:36.2
N:VAL:E:191:20.69:36.82:34.7
CA:VAL:E:191:19.59:36.74:35.61
CB:VAL:E:191:18.22:37.11:35.09
CG1:VAL:E:191:17.03:36.7:35.94
HG11:VAL:E:191:16.87:35.6:35.94
HG12:VAL:E:191:17.19:37.01:36.99
HG13:VAL:E:191:16.08:37.08:35.51
CG2:VAL:E:191:18.15:38.65:35.1
HG21:VAL:E:191:17.31:39.03:34.48
HG22:VAL:E:191:18.29:39.14:36.08
HG23:VAL:E:191:19.03:38.87:34.46

APPENDIX II-continued

ATOMIC COORDINATES FOR MODEL OF CON-INS G1 INSULIN
(CHAINS A AND B) BOUND TO INSULIN RECEPTOR (CHAINS E, F AND X)
Format comprises the following colon-separated fields: (1) atom name, (2)
residue type, (3) chain name, (4) residue number, (5-7) xyz coordinates.

```
OG:SER:E:186:28.91:45.71:23.72
C:SER:E:186:26.2:43.48:24.8
O:SER:E:186:25.98:42.49:24.1
N:HIS:E:187:25.98:43.44:26.13
CA:HIS:E:187:25.82:42.2:26.85
CB:HIS:E:187:27.21:41.62:27.31
ND1:HIS:E:187:28.09:40.71:25.18
CG:HIS:E:187:28.26:41.56:26.21
CE1:HIS:E:187:29.22:40.76:24.47
NE2:HIS:E:187:30.13:41.57:25.12
CD2:HIS:E:187:29.49:42.14:26.2
C:HIS:E:187:24.79:42.39:27.99
O:HIS:E:187:24.64:43.3:28.8
N:CYS:E:188:23.89:41.43:28.15
CA:CYS:E:188:22.84:41.52:29.19
CB:CYS:E:188:21.53:40.8:28.83
SG:CYS:E:188:20.71:41.18:27.27
C:CYS:E:188:23.33:41.03:30.5
O:CYS:E:188:24.3:40.3:30.65
N:GLN:E:189:22.52:41.4:31.54
CA:GLN:E:189:22.75:40.78:32.89
CB:GLN:E:189:21.95:41.49:34
CG:GLN:E:189:22.05:40.89:35.41
CD:GLN:E:189:21.6:41.86:36.6
OE1:GLN:E:189:21.42.88:36.45
NE2:GLN:E:189:22.02:41.49:37.8
C:GLN:E:189:22.53:39.33:32.87
O:GLN:E:189:21.61:38.8:32.17
N:LYS:E:190:23.29:38.5:33.68
CA:LYS:E:190:22.96:37.13:33.93
CB:LYS:E:190:24.21:36.42:34.46
CG:LYS:E:190:25.19:36.21:33.29
CD:LYS:E:190:24.67:35.17:32.28
CE:LYS:E:190:25.86:34.64:31.43
HG12:ILE:E:195:16.11:27.44:42.81
CD:ILE:E:195:14.13:27.67:41.81
C:ILE:E:195:17.24:28.81:44.62
O:ILE:E:195:17.51:27.78:45.21
N:CYS:E:196:18.1:29.36:43.73
CA:CYS:E:196:19.47:28.99:43.44
CB:CYS:E:196:19.82:29.14:41.91
SG:CYS:E:196:18.85:28.06:40.78
C:CYS:E:196:20.48:29.89:44.21
O:CYS:E:196:21.69:29.95:43.94
N:LYS:E:197:19.98:30.7:45.21
CA:LYS:E:197:20.57:31.74:46.01
CB:LYS:E:197:20.98:31.11:47.36
CG:LYS:E:197:19.85:30.36:48.09
CD:LYS:E:197:20.18:29.93:49.58
CE:LYS:E:197:19.2:28.93:50.07
NZ:LYS:E:197:17.88:29.47:50.35
C:LYS:E:197:21.73:32.42:45.4
O:LYS:E:197:21.7:33.44:35
N:SER:E:198:22.95:32.39:46.05
CA:SER:E:198:24.1:32.99:45.34
CB:SER:E:198:25.04:33.93:46.27
OG:SER:E:198:24.31:35.05:46.85
C:SER:E:198:24.96:31.99:44.6
O:SER:E:198:26.04:32.27:44.03
N:HIS:E:199:24.43:30.75:44.49
CA:HIS:E:199:25.17:29.49:44.08
CB:HIS:E:199:24.35:28.16:44.34
ND1:HIS:E:199:22.89:28.14:46.44
CG:HIS:E:199:24.1:28.01:45.8
CE1:HIS:E:199:23.11:28.04:47.7
NE2:HIS:E:199:24.37:27.69:47.98
CD2:HIS:E:199:24.99:27.67:46.75
C:HIS:E:199:25.58:29.47:42.61
O:HIS:E:199:26.6:28.85:42.24
N:GLY:E:200:24.81:30.19:41.77
CA:GLY:E:200:25.06:30.22:40.32
C:GLY:E:200:23.98:29.43:39.54
O:GLY:E:200:23.27:28.57:40.07
N:CYS:E:201:23.88:29.72:38.28
CA:CYS:E:201:22.99:29.24:37.26
C:VAL:E:191:19.53:35.29:36.19
O:VAL:E:191:19.68:34.28:35.47
N:CYS:E:192:19.37:35.12:37.54
CA:CYS:E:192:19.4:33.74:38.08
CB:CYS:E:192:20.8:33.4:38.73
SG:CYS:E:192:21.12:31.64:39.35
C:CYS:E:192:18.35:33.48:39.16
O:CYS:E:192:18.45:34.15:40.23
N:PRO:E:193:17.33:32.58:39.03
CD:PRO:E:193:16.89:32.37:37.78
CA:PRO:E:193:16.41:32.26:40.15
CB:PRO:E:193:15.88:30.86:39.78
CG:PRO:E:193:15.68:31.16:38.22
C:PRO:E:193:16.9:32.23:41.59
O:PRO:E:193:17.9:31.72:42.03
N:THR:E:194:15.98:32.83:42.44
CA:THR:E:194:16.35:33.14:43.84
CB:THR:E:194:15.63:34.33:44.52
OG1:THR:E:194:14.33:34.05:44.94
CG2:THR:E:194:15.44:35.45:43.49
HG21:THR:E:194:16.44:35.66:43.06
HG22:THR:E:194:14.81:35.16:42.61
HG23:THR:E:194:14.92:36.32:43.93
C:THR:E:194:16.41:31.91:44.68
O:THR:E:194:17.02:31.86:45.76
N:ILE:E:195:15.83:30.79:44.25
CA:ILE:E:195:15.95:29.46:44.74
CB:ILE:E:195:14.9:28.64:44.1
CG2:ILE:E:195:13.52:29.33:44.15
HG21:ILE:E:195:13.44:30.13:43.38
HG22:ILE:E:195:12.66:28.64:44.03
HG23:ILE:E:195:13.41:29.7:45.19
CG1:ILE:E:195:15.33:28.23:42.67
HG11:ILE:E:195:15.81:29.11:42.19
OG1:THR:E:202:25.64:24.88:34.97
CG2:THR:E:202:23.96:24.39:36.61
HG21:THR:E:202:23.04:24.75:37.12
HG22:THR:E:202:23.63:23.52:35.99
HG23:THR:E:202:24.67:24.02:37.38
C:THR:E:202:22.75:25.45:34.29
O:THR:E:202:21.53:25.48:34.54
N:ALA:E:203:23.2:24.72:33.22
CA:ALA:E:203:22.44:24.17:32.07
CB:ALA:E:203:22.12:22.7:32.38
C:ALA:E:203:21.23:24.96:31.66
O:ALA:E:203:21.28:26.16:31.48
N:GLU:E:204:20.14:24.25:31.37
CA:GLU:E:204:19.01:24.78:30.71
CB:GLU:E:204:18.05:23.84:29.92
CG:GLU:E:204:18.68:23.13:28.76
CD:GLU:E:204:19.51:21.9:29.23
OE1:GLU:E:204:20.55:21.61:28.63
OE2:GLU:E:204:19.2:21.36:30.39
C:GLU:E:204:18.15:25.59:31.73
O:GLU:E:204:17.63:26.63:31.36
N:GLY:E:205:18.13:25.1:32.98
CA:GLY:E:205:17.31:25.72:34.02
C:GLY:E:205:17.67:25.34:35.37
O:GLY:E:205:16.77:25.2:36.2
N:LEU:E:206:18.97:25.12:35.68
CA:LEU:E:206:19.28:24.47:36.96
CB:LEU:E:206:20.11:23.18:36.73
CG:LEU:E:206:19.3:22.09:36.06
CD1:LEU:E:206:20.22:20.91:35.77
CD2:LEU:E:206:18.19:21.6:37.1
C:LEU:E:206:20.12:25.36:37.75
O:LEU:E:206:20.86:26.22:37.29
N:CYS:E:207:19.96:25.22:39.11
CA:CYS:E:207:20.97:25.78:40.04
CB:CYS:E:207:20.42:25.54:41.43
SG:CYS:E:207:18.82:26.3:41.77
C:CYS:E:207:22.28:25.07:40.02
O:CYS:E:207:22.38:23.99:39.48
N:CYS:E:208:23.35:25.65:40.6
CA:CYS:E:208:24.63:24.99:40.84
```

APPENDIX II-continued

ATOMIC COORDINATES FOR MODEL OF CON-INS G1 INSULIN
(CHAINS A AND B) BOUND TO INSULIN RECEPTOR (CHAINS E, F AND X)
Format comprises the following colon-separated fields: (1) atom name, (2)
residue type, (3) chain name, (4) residue number, (5-7) xyz coordinates.

CB:CYS:E:201:21.96:30.32:36.81
SG:CYS:E:201:20.48:30.49:37.85
C:CYS:E:201:23.63:28.5:36.13
O:CYS:E:201:24.71:28.86:35.58
N:THR:E:202:23.02:27.34:35.78
CA:THR:E:202:23.72:26.31:34.99
CB:THR:E:202:24.65:25.45:35.83
ND1:HIS:E:209:28.17:21.61:46
CG:HIS:E:209:27.34:20.94:45.1
CE1:HIS:E:209:28.57:20.65:46.86
NE2:HIS:E:209:28.14:19.43:46.48
CD2:HIS:E:209:27.35:19.59:45.31
C:HIS:E:209:25.98:23.71:45.12
O:HIS:E:209:26.3:24.89:45.04
N:SER:E:210:25.7:23.18:46.39
CA:SER:E:210:25.57:24.06:47.54
CB:SER:E:210:25.03:23.38:48.78
OG:SER:E:210:25.72:22.2:49.08
C:SER:E:210:26.9:24.74:48.01
O:SER:E:210:26.81:25.79:48.63
N:GLU:E:211:28.08:24.25:47.57
CA:GLU:E:211:29.35:24.92:47.94
CB:GLU:E:211:30.41:23.93:48.44
CG:GLU:E:211:30.06:23.41:49.92
CD:GLU:E:211:28.96:22.29:50.07
OE1:GLU:E:211:29.31:21.13:49.72
OE2:GLU:E:211:27.86:22.64:50.5
C:GLU:E:211:29.91:25.89:46.84
O:GLU:E:211:30.91:26.54:47.07
N:CYS:E:212:29.32:25.95:45.66
CA:CYS:E:212:29.59:26.95:44.66
CB:CYS:E:212:28.91:26.69:43.27
SG:CYS:E:212:29.19:25.15:42.22
C:CYS:E:212:29.26:28.4:44.98
O:CYS:E:212:28.28:28.61:45.71
N:LEU:E:213:30:29.4:44.49
CA:LEU:E:213:29.52:30.71:44.41
CB:LEU:E:213:30.41:31.6:45.28
CG:LEU:E:213:30.25:33.08:45.21
CD1:LEU:E:213:28.84:33.63:45.47
CD2:LEU:E:213:31.25:33.74:46.18
C:LEU:E:213:29.6:31.22:42.98
O:LEU:E:213:30.54:31.01:42.18
N:GLY:E:214:28.5:31.82:42.48
CA:GLY:E:214:28.5:32.58:41.21
C:GLY:E:214:28.19:31.71:39.95
O:GLY:E:214:27.34:32.06:39.13
N:NLG:E:215:29:30.66:39.73
CA:NLG:E:215:29.01:30.01:38.43
CB:NLG:E:215:29.6:30.89:37.3
CG:NLG:E:215:29.34:30.35:35.86
OD1:NLG:E:215:28.45:29.51:35.68
ND2:NLG:E:215:30.19:30.71:34.92
C:NLG:E:215:29.56:28.64:38.57
O:NLG:E:215:30.34:28.33:39.47
CG:PRO:E:222:32.02:19.46:45.64
C:PRO:E:222:33.06:21.42:43.29
O:PRO:E:222:33.73:22.41:43.53
N:THR:E:223:33.47:20.48:42.39
CA:THR:E:223:34.74:20.54:41.73
CB:THR:E:223:35.21:19.16:41.32
OG1:THR:E:223:35.02:18.3:42.41
CG2:THR:E:223:36.72:19.11:40.9
HG21:THR:E:223:37.34:19.8:41.51
HG22:THR:E:223:37.15:18.09:40.84
HG23:THR:E:223:36.88:19.62:39.93
C:THR:E:223:34.62:21.38:40.51
O:THR:E:223:35.64:21.8:39.96
N:LYS:E:224:33.35:21.66:40.11
CA:LYS:E:224:33.24:22.29:38.72
CB:LYS:E:224:32.07:21.48:38.02
CG:LYS:E:224:32.48:20.37:37.86
CD:LYS:E:224:33.57:19.64:36.83
CE:LYS:E:224:33.57:18.14:36.51
NZ:LYS:E:224:34.02:17.31:37.62
CB:CYS:E:208:25.94:25.85:40.79
SG:CYS:E:208:26.18:26.61:39.12
C:CYS:E:208:24.7:24.4:42.3
O:CYS:E:208:23.85:24.63:43.13
N:HIS:E:209:25.71:23.51:42.64
CA:HIS:E:209:25.89:22.8:43.89
CB:HIS:E:209:27.04:21.71:43.85
N:CYS:E:216:29.13:27.76:37.67
CA:CYS:E:216:29.64:26.4:37.56
CB:CYS:E:216:29.05:25.46:38.59
SG:CYS:E:216:27.29:25.15:38.17
C:CYS:E:216:29.67:25.87:36.11
O:CYS:E:216:28.95:26.43:35.25
N:SER:E:217:30.6:24.9:35.77
CA:SER:E:217:30.58:24.34:34.39
CB:SER:E:217:31.98:23.73:33.9
OG:SER:E:217:32.99:24.7:33.73
C:SER:E:217:29.42:23.32:34.24
O:SER:E:217:28.91:23.21:33.13
N:GLN:E:218:29.05:22.57:35.37
CA:GLN:E:218:28.17:21.42:35.46
CB:GLN:E:218:28.9:20.11:35.28
CG:GLN:E:218:29.4:19.64:33.84
CD:GLN:E:218:28.47:19.76:32.65
OE1:GLN:E:218:28.83:20.12:31.56
NE2:GLN:E:218:27.2:19.35:32.87
C:GLN:E:218:27.61:21.38:36.89
O:GLN:E:218:28.32:21.61:37.86
N:PRO:E:219:26.26:21.19:37.04
CD:PRO:E:219:25.38:20.93:35.88
CA:PRO:E:219:25.61:20.77:38.29
CB:PRO:E:219:24.13:20.64:37.92
CG:PRO:E:219:24.16:20.18:36.42
C:PRO:E:219:26.17:19.51:39.02
O:PRO:E:219:26.87:18.72:38.4
N:ASP:E:220:25.77:19.4:40.3
CA:ASP:E:220:25.98:18.12:41.04
CB:ASP:E:220:25.31:16.95:40.33
CG:ASP:E:220:23.89:17.13:39.92
OD1:ASP:E:220:23.44:16.32:39.15
OD2:ASP:E:220:23.24:18.09:40.42
C:ASP:E:220:27.5:17.73:41.42
O:ASP:E:220:27.81:16.57:41.62
N:ASP:E:221:28.39:18.71:41.48
CA:ASP:E:221:29.86:18.6:41.84
CB:ASP:E:221:30.61:18:40.49
CG:ASP:E:221:31.97:17.48:40.85
OD1:ASP:E:221:32.62:16.69:40.06
OD2:ASP:E:221:32.51:17.85:41.93
C:ASP:E:221:30.44:19.95:42.34
O:ASP:E:221:30.23:20.99:41.66
N:PRO:E:222:31.11:20.02:43.52
CD:PRO:E:222:31.15:18.96:44.49
CA:PRO:E:222:31.75:21.26:43.97
CB:PRO:E:222:31.88:21:45.5
CB:CYS:E:228:34.74:28.12:46.97
SG:CYS:E:228:35.67:26.93:45.94
C:CYS:E:228:32.68:29.5:47.25
O:CYS:E:228:32.97:30.69:47.42
N:ARG:E:229:31.52:29.02:47.82
CA:ARG:E:229:30.65:29.51:48.86
CB:ARG:E:229:29.69:28.47:49.35
CG:ARG:E:229:28.83:28.81:50.55
CD:ARG:E:229:27.42:28.23:50.65
NE:ARG:E:229:27.46:26.78:50.8
CZ:ARG:E:229:27.45:26.13:51.98
NH1:ARG:E:229:27.86:26.6:53.1
NH2:ARG:E:229:27.29:24.8:52.03
C:ARG:E:229:31.5:30.03:50.04
O:ARG:E:229:31.35:31.16:50.5
N:ASN:E:230:32.28:29.08:50.63
CA:ASN:E:230:33.22:29.31:51.77
CB:ASN:E:230:32.79:28.43:52.97
CG:ASN:E:230:31.43:28.9:53.5
OD1:ASN:E:230:30.98:30.02:53.47

APPENDIX II-continued

ATOMIC COORDINATES FOR MODEL OF CON-INS G1 INSULIN
(CHAINS A AND B) BOUND TO INSULIN RECEPTOR (CHAINS E, F AND X)
Format comprises the following colon-separated fields: (1) atom name, (2)
residue type, (3) chain name, (4) residue number, (5-7) xyz coordinates.

C:LYS:E:224:32.8:23.76:38.88
O:LYS:E:224:32.48:24.42:37.9
N:CYS:E:225:32.62:24.25:40.12
CA:CYS:E:225:32.37:25.67:40.47
CB:CYS:E:225:32.07:25.85:41.93
SG:CYS:E:225:31.03:24.59:42.71
C:CYS:E:225:33.4:26.61:40.11
O:CYS:E:225:34.56:26.4:40.4
N:VAL:E:226:33.09:27.78:39.42
CA:VAL:E:226:34.02:28.9:39.09
CB:VAL:E:226:33.41:30.06:38.22
CG1:VAL:E:226:34.46:31.08:37.88
HG11:VAL:E:226:34.06:31.83:37.16
HG12:VAL:E:226:34.72:31.63:38.81
HG13:VAL:E:226:35.36:30.68:37.38
CG2:VAL:E:226:32.87:29.42:36.96
HG21:VAL:E:226:31.93:28.84:37.11
HG22:VAL:E:226:32.47:30.24:36.32
HG23:VAL:E:226:33.54:28.97:36.2
C:VAL:E:226:34.7:29.5:40.35
O:VAL:E:226:35.88:29.82:40.25
N:ALA:E:227:33.97:29.56:41.44
CA:ALA:E:227:34.3:30.03:42.72
CB:ALA:E:227:34.09:31.49:42.82
C:ALA:E:227:33.49:29.35:43.82
O:ALA:E:227:32.57:28.62:43.48
N:CYS:E:228:33.82:29.49:45.13
CA:CYS:E:228:33.47:28.67:46.28
CB:LEU:E:233:40.03:22.32:50.6
CG:LEU:E:233:40.83:21.14:51.25
CD1:LEU:E:233:42.18:21.68:51.79
CD2:LEU:E:233:39.99:20.51:52.34
C:LEU:E:233:40.85:21.94:48.17
O:LEU:E:233:39.99:21.22:47.71
N:ASP:E:234:42.11:21.77:47.75
CA:ASP:E:234:42.63:20.8:46.82
CB:ASP:E:234:42.93:19.44:47.57
CG:ASP:E:234:43.93:19.61:48.63
OD1:ASP:E:234:44.09:18.66:49.46
OD2:ASP:E:234:44.73:20.61:48.55
C:ASP:E:234:41.69:20.4:45.6
O:ASP:E:234:41.32:19.26:45.35
N:GLY:E:235:41.19:21.38:44.78
CA:GLY:E:235:40.35:21.28:43.6
C:GLY:E:235:38.88:21.35:43.7
O:GLY:E:235:38.1:21.51:42.76
N:ARG:E:236:38.39:21.42:44.88
CA:ARG:E:236:36.98:21.52:45.18
CB:ARG:E:236:36.32:20.08:45.45
CG:ARG:E:236:36.19:19.57:46.84
CD:ARG:E:236:37.52:19.51:47.61
NE:ARG:E:236:37.38:18.61:48.8
CZ:ARG:E:236:38.36:18.09:49.49
NH1:ARG:E:236:39.6:18.52:49.33
NH2:ARG:E:236:38.11:17.22:50.43
C:ARG:E:236:36.62:22.49:46.29
O:ARG:E:236:37.43:22.8:47.16
N:CYS:E:237:35.39:23.06:46.17
CA:CYS:E:237:34.76:23.95:47.19
CB:CYS:E:237:33.55:24.8:46.49
SG:CYS:E:237:34.21:25.73:44.99
C:CYS:E:237:34.18:23.14:48.33
O:CYS:E:237:33.25:22.32:48.19
N:VAL:E:238:34.68:23.39:49.53
CA:VAL:E:238:34.37:22.73:50.82
CB:VAL:E:238:35.51:21.95:51.44
CG1:VAL:E:238:36.03:20.92:50.37
HG11:VAL:E:238:35.19:20.3:49.98
HG12:VAL:E:238:36.49:21.45:49.51
HG13:VAL:E:238:36.76:20.12:50.63
CG2:VAL:E:238:36.59:22.87:52.04
HG21:VAL:E:238:36.26:23.39:52.96
HG22:VAL:E:238:37.38:22.19:52.42
HG23:VAL:E:238:36.9:23.7:51.37
C:VAL:E:238:33.75:23.79:51.72
ND2:ASN:E:230:30.72:27.95:54.11
C:ASN:E:230:34.63:29.02:51.19
O:ASN:E:230:35.3:29.88:50.7
N:PHE:E:231:35.19:27.76:51.27
CA:PHE:E:231:36.63:27.57:51.13
CB:PHE:E:231:37.28:27.14:52.51
CG:PHE:E:231:36.91:28.02:53.61
CD1:PHE:E:231:37.4:29.27:53.6
CE1:PHE:E:231:37.08:30.25:54.61
CZ:PHE:E:231:36.16:29.85:55.57
CD2:PHE:E:231:36.11:27.6:54.65
CE2:PHE:E:231:35.7:28.51:55.61
C:PHE:E:231:36.99:26.62:49.94
O:PHE:E:231:36.39:25.62:49.74
N:TYR:E:232:38.1:26.94:49.24
CA:TYR:E:232:38.64:26.13:48.23
CB:TYR:E:232:39:27.07:47.06
CG:TYR:E:232:39.7:26.38:45.98
CD1:TYR:E:232:39.12:25.37:45.28
CE1:TYR:E:232:39.79:24.77:44.21
CZ:TYR:E:232:41.08:25.18:43.87
OH:TYR:E:232:41.68:24.55:42.72
CD2:TYR:E:232:41.01:26.8:45.61
CE2:TYR:E:232:41.73:26.2:44.53
C:TYR:E:232:39.84:25.25:48.8
O:TYR:E:232:40.9:25.81:49.2
N:LEU:E:233:39.73:23.95:48.82
CA:LEU:E:233:40.59:22.94:49.28
N:GLU:E:239:32.71:23.41:52.37
CA:GLU:E:239:32.05:24.22:53.4
CB:GLU:E:239:30.81:23.5:53.87
CG:GLU:E:239:30.21:24.12:55.12
CD:GLU:E:239:28.81:23.44:55.33
OE1:GLU:E:239:27.86:23.85:54.59
OE2:GLU:E:239:28.67:22.64:56.24
C:GLU:E:239:32.92:24.61:54.57
O:GLU:E:239:32.92:25.81:54.98
N:THR:E:240:33.78:23.68:55.1
CA:THR:E:240:34.69:24.04:56.18
CB:THR:E:240:34.21:23.69:57.52
OG1:THR:E:240:35.05:24.11:58.59
CG2:THR:E:240:34.22:22.18:57.75
HG21:THR:E:240:33.5:21.7:56.88
HG22:THR:E:240:34.96:21.65:57.97
HG23:THR:E:240:33.31:22.17:58.62
C:THR:E:240:35.99:23.18:55.98
O:THR:E:240:35.93:22.17:55.26
N:CYS:E:241:37.17:23.56:56.59
CA:CYS:E:241:38.36:22.75:56.41
CB:CYS:E:241:39.52:23.67:55.82
SG:CYS:E:241:38.9:24.73:54.54
C:CYS:E:241:38.82:22.09:57.66
O:CYS:E:241:39.42:22.82:58.43
N:PRO:E:242:38.61:20.89:58
CD:PRO:E:242:37.62:20.01:57.35
CA:PRO:E:242:39.23:20.26:59.15
CB:PRO:E:242:38.92:18.76:58.92
CG:PRO:E:242:37.52:18.87:58.29
C:PRO:E:242:40.7:20.44:59.39
O:PRO:E:242:41.36:20.49:58.4
N:PRO:E:243:41.35:20.4:60.58
CD:PRO:E:243:40.74:20.76:61.85
CA:PRO:E:243:42.75:19.92:60.78
CB:PRO:E:243:42.86:19.61:62.31
CG:PRO:E:243:41.98:20.75:62.8
C:PRO:E:243:43.19:18.65:59.96
O:PRO:E:243:42.33:17.8:59.8
N:PRO:E:244:44.41:18.41:59.48
CD:PRO:E:244:44.81:17.3:58.6
CA:PRO:E:244:45.53:19.33:59.65
CB:PRO:E:244:46.75:18.34:59.55
CG:PRO:E:244:46.32:17.47:58.35
C:PRO:E:244:45.6:20.41:58.5
O:PRO:E:244:46.72:20.89:58.26
N:TYR:E:245:44.47:20.84:57.9

APPENDIX II-continued

ATOMIC COORDINATES FOR MODEL OF CON-INS G1 INSULIN
(CHAINS A AND B) BOUND TO INSULIN RECEPTOR (CHAINS E, F AND X)
Format comprises the following colon-separated fields: (1) atom name, (2)
residue type, (3) chain name, (4) residue number, (5-7) xyz coordinates.

O:VAL:E:238:34.19:24.96:51.82
CB:TYR:E:245:43.19:21.63:55.75
CG:TYR:E:245:43.34:20.35:55.14
CD1:TYR:E:245:42.26:19.42:55.26
CE1:TYR:E:245:42.34:18.23:54.51
CZ:TYR:E:245:43.43:18:53.74
OH:TYR:E:245:43.5:16.74:53.17
CD2:TYR:E:245:44.49:20.06:54.39
CE2:TYR:E:245:44.47:18.87:53.64
C:TYR:E:245:44.52:23.18:57.38
O:TYR:E:245:43.87:23.47:58.38
N:TYR:E:246:45.33:24.06:56.76
CA:TYR:E:246:45.6:25.36:57.32
CB:TYR:E:246:47.06:25.63:57.28
CG:TYR:E:246:47.68:24.95:58.45
CD1:TYR:E:246:48.27:23.66:58.27
CE1:TYR:E:246:48.92:22.98:59.35
CZ:TYR:E:246:48.88:23.53:60.61
OH:TYR:E:246:49.3:22.79:61.79
CD2:TYR:E:246:47.77:25.52:59.7
CE2:TYR:E:246:48.24:24.78:60.83
C:TYR:E:246:44.98:26.44:56.45
O:TYR:E:246:45.24:26.58:55.26
N:HIS:E:247:44.07:27.24:57
CA:HIS:E:247:43.33:28.32:56.33
CB:HIS:E:247:42.36:28.85:57.36
ND1:HIS:E:247:39.96:28.32:56.71
CG:HIS:E:247:41.06:28.15:57.58
CE1:HIS:E:247:39.27:27.71:57.23
NE2:HIS:E:247:39.37:27.15:58.43
CD2:HIS:E:247:40.77:27.33:58.6
C:HIS:E:247:44.21:29.41:55.74
O:HIS:E:247:45.27:29.79:56.21
N:PHE:E:248:43.78:29.95:54.57
CA:PHE:E:248:44.55:30.81:53.7
CB:PHE:E:248:45.46:29.93:52.74
CG:PHE:E:248:46.19:30.84:51.8
CD1:PHE:E:248:47.07:31.77:52.41
CE1:PHE:E:248:47.91:32.47:51.54
CZ:PHE:E:248:47.94:32.25:50.18
CD2:PHE:E:248:46.28:30.5:50.47
CE2:PHE:E:248:47.18:31.24:49.63
C:PHE:E:248:43.65:31.84:53.02
O:PHE:E:248:42.63:31.45:52.38
N:GLN:E:249:43.95:33.11:53.17
CA:GLN:E:249:43.32:34.16:52.35
CB:GLN:E:249:43.48:33.99:50.82
CG:GLN:E:249:44.89:34.23:50.26
CD:GLN:E:249:45.6:35.58:50.47
HG12:VAL:E:254:45.87:25.68:49.48
HG13:VAL:E:254:45.3:27:50.63
CG2:VAL:E:254:47.43:26.83:52.39
HG21:VAL:E:254:46.59:27.23:52.99
HG22:VAL:E:254:48.23:26.34:53
HG23:VAL:E:254:47.95:27.72:51.99
C:VAL:E:254:46.91:23.9:52.99
O:VAL:E:254:46.51:23.85:54.14
N:NLG:E:255:47.87:23.06:52.63
CA:NLG:E:255:48.69:22.33:53.62
CB:NLG:E:255:48.98:20.97:53.03
CG:NLG:E:255:50.07:20.82:51.96
OD1:NLG:E:255:50.63:21.8:51.49
ND2:NLG:E:255:50.26:19.66:51.5
C:NLG:E:255:49.85:23.13:54.16
O:NLG:E:255:49.98:24.35:53.89
N:PHE:E:256:50.66:22.51:55.09
CA:PHE:E:256:51.79:23.23:55.72
CB:PHE:E:256:52.27:22.55:56.98
CG:PHE:E:256:53.62:22.97:57.57
CD1:PHE:E:256:54.54:21.91:57.88
CE1:PHE:E:256:55.69:22.13:58.53
CZ:PHE:E:256:55.97:23.38:59.02
CD2:PHE:E:256:53.96:24.23:58.21
CE2:PHE:E:256:55.17:24.51:58.82
C:PHE:E:256:52.97:23.55:54.74

CA:TYR:E:245:44.39:21.77:56.8
OE1:GLN:E:249:45.05:36.53:51.03
NE2:GLN:E:249:46.83:35.62:50
C:GLN:E:249:41.92:34.55:52.78
O:GLN:E:249:41.34:35.5:52.21
N:ASP:E:250:41.36:33.86:53.79
CA:ASP:E:250:40:33.68:54
CB:ASP:E:250:39.36:34.89:54.89
CG:ASP:E:250:40.35:19.06:56.13
OD1:ASP:E:250:40.38:34.18:56.77
OD2:ASP:E:250:40.07:36.45:56.5
C:ASP:E:250:39.1:33.3:52.84
O:ASP:E:250:38:33.82:52.72
N:TRP:E:251:39.56:32.26:52.09
CA:TRP:E:251:38.72:31.78:50.96
CB:TRP:E:251:38.5:32.81:49.85
CG:TRP:E:251:39.55:33.15:48.87
CD1:TRP:E:251:40.38:34.25:48.93
NE1:TRP:E:251:41.23:34.17:47.85
CE2:TRP:E:251:41:33.15:47.08
CD2:TRP:E:251:39.89:32.48:47.59
CE3:TRP:E:251:39.38:31.39:46.88
CZ3:TRP:E:251:40.01:31.07:45.67
CZ2:TRP:E:251:41.65:32.83:45.95
CH2:TRP:E:251:41.09:31.75:45.2
C:TRP:E:251:39.36:30.51:50.4
O:TRP:E:251:38.82:29.87:49.52
N:ARG:E:252:40.9:30.13:50.99
CA:ARG:E:252:41.2:28.92:50.6
CB:ARG:E:252:42.48:29.3:49.89
CG:ARG:E:252:42.28:29.89:48.49
CD:ARG:E:252:43.61:30.1:47.62
NE:ARG:E:252:44.12:28.77:47.27
CZ:ARG:E:252:45.06:28.57:46.4
NH1:ARG:E:252:45.76:29.57:45.84
NH2:ARG:E:252:45.39:27.34:46.16
C:ARG:E:252:41.63:28.09:51.83
O:ARG:E:252:41.81:28.62:52.89
N:CYS:E:253:41.98:26.82:51.63
CA:CYS:E:253:42.65:26.02:52.64
CB:CYS:E:253:41.67:25.16:53.45
SG:CYS:E:253:40.43:26.15:54.32
C:CYS:E:253:43.72:25.25:51.83
O:CYS:E:253:43.53:24.76:50.72
N:VAL:E:254:44.88:25.17:52.49
CA:VAL:E:254:46.15:24.7:51.94
CB:VAL:E:254:46.95:25.82:51.29
CG1:VAL:E:254:46.17:26.49:50.17
HG11:VAL:E:254:46.86:27.19:49.67
C:CYS:E:259:54.27:27.83:53.92
O:CYS:E:259:54.78:28.96:53.99
N:GLN:E:260:55.12:26.8:54.01
CA:GLN:E:260:56.51:26.72:53.84
CB:GLN:E:260:57.06:25.22:54.15
CG:GLN:E:260:56.96:24.64:55.55
CD:GLN:E:260:58.11:23.65:55.81
OE1:GLN:E:260:57.89:22.45:55.57
NE2:GLN:E:260:59.32:24.01:56.33
C:GLN:E:260:57.02:27.21:52.51
O:GLN:E:260:58.02:27.85:52.43
N:ASP:E:261:56.39:26.96:51.33
CA:ASP:E:261:56.69:27.69:50.12
CB:ASP:E:261:55.94:27:48.95
CG:ASP:E:261:56.59:25.71:48.61
OD1:ASP:E:261:55.94:24.88:47.93
OD2:ASP:E:261:57.76:25.52:49.06
C:ASP:E:261:56.4:29.16:50.31
O:ASP:E:261:57.21:29.99:49.84
N:LEU:E:262:55.18:29.46:50.88
CA:LEU:E:262:54.83:30.87:51.1
CB:LEU:E:262:53.4:30.99:51.68
CG:LEU:E:262:52.15:30.82:50.72
CD1:LEU:E:262:50.91:30.56:51.47
CD2:LEU:E:262:51.97:31.9:49.67
C:LEU:E:262:55.82:31.61:51.95

APPENDIX II-continued

ATOMIC COORDINATES FOR MODEL OF CON-INS G1 INSULIN
(CHAINS A AND B) BOUND TO INSULIN RECEPTOR (CHAINS E, F AND X)
Format comprises the following colon-separated fields: (1) atom name, (2)
residue type, (3) chain name, (4) residue number, (5-7) xyz coordinates.

```
O:PHE:E:256:53.54:24.66:54.79
N:SER:E:257:53.31:22.58:53.8
CA:SER:E:257:54.3:22.6:52.75
CB:SER:E:257:54.26:21.28:51.9
OG:SER:E:257:55.13:21.31:50.77
C:SER:E:257:54.04:23.8:51.82
O:SER:E:257:54.92:24.54:51.35
N:PHE:E:258:52.73:24.09:51.52
CA:PHE:E:258:52.33:25.31:50.8
CB:PHE:E:258:50.83:25.22:50.4
CG:PHE:E:258:50.31:26.21:49.29
CD1:PHE:E:258:50.2:27.62:49.45
CE1:PHE:E:258:49.66:28.37:48.44
CZ:PHE:E:258:49.07:27.83:47.32
CD2:PHE:E:258:49.7:25.68:48.12
CE2:PHE:E:258:49.05:26.48:47.15
C:PHE:E:258:52.64:26.54:51.6
O:PHE:E:258:53.17:27.51:51.06
N:CYS:E:259:52.41:26.52:52.98
CA:CYS:E:259:52.78:27.63:53.82
CB:CYS:E:259:52.16:27.44:55.26
SG:CYS:E:259:51.79:29.05:56.1
CA:LYS:E:265:61.66:34.2:49.12
CB:LYS:E:265:63.15:34.43:48.65
CG:LYS:E:265:64.38:34.56:49.65
CD:LYS:E:265:64.13:35.62:50.69
CE:LYS:E:265:64.82:36.96:50.27
NZ:LYS:E:265:64.08:38.15:50.74
C:LYS:E:265:60.69:34.38:47.96
O:LYS:E:265:60.65:33.47:47.12
N:CYS:E:266:60.19:35.6:47.78
CA:CYS:E:266:59.47:35.98:46.54
CB:CYS:E:266:58.94:37.41:46.78
SG:CYS:E:266:57.76:37.49:48.12
C:CYS:E:266:60.13:35.95:45.23
O:CYS:E:266:61.35:36.22:45.02
N:LYS:E:267:59.35:35.56:44.18
CA:LYS:E:267:59.93:35.54:42.82
CB:LYS:E:267:59.37:34.29:42.08
CG:LYS:E:267:59.75:32.98:42.76
CD:LYS:E:267:59.4:31.83:41.86
CE:LYS:E:267:60.01:30.45:42.29
NZ:LYS:E:267:59.58:29.36:41.36
C:LYS:E:267:59.51:36.73:42.08
O:LYS:E:267:60.19:37.12:41.15
N:ASN:E:268:58.3:37.33:42.42
CA:ASN:E:268:57.82:38.5:41.88
CB:ASN:E:268:56.46:38.71:42.53
CG:ASN:E:268:55.68:40.03:42.13
OD1:ASN:E:268:56.08:40.72:41.21
ND2:ASN:E:268:54.55:40.24:42.84
C:ASN:E:268:58.69:39.73:42.02
O:ASN:E:268:59.2:40.04:43.08
N:SER:E:269:58.98:40.47:40.97
CA:SER:E:269:59.9:41.56:41.01
CB:SER:E:269:60.76:41.65:39.69
OG:SER:E:269:59.93:41.72:38.5
C:SER:E:269:59.31:42.91:41.41
O:SER:E:269:60.04:43.94:41.56
N:ARG:E:270:58.02:42.98:41.75
CA:ARG:E:270:57.41:44.26:42.02
CB:ARG:E:270:55.88:44.18:41.84
CG:ARG:E:270:55.41:43.92:40.38
CD:ARG:E:270:53.95:44.27:40.12
NE:ARG:E:270:53.08:43.39:40.94
CZ:ARG:E:270:52.77:42.12:40.68
NH1:ARG:E:270:53.07:41.51:39.54
NH2:ARG:E:270:52.08:41.46:41.58
C:ARG:E:270:57.76:45.04:43.31
O:ARG:E:270:58.32:44.43:44.17
O:GLN:E:276:55.9:34.96:57.48
N:TYR:E:277:55.3:33.91:55.58
CA:TYR:E:277:54.13:33.18:56.1
CB:TYR:E:277:53.27:32.61:54.93
CG:TYR:E:277:52.53:33.61:54.06
O:LEU:E:262:56.03:32.8:51.87
N:HIS:E:263:56.45:30.88:52.94
CA:HIS:E:263:57.53:31.39:53.78
CB:HIS:E:263:57.78:30.49:54.93
ND1:HIS:E:263:60.1:30.15:55.83
CG:HIS:E:263:58.89:30.83:55.82
CE1:HIS:E:263:60.69:30.6:56.97
NE2:HIS:E:263:59.89:31.43:57.67
CD2:HIS:E:263:58.69:31.54:56.94
C:HIS:E:263:58.86:31.77:53.1
O:HIS:E:263:59.58:32.73:53.52
N:HIS:E:264:59.26:30.93:52.12
CA:HIS:E:264:60.42:31.15:51.25
CB:HIS:E:264:60.59:29.96:50.28
ND1:HIS:E:264:62.97:29.88:49.92
CG:HIS:E:264:61.74:30.1:49.31
CE1:HIS:E:264:63.8:29.98:48.87
NE2:HIS:E:264:63.17:30.29:47.72
CD2:HIS:E:264:61.81:30.4:48.03
C:HIS:E:264:60.53:32.48:50.5
O:HIS:E:264:59.53:33.25:50.56
N:LYS:E:265:61.58:32.9:49.82
N:ARG:E:271:57.42:46.34:43.35
CA:ARG:E:271:57.92:47.27:44.37
CB:ARG:E:271:57.46:48.79:44.15
CG:ARG:E:271:58.24:49.42:42.98
CD:ARG:E:271:59.7:49.79:43.3
NE:ARG:E:271:59.82:50.35:44.7
CZ:ARG:E:271:60.5:49.78:45.62
NH1:ARG:E:271:61.4:48.89:45.49
NH2:ARG:E:271:60.28:50.18:46.85
C:ARG:E:271:57.43:46.96:45.76
O:ARG:E:271:58.07:47.27:46.76
N:GLN:E:272:56.13:46.51:45.83
CA:GLN:E:272:55.5:45.85:46.94
CB:GLN:E:272:54.31:45.11:46.42
CG:GLN:E:272:54.64:43.86:45.64
CD:GLN:E:272:53.47:43.44:44.82
OE1:GLN:E:272:53.56:43.42:43.57
NE2:GLN:E:272:52.3:43.18:45.38
C:GLN:E:272:56.27:44.94:47.87
O:GLN:E:272:57.22:44.27:47.5
N:GLY:E:273:55.88:44.87:49.21
CA:GLY:E:273:56.54:44.05:50.2
C:GLY:E:273:56.42:42.62:50.1
O:GLY:E:273:55.53:42.12:49.41
N:CYS:E:274:57.36:41.86:50.67
CA:CYS:E:274:57.39:40.43:50.55
CB:CYS:E:274:58.62:39.89:49.77
SG:CYS:E:274:58.75:38.13:49.78
C:CYS:E:274:57.22:39.91:51.99
O:CYS:E:274:57.91:40.43:52.91
N:HIS:E:275:56.36:38.9:52.19
CA:HIS:E:275:55.99:38.45:53.55
CB:HIS:E:275:54.51:38.58:53.83
ND1:HIS:E:275:53.76:40.88:54.54
CG:HIS:E:275:54.04:39.99:53.52
CE1:HIS:E:275:53:41.89:53.94
NE2:HIS:E:275:52.98:41.66:52.6
CD2:HIS:E:275:53.62:40.47:52.35
C:HIS:E:275:56.38:36.97:53.81
O:HIS:E:275:56.24:36.22:52.88
N:GLN:E:276:56.91:36.68:55.04
CA:GLN:E:276:57.26:35.34:55.54
CB:GLN:E:276:58.48:35.47:56.46
CG:GLN:E:276:59.77:35.74:55.73
CD:GLN:E:276:60.89:35.77:56.8
OE1:GLN:E:276:61.25:36.9:57.19
NE2:GLN:E:276:61.4:34.59:57.34
C:GLN:E:276:56.1:34.72:56.27
O:HIS:E:280:46.62:30.92:62.83
N:ASN:E:281:46.89:30.04:64.84
CA:ASN:E:281:45.51:29.57:64.95
CB:ASN:E:281:44.65:30.79:65.4
CG:ASN:E:281:43.24:30.33:65.7
```

APPENDIX II-continued

ATOMIC COORDINATES FOR MODEL OF CON-INS G1 INSULIN
(CHAINS A AND B) BOUND TO INSULIN RECEPTOR (CHAINS E, F AND X)
Format comprises the following colon-separated fields: (1) atom name, (2)
residue type, (3) chain name, (4) residue number, (5-7) xyz coordinates.

CD1:TYR:E:277:53.23:34.48:53.24
CE1:TYR:E:277:52.59:35.42:52.46
CZ:TYR:E:277:51.23:35.53:52.5
OH:TYR:E:277:50.56:36.37:51.6
CD2:TYR:E:277:51.16:33.78:54.12
CE2:TYR:E:277:50.47:34.65:53.29
C:TYR:E:277:54.37:32.15:57.12
O:TYR:E:277:55.21:31.22:57.01
N:VAL:E:278:53.66:32.22:58.23
CA:VAL:E:278:53.82:31.45:59.48
CB:VAL:E:278:54.28:32.39:60.62
CG1:VAL:E:278:55.85:32.57:60.49
HG11:VAL:E:278:56.37:31.67:60.88
HG12:VAL:E:278:56.14:32.89:59.47
HG13:VAL:E:278:56.03:33.42:61.18
CG2:VAL:E:278:53.6:33.78:60.63
HG21:VAL:E:278:52.61:33.79:60.12
HG22:VAL:E:278:53.31:34.05:61.68
HG23:VAL:E:278:54.21:34.63:60.26
C:VAL:E:278:52.46:30.92:59.8
O:VAL:E:278:51.42:31.1:59.12
N:ILE:E:279:52.38:30.11:60.89
CA:ILE:E:279:51.16:29.43:61.33
CB:ILE:E:279:51.47:27.94:61.61
CG2:ILE:E:279:50.18:27.3:62.13
HG21:ILE:E:279:49.95:27.72:63.13
HG22:ILE:E:279:49.28:27.51:61.52
HG23:ILE:E:279:50.27:26.19:62.06
CG1:ILE:E:279:52.1:27.2:60.43
HG11:ILE:E:279:53.13:27.56:60.2
HG12:ILE:E:279:52.3:5:26.23:60.92
CD:ILE:E:279:51.11:27.15:59.21
C:ILE:E:279:50.67:30.12:62.57
O:ILE:E:279:51.33:30.25:63.61
N:HIS:E:280:49.45:30.64:62.55
CA:HIS:E:280:48.76:31.11:63.75
CB:HIS:E:280:48.76:32.62:63.7
ND1:HIS:E:280:48.36:33.17:66.18
CG:HIS:E:280:47.98:33.28:64.81
CE1:HIS:E:280:47.33:33.71:66.86
NE2:HIS:E:280:46.39:34.26:66.11
CD2:HIS:E:280:46.72:33.99:64.78
C:HIS:E:280:47.36:30.65:63.77
CB:PRO:E:286:51.22:38.05:56.23
CG:PRO:E:286:49.96:37.78:55.45
C:PRO:E:286:52.49:36.98:57.97
O:PRO:E:286:53.71:37.09:57.84
N:GLU:E:287:51.86:37.09:59.14
CA:GLU:E:287:52.6:37.51:60.29
CB:GLU:E:287:52.68:39.06:60.46
CG:GLU:E:287:53.48:39.84:59.33
CD:GLU:E:287:53.27:41.3:59.46
OE1:GLU:E:287:53.34:41.85:60.56
OE2:GLU:E:287:53.06:41.94:58.38
C:GLU:E:287:51.92:37.04:61.55
O:GLU:E:287:50.71:36.94:61.63
N:CYS:E:288:52.77:36.85:62.57
CA:CYS:E:288:52.35:36.65:63.9
CB:CYS:E:288:53.57:36.1:64.72
SG:CYS:E:288:54.3:34.51:64.43
C:CYS:E:288:51.82:37.85:64.47
O:CYS:E:288:52.23:38.95:64.2
N:PRO:E:289:50.83:37.77:65.26
CD:PRO:E:289:49.97:36.59:65.6
CA:PRO:E:289:50.3:38.99:65.93
CB:PRO:E:289:49.16:38.5:66.77
CG:PRO:E:289:48.7:37.22:66.08
C:PRO:E:289:51.25:39.71:66.93
O:PRO:E:289:52.33:39.27:67.23
N:SER:E:290:50.87:40.93:67.44
CA:SER:E:290:51.52:41.59:68.55
CB:SER:E:290:50.64:42.74:69.06
OG:SER:E:290:50.34:43.66:68.02
C:SER:E:290:51.84:40.82:69.86
O:SER:E:290:50.96:40.27:70.59
OD1:ASN:E:281:42.98:29.18:66.01
ND2:ASN:E:281:42.25:31.29:65.77
C:ASN:E:281:44.88:28.78:63.74
O:ASN:E:281:43.79:29.02:63.21
N:ASN:E:282:45.66:27.8:63.21
CA:ASN:E:282:45.21:26.99:62.1
CB:ASN:E:282:43.96:26.07:62.43
CG:ASN:E:282:44.36:24.91:63.35
OD1:ASN:E:282:45.47:24.88:63.84
ND2:ASN:E:282:43.34:24.07:63.54
C:ASN:E:282:45.06:27.77:60.8
O:ASN:E:282:44.45:27.23:59.85
N:LYS:E:283:45.7:28.86:60.62
CA:LYS:E:283:45.9:29.65:59.42
CB:LYS:E:283:45.49:31.11:59.55
CG:LYS:E:283:43.98:31.44:59.81
CD:LYS:E:283:43.27:30.75:60.87
CE:LYS:E:283:41.89:31.41:61.15
NZ:LYS:E:283:41.22:30.81:62.34
C:LYS:E:283:47.38:29.7:58.95
O:LYS:E:283:48.24:29.96:59.75
N:CYS:E:284:47.49:29.78:57.65
CA:CYS:E:284:48.7:30.16:56.99
CB:CYS:E:284:48.89:29.34:55.65
SG:CYS:E:284:50.36:29.83:54.88
C:CYS:E:284:48.64:31.68:56.82
O:CYS:E:284:47.92:32.14:55.91
N:ILE:E:285:49.31:32.47:57.68
CA:ILE:E:285:49.11:33.93:57.78
CB:ILE:E:285:48.47:34.27:59.09
CG2:ILE:E:285:49.43:33.82:60.21
HG21:ILE:E:285:50.3:34.5:60.18
HG22:ILE:E:285:48.95:34:61.2
HG23:ILE:E:285:49.78:32.78:60.12
CG1:ILE:E:285:48.03:35.78:59.19
HG11:ILE:E:285:48.89:36.46:59.12
HG12:ILE:E:285:47.42:35.97:58.29
CD:ILE:E:285:47.18:36.11:60.44
C:ILE:E:285:50.38:34.71:57.5
O:ILE:E:285:51.41:34.09:57.84
N:PRO:E:286:50.49:35.92:56.95
CD:PRO:E:286:49.43:36.48:56.11
CA:PRO:E:286:51.68:36.69:56.74
N:THR:E:293:55.59:35.4:68.65
CA:THR:E:293:56.78:35.13:67.85
CB:THR:E:293:58.04:35.81:68.23
OG1:THR:E:293:59.09:35.52:67.35
CG2:THR:E:293:58.38:35.48:69.74
HG21:THR:E:293:59.11:36.28:69.98
HG22:THR:E:293:57.55:35.54:70.47
HG23:THR:E:293:58.96:34.55:69.93
C:THR:E:293:56.79:33.58:67.45
O:THR:E:293:56.49:32.7:68.25
N:MET:E:294:57.03:33.21:66.17
CA:MET:E:294:56.92:31.8:65.79
CB:MET:E:294:56.88:31.51:64.24
CG:MET:E:294:58.17:32.1:63.56
SD:MET:E:294:58.1:33.85:63.08
CE:MET:E:294:59.75:34.47:63.65
C:MET:E:294:57.96:30.83:66.41
O:MET:E:294:59.16:31.01:66.59
N:ASN:E:295:57.43:29.6:66.85
CA:ASN:E:295:58.2:28.46:67.29
CB:ASN:E:295:57.33:27.36:67.96
CG:ASN:E:295:57.02:27.63:69.42
OD1:ASN:E:295:57.69:28.43:70.08
ND2:ASN:E:295:55.93:27.08:69.97
C:ASN:E:295:59.04:27.84:66.07
O:ASN:E:295:58.55:27.7:64.94
N:SER:E:296:60.27:27.56:66.31
CA:SER:E:296:61.3:26.92:65.44
CB:SER:E:296:62.63:26.58:66.21
OG:SER:E:296:63.38:27.73:66.65
C:SER:E:296:60.82:25.67:64.7
O:SER:E:296:60.38:24.72:65.34

APPENDIX II-continued

ATOMIC COORDINATES FOR MODEL OF CON-INS G1 INSULIN
(CHAINS A AND B) BOUND TO INSULIN RECEPTOR (CHAINS E, F AND X)
Format comprises the following colon-separated fields: (1) atom name, (2)
residue type, (3) chain name, (4) residue number, (5-7) xyz coordinates.

N:GLY:E:291:53.16:40.78:70.21
CA:GLY:E:291:53.67:40.09:71.41
C:GLY:E:291:53.66:38.57:71.17
O:GLY:E:291:53.61:37.77:72.12
N:TYR:E:292:53.64:38.1:69.87
CA:TYR:E:292:53.72:36.71:69.49
CB:TYR:E:292:52.43:36.24:68.63
CG:TYR:E:292:51.24:35.93:69.44
CD1:TYR:E:292:50.37:37:69.87
CE1:TYR:E:292:49.06:36.73:70.36
CZ:TYR:E:292:48.65:35.39:70.48
OH:TYR:E:292:47.38:35.1:70.91
CD2:TYR:E:292:50.68:34.63:69.47
CE2:TYR:E:292:49.44:34.35:70.07
C:TYR:E:292:54.88:36.54:68.52
O:TYR:E:292:55.22:37.41:67.69
CB:LEU:E:299:56.33:28.29:61.26
CG:LEU:E:299:57.55:28.16:60.29
CD1:LEU:E:299:57.25:28.39:58.76
CD2:LEU:E:299:58.82:28.95:60.63
C:LEU:E:299:55.1:28.24:63.4
O:LEU:E:299:54.47:29.13:62.88
N:LEU:E:300:54.7:27.62:64.51
CA:LEU:E:300:53.53:28.08:65.28
CB:LEU:E:300:53.08:27.02:66.27
CG:LEU:E:300:51.76:27.2:67.08
CD1:LEU:E:300:50.61:27.5:66.08
CD2:LEU:E:300:51.51:25.92:67.84
C:LEU:E:300:53.84:29.39:66.08
O:LEU:E:300:54.69:29.58:66.93
N:CYS:E:301:53.04:30.42:65.8
CA:CYS:E:301:52.98:31.67:66.51
CB:CYS:E:301:52.08:32.72:65.74
SG:CYS:E:301:52.82:33.2:64.2
C:CYS:E:301:52.42:31.41:67.89
O:CYS:E:301:51.26:31.02:68.14
N:THR:E:302:53.27:31.79:68.9
CA:THR:E:302:53.07:31.52:70.33
CB:THR:E:302:53.86:30.31:70.79
OG1:THR:E:302:53.07:29.61:71.83
CG2:THR:E:302:55.24:30.69:71.34
HG21:THR:E:302:55.89:31.16:70.56
HG22:THR:E:302:55.24:31.48:72.12
HG23:THR:E:302:55.81:29.81:71.69
C:THR:E:302:53.43:32.84:71.06
O:THR:E:302:54.36:33.53:70.66
N:PRO:E:303:52.72:33.18:72.19
CD:PRO:E:303:51.45:32.6:72.67
CA:PRO:E:303:53.09:34.34:73.08
CB:PRO:E:303:51.99:34.26:74.19
CG:PRO:E:303:50.75:33.67:73.51
C:PRO:E:303:54.49:34.34:73.62
O:PRO:E:303:55.01:33.26:73.9
N:CYS:E:304:55.09:35.51:73.6
CA:CYS:E:304:56.45:35.74:74.02
CB:CYS:E:304:57.19:37.04:73.49
SG:CYS:E:304:56.24:38.57:73.77
C:CYS:E:304:56.66:35.47:75.48
O:CYS:E:304:55.78:35.49:76.36
N:LEU:E:305:57.84:35.01:75.84
CA:LEU:E:305:58.33:34.96:77.24
CB:LEU:E:305:59.61:34.14:77.27
CG:LEU:E:305:59.59:32.71:76.8
CD1:LEU:E:305:60.91:32.05:77.04
N:GLU:F:706:38.27:61.06:49.39
CA:GLU:F:706:39.34:61.4:48.46
CB:GLU:F:706:38.96:62.55:47.43
CG:GLU:F:706:40.08:63.51:46.97
CD:GLU:F:706:39.51:64.62:46.04
OE1:GLU:F:706:38.36:65.09:46.32
OE2:GLU:F:706:40.14:64.98:44.99
C:GLU:F:706:40.59:61.6:49.19
O:GLU:F:706:41.65:61.28:48.76
N:ASP:F:707:40.57:62.44:50.31
CA:ASP:F:707:41.76:62.88:50.99
N:SER:E:297:60.97:25.57:63.45
CA:SER:E:297:60.84:24.41:62.68
CB:SER:E:297:61.56:23.14:63.24
OG:SER:E:297:62.01:22.21:62.19
C:SER:E:297:59.39:24.19:62.25
O:SER:E:297:59.23:23.99:61.03
N:ASN:E:298:58.39:24.27:63.17
CA:ASN:E:298:57:24.06:62.99
CB:ASN:E:298:56.4:23.38:64.26
CG:ASN:E:298:56.79:24.09:65.52
OD1:ASN:E:298:56.25:25.1:65.9
ND2:ASN:E:298:57.68:23.47:66.31
C:ASN:E:298:56.3:25.38:62.68
O:ASN:E:298:55.19:25.39:62.15
N:LEU:E:299:56.95:26.54:62.99
CA:LEU:E:299:56.43:27.87:62.73
CD2:LEU:E:305:58.43:31.95:77.43
C:LEU:E:305:58.47:36.33:77.88
O:LEU:E:305:58.9:37.29:77.31
N:GLY:E:306:58.22:36.4:79.26
CA:GLY:E:306:58.37:37.55:80.16
C:GLY:E:306:57.76:38.82:79.76
O:GLY:E:306:56.85:38.84:78.97
N:PRO:E:307:58.07:40.05:80.14
CD:PRO:E:307:58.91:40.2:81.31
CA:PRO:E:307:57.31:41.23:79.81
CB:PRO:E:307:57.56:42.11:81.04
CG:PRO:E:307:58.98:41.74:81.45
C:PRO:E:307:57.98:41.84:78.56
O:PRO:E:307:58.45:42.99:78.55
N:CYS:E:308:58.03:41.05:77.52
CA:CYS:E:308:58.35:41.4:76.21
CB:CYS:E:308:58.38:40.13:75.3
SG:CYS:E:308:56.9:39.2:75.59
C:CYS:E:308:57.43:42.47:75.67
O:CYS:E:308:56.21:42.26:75.84
N:PRO:E:309:57.83:43.54:74.98
CD:PRO:E:309:59.16:44.06:75.02
CA:PRO:E:309:56.93:44.42:74.29
CB:PRO:E:309:57.9:45.4:73.61
CG:PRO:E:309:59.18:45.49:74.46
C:PRO:E:309:55.92:43.83:73.3
O:PRO:E:309:56.33:42.93:72.61
N:LYS:E:310:54.66:44.26:73.23
CA:LYS:E:310:53.62:43.7:72.47
CB:LYS:E:310:52.18:44.04:73.01
CG:LYS:E:310:51.98:43.4:74.34
CD:LYS:E:310:51.74:41.95:74.22
CE:LYS:E:310:51.28:41.46:75.59
NZ:LYS:E:310:51.27:39.99:75.58
C:LYS:E:310:53.68:44.22:71
OT1:LYS:E:310:53.99:43.38:70.11
OT2:LYS:E:310:53.47:45.43:70.78
N:PHE:F:705:36.51:61.1:51.81
CA:PHE:F:705:37.07:59.86:51.2
CB:PHE:F:705:35.87:59.28:50.29
CG:PHE:F:705:36.24:58.07:49.5
CD1:PHE:F:705:36.59:58.19:48.14
CE1:PHE:F:705:37.13:57.1:47.45
CU:PHE:F:705:37.32:55.86:48.1
CD2:PHE:F:705:36.47:56.86:50.11
CE2:PHE:F:705:36.93:55.73:49.46
C:PHE:F:705:38.28:60.07:50.32
O:PHE:F:705:39.23:59.31:50.43
CA:ASN:F:711:47.1:59.73:51.99
CB:ASN:F:711:46.33:59.87:53.41
CG:ASN:F:711:46.9:61.17:54.13
OD1:ASN:F:711:47.6:61.99:53.51
ND2:ASN:F:711:46.59:61.25:55.41
C:ASN:F:711:47.68:58.36:51.73
O:ASN:F:711:48.94:58.12:51.74
N:VAL:F:712:46.83:57.32:51.55
CA:VAL:F:712:47.22:55.9:51.23
CB:VAL:F:712:46.07:54.82:51.25
CG1:VAL:F:712:46.47:53.39:50.76

APPENDIX II-continued

ATOMIC COORDINATES FOR MODEL OF CON-INS G1 INSULIN
(CHAINS A AND B) BOUND TO INSULIN RECEPTOR (CHAINS E, F AND X)
Format comprises the following colon-separated fields: (1) atom name, (2)
residue type, (3) chain name, (4) residue number, (5-7) xyz coordinates.

CB:ASP:F:707:41.46:64.03:52.01
CG:ASP:F:707:40.74:65.15:51.35
OD1:ASP:F:707:39.87:65.74:52.07
OD2:ASP:F:707:41.65.45:50.17
C:ASP:F:707:42.43:61.7:51.68
O:ASP:F:707:43.68:61.58:51.7
N:TYR:F:708:41.7:60.78:52.26
CA:TYR:F:708:42.23:59.57:52.83
CB:TYR:F:708:41.08:58.83:53.63
CG:TYR:F:708:41.32:57.32:53.87
CD1:TYR:F:708:40.42:56.4:53.18
CE1:TYR:F:708:40.55:55.04:53.48
CU:TYR:F:708:41.54:54.52:54.39
OH:TYR:F:708:41.63:53.11:54.59
CD2:TYR:F:708:42.27:56.75:54.8
CE2:TYR:F:708:42.43:55.37:55.03
C:TYR:F:708:42.9:58.56:51.84
O:TYR:F:708:43.99:58:52.1
N:LEU:F:709:42.23:58.47:50.71
CA:LEU:F:709:42.72:57.91:49.46
CB:LEU:F:709:41.51:57.85:48.46
CG:LEU:F:709:41.82:57.34:46.97
CD1:LEU:F:709:42.47:55.95:47.05
CD2:LEU:F:709:40.54:57.31:46.06
C:LEU:F:709:44.08:58.41:48.99
O:LEU:F:709:45.11:57.68:48.82
N:HSD:F:710:44.18:59.77:48.95
CA:HSD:F:710:45.43:60.49:48.67
CB:HSD:F:710:45.21:62.06:48.59
ND1:HSD:F:710:43.84:63.78:47.34
CG:HSD:F:710:44.55:62.59:47.41
CE1:HSD:F:710:43.39:63.88:46.08
NE2:HSD:F:710:43.8:62.85:45.33
CD2:HSD:F:710:44.53:62.01:46.18
C:HSD:F:710:46.52:60.23:49.72
O:HSD:F:710:47.63:59.93:49.37
N:ASN:F:711:46.17:60.1:51
HG11:VAL:F:715:50.22:55.97:51.92
HG12:VAL:F:715:50.8:54.26:52.26
HG13:VAL:F:715:50.74:55.45:53.52
CG2:VAL:F:715:52.89:55.14:50.83
HG21:VAL:F:715:53.82:55.6:50.45
HG22:VAL:F:715:53.2:54.11:51.09
HG23:VAL:F:715:52.18:55.21:49.96
C:VAL:F:715:53.72:57.87:52.14
O:VAL:F:715:54.56:57.75:51.23
N:PRO:F:716:54.13:58.48:53.3
CD:PRO:F:716:53.38:58.54:54.55
CA:PRO:F:716:55.52:58.68:53.63
CB:PRO:F:716:55.56:59.34:54.99
CG:PRO:F:716:54.37:58.73:55.71
C:PRO:F:716:56.43:57.48:53.54
O:PRO:F:716:55.96:56.34:53.71
N:ARG:F:717:57.75:57.72:53.24
CA:ARG:F:717:58.66:56.71:52.82
CB:ARG:F:717:59.19:56.96:51.37
CG:ARG:F:717:58.07:57.08:50.27
CD:ARG:F:717:57.44:55.7:49.95
NE:ARG:F:717:58.54:54.89:49.47
CU:ARG:F:717:58.85:53.6:49.76
NH1:ARG:F:717:58.09:52.91:50.56
NH2:ARG:F:717:59.9:53:49.31
C:ARG:F:717:59.87:56.5:53.73
O:ARG:F:717:60.49:57.54:54.16
N:PRO:F:718:60.27:55.25:54.02
CD:PRO:F:718:59.49:54.05:53.77
CA:PRO:F:718:61.63:54.88:54.5
CB:PRO:F:718:61.53:53.43:54.95
CG:PRO:F:718:60.47:52.79:54.17
C:PRO:F:718:62.54:55.01:53.29
O:PRO:F:718:62.13:54.82:52.18
N:SER:F:719:63.79:55.5:53.54
CA:SER:F:719:64.81:55.33:52.51
CB:SER:F:719:65.74:56.52:52.38
OG:SER:F:719:65.11:57.83:52.44
HG11:VAL:F:712:46.71:53.48:49.68
HG12:VAL:F:712:47.32:53:51.36
HG13:VAL:F:712:45.66:52.63:50.8
CG2:VAL:F:712:45.43:54.72:52.63
HG21:VAL:F:712:45.01:55.7:52.98
HG22:VAL:F:712:44.48:54.16:52.46
HG23:VAL:F:712:46.1:54.24:53.35
C:VAL:F:712:48.04:55.8:49.92
O:VAL:F:712:49.03:55.1:49.85
N:VAL:F:713:47.59:56.52:48.87
CA:VAL:F:713:48.42:56.58:47.72
CB:VAL:F:713:47.69:57.28:46.53
CG1:VAL:F:713:48.63:57.33:45.33
HG11:VAL:F:713:47.96:57.48:44.45
HG12:VAL:F:713:49.43:58.08:45.48
HG13:VAL:F:713:49.1:56.31:45.23
CG2:VAL:F:713:46.55:56.32:46.23
HG21:VAL:F:713:46.83:55.27:46.43
HG22:VAL:F:713:45.69:56.64:46.85
HG23:VAL:F:713:46.13:56.49:45.22
C:VAL:F:713:49.81:57.26:47.93
O:VAL:F:713:50.83:56.66:47.55
N:PHE:F:714:49.88:58.42:48.62
CA:PHE:F:714:51.01:59.28:48.77
CB:PHE:F:714:50.67:60.72:48.42
CG:PHE:F:714:49.93:60.85:47.16
CD1:PHE:F:714:50.58:60.51:45.98
CE1:PHE:F:714:49.93:60.69:44.72
CU:PHE:F:714:48.73:61.35:44.62
CD2:PHE:F:714:48.68:61.5:47.06
CE2:PHE:F:714:48.18:61.78:45.79
C:PHE:F:714:51.74:59.04:50.09
O:PHE:F:714:52.45:60:50.56
N:VAL:F:715:51.64:57.84:50.69
CA:VAL:F:715:52.29:57.39:51.92
CB:VAL:F:715:52.41:55.91:52.1
CG1:VAL:F:715:50.96:55.35:52.45
CT:NAG:X:720:57.72:52.42:29.41
C3:NAG:X:720:54.42:55.81:29.34
O3:NAG:X:720:54.5:55.8:27.97
C4:NAG:X:720:53.79:57.19:29.86
O4:NAG:X:720:52.51:57.42:29.22
C6:NAG:X:720:53.28:58.62:31.88
O6:NAG:X:720:54.28:59.61:31.56
C1:NAG:X:721:50.32:33.4:28.65
C5:NAG:X:721:51.84:32.26:27.16
O5:NAG:X:721:51.07:32.26:28.41
C2:NAG:X:721:49.37:33.71:27.52
N:NAG:X:721:48.37:34.9:27.67
C:NAG:X:721:47.05:34.83:28.05
O:NAG:X:721:46.49:33.82:28.43
CT:NAG:X:721:46.21:36.08:27.93
C3:NAG:X:721:50.13:33.76:26.22
O3:NAG:X:721:49.28:33.79:25.08
C4:NAG:X:721:51.07:32.58:25.95
O4:NAG:X:721:51.92:32.68:24.8
C6:NAG:X:721:52.8:8:31.02:27.02
O6:NAG:X:721:53.72:30.85:28.14
C1:NAG:X:722:27.17:37.44:47.59
C5:NAG:X:722:26.8:35.84:49.36
O5:NAG:X:722:26.81:36.1:47.95
C2:NAG:X:722:26.03:38.33:48.01
N:NAG:X:722:24.82:38.14:47.21
C:NAG:X:722:23.56:38.6:47.46
O:NAG:X:722:23.14:38.99:48.52
CT:NAG:X:722:22.65:38.53:46.3
C3:NAG:X:722:25.9:38.19:49.52
O3:NAG:X:722:27.05:38.74:50.14
C4:NAG:X:722:25.76:36.77:50
O4:NAG:X:722:24.45:36.26:49.67
C6:NAG:X:722:28.17:35.73:50.1
O6:NAG:X:722:29.12:35:49.36
C1:NAG:X:723:30.04:30.45:33.54
C5:NAG:X:723:29.88:28.78:31.92
O5:NAG:X:723:29.93:29.09:33.31

APPENDIX II-continued

ATOMIC COORDINATES FOR MODEL OF CON-INS G1 INSULIN
(CHAINS A AND B) BOUND TO INSULIN RECEPTOR (CHAINS E, F AND X)
Format comprises the following colon-separated fields: (1) atom name, (2)
residue type, (3) chain name, (4) residue number, (5-7) xyz coordinates.

```
C:SER:F:719:65.77:54.14:52.77
OT1:SER:F:719:66.91:54.24:53.37
OT2:SER:F:719:65.3:53.01:52.44
C1:NAG:X:720:55.48:55.64:31.49
C5:NAG:X:720:53.71:57.27:31.41
O5:NAG:X:720:55.07:56.97:31.77
C2:NAG:X:720:55.75:55.53:29.99
N:NAG:X:720:56.25:54.25:29.59
C:NAG:X:720:57.37:53.77:30.04
O:NAG:X:720:58.06:54.38:30.88
O6:NAG:X:723:28.91:26.68:32.21
C1:NAG:X:724:50.9:19.28:50.25
C5:NAG:X:724:48.85:18.78:49.13
O5:NAG:X:724:50:19.55:49.14
C2:NAG:X:724:51.31:17.79:50.23
N:NAG:X:724:52.44:17.35:51.09
C:NAG:X:724:52.44:17.32:52.44
O:NAG:X:724:51.51:17.63:53.18
CT:NAG:X:724:53.77:16.85:53.01
C3:NAG:X:724:50.08:16.91:50.28
C4:NAG:X:724:49.16:17.31:49.144:NAG:X:724:47.9:16.59:49.41
C6:NAG:X:724:47.87:19.15:47.97
O6:NAG:X:724:47.57:20.51:48.
C2:NAG:X:723:28.84:31.18:32.91
N:NAG:X:723:28.72:32.64:33.2
C:NAG:X:723:28.24:33.18:34.36
O:NAG:X:723:27.43:32.55:35.07
CT:NAG:X:723:28.76:34.47:34.82
C3:NAG:X:723:28.65:30.79:31.45
O3:NAG:X:723:27.46:31.4:31.02
C4:NAG:X:723:28.6:29.26:31.29
O4:NAG:X:723:28.53:28.94:29.9
C6:NAG:X:723:30.06:27.33:31.73
```

The invention claimed is:

1. An insulin analog comprising a human insulin A chain peptide at least 85% identical to wild-type human insulin A chain provided as SEQ ID NO: 24, and a human insulin B chain peptide comprising 90% identity to amino acids 1-22 of wild-type human insulin B chain provided as SEQ ID NO:25 and lacking the last 8 amino acids of the C-terminus of wild-type human insulin B chain, wherein the human insulin B chain peptide comprises a substitution at amino acid 10 and amino acid 20, wherein the substitution at amino acid 20 is G20Y, G20F, or G20P, and wherein the substitution at amino acid 10 is H10E, H10D or H10Q.

2. The insulin analog of claim 1, further comprising at least one substitution in the human insulin A chain peptide.

3. The insulin analog of claim 2, wherein the at least one substitution in the human insulin A chain peptide is T8H, T8Y, T8K, or S9R.

4. The insulin analog of claim 3, further comprising at least two substitutions in the human insulin A chain peptide selected from: T8H, T8Y, T8K, and S9R.

5. The insulin analog of claim 1, wherein the peptide is a des-octapeptide insulin.

6. The insulin analog of claim 1, wherein the human insulin B chain peptide comprises the sequence of FVNQHLCGSELVEALYLVCYER (SEQ ID NO:30).

7. The insulin analog of claim 1, wherein the human insulin A chain comprises the sequence of GIVEQCCHRICSLYQLENYCN (SEQ ID NO: 39).

8. The insulin analog of claim 1, wherein the human insulin A chain comprises the sequence of GIVEQCCHRICSLYQLENYCG (SEQ ID NO: 58).

9. The insulin analog of claim 1, wherein the human insulin A chain peptide and human insulin B chain peptide are bonded via at least one disulfide bond.

10. The insulin analog of claim 1, wherein the peptide is a monomer.

11. A pharmaceutical composition comprising the insulin analog of claim 1 and a pharmaceutically acceptable carrier.

12. A therapeutic protein having a human insulin A chain peptide bonded to a human insulin B chain peptide via at least one disulfide bond, wherein the human insulin A chain comprises the sequence of GIVEQCCHRICSLYQLENYCN (SEQ ID NO:39), and wherein the human insulin B chain peptide comprises the sequence of FVNQHLCG-SELVEALYLVCYER (SEQ ID NO: 30).

13. A therapeutic protein having a human insulin A chain peptide bonded to a human insulin B chain peptide via at least one disulfide bond, wherein the human insulin A chain comprises the sequence of GIVEQCCHRICSLYQLENYCG (SEQ ID NO:58), and wherein the human insulin B chain peptide comprises the sequence of FVNQHLCG-SELVEALYLVCYER (SEQ ID NO: 30).

14. The insulin analog of claim 1, wherein the human insulin B chain comprises an amino acid sequence chosen from SEQ ID NOs: 2-8, 11, 13, 15, 17, 19, 21, 27, and 29-38, and wherein the human insulin A chain peptide and the human insulin B chain peptide are bonded together across at least one pair of cysteine residues.

15. The insulin analog of claim 2, wherein the human insulin A chain comprises an amino acid sequence chosen from SEQ ID NOs: 1, 9-10, 12, 14, 16, 18, 20, 26, 28, 39-41, and 58, and wherein the human insulin A chain peptide and the human insulin B chain peptide are bonded together across at least one pair of cysteine residues.

16. A method for treating an insulin-related condition, comprising administering a therapeutically effective amount of the insulin analog of claim 1 to a subject in need thereof.

17. The method of claim 16, wherein the insulin-related condition is hyperglycemia, insulin resistance, type-1 diabetes, gestational diabetes, or type-2 diabetes.

18. A method for decreasing blood glucose levels, comprising administering a therapeutically effective amount of the insulin analog of claim 1 to a subject in need thereof.

* * * * *